(12) United States Patent
Stewart et al.

(10) Patent No.: US 8,536,157 B2
(45) Date of Patent: Sep. 17, 2013

(54) NON-STEROIDAL COMPOUNDS

(75) Inventors: Alastair Stewart, Victoria (AU); Martin Banwell, Australian Capital Territory (AU); Brenda Leung, Victoria (AU); Anu Augustine, Australian Capital Territory (AU); Jacki Kitching, Australian Capital Territory (AU); Thomasz Bilski, Australian Capital Territory (AU)

(73) Assignee: The University of Melbourne, Victoria (AU)

( * ) Notice: Subject to any disclaimer, the term of this patent is extended or adjusted under 35 U.S.C. 154(b) by 477 days.

(21) Appl. No.: 12/937,148

(22) PCT Filed: Apr. 14, 2008
(Under 37 CFR 1.47)

(86) PCT No.: PCT/AU2008/000519
§ 371 (c)(1),
(2), (4) Date: Mar. 28, 2011

(87) PCT Pub. No.: WO2008/124878
PCT Pub. Date: Oct. 23, 2008

(65) Prior Publication Data
US 2012/0046255 A1 Feb. 23, 2012

(30) Foreign Application Priority Data

Apr. 13, 2007 (AU) .................... 2007901958

(51) Int. Cl.
| | | |
|---|---|---|
| A61K 31/56 | (2006.01) |
| A61K 31/416 | (2006.01) |
| A61K 31/36 | (2006.01) |
| A61K 31/27 | (2006.01) |
| A61K 31/15 | (2006.01) |
| A01N 37/44 | (2006.01) |
| C07D 271/12 | (2006.01) |
| C07D 231/54 | (2006.01) |
| C07D 317/48 | (2006.01) |
| C07D 229/38 | (2006.01) |
| C07D 233/00 | (2006.01) |
| C07D 251/32 | (2006.01) |

(52) U.S. Cl.
USPC ........... 514/171; 514/364; 514/406; 514/465; 514/490; 514/640; 514/539; 514/548; 548/126; 548/356.5; 549/442; 560/35; 564/256

(58) Field of Classification Search
USPC ................ 514/171, 364, 406, 465, 490, 640, 514/539; 548/126, 356.5; 549/442; 560/27, 560/35; 564/256
See application file for complete search history.

(56) References Cited

U.S. PATENT DOCUMENTS
4,566,901 A * 1/1986 Martin et al. ................. 504/112

FOREIGN PATENT DOCUMENTS
WO 2004/101595 11/2004

OTHER PUBLICATIONS
International Search Report of PCT/AU2008/000519 mailed Jun. 11, 2008.
Written Opinion of PCT/AU2008/000519 mailed Jun. 11, 2008.

* cited by examiner

*Primary Examiner* — Jennifer M Kim
(74) *Attorney, Agent, or Firm* — Baker Donelson Bearman Caldwell & Berkowitz, PC

(57) ABSTRACT

The present invention relates to non-steroidal compounds useful in the treatment of inflammatory conditions and pharmaceutical compositions comprising them. A representative example of these compounds is

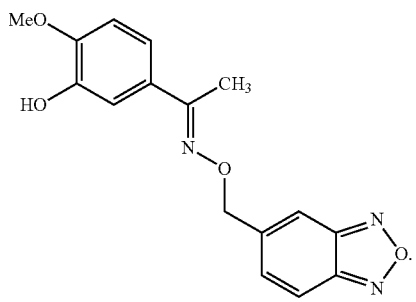

13 Claims, 3 Drawing Sheets

FIGURE 1
Figure 1A
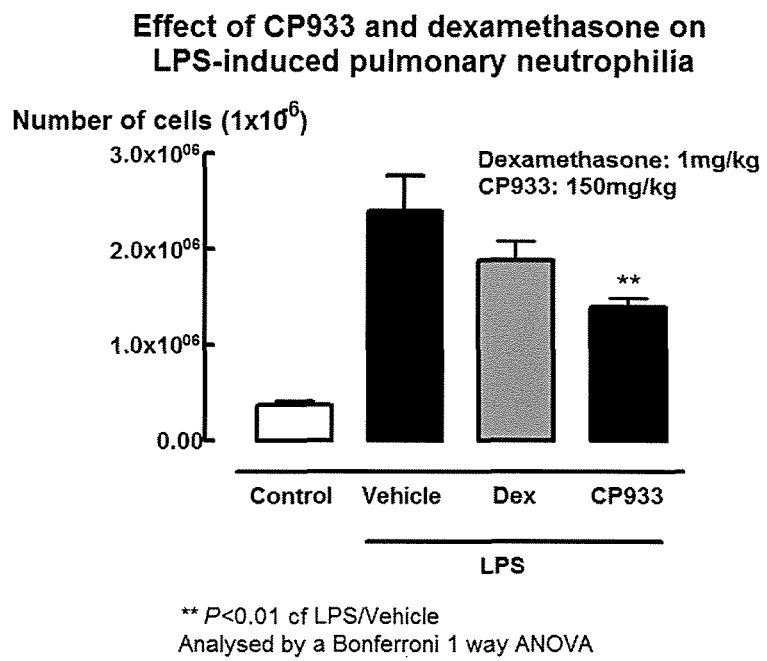
Figure 1B
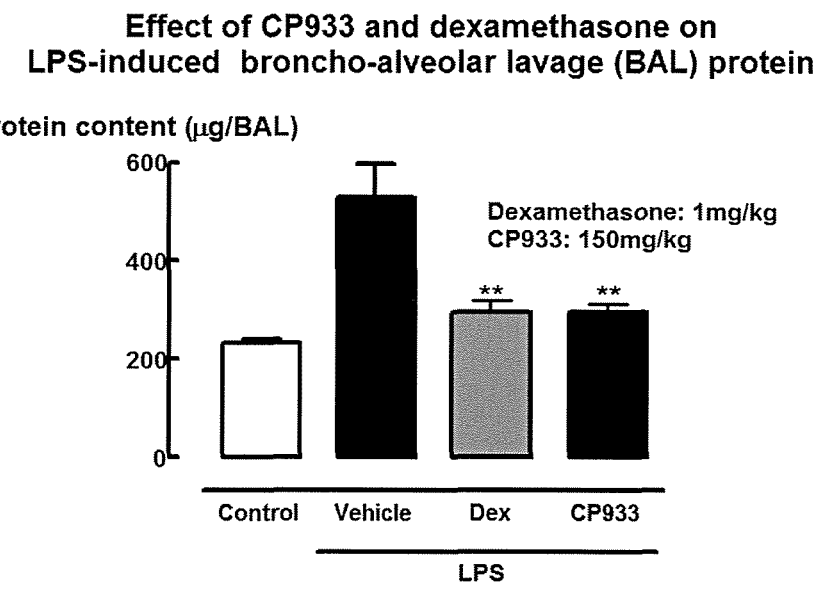

NON-STEROIDAL COMPOUNDS

CROSS REFERENCE TO RELATED APPLICATIONS

This application is a §371 National Stage Application of PCT/AU2008/000519 filed Apr.14, 2008.

FIELD OF THE INVENTION

The present invention relates to non-steroidal compounds useful in the treatment of inflammatory conditions.

BACKGROUND OF THE INVENTION

Inflammatory conditions such as asthma, psoriasis and the like are treatable by glucocorticoids. There are risks associated with the use of steroid-based treatments and there is therefore a need for non-steroidal compounds useful in the treatment of inflammatory conditions. The present inventors have identified a class of compounds useful in the treatment of inflammatory conditions which are not steroid based.

SUMMARY OF THE INVENTION

Accordingly, in a first aspect, the present invention provides a compound of Formula I, or pharmaceutically acceptable salts, derivatives or prodrugs thereof,

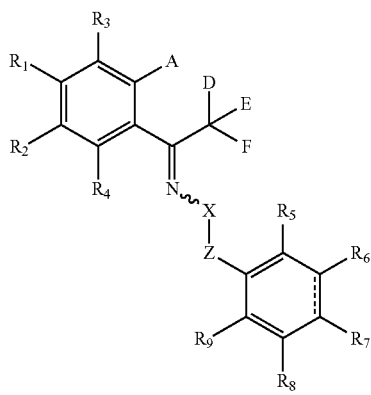

I wherein:
A is H, halo, alkyl, cycloalkyl, aryl, arylalkyl, heterocyclyl, heteroaryl or A together with D may form part of a cyclic group as defined below;
D is H, halo, alkyl, or D together with A may form part of a cyclic group as defined below;
E is H, halo, alkyl, or E together with D or with F may form part of a cyclic group as defined below, or, E, if required by considerations of valency, is absent;
F is H, halo, alkyl, or F together with $R_{10}$ may form part of a cyclic group as defined below;
$R_1$ is selected from the group consisting of H, halo, OH, alkoxy, $OSO_2NH_2$, $OSO_2NHalkyl$ and $OSO_2N(alkyl)_2$ or may form part of a cyclic group as defined below;
$R_2$ is selected from the group consisting of H, halo, OH, alkoxy, $OalkylC(O)Oalkyl$, $OSO_2NH_2$, $OSO_2NHalkyl$ and $OSO_2N(alkyl)_2$ or may form part of a cyclic group as defined below;
$R_3$ is selected from the group consisting of H; halo, alkyl;
$R_4$ is selected from the group consisting of H; halo, alkyl;
$R_5$ is selected from the group consisting of H; halo, and alkyl;
$R_6$ is selected from the group consisting of H, halo, alkyl, $CO_2alkyl$, $OCF_3$, or $R_6$ together with $R_7$ may form part of a cyclic group as defined below;
$R_7$ is selected from the group consisting of H, halo, $CO_2alkyl$, $NO_2$, $C_{1-3}alkyl$, and CN, or $R_7$ together with $R_6$ may form part of a cyclic group as defined below;
$R_8$ is selected from the group consisting of H, halo, alkyl, $CO_2alkyl$, and $OCF_3$;
$R_9$ is selected from the group consisting of H; halo, and alkyl;
X is selected from the group consisting of —O— or $N(R_{10})$;
$R_{10}$ is H or $R_{10}$ together with F may form part of a cyclic group as defined below;
Z is absent or is —$CH_2$—;
A and D may together form a —$CH_2$— or —$(CH_2)_2$— group linking the two carbons to which they are respectively attached;
E and D or E and F may together form a —$(CH_2)_4$— or —$(CH_2)_5$— group linking the carbon atom to which they are respectively attached;
F and $R_{10}$ may together form a =C— group linking the carbon and nitrogen atoms to which they are respectively attached;
$R_1$ and $R_2$ may together form a —O—$CH_2$—O— linker linking the carbon atoms to which they are respectively attached;
$R_6$ and $R_7$ may together form a =N—O—N= group linking the two carbon atoms to which they are respectively attached;
wherein alkyl, cycloalkyl, aryl, arylalkyl, heterocyclyl, heteroaryl and the cyclic groups formed may be optionally substituted with one or more substituents selected from the group consisting of halo, hydroxy, alkyl, haloalkyl, hydroxyalkyl, aryl, alkylaryl, $NO_2$, $NH_2$, NHalkyl, $N(alkyl)_2$, $OCF_3$, $CF_3$, CN, alkoxy, $OSO_2NH_2$, $OSO_2NHalkyl$ and $OSO_2N(alkyl)_2$, C(O)OH, C(O)Oalkyl, C(O)Ocycloalkyl, C(O)Oaryl, C(O)Oarylalkyl, C(O)Oheterocyclyl, C(O)Oheteroaryl, alkylC(O)Oalkyl, alkylC(O)Ocycloalkyl, alkylC(O)Oaryl, alkylC(O)Oarylalkyl, alkylC(O)Oheterocyclyl, alkylC(O)Oheteroaryl, $CONH_2$, CONH(alkyl), CON(alkyl)$_2$, NHC(O)OH, NHC(O)Oalkyl, NHC(O)Ocycloalkyl, NHC(O)Oaryl, NHC(O)Oarylalkyl, NHC(O)Oheterocyclyl, NHC(O)Oheteroaryl, alkylNHC(O)Oalkyl, alkylNHC(O)Ocycloalkyl, alkylNHC(O)Oaryl, alkylNHC(O)Oarylalkyl, alkylNHC(O)Oheterocyclyl, and alkylNHC(O)Oheteroaryl; and
wherein cycloalkyl, aryl, arylalkyl, heterocyclyl, heteroaryl and the cyclic groups formed may form part of an optionally substituted polycyclic or polyaryl group.

In a second aspect, the present invention provides a pharmaceutical composition comprising a compound of formula I and a pharmaceutically acceptable carrier, diluent or excipient.

In a third aspect, the present invention provides a method of treating a condition or disease comprising an inflammatory component in a subject comprising the administration of an effective amount of a compound according to the first aspect or a pharmaceutical composition according to the second aspect to the subject.

BRIEF DESCRIPTION OF THE FIGURES

FIG. 1: FIG. 1A of FIG. 1 shows the effect of CP933, a preferred compound in accordance with the first aspect of the present invention, together with dexamethasone on LPS-induced pulmonary neutrophilia. FIG. 1B of FIG. 1 shows the effect of CP933 and dexamethasone on LPS-induced broncho-alveolar lavage (BAL) protein.

DETAILED DESCRIPTION OF THE INVENTION

Figure 2:
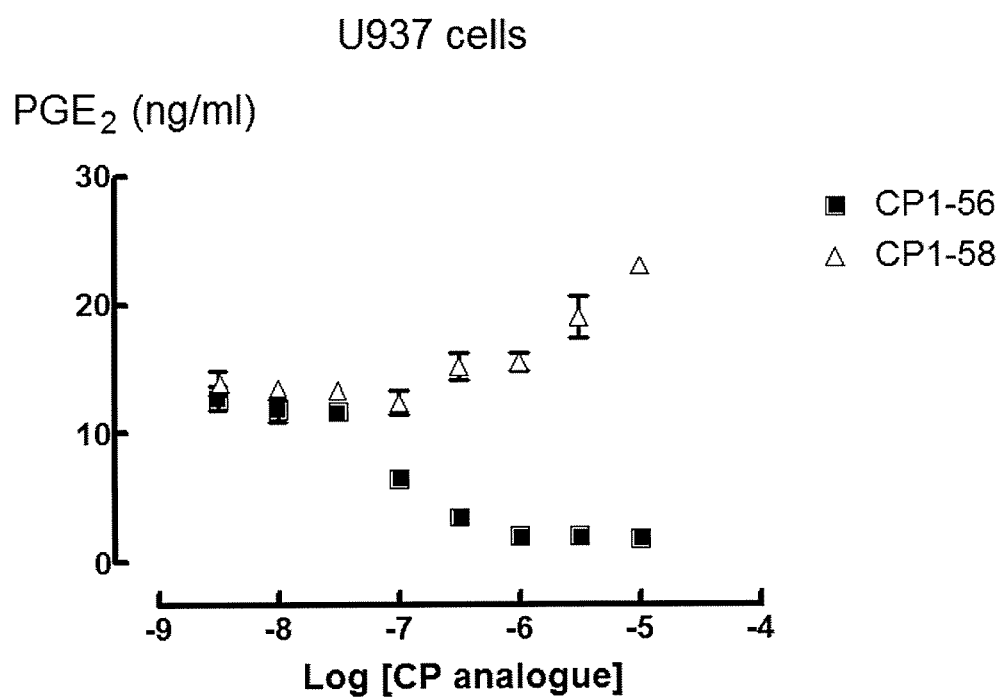
FIG. 2: Shows the evaluation of CP1-56 and CP1-58, compounds of general formula I in accordance with the first aspect of the present invention, for their actions on the release of $PGE_2$ from the human U937 macrophage cell line.

In a first aspect, the present invention provides a compound of Formula I, or pharmaceutically acceptable salts, derivatives or prodrugs thereof,

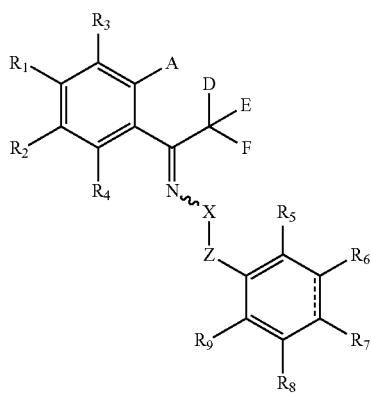

wherein:
A is H, halo, alkyl, cycloalkyl, aryl, arylalkyl, heterocyclyl, heteroaryl or A together with D may form part of a cyclic group as defined below;
D is H, halo, alkyl, or D together with A may form part of a cyclic group as defined below;
E is H, halo, alkyl, or E together with D or with F may form part of a cyclic group as defined below, or, E, if required by considerations of valency, is absent;
F is H, halo, alkyl, or F together with $R_{10}$ may form part of a cyclic group as defined below;
$R_1$ is selected from the group consisting of H, halo, OH, alkoxy, $OSO_2NH_2$, $OSO_2NHalkyl$ and $OSO_2N(alkyl)_2$ or may form part of a cyclic group as defined below;
$R_2$ is selected from the group consisting of H, halo, OH, alkoxy, OalkylC(O)Oalkyl, $OSO_2NH_2$, $OSO_2NHalkyl$ and $OSO_2N(alkyl)_2$ or may form part of a cyclic group as defined below;
$R_3$ is selected from the group consisting of H; halo, alkyl;
$R_4$ is selected from the group consisting of H; halo, alkyl;
$R_5$ is selected from the group consisting of H; halo, and alkyl;
$R_6$ is selected from the group consisting of H, halo, alkyl, $CO_2$alkyl, $OCF_3$, or $R_6$ together with $R_7$ may form part of a cyclic group as defined below;
$R_7$ is selected from the group consisting of H, halo, $CO_2$alkyl, $NO_2$, $C_{1-3}$alkyl, and CN, or $R_7$ together with $R_6$ may form part of a cyclic group as defined below;
$R_8$ is selected from the group consisting of H, halo, alkyl, $CO_2$alkyl, and $OCF_3$;
$R_9$ is selected from the group consisting of H; halo, and alkyl;
X is selected from the group consisting of —O— or $N(R_{10})$;
$R_{10}$ is H or $R_{10}$ together with F may form part of a cyclic group as defined below;
Z is absent or is —$CH_2$—;
A and D may together form a —$CH_2$— or —$(CH_2)_2$— group linking the two carbons to which they are respectively attached;
E and D or E and F may together form a —$(CH_2)_4$— or —$(CH_2)_5$— group linking the carbon atom to which they are respectively attached;
F and $R_{10}$ may together form a =C— group linking the carbon and nitrogen atoms to which they are respectively attached;
$R_1$ and $R_2$ may together form a —O—$CH_2$—O— linker linking the carbon atoms to which they are respectively attached;
$R_6$ and $R_7$ may together form a =N—O—N= group linking the two carbon atoms to which they are respectively attached;
wherein alkyl, cycloalkyl, aryl, arylalkyl, heterocyclyl, heteroaryl and the cyclic groups formed may be optionally substituted with one or more substituents selected from the group consisting of halo, hydroxy, alkyl, haloalkyl, hydroxyalkyl, aryl, alkylaryl, $NO_2$, $NH_2$, NHalkyl, N(alkyl)$_2$, $OCF_3$, $CF_3$, CN, alkoxy, $OSO_2NH_2$, $OSO_2NHalkyl$ and $OSO_2N(alkyl)_2$, C(O)OH, C(O)Oalkyl, C(O)Ocycloalkyl, C(O)Oaryl, C(O)Oarylalkyl, C(O)Oheterocyclyl, C(O)Oheteroaryl, alkylC(O)Oalkyl, alkylC(O)Ocycloalkyl, alkylC(O)Oaryl, alkylC(O)Oarylalkyl, alkylC(O)Oheterocyclyl, alkylC(O)Oheteroaryl, $CONH_2$, CONH(alkyl), CON(alkyl)$_2$, NHC(O)OH, NHC(O)Oalkyl, NHC(O)Ocycloalkyl, NHC(O)Oaryl, NHC(O)Oarylalkyl, NHC(O)Oheterocyclyl, NHC(O)Oheteroaryl, alkylNHC(O)Oalkyl, alkylNHC(O)Ocycloalkyl, alkylNHC(O)Oaryl, alkylNHC(O)Oarylalkyl, alkylNHC(O)Oheterocyclyl, and alkylNHC(O)Oheteroaryl; and
wherein cycloalkyl, aryl, arylalkyl, heterocyclyl, heteroaryl and the cyclic groups formed may form part of an optionally substituted polycyclic or polyaryl group.

Preferably the one or more substituents is selected from the group consisting of halo, hydroxy, alkyl, hydroxyalkyl, $NO_2$, $NH_2$, $OCF_3$, $CF_3$, CN, alkoxy, C(O)Oalkyl, $OSO_2NH_2$, and NHC(O)alkyl.

Preferably alkyl is $C_{1-6}$alkyl, more preferably $C_{1-3}$alkyl and even more preferably alkyl is ethyl or methyl.

Preferably alkoxy is $C_{1-6}$alkoxy, more preferably $C_{1-3}$alkoxy and even more preferably alkoxy is iso-propyloxy, ethoxy or methoxy.

Preferably cycloalkyl is cyclopentyl or cyclohexyl.

Preferably aryl is phenyl.

Preferably arylalkyl is aryl, $C_{1-6}$alkyl, even more preferably arylalkyl is benzyl.

Preferably heterocyclyl and heteroaryl are 5- or 6-membered rings.

Preferably, A is H, halo preferably I or Br, optionally substituted cycloalkyl, optionally substituent aryl or together with D forms a —$CH_2$— or —$(CH_2)_2$— group linking the two carbons to which they are respectively attached.

Preferably, D is H, alkyl or together with A forms a —$CH_2$— or —$(CH_2)_2$— group linking the two carbons to which they are respectively attached.

Preferably, E is H, or E together with D or with F forms part of a cyclic group. Preferably the cyclic group formed by E together with D or with F is substituted with one or more optional substituents selected from alkyl, hydroxy and hydroxyalkyl.

Preferably, F is H, alkyl or together with $R_{10}$ forms a =C— group linking the carbon and nitrogen atoms to which they are respectively attached.

Preferably, $R_1$ is OH, F, $OCH_3$, $OSO_2NH_2$ or together with $R_2$ forms a —O—$CH_2$—O— linker linking the carbon atoms to which they are respectively attached.

Preferably, $R_2$ is OH, F, $OCH_3$, iso-propyloxy, $OSO_2NH_2$ or together with $R_1$ forms a —O—$CH_2$—O— linker linking the carbon atoms to which they are respectively attached.

Preferably, $R_3$ and $R_4$ are each independently H.

Preferably, $R_5$ is H or F.

Preferably, $R_6$ is H, F, $CH_3$, $OCF_3$, or together with $R_7$ forms a =N—O—N= group linking the two carbon atoms to which they are respectively attached.

Preferably, $R_7$ is $NO_2$, $CO_2CH_3$, F, CN or together with $R_6$ forms a =N—O—N= group linking the two carbon atoms to which they are respectively attached.

Preferably, $R_8$ is H, F, $CH_3$, or $OCF_3$.

Preferably, $R_9$ is H or F.

Particularly preferred compounds of Formula I are selected from the group consisting of:

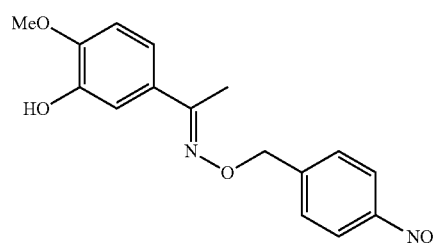

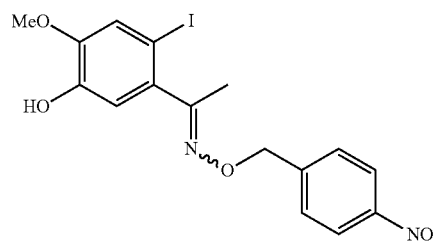

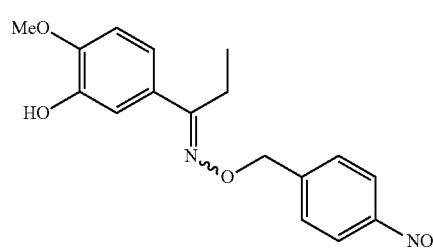

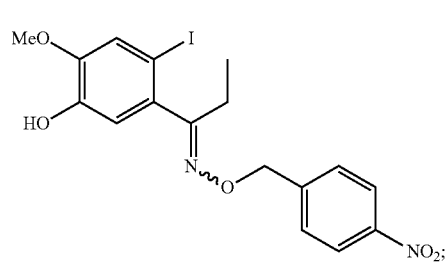

-continued

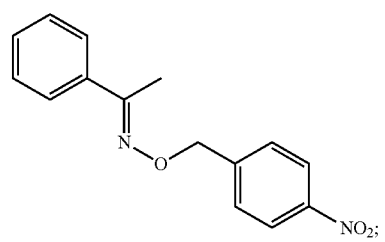

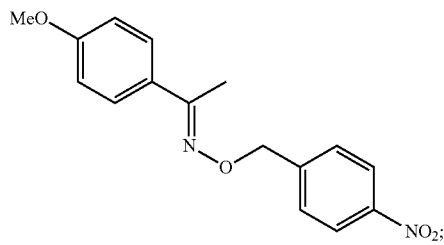

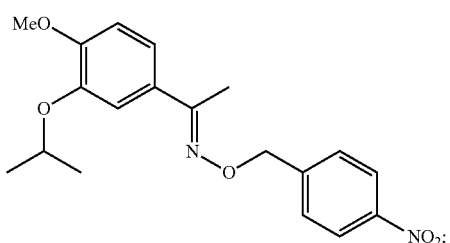

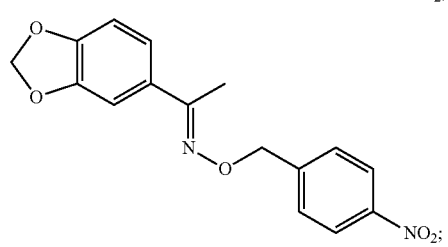

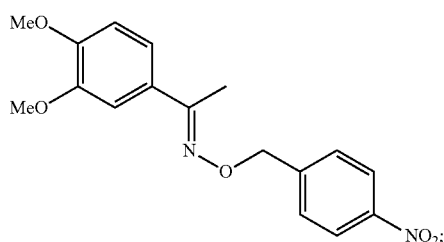

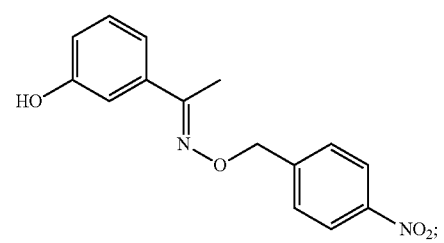

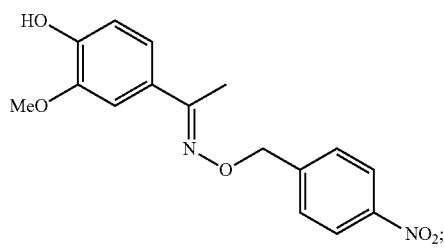

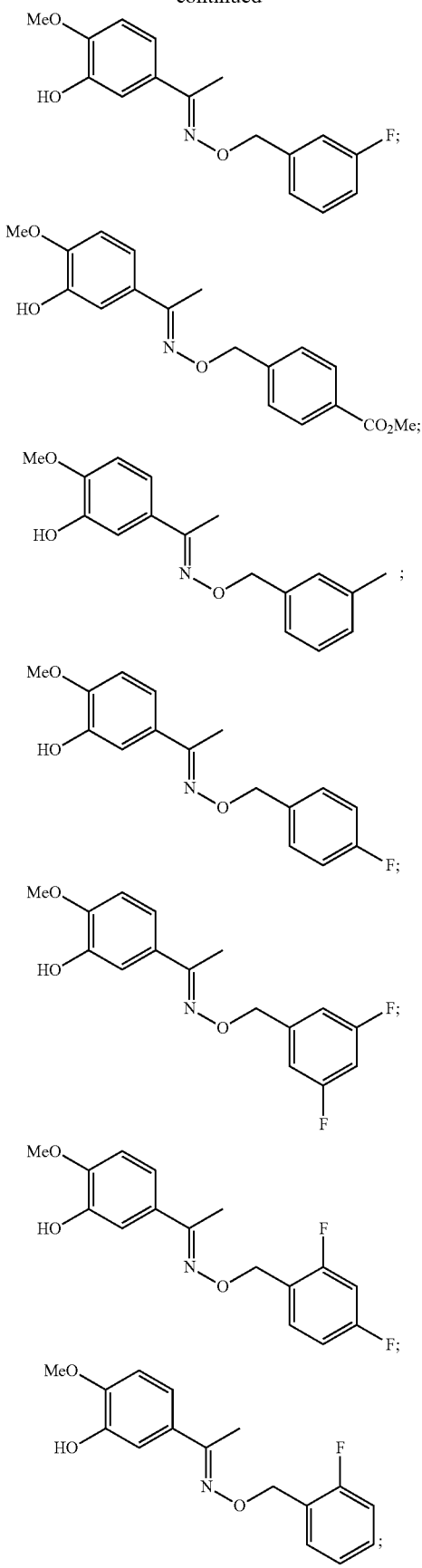
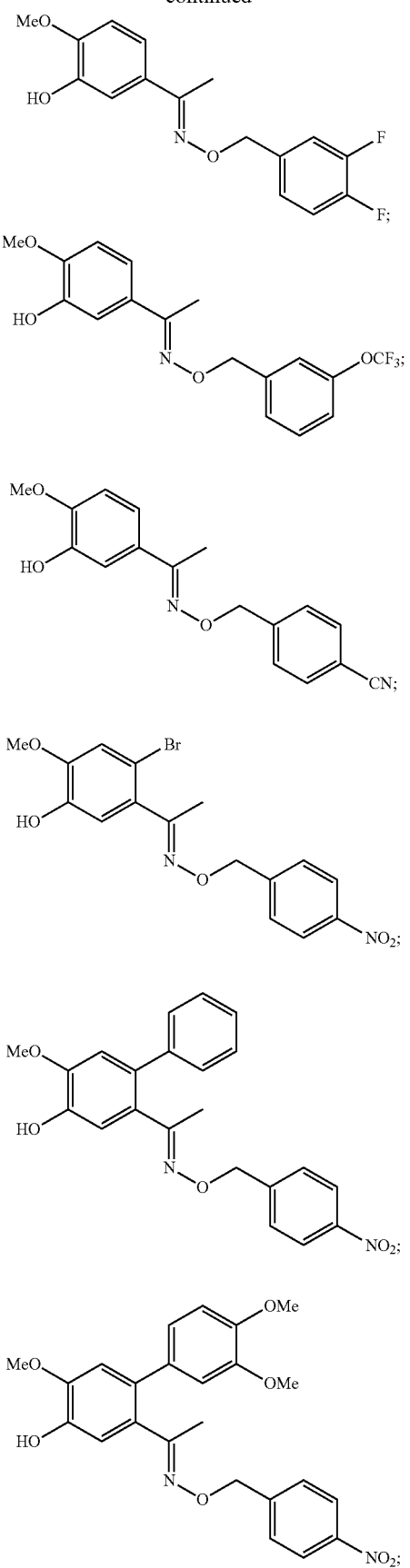

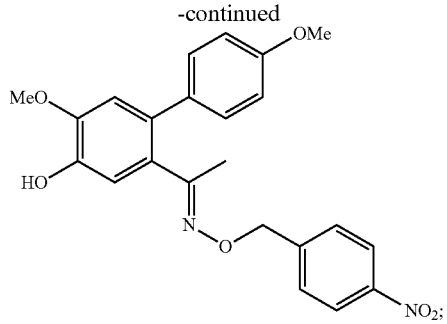
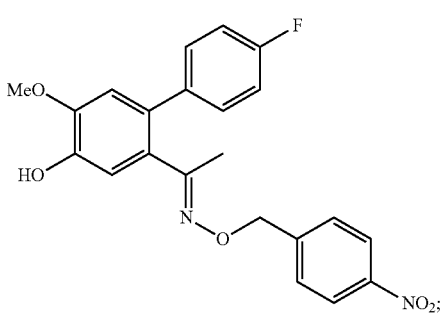
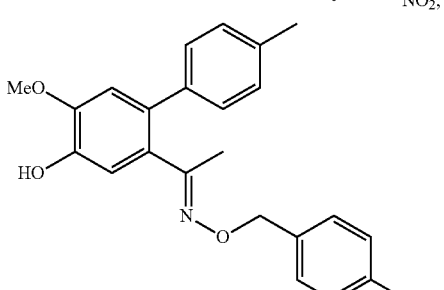
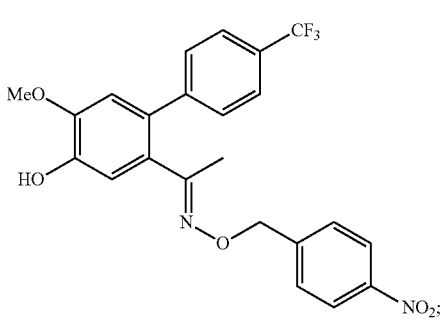
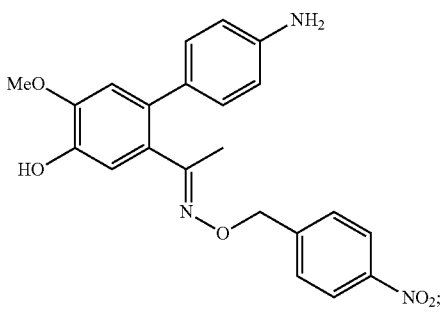
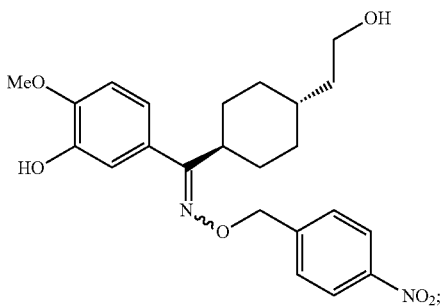

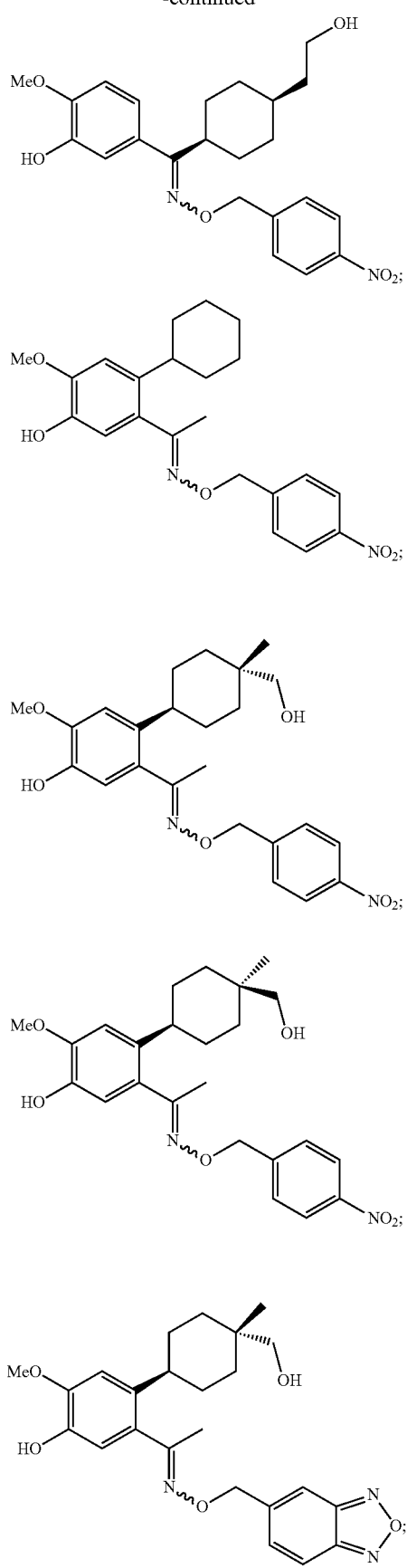
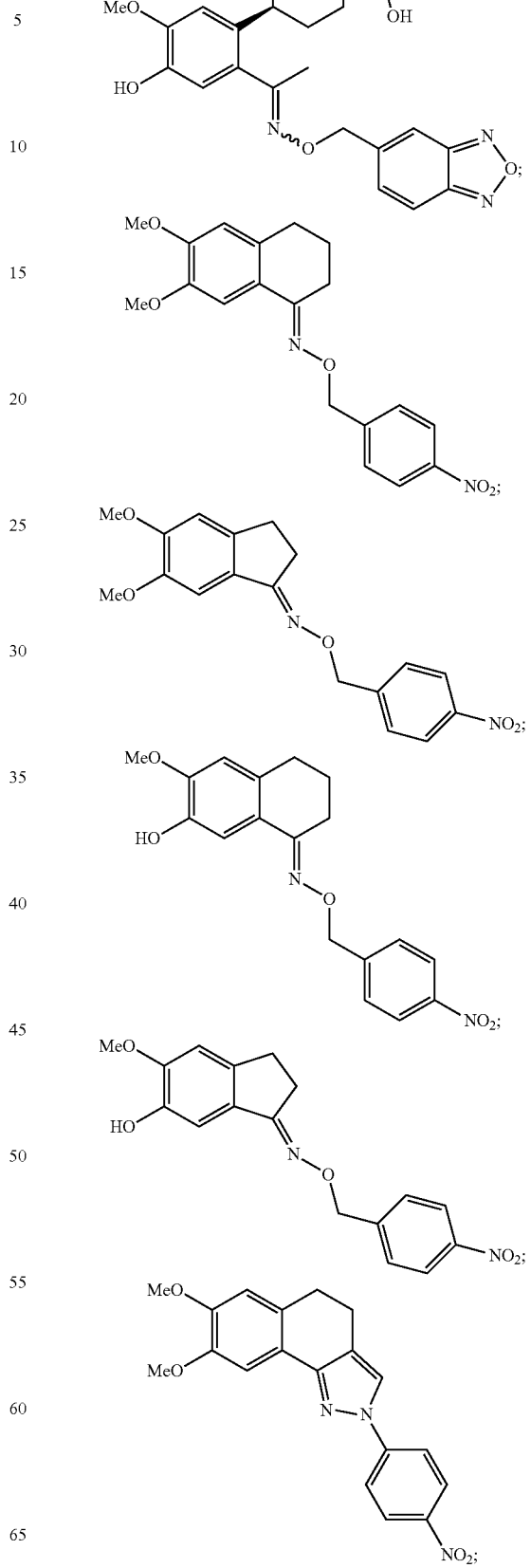

13
-continued
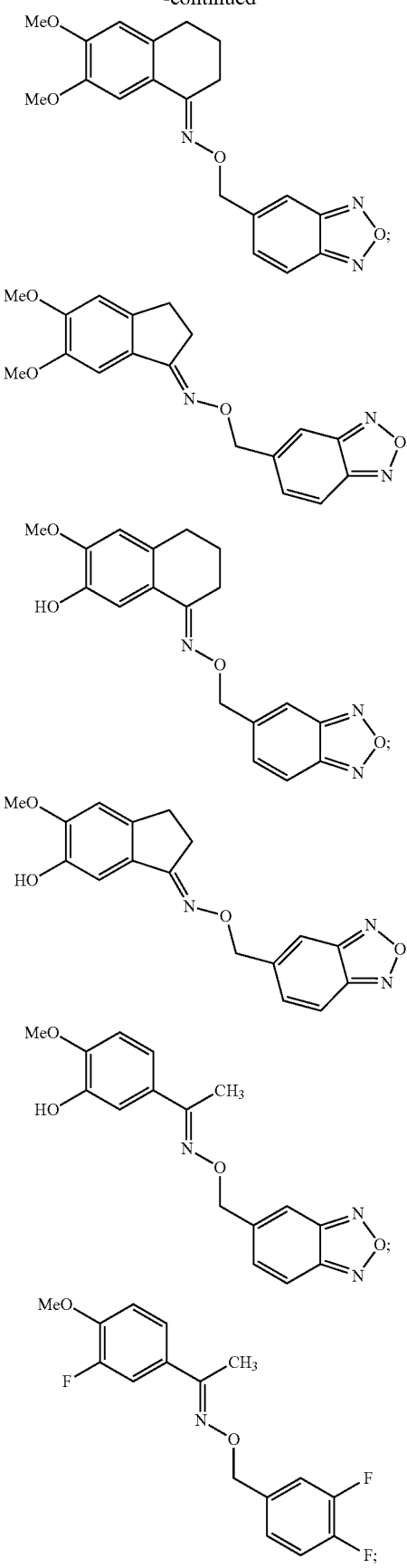
14
-continued
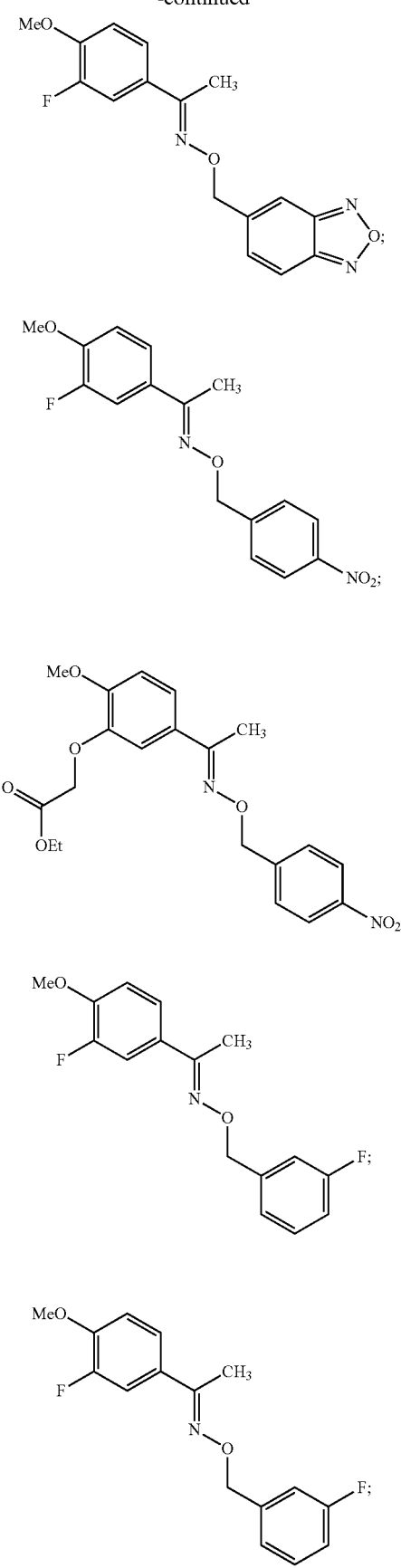

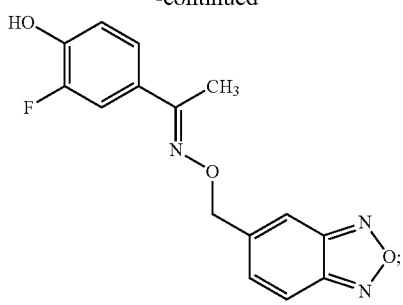
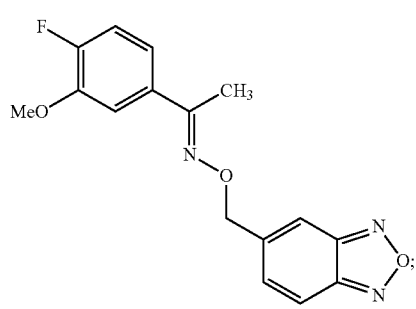
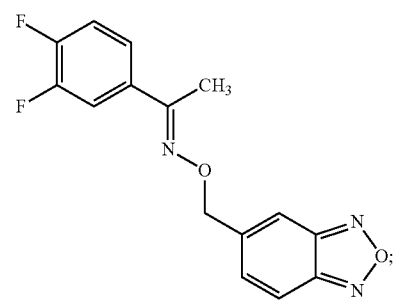
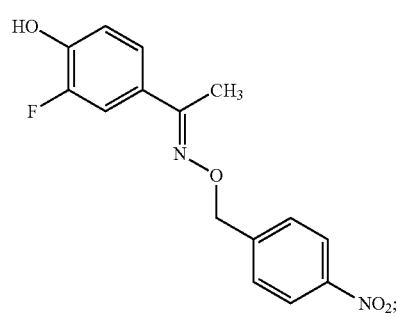
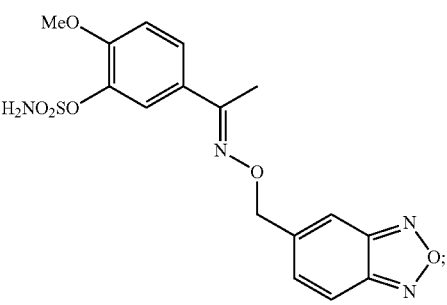
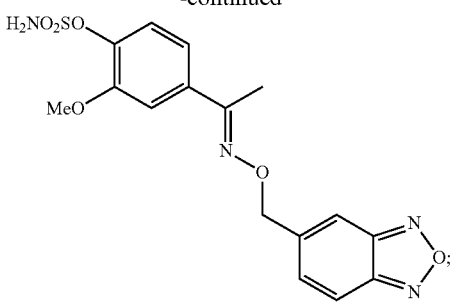
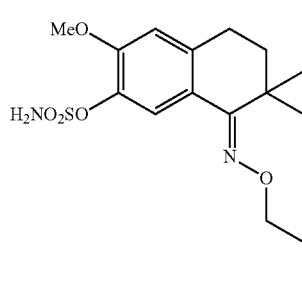
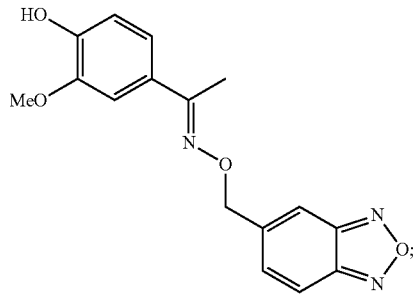
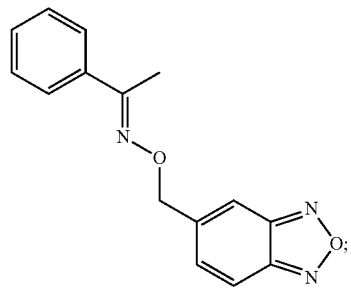
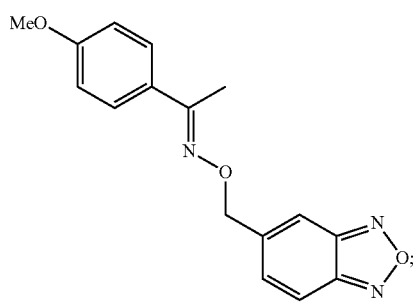

-continued

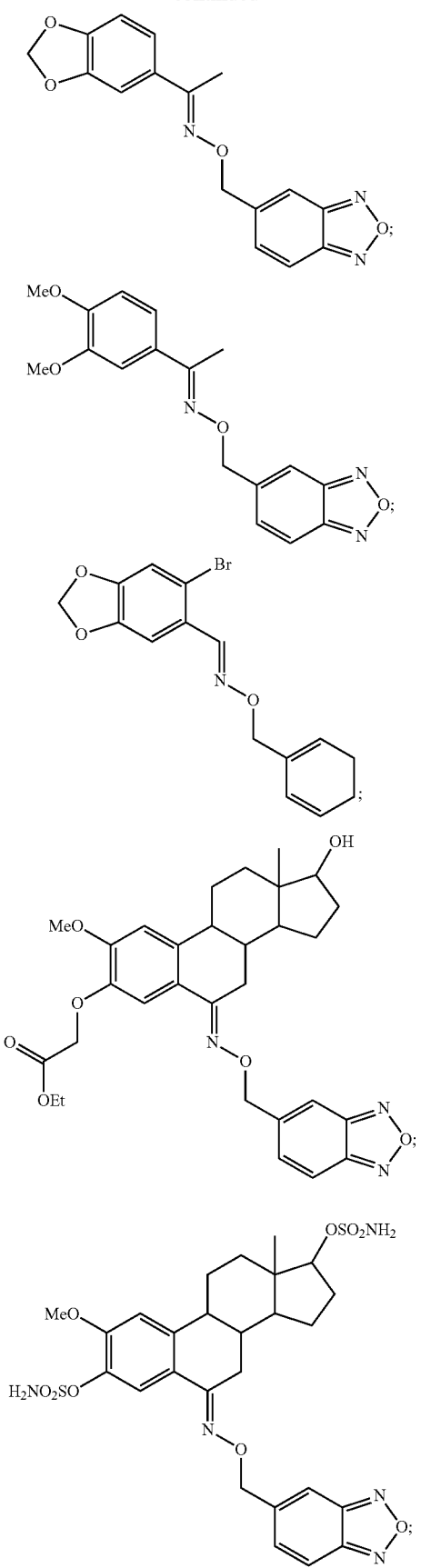

-continued

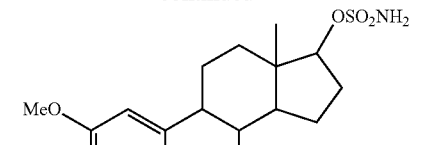
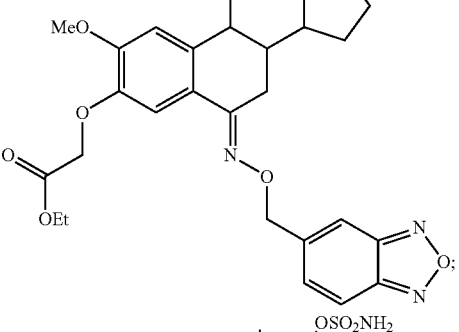
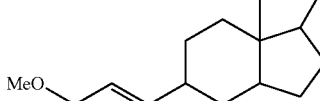
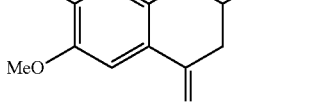
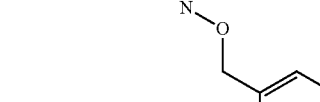

It will be understood that the sulfamated compounds of general formula I may be synthesised from compounds possessing a hydroxy group, preferably a phenolic group. Sulfamation of a hydroxy group may be performed using conventional techniques known to those skilled in the art.

In a preferred embodiment, the compounds of Formula I have the "E" conformation around the C=N double bond.

It is also preferred that the compounds of Formula I are in substantially pure isomeric form at one of more asymmetric centres.

As used herein, the term "halo" or "halogen" refers to fluorine (fluoro), chlorine (chloro), bromine (bromo) or iodine (iodo).

As used herein, the term "alkyl" either used alone or in compound terms such as NH(alkyl) or N(alkyl)$_2$, refers to monovalent straight chain or branched hydrocarbon groups. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

The term "aryl" as used herein, refers to a $C_6$-$C_{10}$ aromatic hydrocarbon group, for example phenyl or naphthyl.

The term "arylalkyl" includes, for example, benzyl.

The term "cycloalkyl" refers to a $C_3$-$C_{10}$ cyclic hydrocarbon and includes, for example, cyclopentyl and cyclohexyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. Suitable heteroatoms include O, N and S, S(O) and S($O_2$). Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, tetrahydrofuranyl, tetrahydropyranyl, tetrahydropyrrolyl, lactams, sultams etc.

The term "heteroaryl" includes a 5- or 6-membered heteroaromatic ring containing one or more heteroatoms selected from O, N and S. Suitable examples of heteroaryl groups include tetrazolyl, 1,2,3-triazolyl, 1,2,4-triazolyl, imidazolyl, pyrazolyl, pyridinyl, pyrimidinyl, oxazolyl, oxadiazolyl etc. The heteroaromatic ring may be fused to another 5- or 6-membered aromatic ring to form a bicyclic aromatic system eg benzofuran.

Each alkyl, alkenyl, alkynyl, cycloalkyl, aryl, heterocyclyl, or heteroaryl group may be optionally substituted with halo, hydroxy, alkyl, haloalkyl, hydroxyalkyl, aryl, alkylaryl, $NO_2$, $NH_2$, NHalkyl, N(alkyl)$_2$, $OCF_3$, $CF_3$, CN, alkoxy, $OSO_2NH_2$, $OSO_2NH$alkyl and $OSO_2N$(alkyl)$_2$, C(O)OH, C(O)Oalkyl, C(O)Ocycloalkyl, C(O)Oaryl, C(O)Oarylalkyl, C(O)Oheterocyclyl, C(O)Oheteroaryl, alkylC(O)Oalkyl, alkylC(O)Ocycloalkyl, alkylC(O)Oaryl, alkylC(O)Oarylalkyl, alkylC(O)Oheterocyclyl, alkylC(O)Oheteroaryl, $CONH_2$, CONH(alkyl), CON(alkyl)$_2$, NHC(O)OH, NHC(O)Oalkyl, NHC(O)Ocycloalkyl, NHC(O)Oaryl, NHC(O)Oarylalkyl, NHC(O)Oheterocyclyl, NHC(O)Oheteroaryl, alkylNHC(O)Oalkyl, alkylNHC(O)Ocycloalkyl, alkylNHC(O)Oaryl, alkylNHC(O)Oarylalkyl, alkylNHC(O)Oheterocyclyl, and alkylNHC(O)Oheteroaryl. For example, an optionally substituted aryl group may be 4-methylphenyl or 4-hydroxyphenyl group, and an optionally substituted alkyl group may be 2-hydroxyethyl, trifluoromethyl, or difluoromethyl. Each aryl may optionally be fused with a dioxolane ring. Any of the above substituents may additionally be substituted by optional substituents.

Optional substituents also includes suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or a pharmaceutically active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

This invention also encompasses pharmaceutical compositions containing prodrugs of compounds of formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions). The compounds of the present invention may also be administered intranasally or via inhalation, for example by atomiser, aerosol or nebulizer means. Particularly preferred modes of administration include parental, oral and inhalation.

In a second aspect, the present invention provides a pharmaceutical composition comprising a compound of the first aspect and a pharmaceutically acceptable carrier, diluent or excipient.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of inflammatory conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Suitable agents for use in combination with the compounds of the present invention include, for example, the glucocorticoids. Accordingly, in a preferred embodiment, the pharmaceutical composition further comprises a glucocorticoid. In still another preferred embodiment, the pharmaceutical composition further comprises a β2-adrenoceptor agonist.

When other therapeutic agents are employed in combination with the compounds of the present invention they may be used for example in amounts as noted in the Physician Desk Reference (PDR) or as otherwise determined by one of ordinary skill in the art.

In a third aspect, the present invention provides a method of treating a condition or disease comprising an inflammatory component in a subject comprising the administration of an effective amount of a compound according to the first aspect or a pharmaceutical composition according to the second aspect to the subject.

Representative conditions or diseases comprising an inflammatory component include, but are not limited to, (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

Conditions and diseases comprising an inflammatory component which are arranged in accordance with the system of the body which they affect are listed in Table 1 below.

TABLE 1

|  | Acute | Chronic |
|---|---|---|
| Circulatory system | Infarction/re-perfusion injury | Atherosclerosis |
| Digestive system | Gastric ulceration | Crohn's Disease |
| Excretory system | Acute interstitial nephritis | Chronic renal failure |
| Endocrine system | Pancreatitis | Thyroiditis |
| Integumentary system | Burns | Psoriasis |
| Muscular system | Acute myositis | Polymyositis |
| Nervous system | Meningitis | Multiple Sclerosis |
| Reproductive system | Pyometra | Vaginitis |

TABLE 1-continued

| | Acute | Chronic |
|---|---|---|
| Respiratory system | Acute Respiratory Distress Syndrome | Cystic Fibrosis |
| Skeletal system | Osteomyelitis | Arthritis |

In a further embodiment, the inflammatory disease is selected from the group consisting of chronic inflammatory disease and acute inflammatory disease.

In another embodiment, the disease or condition is associated with hypersensitivity.

Preferably, the hypersensitivity is selected from the group consisting of Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and delayed type hypersensitivity.

More preferably, the delayed type hypersensitivity is selected from the group consisting of contact dermatitis and drug eruption.

More preferably, the T lymphocyte-mediated hypersensitivity is selected from the group consisting of helper T lymphocyte mediated hypersensitivity and cytotoxic T lymphocyte mediated hypersensitivity.

Yet more preferably, the helper T lymphocyte-mediated hypersensitivity is selected from the group consisting of $T_{h1}$ lymphocyte mediated hypersensitivity and $T_{h2}$ lymphocyte mediated hypersensitivity.

In another embodiment, the disease or condition is associated with autoimmune disease.

Preferably, the autoimmune disease is selected from the group consisting of cardiovascular disease, rheumatoid disease, glandular disease, gastrointestinal disease, cutaneous disease, hepatic disease, neurological disease, muscular disease, nephric disease, disease related to reproduction, connective tissue disease and systemic disease.

More preferably, the cardiovascular disease is selected from the group consisting of occlusive disease, atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity in Chagas' disease and anti-helper T lymphocyte autoimmunity.

More preferably, the rheumatoid disease is selected from the group consisting of rheumatoid arthritis and ankylosing spondylitis.

More preferably, the glandular disease is selected from the group consisting of pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

More preferably, the gastrointestinal disease is selected from the group consisting of colitis, ileitis, Crohn's disease, chronic inflammatory intestinal disease and celiac disease.

More preferably, the cutaneous disease is selected from the group consisting of autoimmune bullous skin disease, pemphigus vulgaris, bullous pemphigoid and pemphigus foliaceus.

More preferably, the hepatic disease is selected from the group consisting of autoimmune hepatitis and primary biliary cirrhosis.

More preferably, the neurological disease is selected from the group consisting of neurodegenerative disease, multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis and stiff-man syndrome.

More preferably, the muscular disease is selected from the group consisting of autoimmune myositis, primary Sjogren's syndrome and smooth muscle autoimmune disease.

More preferably, the nephric disease is autoimmune interstitial nephritis.

More preferably, the disease related to reproduction is repeated fetal loss.

More preferably, the connective tissue disease is selected from the group consisting of autoimmune ear disease and autoimmune disease of the inner ear.

More preferably, the systemic disease is selected from the group consisting of systemic lupus erythematosus and systemic sclerosis.

In a further embodiment, the disease or condition is associated with an infectious disease.

Preferably, the infectious disease is selected from the group consisting of chronic infectious disease, subacute infectious disease, acute infectious disease, viral disease, bacterial disease, protozoan disease, parasitic disease, fungal disease, mycoplasma disease and prion disease.

In a further embodiment, the disease or condition is associated with a disease associated with transplantation of a graft.

Preferably, the disease is selected from the group consisting of graft rejection, chronic graft rejection, subacute graft rejection, hyperacute graft rejection, acute graft rejection and graft versus host disease.

Preferably, the graft is selected from the group consisting of a syngeneic graft, an allograft and a xenograft.

Preferably, the graft is selected from the group consisting of a cellular graft, a tissue graft, an organ graft and an appendage graft.

More preferably, the cellular graft is selected from the group consisting of a stem cell graft, a progenitor cell graft, a hematopoietic cell graft, an embryonic cell graft and a nerve cell graft.

More preferably, the tissue graft is selected from the group consisting of a skin graft, a bone graft, a nerve graft, an intestine graft, a corneal graft, a cartilage graft, a cardiac tissue graft, a cardiac valve graft, a dental graft, a hair follicle graft and a muscle graft.

More preferably, the organ graft is selected from the group consisting of a kidney graft, a heart graft, a skin graft, a liver graft, a pancreatic graft, a lung graft and an intestine graft.

More preferably, the appendage graft is selected from the group consisting of an arm graft, a leg graft, a hand graft, a foot graft, a finger graft, a toe graft and a sexual organ graft.

In a further embodiment, the disease or condition is associated with an allergic disease.

Preferably, the allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

In another embodiment, the disease or condition is associated with a neurodegenerative disease.

In a further embodiment, the disease or condition is associated with a cardiovascular disease.

In a further embodiment, the disease or condition is associated with a gastrointestinal disease.

In a further embodiment, the disease or condition is associated with a.

Preferably, the is selected from the group consisting of a malignant, a benign, a solid, a metastatic and a non-solid.

In a further embodiment, the disease or condition is associated with septic shock.

In a further embodiment, the disease or condition is associated with anaphylactic shock.

In a further embodiment, the disease or condition is associated with toxic shock syndrome.

In a further embodiment, the disease or condition is associated with cachexia.

In a further embodiment, the disease or condition is associated with necrosis.

In a further embodiment, the disease or condition is associated with gangrene.

In a further embodiment, the disease or condition is associated with a prosthetic implant.

Preferably, the prosthetic implant is selected from the group consisting of a breast implant, a silicone implant, a dental implant, a penile implant, a cardiac implant, an artificial joint, a bone fracture repair device, a bone replacement implant, a drug delivery implant, a catheter, a pacemaker and a respirator tube.

In a further embodiment, the disease or condition is associated with menstruation.

In a further embodiment, the disease or condition is associated with an ulcer.

Preferably, the ulcer is selected from the group consisting of a skin ulcer, a bed sore, a gastric ulcer, a peptic ulcer, a buccal ulcer, a nasopharyngeal ulcer, an esophageal ulcer, a duodenal ulcer and a gastrointestinal ulcer.

In a further embodiment, the disease or condition is associated with an injury.

Preferably, the injury is selected from the group consisting of an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound.

In a further embodiment, the disease or condition is a musculo-skeletal inflammation.

Preferably, the musculo-skeletal inflammation is selected from the group consisting of a muscle inflammation, myositis, a tendon inflammation, tendinitis, a ligament inflammation, a cartilage inflammation, a joint inflammation, a synovial inflammation, carpal tunnel syndrome and a bone inflammation.

In a further embodiment, the disease or condition is selected from the group consisting of an idiopathic inflammation and an inflammation of unknown etiology.

Preferably, the disease or condition comprising an inflammatory component is selected from the group consisting of arthritis, nephritis, asthma, bronchitis, chronic granulomatous disease, and psoriasis. More preferably, the disease or condition is asthma.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens). Preferably, the subject is a human.

The term "effective amount" means the amount of the subject composition that will elicit the biological or medical response of a tissue, system, animal or human that is being sought by the researcher, veterinarian, medical doctor or other clinician.

The terms "administration of" and or "administering a" compound should be understood to mean providing a compound of the invention to the individual in need of treatment.

In the treatment or prevention of inflammatory conditions, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood, preferred forms thereof will now be described with reference to the following non-limiting examples.

EXAMPLES

Compound Synthesis
I) Synthesis of Precursors

3-Isopropoxy-4-methoxybenzaldehyde (2)

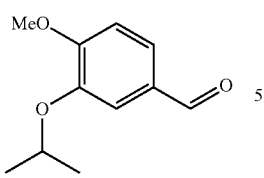

2

Following protocols reported by Ishii et al.,[1] a solution of isovanillin (1) (5.00 g, 32.9 mmol) in DMF (15 mL) was treated with $K_2CO_3$ (7.26 g, 52.6 mmol) and isopropyl bromide (4.6 mL, 49.0 mmol). The resulting mixture was stirred at 18° C. under a nitrogen atmosphere for 42 h then poured into $H_2O$ (100 mL) and extracted with $Et_2O$ (3×20 mL). The combined organic fractions were dried ($MgSO_4$), filtered and concentrated under reduced pressure to afford the title compound 2[1] (6.32 g, quant.) as a pale-yellow and low-melting solid.

$^1$H NMR (300 MHz) δ 9.80 (s, 1H), 7.40 (m, 2H), 6.95 (d, J 8.1 Hz, 1H), 4.61 (septet, J 6.0 Hz, 1H), 3.90 (s, 3H), 1.36 (d, J 6.0 Hz, 6H).

1-(3-Isopropoxy-4-methoxyphenyl)ethanol (3)

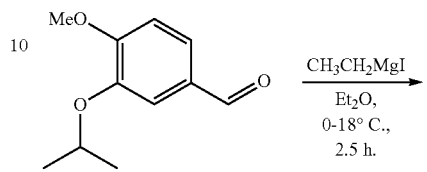

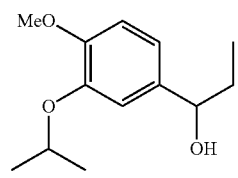

3

Following protocols reported by Ishii et al.,[1] a mixture of Mg turnings (325 mg, 13.4 g·atom) in dry $Et_2O$ (4.0 mL) was stirred at 0° C. under a nitrogen atmosphere then treated, dropwise, with a solution of iodomethane (0.97 mL, 15.6 mmol) in dry $Et_2O$ (3.0 mL). After 0.5 h a solution of aldehyde 2 (1.00 g, 5.15 mmol) in dry $Et_2O$ (8.0 mL) was added, dropwise, to the reaction mixture that was then allowed to warm to 18° C. and then stirred at this temperature for a further 1 h. After this time $NH_4Cl$ (15 mL of a 20% w/v aqueous solution) then $Et_2O$ (10 mL) were added to the reaction mixture. The separated organic phase was washed with $H_2O$ (1×15 mL) then dried ($MgSO_4$), filtered and concentrated under reduced pressure to afford the title compound 3[1] (938 mg, 87%) as a pale-yellow oil.

$^1$H NMR (300 MHz) δ 6.79-6.93 (complex m, 3H), 4.79 (q, J 6.3 Hz, 1H), 4.53 (septet, J 6.3 Hz, 1H), 3.81 (s, 3H), 2.15 (broad s, 1H), 1.44 (d, J 6.3 Hz, 3H), 1.35 (d, J 6.3 Hz, 6H).

1-(3-Isopropoxy-4-methoxyphenyl)propanol (4)

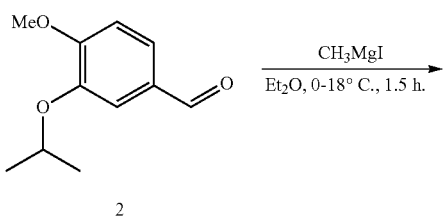

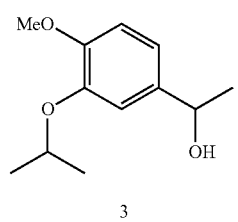

4

A mixture of Mg turnings (651 mg, 26.8 g·atom) in dry $Et_2O$ (6.0 mL) was stirred at 0° C. under a nitrogen atmosphere then treated, dropwise, with a solution of iodomethane (2.47 mL, 30.9 mmol) in dry $Et_2O$ (4.0 mL). After 0.5 h a solution of aldehyde 2 (2.00 g, 10.3 mmol) in dry $Et_2O$ (10 mL) was added, dropwise, to the reaction mixture that was then allowed to warm to 18° C. Stirring was continued at this temperature a further 2 h after which time $NH_4Cl$ (20 mL of a 20% w/v aqueous solution) then $Et_2O$ (20 mL) were added to the reaction mixture. The separated organic component was washed with $H_2O$ (1×15 mL) then dried ($MgSO_4$), filtered and concentrated under reduced pressure to afford the title compound 4 (1.87 g, 81%) as a pale-yellow oil.

$^1$H NMR (300 MHz) δ 6.89-6.81 (complex m, 3H), 4.52 (septet, J 6.0 Hz, 1H), 4.47 (t, J 6.6 Hz, 1H), 3.81 (s, 3H), 2.11 (broad s, 1H), 1.83-1.62 (complex m, 2H), 1.34 (d, J 6.0 Hz, 6H), 0.87 (t, J 7.5 Hz, 3H).

$^{13}$C NMR (75 MHz) δ 149.6 (C), 147.0 (C), 137.1 (C), 118.6 (CH), 113.4 (CH), 111.4 (CH), 75.6 (CH), 71.2 (CH), 55.9 ($CH_3$), 31.7 ($CH_2$), 21.9 (9) ($CH_3$), 21.9 (5) ($CH_3$), 10.1 ($CH_3$).

IR $v_{max}$/cm$^{-1}$ 3524, 2974, 2932, 1508, 1261, 1136.

Mass Spectrum (EI) m/z 224 (M$^+$., 18), 153 (100).

HRMS Found: M$^+$., 224.1413. $C_{13}H_{20}O_3$ requires M$^+$., 224.1412.

The material was used, as obtained, in the next step of the reaction sequence.

2-Iodo-5-isopropoxy-4-methoxybenzaldehyde (5)

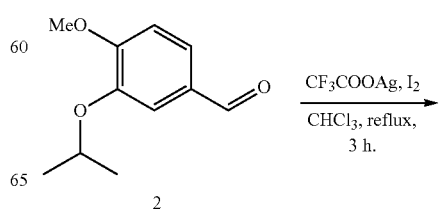

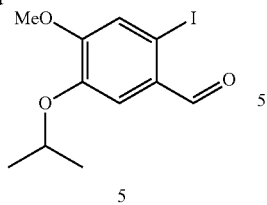

Following protocols reported by Banwell et al.,[2] a solution of aldehyde 2 (10.0 g, 51.5 mmol) in dry chloroform (70 mL) was treated with silver trifluoroacetate (12.0 g, 54.4 mmol) and the resulting mixture stirred at reflux under a nitrogen atmosphere. Iodine (14.4 g, 56.7 mmol) was then added, in three equal portions over 15 minutes, then the ensuing mixture stirred at reflux for a further 3 h before being cooled to 18° C. and filtered through Celite™. The yellow solid thus retained was washed with $CHCl_3$ (50 mL) and the combined filtrates washed with $Na_2S_2O_5$ (1×40 mL of a 10% w/v aq. solution), $NaHCO_3$ (1×40 mL of a 10% w/v aqueous solution) and $H_2O$ (1×40 mL). The separated organic phase was then dried ($MgSO_4$), filtered and concentrated under reduced pressure to afford the title compound 5[2] (13.9 g, 84%) as a cream solid, m.p. 74.0-77.8° C. (lit.[2] 75-76° C.).

$^1$H NMR (300 MHz) δ 9.84 (s, 1H), 7.41 (s, 1H), 7.30 (s, 1H), 4.63 (septet, J 6.0 Hz, 1H), 3.92 (s, 3H), 1.38 (d, J 6.0 Hz, 6H).

1-(2-Iodo-5-isopropoxy-4-methoxyphenyl)ethanol
(6)

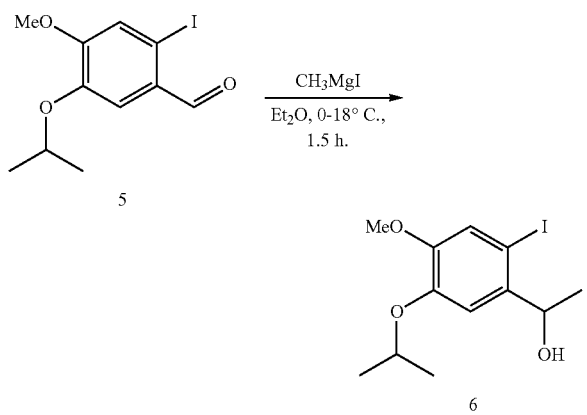

A mixture of Mg turnings (195 mg, 8.02 g·atom) in dry $Et_2O$ (3.0 mL) was stirred at 0° C. under a nitrogen atmosphere then treated, dropwise, with a solution of iodomethane (0.58 mL, 9.31 mmol) in dry $Et_2O$ (7.5 mL). After 0.5 h a solution of aldehyde 5 (1.00 g, 3.12 mmol) in dry $Et_2O$ (7.5 mL) was added, dropwise, and the ensuing mixture then allowed to warm to 18° C. Stirring was continued at this temperature for a further 1 h then the reaction mixture was treated with $NH_4Cl$ (5 mL of a 20% w/v aqueous solution) and $Et_2O$ (10 mL). The separated organic phase was washed with $H_2O$ (1×5 mL) then dried ($MgSO_4$), filtered and concentrated under reduced pressure to afford the title compound 6 (1.05 g, quant.) as a pale-yellow oil.

$^1$H NMR (300 MHz) δ 7.17 (s, 1H), 7.09 (s, 1H), 4.95 (q, J 6.3 Hz, 1H), 4.55 (septet, J 6.0 Hz, 1H), 3.81 (s, 3H), 2.17 (broad s, 1H), 1.39 (d, J 6.3 Hz, 3H), 1.35 (d, J 6.0 Hz, 6H).

$^{13}$C NMR (75 MHz) δ 150.0 (C), 147.9 (C), 139.9 (C), 121.8 (CH), 113.0 (CH), 85.0 (C), 73.4 (CH), 71.4 (CH), 56.2 ($CH_3$), 23.8 ($CH_3$), 22.0 ($CH_3$), 21.9 ($CH_3$).

IR $v_{max}$/cm$^{-1}$ 3429, 2974, 2928, 1493, 1253, 1157, 1110.

Mass Spectrum (EI) m/z 336 (M$^+$., 34), 279 (100).

HRMS Found: M$^+$., 336.0219. $C_{12}H_{17}IO_3$ requires M$^+$., 336.0222.

The material was used, as obtained, in the next step of the reaction sequence.

1-(2-Iodo-5-isopropoxy-4-methoxyphenyl)propanol
(7)

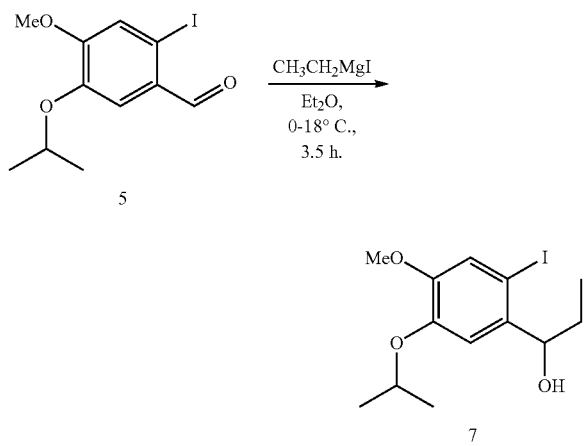

A mixture of Mg turnings (585 mg, 24.1 g·atom) in dry $Et_2O$ (8.0 mL) was stirred at 0° C. under a nitrogen atmosphere then treated, dropwise, with a solution of iodomethane (2.25 mL, 28.1 mmol) in dry $Et_2O$ (7.0 mL). After 0.5 h a solution of aldehyde 5 (3.00 g, 9.38 mmol) in dry $Et_2O$ (10 mL) was added, dropwise, to the mixture that was then allowed to warm to 18° C. Stirring was continued at this temperature for 3 h then the reaction mixture was treated with $NH_4Cl$ (10 mL of a 20% w/v aqueous solution) followed by $Et_2O$ (20 mL). The separated organic phase was washed with $H_2O$ (1×10 mL) then dried ($MgSO_4$), filtered and concentrated under reduced pressure to afford the title compound 7 (3.19 g, 97%) as an orange oil.

$^1$H NMR (300 MHz) δ 7.19 (s, 1H), 7.04 (s, 1H), 4.74 (m, J 7.5 Hz and 4.8 Hz, 1H), 4.55 (septet, J 6.3 Hz, 1H), 3.82 (s, 3H), 1.96 (broad s, 1H), 1.79-1.60 (complex m, 2H), 1.35 (d, J 6.3 Hz, 6H), 0.99 (t, J 7.5 Hz, 3H).

$^{13}$C NMR (75 MHz) δ 149.7 (C), 147.5 (C), 138.8 (C), 121.6 (CH), 113.6 (CH), 85.7 (C), 78.1 (CH), 71.2 (CH), 56.0 ($CH_3$), 30.8 ($CH_2$), 21.9 ($CH_3$), 21.7 ($CH_3$), 10.0 ($CH_3$).

IR $v_{max}$/cm$^{-1}$ 3429, 2974, 2932, 1493, 1252, 1204, 1156, 1110.

Mass Spectrum (EI) m/z 350 (M$^+$., 95), 279 (100).

HRMS Found: M$^+$., 350.0379. $C_{13}H_{19}IO_3$ requires M$^+$., 350.0379.

The material was used, as obtained, in the next step of the reaction sequence.

3'-Isopropoxy-4'-methoxyacetophenone (8)

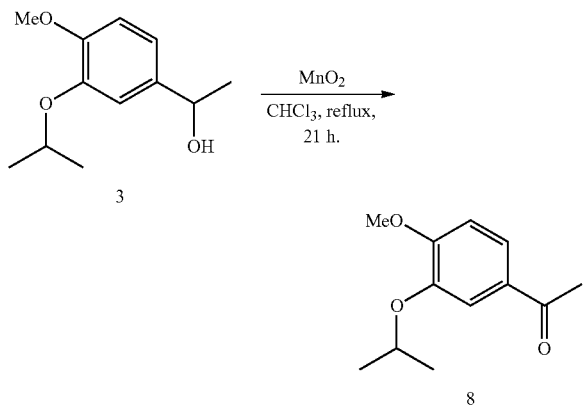

A magnetically stirred solution of alcohol 3 (565 mg, 2.69 mmol) in CHCl$_3$ (20 mL) was treated with activated MnO$_2$ (2.34 g, 27.5 mmol) and the resulting mixture heated at reflux under a nitrogen atmosphere for 21 h. The mixture was then cooled, filtered through a pad of Celite™ and the solids thus retained washed with CHCl$_3$ (1×20 mL). The combined filtrates were concentrated under reduced pressure to afford the title compound 8[3] (559 mg, 99%) as a pale-yellow solid, m.p. 56.1-58.0° C. (lit.[3] m.p. 56° C.).

$^1$H NMR (300 MHz) δ 7.53-7.57 (complex m, 2H), 6.88 (d, J 8.1 Hz, 1H), 4.63 (septet, J 6.3 Hz, 1H), 3.91 (s, 3H), 2.55 (s, 3H), 1.38 (d, J 6.3 Hz, 6H).

2'-Iodo-5'-isopropoxy-4'-methoxyacetophenone (9)

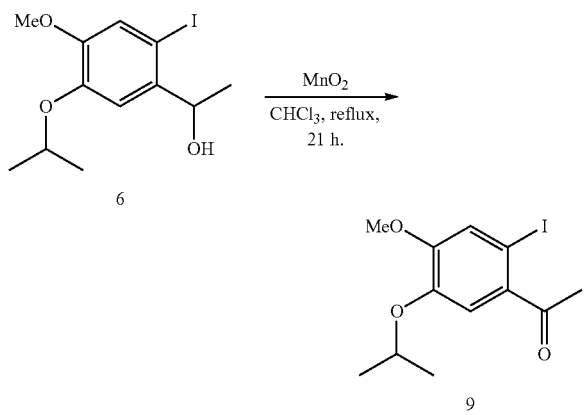

A magnetically stirred solution of alcohol 6 (1.05 g, 3.12 mmol) in CHCl$_3$ (20 mL) was treated with activated MnO$_2$ (2.72 g, 31.3 mmol) and the resulting mixture heated at reflux under a nitrogen atmosphere for 21 h. The mixture was then cooled, filtered through a pad of Celite™ and the solids thus retained washed with CHCl$_3$ (20 mL). The combined filtrates were then concentrated under reduced pressure and the ensuing mixture of product ketone and precursor alcohol subjected to flash chromatography (15:85 v/v ethyl acetate/hexane elution) and thus affording two fractions, A and B.

Concentration of fraction A (R$_f$ 0.7 in 1:1 v/v ethyl acetate/hexane) afforded the title compound 9 (687 mg, 66% at 81% conversion) as a pale-yellow oil.

$^1$H NMR (300 MHz) δ 7.34 (s, 1H), 7.14 (s, 1H), 4.53 (septet, J 6.0 Hz, 1H), 3.87 (s, 3H), 2.60 (s, 3H), 1.35 (d, J 6.0 Hz, 6H).

$^{13}$C NMR (75 MHz) δ 199.3 (C), 152.8 (C), 146.8 (C), 134.8 (C), 124.1 (CH), 117.1 (CH), 82.0 (C), 72.0 (CH), 56.2 (CH$_3$), 29.0 (CH$_3$), 21.9 (2×CH$_3$).

IR $v_{max}$/cm$^{-1}$ 2976, 2932, 1687, 1584, 1497, 1257.

Mass Spectrum (EI) m/z 334 (M$^+$., 35), 277 (100).

HRMS Found: M$^+$., 334.0065. C$_{12}$H$_{15}$IO$_3$ requires M$^+$., 334.0066.

Concentration of fraction B (R$_f$ 0.6 in 1:1 v/v ethyl acetate/hexane) afforded the starting alcohol 6 (200 mg, 19% recovery) as a pale-yellow oil that was identical, as judged by $^1$H NMR spectroscopic analysis, with authentic material.

3'-Isopropoxy-4'-methoxypropiophenone (10)

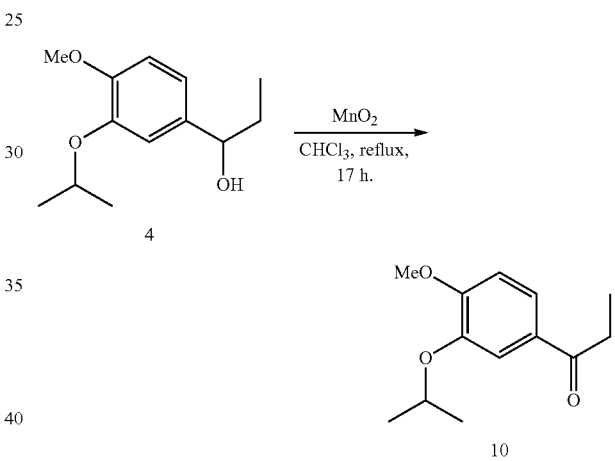

A magnetically stirred solution of alcohol 4 (500 mg, 2.23 mmol) in CHCl$_3$ (15 mL) was treated with activated MnO$_2$ (1.94 g, 22.3 mmol) and the resulting mixture heated at reflux under a nitrogen atmosphere for 17 h. The cooled reaction mixture was filtered through a pad of Celite™ that was then washed with CHCl$_3$ (1×15 mL). The combined filtrates were concentrated under reduced pressure to afford the title compound 10 (466 mg, 94%) as a white solid, m.p. 58.1-58.7° C.

$^1$H NMR (300 MHz) δ 7.58-7.54 (complex m, 2H), 6.87 (d, J 8.1 Hz, 1H), 4.62 (septet, J 6.0 Hz, 1H), 3.90 (s, 3H), 2.94 (q, J 7.2 Hz, 2H), 1.37 (d, J 6.0 Hz, 6H), 1.20 (t, J 7.2 Hz, 3H).

$^{13}$C NMR (75 MHz) δ 199.5 (C), 154.2 (C), 147.0 (C), 129.9 (C), 122.5 (CH), 114.0 (CH), 110.4 (CH), 71.2 (CH), 56.0 (CH$_3$), 31.2 (CH$_2$), 21.9 (2×CH$_3$), 8.5 (CH$_3$).

IR $v_{max}$/cm$^{-1}$ 2977, 2937, 1678, 1594, 1583, 1512, 1423, 1264.

Mass Spectrum (EI) m/z 222 (M$^+$., 10), 151 (100).

HRMS Found: M$^+$., 222.1255. C$_{13}$H$_{18}$O$_3$ requires M$^+$., 222.1256.

Elemental Analysis Found: C, 70.19; H, 7.88%. C$_{13}$H$_{18}$O$_3$ requires C, 70.24; H, 8.16%.

This material was used, as obtained, in the next step of the reaction sequence.

2'-Iodo-5'-isopropoxy-4'-methoxypropiophenone (11)

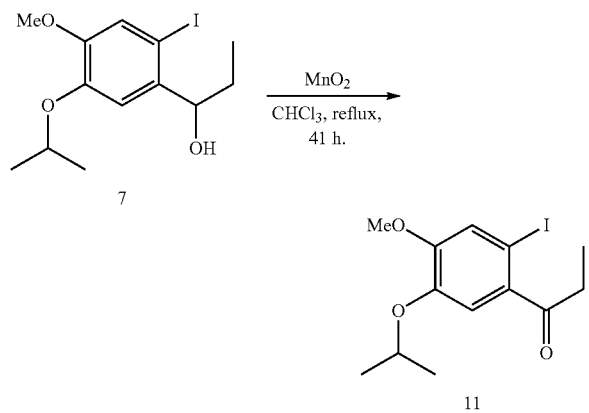

A magnetically stirred solution of alcohol 7 (985 mg, 2.81 mmol) in CHCl$_3$ (15 mL) was treated with activated MnO$_2$ (2.45 g, 28.2 mmol) and the resulting mixture heated at reflux under a nitrogen atmosphere for 41 h. The cooled reaction mixture was filtered through a pad of Celite™ that was then washed with CHCl$_3$ (1×15 mL). The combined filtrates were concentrated under reduced pressure and the ensuing mixture of product ketone and precursor alcohol subjected to flash chromatography (15:85 v/v ethyl acetate/hexane elution) and thus affording two fractions, A and B.

Concentration of fraction A (R$_f$ 0.7 in 1:1 v/v ethyl acetate/hexane) afforded the title compound 11 (555 mg, 57% at 79% conversion) as a pale-yellow oil.

$^1$H NMR (300 MHz) δ 7.30 (s, 1H), 7.02 (s, 1H), 4.50 (septet, J 6.0 Hz, 1H), 3.84 (s, 3H), 2.89 (q, J 7.2 Hz, 2H), 1.33 (d, J 6.0 Hz, 6H), 1.17 (t, J 7.2 Hz, 3H).

$^{13}$C NMR (75 MHz) δ 203.1 (C), 152.4 (C), 146.8 (C), 135.5 (C), 123.7 (CH), 116.1 (CH), 81.4 (C), 71.9 (CH), 56.1 (CH$_3$), 34.4 (CH$_2$), 21.8 (2×CH$_3$), 8.4 (CH$_3$).

IR $v_{max}$/cm$^{-1}$ 2976, 2936, 1692, 1585, 1496, 1372, 1256, 1165.

Mass Spectrum (EI) m/z 348 (M$^+$., 70), 277 (100).

HRMS Found: M$^+$., 348.0222. C$_{13}$H$_{17}$IO$_3$ requires M$^+$., 348.0222.

Concentration of fraction B (R$_f$ 0.6 in 1:1 v/v ethyl acetate/hexane) afforded the starting alcohol 7 (205 mg, 21% recovery) as a pale-orange oil and identical, as judged by $^1$H NMR spectroscopic analysis, with authentic material.

3'-Hydroxy-4'-methoxyacetophenone (12)

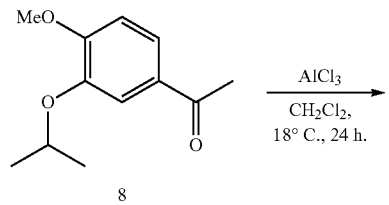

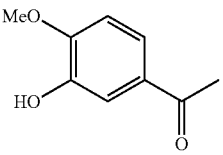

A solution of ketone 8 (250 mg, 1.20 mmol) in dry CH$_2$Cl$_2$ (3 mL) was treated with AlCl$_3$ (208 mg, 1.56 mmol) and the resulting mixture stirred at 18° C. under a nitrogen atmosphere for 24 h then partitioned between H$_2$O (10 mL) and additional CH$_2$Cl$_2$ (10 mL). The separated aqueous phase was extracted with CH$_2$Cl$_2$ (1×10 mL) and the combined organic fractions then dried (MgSO$_4$), filtered and concentrated under reduced pressure. The ensuing light-yellow oil was subjected to flash chromatography (1:4 v/v ethyl acetate/hexane) to afford the title compound 12$^4$ (172 mg, 86%) as a white solid, m.p. 88.6-90.5° C. (lit.$^4$ m.p. 92-93° C.), R$_f$ 0.4 in 1:1 v/v ethyl acetate/hexane.

$^1$H NMR (300 MHz) δ 7.53-7.56 (complex m, 2H), 6.89 (d, J 7.5 Hz, 1H), 5.73 (broad s, 1H), 3.96 (s, 3H), 2.54 (s, 3H).

5'-Hydroxy-2'-iodo-4'-methoxyacetophenone (13)

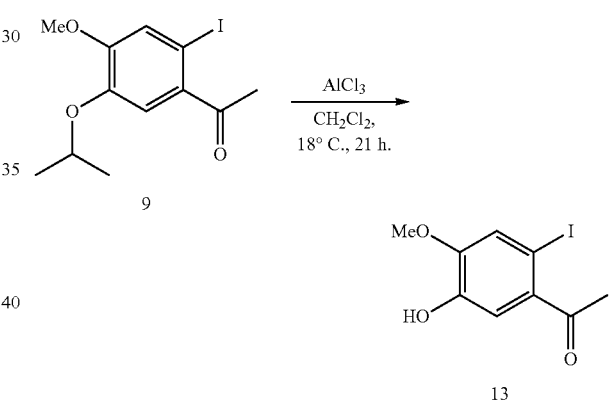

A solution of ketone 9 (625 mg, 1.87 mmol) in dry CH$_2$Cl$_2$ (5 mL), was treated with AlCl$_3$ (325 mg, 2.44 mmol) and the resulting mixture stirred at 18° C. under a nitrogen atmosphere for 21 h then partitioned between H$_2$O (10 mL) and additional CH$_2$Cl$_2$ (10 mL). The separated aqueous phase was extracted with CH$_2$Cl$_2$ (1×10 mL) and the combined organic fractions were then dried (MgSO$_4$), filtered and concentrated under reduced pressure. The ensuing residue was subjected to flash chromatography (1:4 v/v ethyl acetate/hexane elution) to afford the title compound 13 (411 mg, 75%) as a pale-yellow solid, m.p. 109.4-110.6° C., R$_f$ 0.5 in 1:1 v/v ethyl acetate/hexane.

$^1$H NMR (300 MHz) δ 7.30 (s, 1H), 7.21 (s, 1H), 6.13 (broad s, 1H), 3.87 (s, 3H), 2.53 (s, 3H).

$^{13}$C NMR (75 MHz) δ 199.3 (C), 149.2 (C), 145.2 (C), 134.2 (C), 123.1 (CH), 116.1 (CH), 79.8 (C), 56.2 (CH$_3$), 28.7 (CH$_3$).

IR $v_{max}$/cm$^{-1}$ 3196, 1672, 1599, 1563, 1495, 1277, 1193, 1174.

Mass Spectrum (EI) m/z 292 (M$^+$., 98), 277 (100).

HRMS Found: M$^+$., 291.9584. C$_9$H$_9$$^{127}$IO$_3$ requires M$^+$., 291.9596.

3'-Hydroxy-4'-methoxypropiophenone (14)

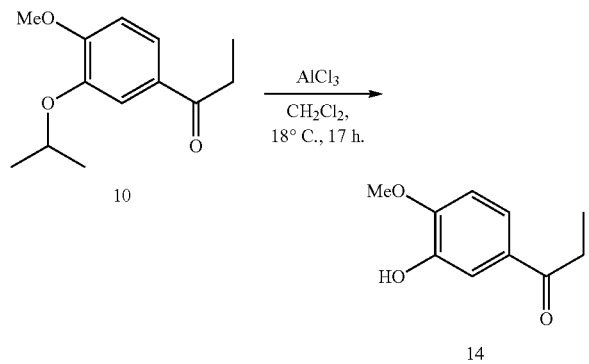

A solution of ketone 10 (414 mg, 1.86 mmol) in dry CH$_2$Cl$_2$ (5 mL) was treated with AlCl$_3$ (323 mg, 2.42 mmol) and the resulting mixture stirred at 18° C. under a nitrogen atmosphere for 17 h then partitioned between H$_2$O (10 mL) and additional CH$_2$Cl$_2$ (10 mL). The separated aqueous phase was extracted with CH$_2$Cl$_2$ (1×10 mL) and the combined organic fractions then dried (MgSO$_4$), filtered and concentrated under reduced pressure. The resulting mixture of product phenol and precursor ether was subjected to flash chromatography (15:85 v/v ethyl acetate/hexane elution) and thus affording two fractions, A and B.

Concentration of fraction A (R$_f$ 0.5 in 1:1 v/v ethyl acetate/hexane) afforded the title compound 14 (131 mg, 39% at 50% conversion) as a white solid, m.p. 92.2-93.7° C.

$^1$H NMR (300 MHz) δ 7.54-7.51 (complex m, 2H), 6.86 (d, J 9.3 Hz, 1H), 5.99 (broad s, 1H), 3.92 (s, 3H), 2.92 (q, J 7.2 Hz, 2H), 1.18 (t, J 7.2 Hz, 3H).

$^{13}$C NMR (75 MHz) δ 199.9 (C), 150.6 (C), 145.3 (C), 130.3 (C), 121.3 (CH), 114.1 (CH), 109.8 (CH), 55.3 (CH$_3$), 31.3 (CH$_2$), 8.3 (CH$_3$).

IR $v_{max}$/cm$^{-1}$ 3356, 3261, 2975, 2938, 1669, 1582, 1518, 1433, 1282, 1196, 1175, 1123, 1021, 796.

Mass Spectrum (EI) m/z 180 (M$^+$., 18), 151 (100).

HRMS Found: M$^+$., 180.0786. C$_{10}$H$_{12}$O$_3$ requires M$^+$., 180.0786.

Elemental Analysis Found: C, 66.76; H, 6.41. C$_{10}$H$_{12}$O$_3$ requires C, 66.65; H, 6.71%.

Concentration of fraction B (R$_f$ 0.6 in 1:1 v/v ethyl acetate/hexane) afforded the starting ether 10 (207 mg, 50% recovery) as a white solid that was identical, as judged by $^1$H NMR spectroscopic analysis, with authentic material.

5'-Hydroxy-2'-iodo-4'-methoxypropiophenone (15)

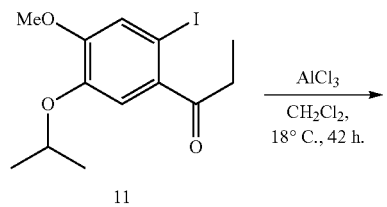

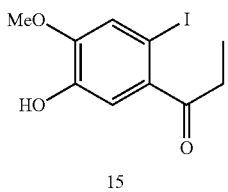

A solution of ketone 11 (460 mg, 1.32 mmol) in dry CH$_2$Cl$_2$ (3.0 mL) was treated with AlCl$_3$ (265 mg, 1.99 mmol) and the resulting mixture stirred at 18° C. under a nitrogen atmosphere for 42 h then partitioned between H$_2$O (10 mL) and CH$_2$Cl$_2$ (10 mL). The separated aqueous phase was extracted with CH$_2$Cl$_2$ (1×10 mL) and the combined organic phases then dried (MgSO$_4$), filtered and concentrated under reduced pressure. The resulting mixture of product phenol and precursor ether was subjected to flash chromatography (15:85 v/v ethyl acetate/hexane elution) and thus affording two fractions, A and B.

Concentration of fraction A (R$_f$ 0.6 in 1:1 v/v ethyl acetate/hexane) afforded the title compound 15 (234 mg, 58% at 79% conversion) as a cream solid, m.p. 86.8-88.3° C.

$^1$H NMR (300 MHz) δ 7.31 (s, 1H), 7.12 (s, 1H), 5.78 (broad s, 1H), 3.90 (s, 3H), 2.86 (q, J 7.2 Hz, 2H), 1.18 (t, J 7.2 Hz, 3H).

$^{13}$C NMR (75 MHz) δ 203.0 (C), 148.6 (C), 145.4 (C), 135.6 (C), 122.7 (CH), 115.0 (CH), 79.4 (C), 56.3 (CH$_3$), 34.3 (CH$_2$), 8.3 (CH$_3$).

IR $v_{max}$/cm$^{-1}$ 3393, 2976, 2937, 1688, 1604, 1564, 1497, 1271, 1166.

Mass Spectrum (EI) m/z 306 (M$^+$., 35), 277 (100).

HRMS Found: M$^+$., 305.9751. C$_{10}$H$_{11}$IO$_3$ requires M$^+$., 305.9753.

Elemental Analysis Found: C, 39.34; H, 3.46. C$_{10}$H$_{11}$IO$_3$ requires C, 39.24; H, 3.62%.

Concentration of fraction B (R$_f$ 0.7 in 1:1 v/v ethyl acetate/hexane) afforded the starting ether 11 (98 mg, 21% recovery) as a pale-yellow oil that was identical, as judged by $^1$H NMR spectroscopic analysis, with authentic material.

N-(4-Nitrobenzyloxy)phthalimide (18)

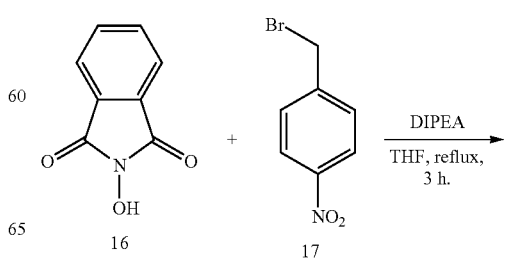

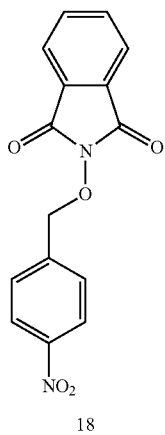

18

A magnetically stirred solution of N-hydroxyphthalimide (16) (11.2 g, 68.7 mmol) in THF (200 mL) was treated with 4-nitrobenzylbromide (17) (13.5 g, 62.5 mmol) and N,N-diisopropylethylamine (21.8 mL) and the resulting mixture heated at reflux for 24 h. The reaction mixture was then cooled and the solvent removed under reduced pressure. The ensuing residue was partitioned between $H_2O$ (150 mL) and $CH_2Cl_2$ (150 mL), the organic phase separated and the aqueous phase extracted with $CH_2Cl_2$ (1×100 mL) The combined organic fractions were dried ($MgSO_4$), filtered and concentrated under reduced pressure and the resulting solid triturated with MeOH (150 mL). The ensuing solid was removed by filtration to afford the title compound 18[5] (18.1 g, 97%) as a cream solid, m.p. 194.1-195.1° C. (lit.[5] m.p. 197-198° C.).

$^1$H NMR (300 MHz) δ 8.24 (d, J 8.7 Hz, 2H), 7.84-7.22 (complex m, 6H), 5.31 (s, 2H).

O-(4-Nitrobenzyl)hydroxylamine Hydrochloride (19)

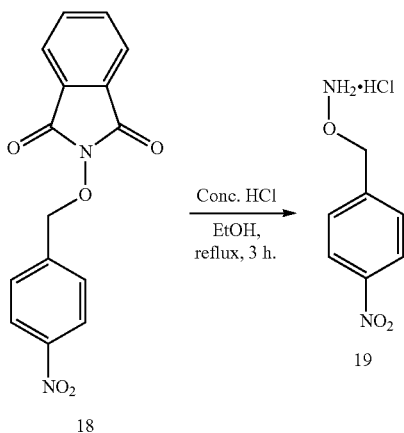

A magnetically stirred suspension of compound 18 (2.00 g, 6.71 mmol) in EtOH (10 mL) was treated with HCl (20 mL of a conc. aqueous solution) and the resulting mixture heated at reflux for 3 h. The reaction mixture was then cooled slightly, $H_2O$ (30 mL) added and the ensuing mixture washed with $CHCl_3$ (1×20 mL). The separated aqueous fraction was concentrated under reduced pressure to afford the title compound 19[6] (1.37 g, quant.) as a cream solid, m.p. 179.1-205.9° C. (lit.[6] m.p. 217° C.).

$^1$H NMR (300 MHz, DMSO-$d_6$) δ 11.37 (broad s, 2H), 8.26 (d, J 8.6 Hz, 2H), 8.68 (d, J 8.6 Hz, 2H), 5.22 (s, 2H).

(E)-3'-Hydroxy-4'-methoxyacetophenone O-4-Nitrobenzyl Oxime (CP30218)

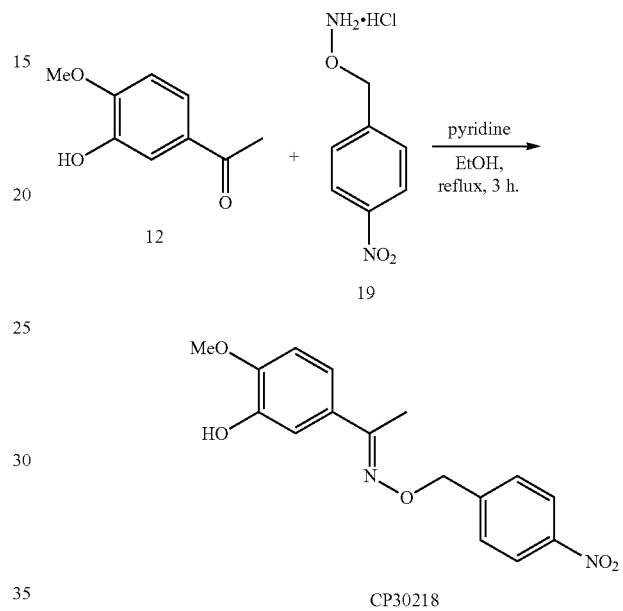

A solution of ketone 12 (200 mg, 1.20 mmol) in EtOH (2.0 mL) was treated with compound 19 (0.27 g, 1.32 mmol) and pyridine (0.5 mL) and the resulting mixture heated at reflux for 3 h then cooled and the solvent evaporated under reduced pressure. The ensuing residue was partitioned between $CH_2Cl_2$ (10 mL) and $H_2O$ (10 mL). The separated aqueous fraction was extracted with $CH_2Cl_2$ (1×5.0 ml) and the combined organic fractions were dried ($MgSO_4$) then filtered and concentrated under reduced pressure to give a light-yellow solid. Recrystallisation (isopropanol) of this material afforded the title compound CP30218 (340 mg, 89%) as pale-yellow crystals, m.p. 105.0-105.7° C.

$^1$H NMR (300 MHz) δ 8.21 (d, J 8.7 Hz, 2H), 7.54 (d, J 8.7 Hz, 2H), 7.24 (d, J 2.1 Hz, 1H), 7.11 (dd, J 8.4 and 2.1 Hz, 1H), 6.82 (d, J 8.4 Hz, 1H), 5.61 (broad s, 1H), 5.29 (s, 2H), 3.90 (s, 3H), 2.26 (s, 3H).

$^{13}$C NMR (75 MHz) δ 155.3 (C), 147.6 (C), 147.3 (C), 146.1 (C), 145.3 (C), 129.4 (C), 128.1 (2×CH), 123.5 (2×CH), 118.3 (CH), 112.2 (CH), 110.1 (CH), 74.4 ($CH_2$), 55.9 ($CH_3$), 12.8 ($CH_3$).

IR $v_{max}$/cm$^{-1}$ 3500, 1605, 1518, 1345, 1290, 1260, 1216, 1054, 860.

Mass Spectrum (EI) m/z 316 (M$^+$., 95), 107 (100).

HRMS Found: M$^+$., 316.1063. $C_{16}H_{16}N_2O_5$ requires M$^+$., 316.1059.

Elemental Analysis Found: C, 60.52; H, 5.07; N, 8.73. $C_{16}H_{16}N_2O_5$ requires C, 60.75; H, 5.10; N, 8.86%.

5'-Hydroxy-2'-iodo-4'-methoxyacetophenone O-4-Nitrobenzyl Oxime (CP30220)

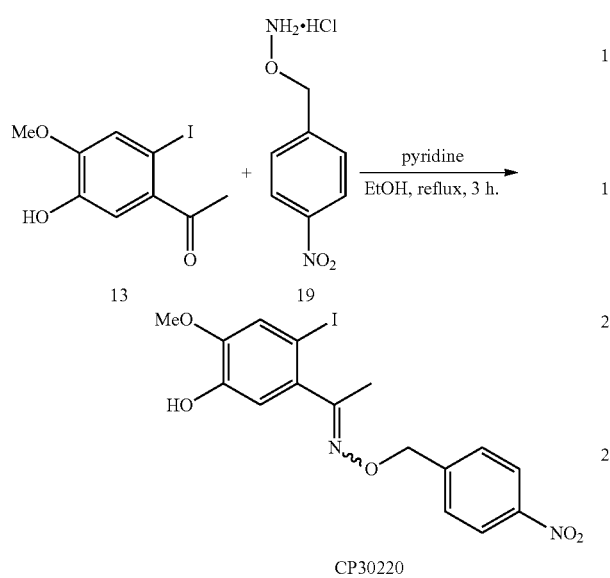

CP30220

A magnetically stirred solution of ketone 13 (350 mg, 1.20 mmol) in EtOH (2.0 mL) was treated with compound 19 (270 mg, 1.32 mmol) and pyridine (0.25 mL) then the resulting mixture was stirred at reflux for 3 h before being cooled and the solvent evaporated under reduced pressure. The ensuing residue was partitioned between $CH_2Cl_2$ (10 mL) and $H_2O$ (10 mL) then the organic layer separated. The aqueous fraction was extracted with $CH_2Cl_2$ (1×10 ml) and the combined organic fractions were then dried ($MgSO_4$), filtered and concentrated under reduced pressure. The resulting mixture was subjected to flash chromatography (15:85 v/v ethyl acetate/hexane elution) to afford a ca. 3:1 mixture of the E- and Z-isomeric forms of compound CP30220 (513 mg, 97%) as a yellow oil-foam, $R_f$ 0.5 in 1:1 v/v ethyl acetate/hexane. This mixture was subjected to semi-preparative HPLC (22×250 mm Alltima C18 column, 7:3 v/v acetonitrile/water containing 0.1% v/v TFA) and two fractions, A and B, thereby obtained.

Recrystallisation (acetonitrile/water) of the solid derived concentration of fraction A gave the E-isomer of the title compound as a pale-yellow crystalline solid, m.p. 98.1-101.1° C., $R_t$ 16.0 min.

$^1$H NMR (300 MHz) δ 8.22 (d, J 8.7 Hz, 2H), 7.56 (d, J 8.7 Hz, 2H), 7.21 (s, 1H), 6.77 (s, 1H), 5.31 (s, 2H), 3.87 (s, 3H), 2.24 (s, 3H), signal due to Ar—OH not observed.

$^{13}$C NMR (75 MHz) δ 159.7 (C), 147.3 (C), 145.9 (C), 145.7 (C), 135.3 (C), 128.0 (2×CH), 123.6 (2×CH), 121.1 (CH), 115.5 (CH), 82.6 (C), 74.4 ($CH_2$), 56.2 ($CH_3$), 17.1 ($CH_3$), signal due to 1×C obscured or overlapping.

IR $v_{max}$/cm$^{-1}$ 3468, 2925, 1606, 1520, 1495, 1344, 1306, 1256, 1202, 859.

Mass Spectrum (EI) m/z 442 (M$^+$., 60), 315 (42), 164 (100).

HRMS Found: M$^+$., 442.0023. $C_{16}H_{15}IN_2O_5$ requires M$^+$., 442.0026.

Elemental Analysis Found: C, 43.26; H, 3.44; N, 6.28. $C_{16}H_{15}IN_2O_5$ requires C, 43.46; H, 3.42; N, 6.33%.

Concentration of fraction B gave the Z-isomer of the title compound as a pale-yellow solid, m.p. 121.2-126.6° C., $R_t$ 13.9 min.

$^1$H NMR (300 MHz) δ 8.19 (d, J 8.7 Hz, 2H), 7.49 (d, J 8.7 Hz, 2H), 7.25 (s, 1H), 6.65 (s, 1H), 5.66 (broad s, 1H), 5.14 (s, 2H), 3.90 (s, 3H), 2.11 (s, 3H).

$^{13}$C NMR (75 MHz) δ 157.6 (C), 146.8 (C), 146.0 (C), 134.8 (C), 128.1 (2×CH), 123.5 (2×CH), 120.6 (CH), 113.3 (CH), 80.2 (C), 74.2 ($CH_2$), 56.2 ($CH_3$), 21.3 ($CH_3$), signals due to 2×C obscured or overlapping.

IR $v_{max}$/cm$^{-1}$ 3437, 2915, 1607, 1566, 1519, 1495, 1345, 1292, 1255, 1200, 1054, 887, 736.

Mass Spectrum (EI) m/z 442 (M$^+$., 45), 315 (38), 164 (100).

HRMS Found: M$^+$., 442.0021. $C_{16}H_{15}IN_2O_5$ requires M$^+$., 442.0026.

Elemental Analysis Found: C, 43.39; H, 3.45; N, 6.21. $C_{16}H_{15}IN_2O_5$ requires C, 43.46; H, 3.42; N, 6.33%.

3'-Hydroxy-4'-methoxypropiophenone O-4-Nitrobenzyl Oxime (CP30221)

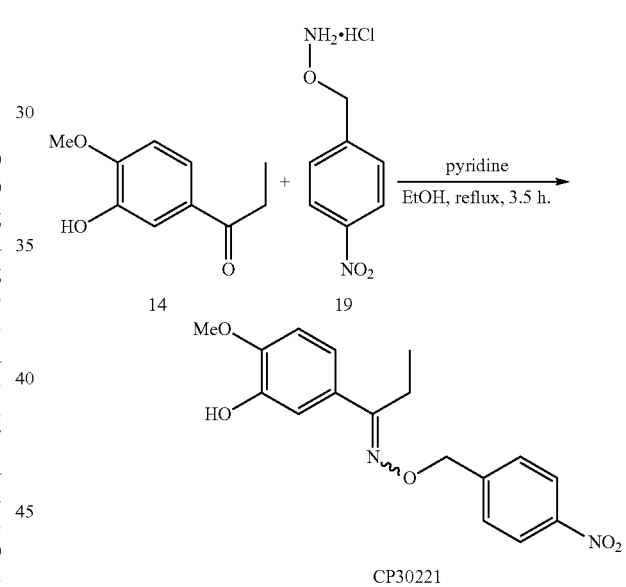

CP30221

A magnetically stirred solution of ketone 14 (216 mg, 1.20 mmol) in EtOH (2.0 mL) was treated with compound 19 (0.270 g, 1.32 mmol) and pyridine (0.25 mL). The resulting mixture heated at reflux for 3.5 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (1×10 ml). The combined organic fractions were dried ($MgSO_4$), filtered and concentrated under reduced pressure. The resulting mixture was subjected to flash chromatography (15:85 v/v ethyl acetate/hexane elution) to afford a ca. 7:1 mixture of the E- and Z-isomeric forms of the title compound CP30221 (370 mg, 93%) as a yellow oil, $R_f$ 0.5 in 1:1 v/v ethyl acetate/hexane.

$^1$H NMR (300 MHz) δ (major isomer) 8.21 (d, J 8.7 Hz, 2H), 7.55 (d, J 8.7 Hz, 2H), 7.22 (d, J 2.1 Hz, 1H), 7.11 (dd, J 8.4 and 2.1 Hz, 1H), 6.82 (d, J 8.4 Hz, 1H), 5.28 (s, 2H), 3.89 (s, 3H), 2.76 (q, J 7.5 Hz, 2H), 1.15 (t, J 7.5 Hz, 3H), signal due to Ar—OH not observed; δ (minor isomer) 7.45 (d, J 8.7 Hz, 2H), 7.06 (d, J 1.5 Hz, 1H), 6.97 (dd, J 8.4 and 1.5 Hz, 1H), 6.88 (d, J 8.4 Hz, 1H), 5.17 (s, 2H), 3.92 (s, 3H), 2.51 (q, J 7.5 Hz, 2H), 1.03 (t, J 7.5 Hz, 3H), signals due to two Ar—H obscured or overlapping, signal due to Ar—OH not observed.

$^{13}$C NMR (75 MHz) δ (major isomer) 160.3 (C), 147.6 (C), 147.2 (C), 146.1 (C), 145.4 (C), 128.3 (C), 128.1 (2×CH), 123.5 (2×CH), 118.4 (CH), 112.3 (CH), 110.2 (CH), 74.4 (CH$_2$), 55.9 (CH$_3$), 20.1 (CH$_2$), 11.2 (CH$_3$); δ (minor isomer) 155.9 (C), 146.9 (C), 145.0 (C), 127.9 (2×CH), 123.4 (2×CH), 120.1 (CH), 114.4 (CH), 110.0 (CH), 74.1 (CH$_2$), 55.8 (CH$_3$), 28.6 (CH$_2$), 11.9 (CH$_3$), signals due to 3×C obscured or overlapping.

IR $v_{max}$/cm$^{-1}$ 3492, 2973, 2937, 1606, 1574, 1516, 1345, 1265, 1015, 852.

Mass Spectrum (EI) m/z 330 (M$^+$., 100).

HRMS Found: M$^+$., 330.1213. C$_{17}$H$_{18}$N$_2$O$_5$ requires M$^+$., 330.1216.

5'-Hydroxy-2'-iodo-4'-methoxypropiophenone O-4-Nitrobenzyl Oxime (CP30222)

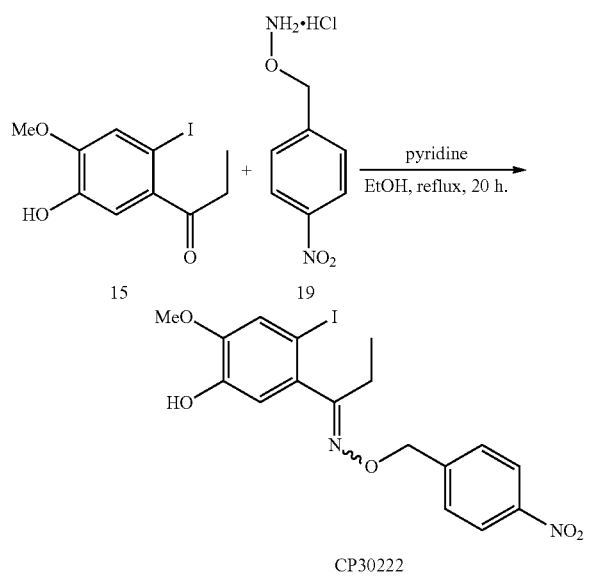

CP30222

A magnetically stirred solution of ketone 15 (367 mg, 1.20 mmol) in EtOH (2.0 mL) was treated with compound 19 (270 mg, 1.32 mmol) and pyridine (0.25 mL) and the resulting mixture stirred at reflux for 20 h then cooled and the solvent removed under reduced pressure. The ensuing residue was partitioned between CH$_2$Cl$_2$ (10 mL) and H$_2$O (10 mL) then the separated aqueous phase extracted with CH$_2$Cl$_2$ (1×10 ml) and the combined organic fractions dried (MgSO$_4$), filtered and concentrated under reduced pressure. The resulting mixture was subjected to flash chromatography (15:85 v/v ethyl acetate/hexane elution) to afford a ca. 2:1 mixture of the E- and Z-isomeric forms of the title compound CP30222 (473 mg, 86%) as a yellow oil, R$_f$ 0.5 in 1:1 v/v ethyl acetate/hexane.

$^1$H NMR (300 MHz) δ (major isomer) 8.21 (d, J 8.7 Hz, 2H), 7.55 (d, J 8.7 Hz, 2H), 7.21 (s, 1H), 6.75 (s, 1H), 5.69 (broad s, 1H), 5.29 (s, 2H), 3.86 (s, 3H), 2.75 (q, J 7.5 Hz, 2H), 1.02 (t, J 7.5 Hz, 3H); δ (minor isomer) 8.17 (d, J 8.7 Hz, 2H), 7.48 (d, J 8.7 Hz, 2H), 7.25 (s, 1H), 6.61 (s, 1H), 5.69 (broad s, 1H), 5.14 (s, 2H), 3.88 (s, 3H), 2.46 (q, J 7.5 Hz, 2H), 1.09 (t, J 7.5 Hz, 3H).

$^{13}$C NMR (75 MHz) δ (major isomer) 164.4 (C), 147.2 (C), 146.8 (C), 146.0 (C), 145.6 (C), 133.8 (C), 128.0 (2×CH), 123.5 (2×CH), 120.9 (CH), 115.9 (CH), 83.5 (C), 74.2 (CH$_2$), 56.2 (CH$_3$), 23.3 (CH$_2$), 9.9 (CH$_3$); δ (minor isomer) 161.3 (C), 147.2 (C), 147.1 (C), 145.9 (C), 145.7 (C), 133.7 (C), 128.1 (2×CH), 123.3 (2×CH), 120.6 (CH), 114.0 (CH), 81.1 (C), 74.1 (CH$_2$), 56.1 (CH$_3$), 28.5 (CH$_2$), 10.7 (CH$_3$).

IR $v_{max}$/cm$^{-1}$ 3469, 2972, 2936, 1606, 1567, 1520, 1496, 1345, 1258, 1200, 1026, 1014, 848, 785.

Mass Spectrum (EI) m/z 456 (M$^+$., 45), 178 (100).

HRMS Found: M$^+$., 456.0182. C$_{17}$H$_{17}$IN$_2$O$_5$ requires M$^+$., 456.0182.

II) Synthesis of CP30218 Analogues

A) General Procedure for the Synthesis of Compounds CP30252-5, 30257, 30260-61

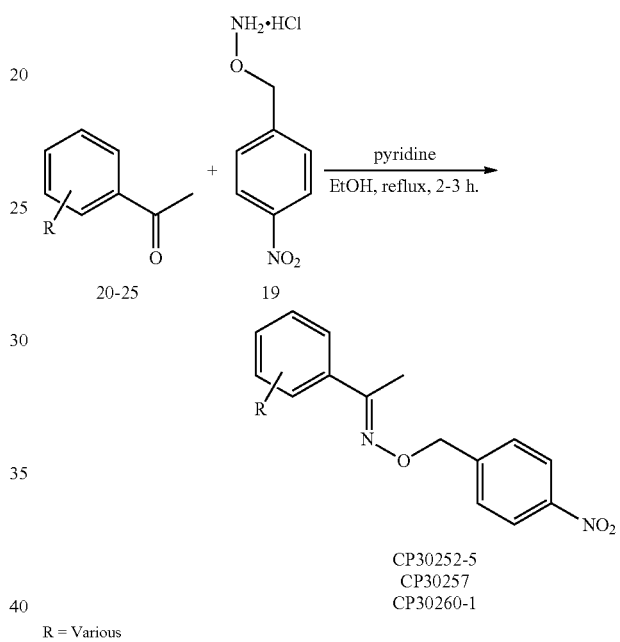

CP30252-5
CP30257
CP30260-1

R = Various

A solution of the relevant acetophenone, 20-25 (150 mg), in EtOH (2.0 mL) was treated with O-(4-nitrobenzyl)hydroxylamine hydrochloride (19) (~1.1 equivalents) and pyridine (500 μL) then the resulting mixture stirred at reflux for 2-3 h. The reaction mixture was then cooled and the target compound isolated as specified below.

(E)-Acetophenone O-4-Nitrobenzyl Oxime (CP30252)

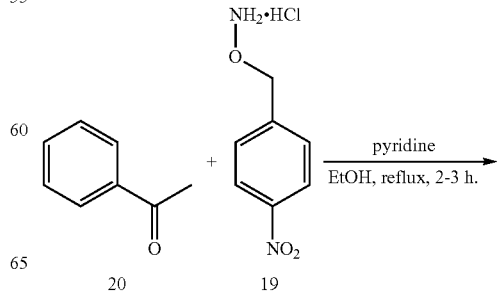

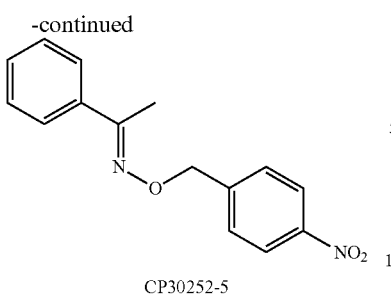
CP30252-5

Acetophenone (20) (150 mg, 1.25 mmol) was condensed with compound 19 (280 mg, 1.37 mmol) according to the general procedure II-A defined above. After heating the reaction mixture for 2 h it was cooled and the solvent removed under reduced pressure. The resulting solid was filtered off and washed with cold isopropanol (3.0 mL) to afford the title compound CP30252 (258 mg, 77%) as a pale-yellow solid, m.p. 91.3-92.3° C.

$^1$H NMR (300 MHz) δ 8.23 (d, J 8.7 Hz, 2H), 7.64-7.50 (complex m, 2H), 7.56 (d, J 8.7 Hz, 2H), 7.38-7.35 (complex m, 3H), 5.33 (s, 2H), 2.31 (s, 3H).

$^{13}$C NMR (75 MHz) δ 155.9 (C), 147.3 (C), 145.9 (C), 136.1 (C), 129.3 (CH), 128.4 (2×CH), 128.2 (2×CH), 126.0 (2×CH), 123.6 (2×CH), 74.6 (CH$_2$), 12.9 (CH$_3$).

IR $v_{max}$/cm$^{-1}$ 3080, 2877, 1606, 1515, 1344, 1038, 932, 763.

Mass Spectrum (EI) m/z 270 (M$^+$., 90), 136 (98), 106 (100)

HRMS Found: M$^+$., 270.1006. C$_{15}$H$_{14}$N$_2$O$_3$ requires M$^+$., 270.1004.

Elemental Analysis Found: C, 66.62; H, 5.20; N, 10.23. C$_{15}$H$_{14}$N$_2$O$_3$ requires C, 66.66; H, 5.22; N, 10.36%.

(E)-4'-Methoxyacetophenone O-4-Nitrobenzyl Oxime (CP30253)

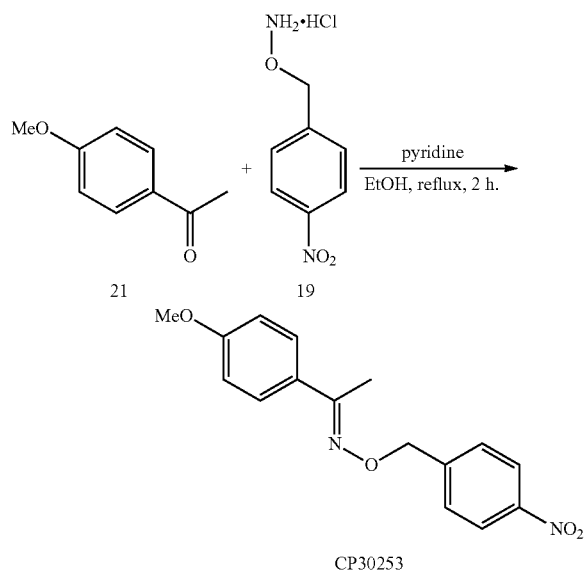

4'-Methoxyacetophenone (21) (150 mg, 1.00 mmol) was condensed with compound 19 (225 mg, 1.10 mmol) according to the general procedure II-A defined above. After heating the reaction mixture for 2 h it was cooled and the resulting solid filtered off and washed with cold isopropanol (3.0 mL) to afford the title compound CP30253 (204 mg, 68%) as a pale-yellow solid, m.p. 88.2-89.5° C.

$^1$H NMR (300 MHz) δ 8.22 (d, J 8.7 Hz, 2H), 7.57 (d, J 9.0 Hz, 2H), 7.56 (d, J 8.7 Hz, 2H), 6.88 (d, J 9.0 Hz, 2H), 5.30 (s, 2H), 3.82 (s, 3H), 2.28 (s, 3H).

$^{13}$C NMR (75 MHz) δ 160.5 (C), 155.5 (C), 146.1 (C), 128.6 (C), 128.1 (2×CH), 127.4 (2×CH), 123.6 (2×CH), 113.8 (2×CH), 74.4 (CH$_2$), 55.3 (CH$_3$), 12.8 (CH$_3$), signal due to 1×C obscured or overlapping.

IR $v_{max}$/cm$^{-1}$ 2959, 2923, 2836, 1603, 1512, 1455, 1340, 1244, 1179, 1064, 934, 827, 934.

Mass Spectrum (EI) m/z 300 (M$^+$., 100)

HRMS Found: M$^+$., 300.1116. C$_{16}$H$_{16}$N$_2$O$_4$ requires M$^+$., 300.1110.

Elemental Analysis Found: C, 64.08; H, 5.27; N, 9.24. C$_{16}$H$_{16}$N$_2$O$_4$ requires C, 63.99; H, 5.37; N, 9.33%.

(E)-3'-Isopropoxy-4'-methoxyacetophenone O-4-Nitrobenzyl Oxime (CP30254)

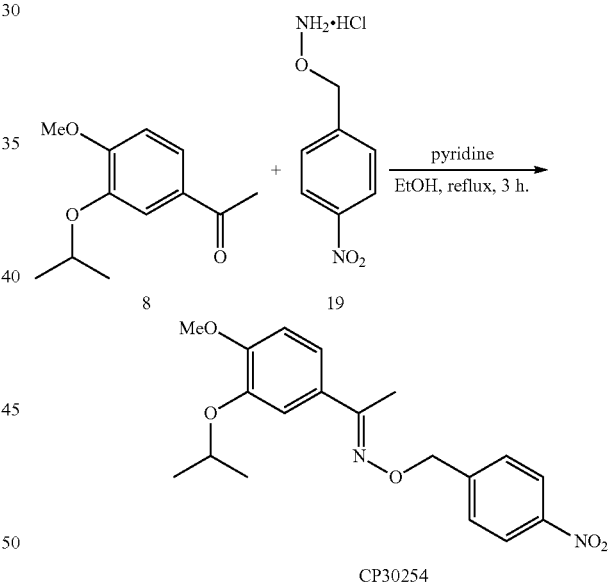

3'-Isopropoxy-4'-methoxyacetophenone (8) (150 mg, 0.720 mmol) was condensed with compound 19 (162 mg, 0.792 mmol) according to the general procedure II-A defined above. After being heated for 3 h the reaction mixture was cooled and the solvent removed under reduced pressure. The ensuing yellow oil was dissolved in CH$_2$Cl$_2$ (20 mL) and the resulting solution washed with H$_2$O (2×15 mL) then dried (MgSO$_4$), filtered and concentrated under reduced pressure. The oil thus obtained was subjected to flash chromatography (15:85 v/v ethyl acetate/hexane elution) to afford the title compound CP30254 (229 mg, 89%) as a pale-yellow oil, which solidified upon extensive standing, m.p. 44.5-46.1° C., R$_f$ 0.5 in 1:1 v/v ethyl acetate/hexane.

$^1$H NMR (300 MHz) δ 8.21 (d, J 9.0 Hz, 2H), 7.55 (d, J 9.0 Hz, 2H), 7.24 (d, J 2.1 Hz, 1H), 7.15 (dd, J 8.4 and 2.1 Hz, 1H), 6.84 (d, J 8.4 Hz, 1H), 5.30 (s, 2H), 4.54 (septet, J 6.0 Hz, 1H), 3.89 (s, 3H), 2.27 (s, 3H), 1.36 (d, J 6.0 Hz, 6H).

$^{13}$C NMR (75 MHz) δ 155.4 (C), 151.6 (C), 147.4 (C), 146.9 (C), 146.0 (C), 128.7 (C), 128.1 (2×CH), 123.5 (2×CH), 119.5 (CH), 113.4 (CH), 111.2 (CH), 74.4 (CH$_2$), 71.5 (CH), 55.9 (CH$_3$), 22.0 (2×CH$_3$), 12.8 (CH$_3$).

IR ν$_{max}$/cm$^{-1}$ 2976, 2932, 2838, 1603, 1520, 1345, 1268, 1253, 1220, 1147, 1110, 1056, 860, 735.

Mass Spectrum (EI) m/z 358 (M$^+$., 82), 316 (92), 43 (100)

HRMS found: M$^+$., 358.1530. C$_{19}$H$_{22}$N$_2$O$_5$ requires M$^+$., 358.1529.

Elemental Analysis Found: C, 63.49; H, 6.25; N, 7.78. C$_{19}$H$_{22}$N$_2$O$_5$ requires C, 63.68; H, 6.19; N, 7.82%.

(E)-3',4'-Methylenedioxyacetophenone O-4-Nitrobenzyl Oxime (CP30255)

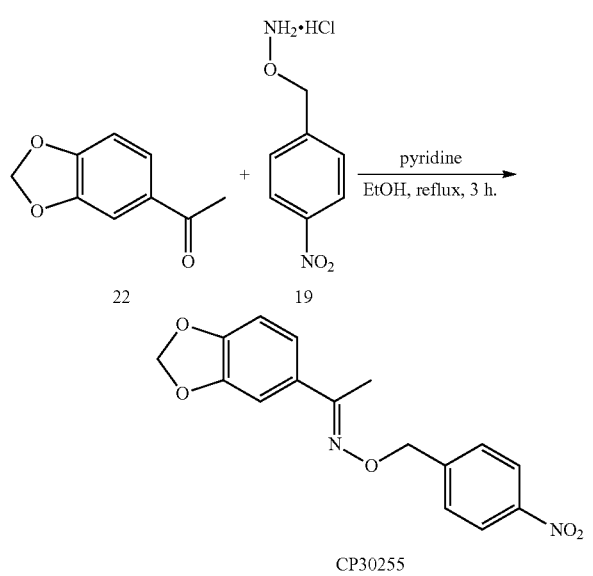

CP30255

3',4'-Methylenedioxyacetophenone (22) (150 mg, 0.914 mmol) was condensed with compound 19 (206 mg, 1.01 mmol) according to the general procedure II-A defined above. After being heated for 3 h the reaction mixture was cooled and the resulting solid filtered off and washed with cold isopropanol (3.0 mL) to afford the title compound CP30255 (250 mg, 87%) as a yellow solid, m.p. 158.7-160.5° C.

$^1$H NMR (300 MHz) δ 8.22 (d, J 8.7 Hz, 2H), 7.54 (d, J 8.7 Hz, 2H), 7.17 (d, J 1.5 Hz, 1H), 7.08 (dd, J 8.4 and 1.5 Hz, 1H), 6.78 (d, J 8.4 Hz, 1H), 5.97 (s, 2H), 5.29 (s, 2H), 2.26 (s, 3H).

$^{13}$C NMR (75 MHz) δ 155.3 (C), 148.7 (C), 147.9 (C), 146.0 (C), 130.3 (C), 128.2 (2×CH), 123.6 (2×CH), 120.4 (CH), 108.0 (CH), 106.2 (CH), 101.3 (CH$_2$), 74.5 (CH$_2$), 12.9 (CH$_3$), signal due to 1×C obscured or overlapping.

IR ν$_{max}$/cm$^{-1}$ 2910, 1603, 1515, 1449, 1349, 1233, 1074, 1044, 937, 877, 831, 809, 733.

Mass Spectrum (EI) m/z 314 (M$^+$., 100).

HRMS Found: M$^+$., 314.0901. C$_{16}$H$_{14}$N$_2$O$_5$ requires M$^+$., 314.0903.

Elemental Analysis Found: C, 61.24; H, 4.50; N, 8.79. C$_{16}$H$_{14}$N$_2$O$_5$ requires C, 61.14; H, 4.49; N, 8.91%.

(E)-3',4'-Dimethoxyacetophenone O-4-Nitrobenzyl Oxime (CP30257)

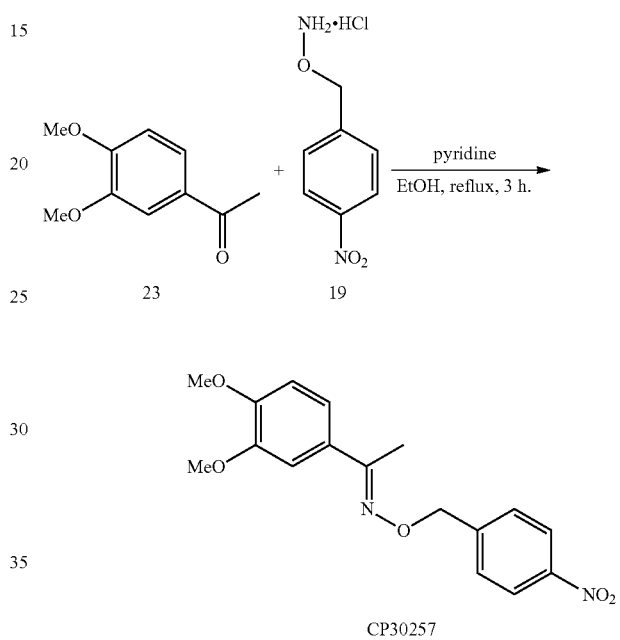

CP30257

3',4'-Dimethoxyacetophenone (23) (150 g, 0.832 mmol) was condensed with compound 19 (187 mg, 0.914 mmol) according to the general procedure II-A defined above. After being heated for 3 h the mixture was cooled and the resulting solid filtered off and washed with cold isopropanol (3.0 mL) to afford the title compound CP30257 (222 mg, 81%) as a white solid, m.p. 118.4-121.0° C.

$^1$H NMR (300 MHz) δ 8.22 (d, J 9.0 Hz, 2H), 7.55 (d, J 9.0 Hz, 2H), 7.24 (d, J 2.1 Hz, 1H), 7.14 (dd, J 8.4 and 2.1 Hz, 1H), 6.84 (d, J 8.4 Hz, 1H), 5.32 (s, 2H), 3.90 (s, 6H), 2.29 (s, 3H).

$^{13}$C NMR (75 MHz) δ 155.5 (C), 150.3 (C), 148.8 (C), 146.0 (C), 128.8 (C), 128.1 (2×CH), 123.6 (2×CH), 119.3 (CH), 110.5 (CH), 108.6 (CH), 74.5 (CH$_2$), 55.9 (CH$_3$), 55.8 (CH$_3$), 12.8 (CH$_3$), signal due to 1×C obscured or overlapping.

IR ν$_{max}$/cm$^{-1}$ 3082, 2941, 2839, 1603, 1576, 1519, 1508, 1450, 1415, 1350, 1279, 1254, 1230, 1155, 1062, 1022, 952, 859.

Mass Spectrum (EI) m/z 330 (M$^+$., 43), 43 (100)

HRMS Found: M$^+$., 330.1217. C$_{17}$H$_{18}$N$_2$O$_5$ requires M$^+$., 330.1216.

Elemental Analysis Found: C, 61.75; H, 5.76; N, 8.54. C$_{17}$H$_{18}$N$_2$O$_5$ requires C, 61.81; H, 5.49; N, 8.48%.

(E)-3'-Hydroxyacetophenone O-4-Nitrobenzyl Oxime (CP30260)

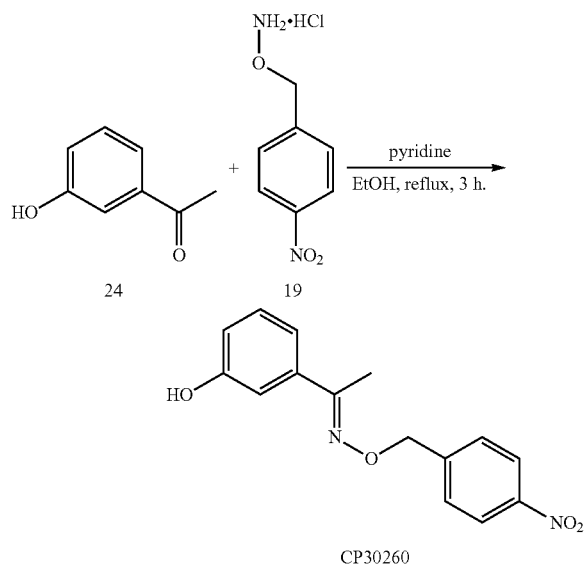

3'-Hydroxyacetophenone (24) (150 mg, 1.10 mmol) was condensed with compound 19 (248 mg, 1.21 mmol) according to the general procedure II-A defined above. After being heated for 3 h the reaction mixture was cooled and the solvent removed under reduced pressure. The resulting solid was filtered off and washed with cold isopropanol (3.0 mL) to afford the title compound CP30260 (257 mg, 82%) as a white solid, m.p. 123.6-125.3° C.

$^1$H NMR (300 MHz) δ 8.22 (d, J 8.7 Hz, 2H), 7.54 (d, J 8.1 Hz, 2H), 7.24-7.10 (complex m, 3H), 6.84 (m, 1H), 5.32 (s, 2H), 2.28 (s, 3H), signal due to Ar—OH not observed.

$^{13}$C NMR (75 MHz) δ 155.8 (C), 155.5 (C), 145.8 (C), 137.6 (C), 129.7 (CH), 128.2 (2×CH), 123.6 (2×CH), 118.7 (CH), 116.5 (CH), 112.8 (CH), 74.6 (CH$_2$), 13.0 (CH$_3$), signal due to 1×C obscured or overlapping.

IR $v_{max}$/cm$^{-1}$ 3436, 1602, 1579, 1512, 1453, 1342, 1324, 1206, 1064, 952, 884, 862, 786, 733.

Mass Spectrum (EI) m/z 286 (M$^+$., 93), 136 (100)

HRMS Found: M$^+$., 286.0956. C$_{15}$H$_{14}$N$_2$O$_4$ requires M$^+$., 286.0954.

Elemental Analysis Found: C, 62.68; H, 5.27; N, 9.69. C$_{15}$H$_{14}$N$_2$O$_4$ requires C, 62.93; H, 4.93; N, 9.79%.

(E)-4'-Hydroxy-3'-methoxyacetophenone O-4-Nitrobenzyl Oxime (CP30261)

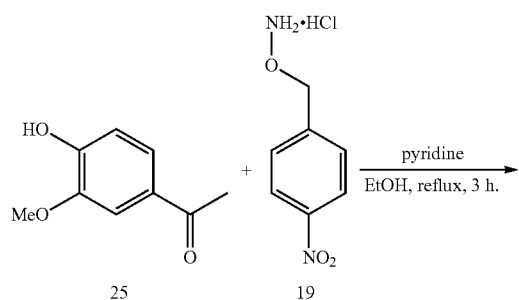

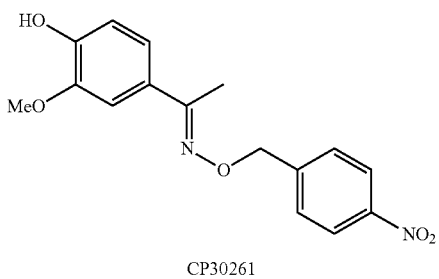

4'-Hydroxy-3'-methoxyacetophenone (25) (150 mg, 0.903 mmol) was condensed with compound 19 (0.203 g, 0.992 mmol) according to the general procedure II-A defined above. After being heated for 3 h the reaction mixture was cooled and the solvent removed under reduced pressure. The ensuing residue was dissolved in CH$_2$Cl$_2$ (20 mL), washed with H$_2$O (2×15 mL) then dried (MgSO$_4$), filtered and concentrated under reduced pressure. The residue thus obtained was subjected to flash chromatography (1:9 v/v ethyl acetate/hexane elution) to afford the title compound CP30261 (158 mg, 55%) as a yellow solid, m.p. 118.4-121.1° C., R$_f$ 0.5 in 1:1 v/v ethyl acetate/hexane.

$^1$H NMR (300 MHz) δ 8.22 (d, J 8.7 Hz, 2H), 7.55 (d, J 8.7 Hz, 2H), 7.22 (d, J 1.8 Hz, 1H), 7.10 (dd, J 8.4 and 1.8 Hz, 1H), 6.89 (d, J 8.4 Hz, 1H), 5.74 (broad s, 1H), 5.32 (s, 2H), 3.91 (s, 3H), 2.28 (s, 3H).

$^{13}$C NMR (75 MHz) δ 155.7 (C), 147.0 (C), 146.4 (C), 146.0 (C), 128.3 (C), 128.1 (2×CH), 123.6 (2×CH), 120.0 (CH), 114.0 (CH), 108.0 (CH), 74.5 (CH$_2$), 55.9 (CH$_3$), 12.9 (CH$_3$), signal due to 1×C obscured or overlapping.

IR $v_{max}$/cm$^{-1}$ 3496, 3079, 2939, 2849, 1604, 1518, 1464, 1421, 1345, 1317, 1258, 1222, 1055, 1032, 860.

Mass Spectrum (EI) m/z 316 (M$^+$., 60), 57 (100)

HRMS Found: M$^+$., 316.1060. C$_{16}$H$_{16}$N$_2$O$_5$ requires M$^+$., 316.1059.

Elemental Analysis Found: C, 60.66; H, 5.38; N, 8.90. C$_{16}$H$_{16}$N$_2$O$_5$ requires C, 60.75; H, 5.10; N, 8.86%.

B) General Procedure for the Synthesis of Compounds CP30262-4, 30266, 30274-5, 30280-83

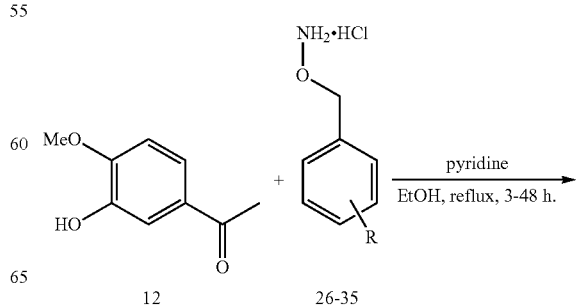

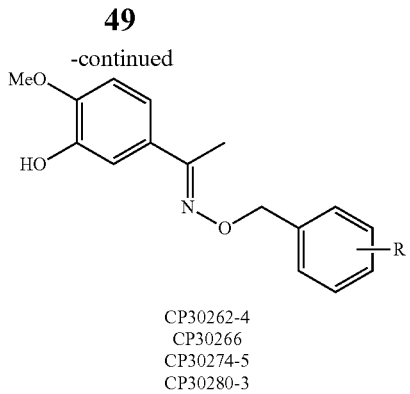

CP30262-4
CP30266
CP30274-5
CP30280-3

R = Various

A magnetically stirred solution of 3-hydroxy-4-methoxyacetophenone (12) (50 mg, 0.301 mmol) in EtOH (600 μL) was treated with the relevant hydroxylamine hydrochloride, viz. one of compounds 26-35 (~1.1 equivalents), and pyridine (150 μL) and the resulting mixture heated at reflux for 3-48 then cooled and the target compound isolated as defined below.

(E)-3'-Hydroxy-4'-methoxyacetophenone O-3-Fluorobenzyl Oxime (CP30262)

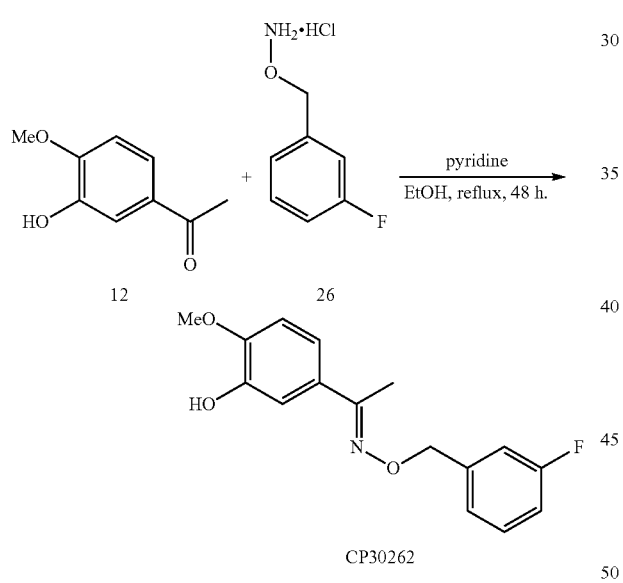

Acetophenone 12 (50 mg, 0.301 mmol) was condensed with O-(3-fluorobenzyl)hydroxylamine hydrochloride (26) (59 mg, 0.332 mmol) according to the general procedure II-B defined above. After being heated at reflux for 48 h the reaction mixture was cooled and the solvent removed under reduced pressure. The ensuing residue was dissolved in CH$_2$Cl$_2$ (15 mL), washed with H$_2$O (2×10 mL) then dried (MgSO$_4$), filtered and concentrated under reduced pressure. The oil thus obtained was subjected to flash chromatography (1:19 v/v ethyl acetate/hexane elution) to afford the title compound CP30262 (71 mg, 82%) as a pale-pink oil, R$_f$ 0.6 in 1:1 v/v ethyl acetate/hexane.

$^1$H NMR (300 MHz) δ 7.35-7.26 (complex m, 2H), 7.18-7.10 (complex m, 1H), 6.99 (m, 1H), 6.82 (d, J 8.4 Hz, 1H), 5.20 (s, 2H), 3.90 (s, 3H), 2.24 (s, 3H), signal due to Ar—OH not observed.

$^{13}$C NMR (75 MHz) δ 162.8 (d, J$_{C,F}$ 244 Hz, C), 154.8 (C), 147.5 (C), 145.3 (C), 140.9 (d, J$_{C,F}$ 7 Hz, C), 129.8 (C), 129.7 (d, J$_{C,F}$ 7 Hz, CH), 123.3 (d, J$_{C,F}$ 2 Hz, CH), 118.3 (CH), 114.7 (d, J$_{C,F}$ 19 Hz, CH), 114.4 (d, J$_{C,F}$ 18 Hz, CH), 112.2 (CH), 110.1 (CH), 75.1 (d, J$_{C,F}$ 2 Hz, CH$_2$), 55.9 (CH$_3$), 12.8 (CH$_3$).

IR ν$_{max}$/cm$^{-1}$ 3525, 2934, 1619, 1591, 1510, 1488, 1450, 1318, 1290, 1259, 1216, 1138, 1027, 872.

Mass Spectrum (EI) m/z 289 (M$^+$., 65), 109 (100)

HRMS Found: M$^+$., 289.1103. C$_{16}$H$_{16}$FNO$_3$ requires M$^+$., 289.1114.

(E)-3'-Hydroxy-4'-methoxyacetophenone O-4-Carbomethoxybenzyl Oxime (CP30263)

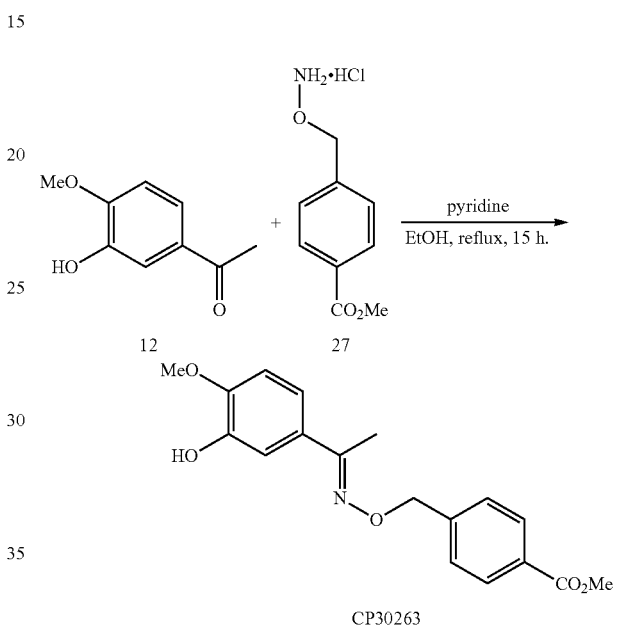

Acetophenone 12 (50 mg, 0.301 mmol) was condensed with O-(4-carbomethoxybenzyl)hydroxylamine hydrochloride (27) (72 mg, 0.331 mmol) according to the general procedure II-B defined above. After being heated at reflux for 15 h the reaction mixture was cooled and the solvent removed under reduced pressure. The ensuing residue was dissolved in CH$_2$Cl$_2$ (15 mL) and the resulting solution washed with H$_2$O (2×10 mL) then dried (MgSO$_4$), filtered and concentrated under reduced pressure. The residue thus obtained was subjected to flash chromatography (1:9 v/v ethyl acetate/hexane elution) to afford the title compound CP30263 (71 mg, 82%) as a white solid, m.p. 97.7-98.7° C., R$_f$ 0.5 in 1:1 v/v ethyl acetate/hexane.

$^1$H NMR (300 MHz) δ 8.03 (d, J 8.4 Hz, 2H), 7.46 (d, J 8.4 Hz, 2H), 7.25 (d, J 2.4 Hz, 1H), 7.12 (dd, J 8.4 and 2.4 Hz, 1H), 6.81 (d, J 8.4 Hz, 1H), 5.60 (broad s, 1H), 5.26 (s, 2H), 3.91 (s, 3H), 3.90 (s, 3H), 2.24 (s, 3H).

$^{13}$C NMR (75 MHz) δ 167.0 (C), 154.9 (C), 147.5 (C), 145.4 (C), 143.6 (C), 129.8 (C), 129.6 (2×CH), 129.3 (C), 127.6 (2×CH), 118.3 (CH), 112.2 (CH), 110.2 (CH), 75.2 (CH$_2$), 55.9 (CH$_3$), 52.1 (CH$_3$), 12.8 (CH$_3$).

IR ν$_{max}$/cm$^{-1}$ 3435, 3004, 2951, 2841, 1719, 1613, 1577, 1510, 1436, 1318, 1282, 1216, 1110, 1052, 1018, 868, 762.

Mass Spectrum (EI) m/z 329 (M$^+$., 40), 149 (100).

HRMS Found: M$^+$., 329.1271. C$_{18}$H$_{19}$NO$_5$ requires M$^+$., 329.1263.

Elemental Analysis Found: C, 65.75; H, 5.72; N, 4.24. C$_{18}$H$_{19}$NO$_5$ requires C, 65.64; H, 5.81; N, 4.25%.

(E)-3'-Hydroxy-4'-methoxyacetophenone O-3-Methylbenzyl Oxime (CP30264)

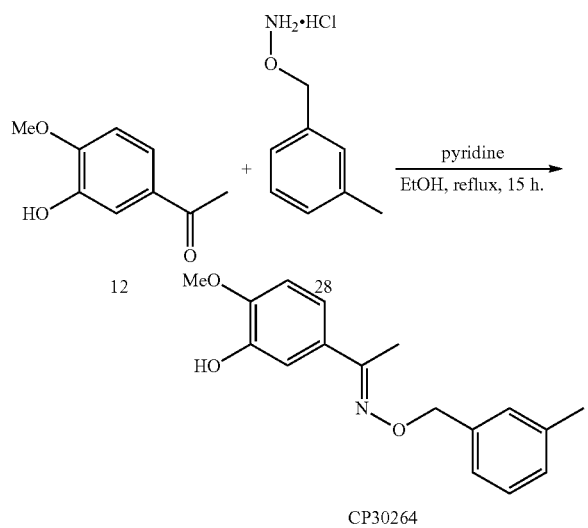

Acetophenone 12 (50 mg, 0.301 mmol) was condensed with O-(3-methylbenzyl)hydroxylamine hydrochloride (28) (57 mg, 0.328 mmol) according to the general procedure II-B defined above. After being heated for 15 h the reaction mixture was cooled and the solvent removed under reduced pressure. The ensuing residue was dissolved in $CH_2Cl_2$ (15 mL), washed with $H_2O$ (2×10 mL) then dried ($MgSO_4$), filtered and concentrated under reduced pressure. The oil thus obtained was subjected to flash chromatography (1:19 v/v ethyl acetate/hexane elution) to afford the title compound CP30264 (78 mg, 91%) as a pale-orange oil, $R_f$ 0.6 in 1:1 v/v ethyl acetate/hexane.

$^1$H NMR (300 MHz) δ 7.29-7.23 (complex m, 4H), 7.18-7.11 (complex m, 2H), 6.82 (d, J 8.7 Hz, 1H), 5.60 (broad s, 1H), 5.18 (s, 2H), 3.90 (s, 3H), 2.37 (s, 3H), 2.22 (s, 3H).

$^{13}$C NMR (75 MHz) δ 154.3 (C), 147.4 (C), 145.3 (C), 137.9 (C), 130.1 (C), 128.9 (CH), 128.4 (CH), 128.2 (CH), 125.2 (CH), 118.2 (CH), 112.3 (CH), 110.1 (CH), 76.1 ($CH_2$), 55.9 ($CH_3$), 21.4 ($CH_3$), 12.8 ($CH_3$), signal due to 1×C obscured or overlapping.

IR $v_{max}$/cm$^{-1}$ 3515, 3011, 2933, 2871, 2841, 1610, 1578, 1510, 1440, 1369, 1318, 1290, 1260, 1215, 1028, 952, 886, 865, 804, 764.

Mass Spectrum (EI) m/z 285 (M$^+$., 28), 105 (100)

HRMS Found: M$^+$., 285.1366. $C_{17}H_{19}NO_3$ requires M$^+$., 285.1365.

(E)-3'-Hydroxy-4'-methoxyacetophenone O-4-Fluorobenzyl Oxime (CP30266)

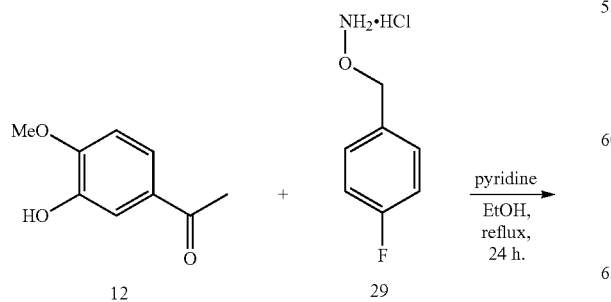

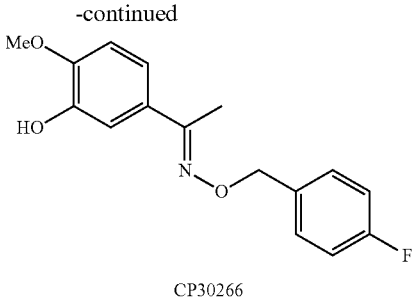

CP30266

Acetophenone 12 (50 mg, 0.301 mmol) was condensed with O-(4-fluorobenzyl)hydroxylamine hydrochloride (29) (58 mg, 0.327 mmol) according to the general procedure II-B defined above. After being heated for 24 h the reaction mixture was cooled and the solvent removed under reduced pressure. The ensuing residue was dissolved in $CH_2Cl_2$ (15 mL) and the resulting solution washed with $H_2O$ (2×10 mL) then dried ($MgSO_4$), filtered and concentrated under reduced pressure. The oil thus obtained was subjected to flash chromatography (1:19 v/v ethyl acetate/hexane elution) to afford the title compound CP30266 (70 mg, 80%) as a pale-purple waxy-oil, $R_f$ 0.5 in 1:1 v/v ethyl acetate/hexane.

$^1$H NMR (300 MHz) δ 7.41-7.36 (complex m, 2H), 7.27 (d, J 2.4 Hz, 1H), 7.13 (dd, J 8.4 and 2.4 Hz, 1H), 7.07-7.01 (complex m, 2H), 6.82 (d, J 8.4 Hz, 1H), 5.61 (broad s, 1H), 5.16 (s, 2H), 3.90 (s, 3H), 2.21 (s, 3H).

$^{13}$C NMR (75 MHz) δ 162.3 (d, $J_{C,F}$ 244 Hz, C), 154.6 (C), 147.4 (C), 145.3 (C), 133.9 (d, $J_{C,F}$ 3 Hz, C), 130.0 (d, $J_{C,F}$ 8 Hz, 2×CH), 129.9 (C), 118.2 (CH), 115.1 (d, $J_{C,F}$ 21 Hz, 2×CH), 112.2 (CH), 110.1 (CH), 75.2 ($CH_2$), 55.9 ($CH_3$), 12.7 ($CH_3$).

IR $v_{max}$/cm$^{-1}$ 3524, 2935, 1604, 1578, 1510, 1440, 1369, 1319, 1290, 1260, 1221, 1028, 868, 764.

Mass Spectrum (EI) m/z 289 (M$^+$., 75), 109 (100).

HRMS Found: M$^+$., 289.1114. $C_{16}H_{16}FNO_3$ requires M$^+$., 289.1114.

(E)-3'-Hydroxy-4'-methoxyacetophenone O-3,5-Difluorobenzyl Oxime (CP30274)

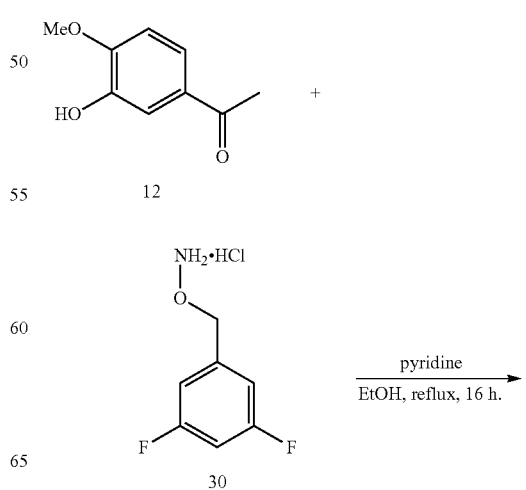

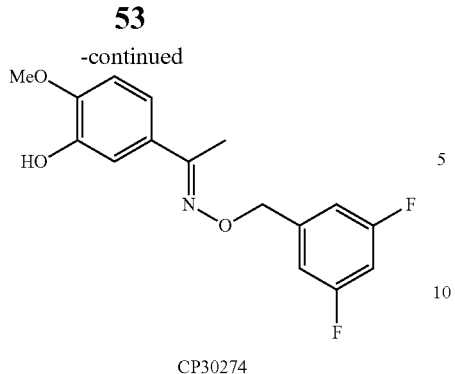

CP30274

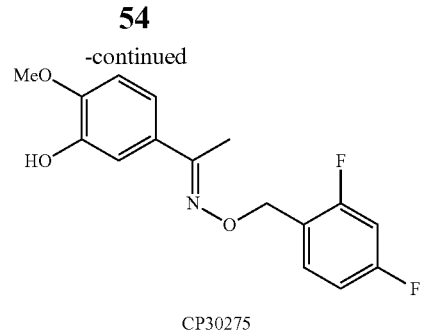

CP30275

Acetophenone 12 (50 mg, 0.301 mmol) was condensed with O-(3,5-difluorobenzyl)hydroxylamine hydrochloride (30) (65 mg, 0.332 mmol) according to the general procedure II-B defined above. After being heated for 16 h the reaction mixture was cooled and the solvent removed under reduced pressure. The ensuing residue was dissolved in CH$_2$Cl$_2$ (15 mL) and the resulting solution washed with H$_2$O (2×10 mL) then dried (MgSO$_4$), filtered and concentrated under reduced pressure. The oil thus obtained was subjected to flash chromatography (1:19 v/v ethyl acetate/hexane elution) to afford the title compound CP30274 (87 mg, 94%) as a pale-orange oil, which solidified upon extensive standing as a cream solid, m.p. 47.7-50.2° C., R$_f$ 0.5 in 1:1 v/v ethyl acetate/hexane.

$^1$H NMR (300 MHz) δ 7.25 (d, J 2.1 Hz, 1H), 7.13 (dd, J 8.4 and 2.1 Hz, 1H), 6.93-6.88 (complex m, 2H), 6.82 (d, J 8.4 Hz, 1H), 6.72 (m, 1H), 5.59 (broad s, 1H), 5.17 (s, 2H), 3.90 (s, 3H), 2.25 (s, 3H).

$^{13}$C NMR (75 MHz) δ 162.9 (dd, J$_{C,F}$ 247 and 13 Hz, 2×C), 155.1 (C), 147.6 (C), 145.3 (C), 142.5 (t, J$_{C,F}$ 9 Hz, C), 129.6 (C), 118.3 (CH), 112.2 (CH), 110.3-110.0 (m, 3×CH), 102.8 (t, J$_{C,F}$ 26 Hz, CH), 74.5 (t, J$_{C,F}$ 2 Hz, CH$_2$), 55.9 (CH$_3$), 12.7 (CH$_3$).

IR v$_{max}$/cm$^{-1}$ 3536, 3085, 2936, 2843, 1627, 1597, 1510, 1460, 1441, 1369, 1319, 1291, 1260, 1215, 1117, 1060, 1018, 961, 867.

Mass Spectrum (EI) m/z 307 (M$^+$., 100).

HRMS Found: M$^+$., 307.1013. C$_{16}$H$_{15}$F$_2$NO$_3$ requires M$^+$., 307.1020.

Elemental Analysis Found: C, 62.63; H, 5.20; N, 4.47. C$_{16}$H$_{15}$F$_2$NO$_3$ requires C, 62.54; H, 4.92; N, 4.56%.

(E)-3'-Hydroxy-4'-methoxyacetophenone O-2,4-Difluorobenzyl Oxime (CP30275)

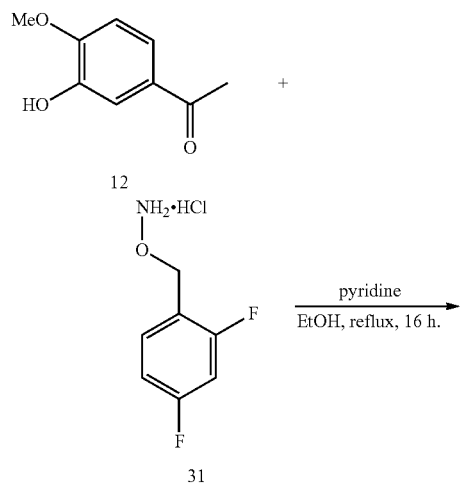

Acetophenone 12 (50 mg, 0.301 mmol) was condensed with O-(2,4-difluorobenzyl)hydroxylamine hydrochloride (31) (65 mg, 0.332 mmol) according to the general procedure II-B defined above. After being heated at reflux for 16 h the reaction mixture was cooled and the solvent removed under reduced pressure. The ensuing residue was dissolved in CH$_2$Cl$_2$ (15 mL) and the resulting solution washed with H$_2$O (2×10 mL) then dried (MgSO$_4$), filtered and concentrated under reduced pressure. The oil thus obtained was subjected to flash chromatography (1:19 v/v ethyl acetate/hexane) to afford the title compound CP30275 (88 mg, 96%) as a pale-orange oil, which solidified upon extensive standing as a cream solid, m.p. 64.8-68.0° C., R$_f$ 0.5 in 1:1 v/v ethyl acetate/hexane.

$^1$H NMR (300 MHz) δ 7.43 (m, 1H), 7.26 (m, 1H), 7.13 (dd, J 8.4 and 2.4 Hz, 1H), 6.90-6.78 (complex m, 3H), 5.57 (broad s, 1H), 5.22 (s, 2H), 3.90 (s, 3H), 2.20 (s, 3H).

$^{13}$C NMR (75 MHz) δ 162.6 (dd, J$_{C,F}$ 247 and 12 Hz, C), 160.9 (dd, J$_{C,F}$ 249 and 12 Hz, C), 154.8 (C), 147.5 (C), 145.3 (C), 131.6 (dd, J$_{C,F}$ 10 and 6 Hz, CH), 129.7 (CH), 121.2 (dd, J$_{C,F}$ 15 and 4 Hz, C), 118.3 (CH), 112.2 (CH), 111.0 (dd, J$_{C,F}$ 21 and 4 Hz, CH), 110.1 (CH), 103.6 (t, J$_{C,F}$ 25 Hz, CH), 68.9 (d, J$_{C,F}$ 3 Hz, CH$_2$), 55.9 (CH$_3$), 12.6 (CH$_3$).

IR v$_{max}$/cm$^{-1}$ 3536, 3079, 2939, 2843, 1621, 1606, 1579, 1506, 1456, 1431, 1371, 1319, 1278, 1262, 1216, 1139, 1100, 1028, 995, 961, 866, 803, 764.

Mass Spectrum (EI) m/z 307 (M$^+$., 100).

HRMS Found: M$^+$., 307.1020. C$_{16}$H$_{15}$F$_2$NO$_3$ requires M$^+$., 307.1020.

Elemental Analysis Found: C, 62.48; H, 4.99; N, 4.42. C$_{16}$H$_{15}$F$_2$NO$_3$ requires C, 62.54; H, 4.92; N, 4.56%.

(E)-3'-Hydroxy-4'-methoxyacetophenone O-2-Fluorobenzyl Oxime (CP30280)

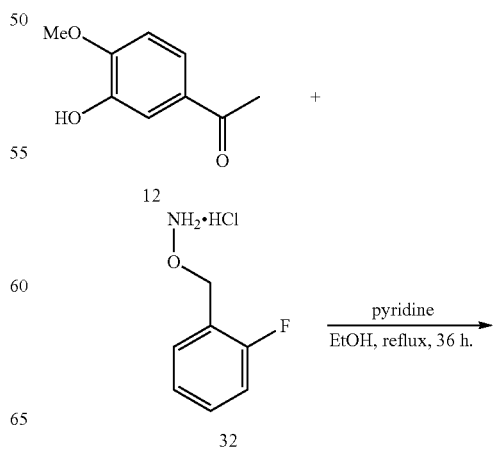

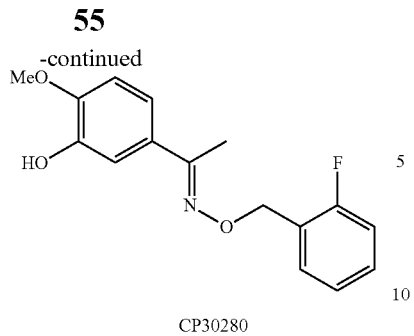

CP30280

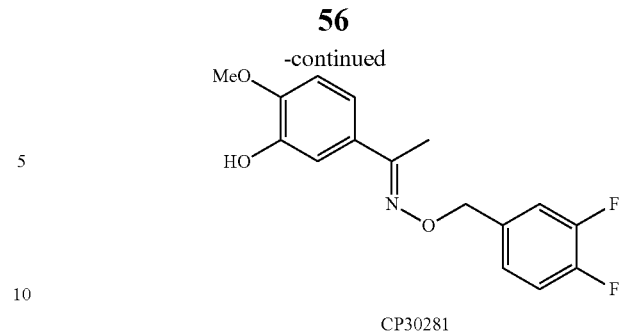

CP30281

Acetophenone 12 (50 mg, 0.301 mmol) was condensed with O-(2-fluorobenzyl)hydroxylamine hydrochloride (32) (58 mg, 0.327 mmol) according to the general procedure II-B defined above. After being heated for 36 h the reaction mixture was cooled and the solvent removed under reduced pressure. The ensuing residue was dissolved in $CH_2Cl_2$ (15 mL) and the resulting solution washed with $H_2O$ (2×10 mL) then dried ($MgSO_4$), filtered and concentrated under reduced pressure. The oil thus obtained was subjected to flash chromatography (1:19 v/v ethyl acetate/hexane) to afford the title compound CP30280 (79 mg, 91%) as a pale-yellow oil, $R_f$ 0.5 in 1:1 v/v ethyl acetate/hexane.

$^1$H NMR (300 MHz) δ 7.46 (m, 1H), 7.32-7.25 (complex m, 2H), 7.16-7.03 (complex m, 3H), 6.82 (d, J 8.4 Hz, 1H), 5.58 (broad s, 1H), 5.28 (s, 2H), 3.90 (s, 3H), 2.22 (s, 3H).

$^{13}$C NMR (75 MHz) δ 160.8 (d, $J_{C,F}$ 246 Hz, C), 154.7 (C), 147.4 (C), 145.3 (C), 130.5 (d, $J_{C,F}$ 4 Hz, CH), 129.8 (C), 129.4 (d, $J_{C,F}$ 8 Hz, CH), 125.2 (d, $J_{C,F}$ 15 Hz, C), 123.9 (d, $J_{C,F}$ 3 Hz, CH), 118.3 (CH), 115.2 (d, $J_{C,F}$ 22 Hz, CH), 112.2 (CH), 110.1 (CH), 69.5 (d, $J_{C,F}$ 4 Hz, $CH_2$), 55.8 ($CH_3$), 12.6 ($CH_3$).

IR $v_{max}$/cm$^{-1}$ 3526, 2937, 2842, 1619, 1579, 1510, 1492, 1456, 1440, 1370, 1318, 1290, 1260, 1217, 1138, 1026, 869, 760.

Mass Spectrum (EI) m/z 289 (M$^+$., 65), 109 (100).

HRMS Found: M$^+$., 289.1112. $C_{16}H_{16}FNO_3$ requires M$^+$., 289.1114.

(E)-3'-Hydroxy-4'-methoxyacetophenone O-3,4-Difluorobenzyl Oxime (CP30281)

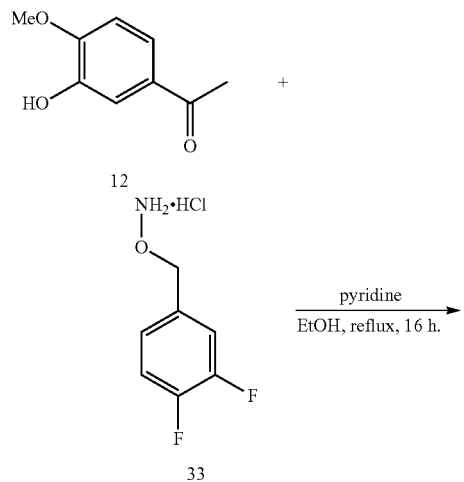

Acetophenone 12 (50 mg, 0.301 mmol) was condensed with O-(3,4-difluorobenzyl)hydroxylamine hydrochloride (33) (65 mg, 0.332 mmol) according to the general procedure II-B defined above. After being heated at reflux for 16 h the reaction mixture was cooled and the solvent removed under reduced pressure. The ensuing residue was dissolved in $CH_2Cl_2$ (15 mL) and the resulting solution washed with $H_2O$ (2×10 mL) then dried ($MgSO_4$), filtered and concentrated under reduced pressure. The oil thus obtained was subjected to flash chromatography (1:19 v/v ethyl acetate/hexane elution) to afford the title compound CP30281 (86 mg, 93%) as a pale-pink oil, $R_f$ 0.5 in 1:1 v/v ethyl acetate/hexane.

$^1$H NMR (300 MHz) δ 7.28-7.10 (complex m, 5H), 6.82 (d, J 8.7 Hz, 1H), 5.56 (broad s, 1H), 5.14 (s, 2H), 3.90 (s, 3H), 2.22 (s, 3H).

$^{13}$C NMR (75 MHz) δ 154.9 (C), 150.1 (dd, $J_{C,F}$ 246 and 13 Hz, C), 149.8 (dd, $J_{C,F}$ 246 and 13 Hz, C), 147.5 (C), 145.3 (C), 135.3 (dd, $J_{C,F}$ 5 and 4 Hz, C), 129.6 (C), 123.9 (dd, $J_{C,F}$ 6 and 3 Hz, CH), 118.3 (CH), 116.9 (dd, $J_{C,F}$ 17 and 5 Hz, CH), 112.2 (CH), 110.1 (CH), 74.6 (d, $J_{C,F}$ 1 Hz, $CH_2$), 55.9 ($CH_3$), 12.7 ($CH_3$), signal due to 1×C obscured or overlapping.

IR $v_{max}$/cm$^{-1}$ 3541, 2937, 2844, 1611, 1579, 1519, 1435, 1370, 1319, 1288, 1260, 1213, 1140, 1115, 1028, 873, 806, 764.

Mass Spectrum (EI) m/z 307 (M$^+$., 62), 127 (100).

HRMS Found: M$^+$., 307.1020. $C_{16}H_{15}F_2NO_3$ requires M$^+$., 307.1020.

(E)-3'-Hydroxy-4'-methoxyacetophenone O-3-Trifluoromethoxybenzyl Oxime (CP30282)

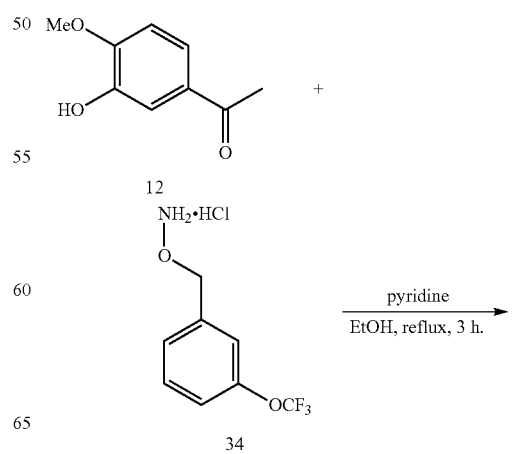

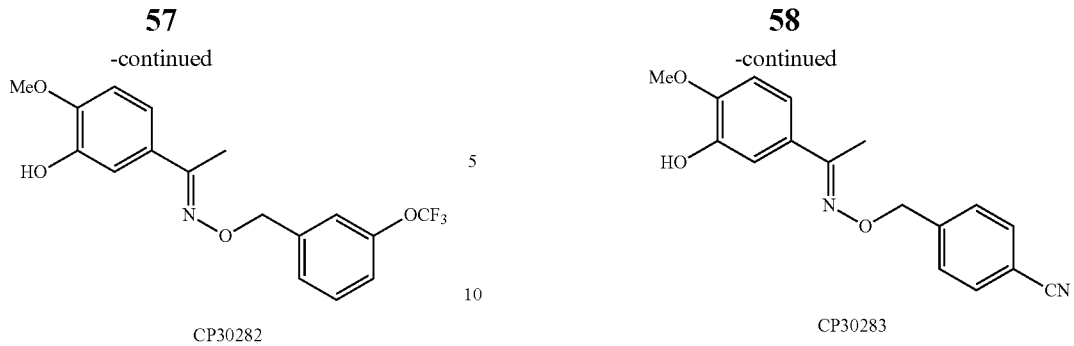

CP30282

Acetophenone 12 (50 mg, 0.301 mmol) was condensed with O-(3-trifluoromethoxybenzyl)hydroxylamine hydrochloride (34) (81 mg, 0.332 mmol) according to the general procedure II-B defined above. After being heated for 3 h the reaction mixture was cooled and the solvent removed under reduced pressure. The ensuing residue was dissolved in $CH_2Cl_2$ (15 mL) and the resulting solution washed with $H_2O$ (2×10 mL) then dried ($MgSO_4$), filtered and concentrated under reduced pressure. The oil thus obtained was subjected to flash chromatography (1:19 v/v ethyl acetate/hexane elution) to afford the title compound CP30282 (95 mg, 89%) as a pale-orange oil, $R_f$ 0.6 in 1:1 v/v ethyl acetate/hexane.

$^1$H NMR (300 MHz) δ 7.40-7.26 (complex m, 4H), 7.15-7.12 (complex m, 2H), 6.82 (d, J 8.1 Hz, 1H), 5.59 (broad s, 1H), 5.22 (s, 2H), 3.90 (s, 3H), 2.24 (s, 3H).

$^{13}$C NMR (75 MHz) δ 155.0 (C), 149.2 (C), 147.5 (C), 145.3 (C), 140.7 (C), 129.7 (C), 129.6 (CH), 126.1 (CH), 120.4 (d, $J_{C,F}$ 256 Hz, C), 120.3 (CH), 119.9 (CH), 118.3 (CH), 112.2 (CH), 110.1 (CH), 74.9 ($CH_2$), 55.9 ($CH_3$), 12.8 ($CH_3$).

IR $v_{max}$/cm$^{-1}$ 3436, 2931, 1579, 1510, 1259, 1215, 1662, 1027.

Mass Spectrum (EI) m/z 355 (M$^+$., 85), 175 (100).

HRMS Found: M$^+$., 355.1032. $C_{17}H_{16}F_3NO_4$ requires M$^+$., 355.1031.

(E)-3'-Hydroxy-4'-methoxyacetophenone O-4-Cyanobenzyl Oxime (CP30283)

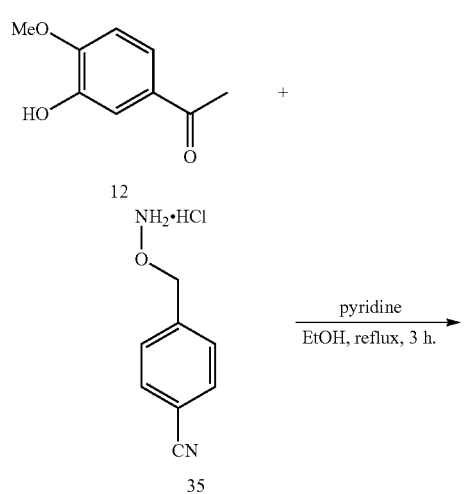

Acetophenone 12 (30 mg, 0.181 mmol) was condensed with O-(4-cyanobenzyl)hydroxylamine hydrochloride (35) (37 mg, 0.200 mmol) according to the general procedure II-B defined above. After being heated for 3 h the reaction mixture was cooled and the solvent removed under reduced pressure. The ensuing solid was filtered off and washed with cold isopropanol (3.0 mL) to afford the title compound CP30283 (27 mg, 51%) as a white solid, m.p. 125.9-129.7° C.

$^1$H NMR (300 MHz) δ 7.65 (d, J 8.1 Hz, 2H), 7.49 (d, J 8.1 Hz, 2H), 7.24 (d, J 2.1 Hz, 1H), 7.11 (dd, J 8.4 and 2.1 Hz, 1H), 6.82 (d, J 8.4 Hz, 1H), 5.63 (broad s, 1H), 5.25 (s, 2H), 3.90 (s, 3H), 2.24 (s, 3H).

$^{13}$C NMR (75 MHz) δ 155.2 (C), 147.6 (C), 145.4 (C), 144.0 (C), 132.2 (2×CH), 129.6 (C), 128.1 (2×CH), 118.9 (C), 118.3 (CH), 112.2 (CH), 111.3 (C), 110.1 (CH), 74.8 ($CH_2$), 56.0 ($CH_3$), 12.8 ($CH_3$).

IR $v_{max}$/cm$^{-1}$ 3401, 2233, 1577, 1509, 1439, 1370, 1319, 1292, 1261, 1212, 1058, 949, 900, 804.

Mass Spectrum (EI) m/z 296 (M$^+$., 100).

HRMS Found: M$^+$., 296.1160. $C_{17}H_{16}N_2O_3$ requires M$^+$., 296.1161.

Elemental Analysis Found: C, 68.51; H, 5.40; N, 9.19. $C_{17}H_{16}N_2O_3$ requires C, 68.91; H, 5.44; N, 9.45%.

III) Synthesis of CP30220 Bromo-Analogue

2-Bromo-5-isopropoxy-4-methoxybenzaldehyde (36)

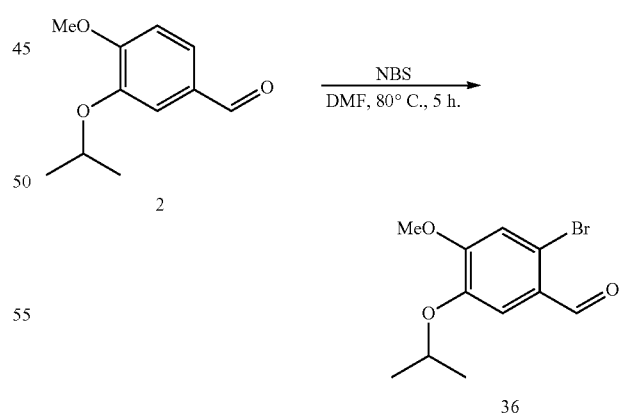

Following protocols reported by Flynn et al.,[7] a solution of aldehyde 2 (2.0 g, 10.3 mmol) in dry DMF (2.5 mL) was treated with N-bromosuccinimide (2.57 g, 14.4 mmol) and the resulting mixture stirred magnetically at 80° C. for 5 h then cooled, diluted with $Et_2O$ (50 mL), washed with $Na_2S_2O_5$ (1×10 mL of 10% w/v aqueous solution) and then $H_2O$ (1×40 mL). The separated organic phase was then dried (MgSO₄), filtered and concentrated under reduced pressure. The ensuing residue was subjected to flash chromatography (5:95 v/v ethyl acetate/hexane elution) to afford the title compound 36[7] (2.16 g, 77%) as a pale-yellow solid, m.p. 71-75° C. (lit.[7] 78-79° C.), $R_f$ 0.7 in 1:1 v/v ethyl acetate/hexane.

$^1$H NMR (300 MHz) δ 10.17 (s, 1H), 7.41 (s, 1H), 7.04 (s, 1H), 4.62 (septet, J 6.0 Hz, 1H), 3.93 (s, 3H), 1.38 (d, J 6.0 Hz, 6H).

1-(2-Bromo-5-isopropoxy-4-methoxyphenyl)ethanol (37)

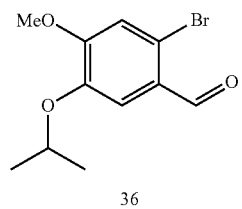

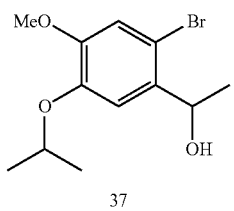

A mixture of Mg turnings (231 mg, 9.51 g·atom) in dry Et₂O (3.0 mL) was stirred at 0° C. under a nitrogen atmosphere then treated, dropwise, with a solution of iodomethane (680 μL, 10.9 mmol) in dry Et₂O (2.0 mL). After 0.5 h a solution of aldehyde 36 (1.00 g, 3.66 mmol) in dry Et₂O (10 mL) was added, dropwise, to the reaction mixture that was then allowed to warm to 18° C. at which temperature it was stirred for a further 1 h. After this time NH₄Cl (15 mL of a 20% w/v aqueous solution) then Et₂O (20 mL) were added to the reaction mixture. The separated organic phase was washed with H₂O (1×20 mL) then dried (MgSO₄), filtered and concentrated under reduced pressure to afford the title compound 37 (1.05 g, 99%) as an orange oil.

$^1$H NMR (300 MHz) δ 7.10 (s, 1H), 6.94 (s, 1H), 5.12 (q, J 6.3 Hz, 1H), 4.53 (septet, J 6.0 Hz, 1H), 3.81 (s, 3H), 2.21 (broad s, 1H), 1.41 (d, J 6.3 Hz, 3H), 1.34 (d, J 6.0 Hz, 6H).

$^{13}$C NMR (75 MHz) δ 149.8 (C), 146.8 (C), 136.6 (C), 115.6 (CH), 113.4 (CH), 111.5 (C), 71.6 (CH), 68.8 (CH), 56.1 (CH₃), 23.6 (CH₃), 21.9 (4) (CH₃), 21.8 (6) (CH₃).

IR $v_{max}$/cm$^{-1}$ 3402, 2975, 2929, 1599, 1496, 1439, 1385, 1254, 1206, 1158, 1109, 1031, 978, 918, 884, 831, 799.

Mass Spectrum (EI) m/z 290 and 288 (M⁺., 53 and 55), 233 and 231 (95 and 100), 124 (75).

HRMS Found: M⁺., 290.0345. C₁₂H₁₇$^{81}$BrO₃ requires M⁺., 290.0341. Found: M⁺., 288.0363. C₁₂H₁₇$^{79}$BrO₃ requires M⁺., 288.0361.

This material was used, as obtained, in the next step of the reaction sequence.

2'-Bromo-5'-isopropoxy-4'-methoxyacetophenone (38)

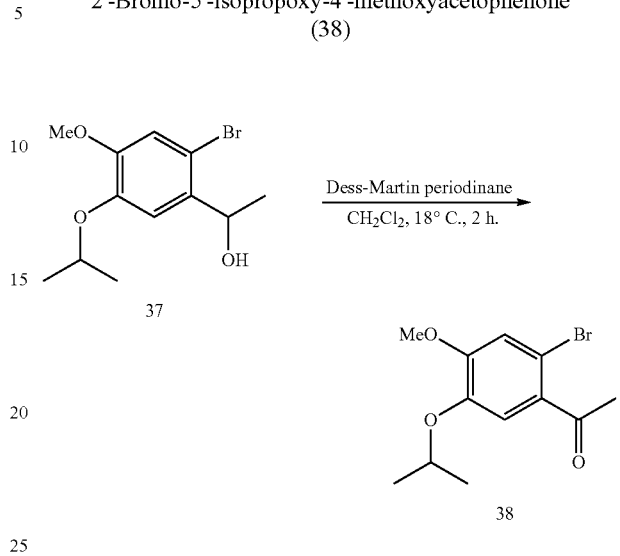

A magnetically stirred solution of alcohol 37 (520 mg, 1.80 mmol) in CH₂Cl₂ (10 mL), maintained at 0° C. was treated with Dess-Martin periodinane (1.14 g, 2.69 mmol). The resulting mixture was warmed to 18° C., stirred at this temperature for 2 h then concentrated, under reduced pressure, onto TLC-grade silica (ca. 500 mg). The resulting free-flowing solid was subjected to flash chromatography (1:19 v/v ethyl acetate/hexane elution) to afford the title compound 38 (361 mg, 70%) as a pale-yellow solid, m.p. 59.0-59.9° C., $R_f$ 0.6 in 1:1 v/v ethyl acetate/hexane.

$^1$H NMR (300 MHz) δ 7.18 (s, 1H), 7.05 (s, 1H), 4.55 (septet, J 6.0 Hz, 1H), 3.89 (s, 3H), 2.65 (s, 3H), 1.36 (d, J 6.0 Hz, 6H).

$^{13}$C NMR (75 MHz) δ 199.3 (C), 152.9 (C), 146.2 (C), 132.4 (C), 116.9 (CH), 116.7 (CH), 111.9 (C), 71.8 (CH), 56.2 (CH₃), 30.3 (CH₃), 21.8 (2×CH₃).

IR $v_{max}$/cm$^{-1}$ 2977, 2932, 1690, 1589, 1500, 1440, 1375, 1257, 1204, 1176, 1110, 1026, 953, 904, 842.

Mass Spectrum (EI) m/z 288 and 286 (M⁺., 44 and 43), 231 and 229 (98 and 100).

HRMS Found: M⁺., 288.0186. C₁₂H₁₅$^{81}$BrO₃ requires M⁺., 288.0184. Found: M⁺., 286.0207. C₁₂H₁₅$^{79}$BrO₃ requires M⁺., 286.0205.

Elemental Analysis Found: C, 50.08; H, 5.17. C₁₂H₁₅BrO₃ requires C, 50.19; H, 5.27%.

2'-Bromo-5'-hydroxy-4'-methoxyacetophenone (39)

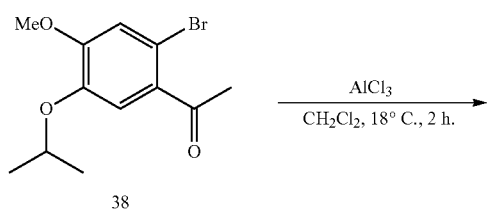

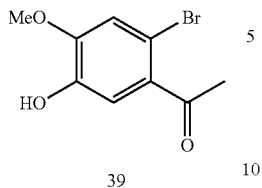

A solution of ketone 38 (220 mg, 0.766 mmol) in dry $CH_2Cl_2$ (2.0 mL) was treated with $AlCl_3$ (306 mg, 2.29 mmol) and the resulting mixture stirred at 18° C. under a nitrogen atmosphere for 2 h. The ensuing mixture was partitioned between $H_2O$ (5 mL) and $CH_2Cl_2$ (5 mL) then the separated aqueous phase extracted with $CH_2Cl_2$ (1×15 mL). The combined organic fractions were dried ($MgSO_4$), filtered and concentrated under reduced pressure and the ensuing residue subjected to flash chromatography (15:85 v/v ethyl acetate/hexane elution) to afford the title compound 39 (184 mg, 98%) as a pale-yellow solid, m.p. 109.7-111.4° C., $R_f$ 0.4 in 1:1 v/v ethyl acetate/hexane.

$^1$H NMR (300 MHz) δ 7.21 (s, 1H), 7.06 (s, 1H), 5.63 (broad s, 1H), 3.94 (s, 3H), 2.60 (s, 3H).

$^{13}$C NMR (75 MHz) δ 199.2 (C), 148.9 (C), 144.6 (C), 132.9 (C), 116.1 (CH), 115.9 (CH), 110.1 (C), 56.3 ($CH_3$), 30.0 ($CH_3$).

IR $v_{max}$/cm$^{-1}$ 3391, 1681, 1609, 1567, 1501, 1275, 1197, 1177, 1025.

Mass Spectrum (EI) m/z 246 and 244 (M$^+$., 47 and 48), 231 and 229 (98 and 100).

HRMS Found: M$^+$., 245.9721. $C_9H_9{}^{81}BrO_3$ requires M$^+$., 245.9715. Found: M$^+$., 243.9737. $C_9H_9{}^{79}BrO_3$ requires M$^+$., 243.9735.

Elemental Analysis Found: C, 44.15; H, 3.62. $C_9H_9BrO_3$ requires C, 44.11; H, 3.70%.

(E)-2'-Bromo-5'-hydroxy-4'-methoxyacetophenone O-4-Nitrobenzyl Oxime (CP302108-Major)

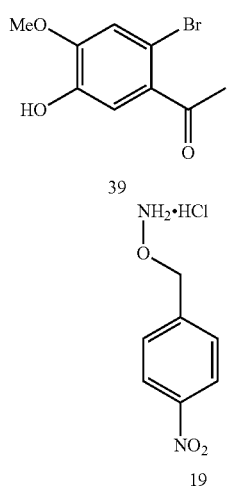

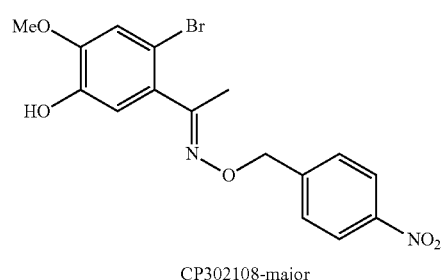

A magnetically stirred solution of ketone 39 (162 mg, 0.661 mmol) in EtOH (2.0 mL) was treated with compound 19 (271 mg, 1.32 mmol) and imidazole (68 mg, 0.999 mmol) then the resulting mixture stirred at reflux for 2 h before being cooled and concentrated under reduced pressure. The ensuing residue was partitioned between $CH_2Cl_2$ (10 mL) and $H_2O$ (10 mL) and the separated aqueous fraction extracted with $CH_2Cl_2$ (1×10 ml). The combined organic fractions were then dried ($MgSO_4$), filtered and concentrated under reduced pressure. The resulting mixture was subjected to flash chromatography (15:85 v/v ethyl acetate/hexane) to afford a ca. 3:1 mixture of the E- and Z-isomeric foams of the title compound CP302108 (229 mg, 88%) as a pale-yellow solid, $R_f$ 0.5 in 1:1 v/v ethyl acetate/hexane. Recrystallisation of this material (twice from isopropanol) afforded the major isomer, CP302108-major, as a pale-yellow solid, m.p. 136.8-138.4° C.

$^1$H NMR (300 MHz) δ 8.21 (d, J 9.0 Hz, 2H), 7.53 (d, J 9.0 Hz, 2H), 7.00 (s, 1H), 6.81 (s, 1H), 5.65 (broad s, 1H), 5.30 (s, 2H), 3.87 (s, 3H), 2.26 (s, 3H).

$^{13}$C NMR (75 MHz) δ 158.1 (C), 147.3 (C), 145.9 (C), 144.8 (C), 131.2 (C), 128.0 (2×CH), 123.6 (2×CH), 115.9 (CH), 115.2 (CH), 110.9 (C), 74.4 ($CH_2$), 56.3 ($CH_3$), 17.0 ($CH_3$), signal due to 1×C obscured or overlapping.

IR $v_{max}$/cm$^{-1}$ 3467, 2918, 1606, 1520, 1498, 1344, 1309, 1259, 1203, 1108, 1055, 1029, 860, 793.

Mass Spectrum (EI) m/z 396 and 394 (M$^+$., both 52), 315 (78), 164 (95), 106 (100).

HRMS Found: M$^+$., 396.0146. $C_{16}H_{15}BrN_2O_5$ requires M$^+$., 396.0144. Found: M$^+$., 394.0170. $C_{16}H_{15}{}^{79}BrN_2O_5$ requires M$^+$., 394.0164.

Elemental Analysis Found: C, 48.86; H, 3.80; N, 6.90. $C_{16}H_{15}BrN_2O_3$ requires C, 48.63; H, 3.83; N, 7.09%.

IV) Synthesis of CP30220 Aryl-Analogues
General Procedure for the Synthesis of Compounds CP30329, 30331, 30338-40, 30342-46

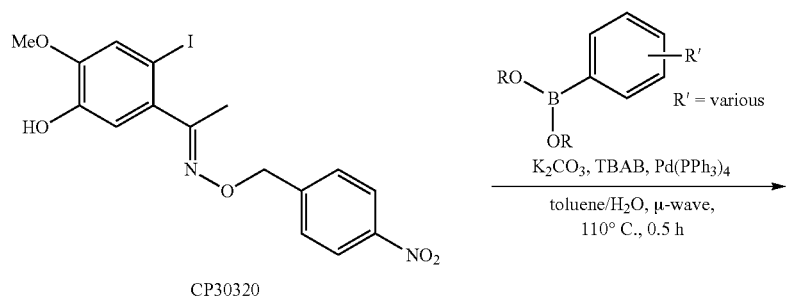

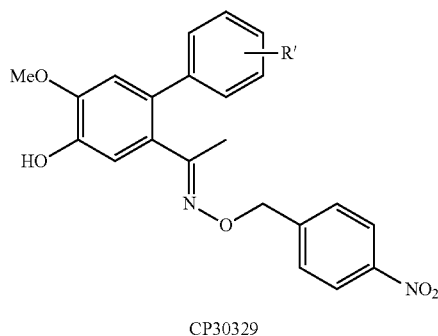

CP30329
CP30331
CP30338-40
CP30342-46

A solution of E-5'-hydroxy-2'-iodo-4'-methoxy acetophenone O-4-nitrobenzyl oxime (CP30220) (80 mg, 0.181 mmol) in toluene (1.5 mL) and $H_2O$ (1.5 mL), maintained under a nitrogen atmosphere, was treated with $K_2CO_3$ (75 mg, 0.543 mmol), tetrabutylammonium bromide (6 mg, 0.019 mmol), tetrakis(triphenylphosphine)palladium(0) (21 mg, 0.018 mmol) and the relevant arylboronic acid (ca. 2 equivalents). The resulting mixture was then subjected to microwave irradiation (110° C., 30 min), cooled then filtered and the palladium residue thus retained washed with EtOAc (1×5 mL). The organic layer was then separated, dried ($MgSO_4$), filtered and concentrated under reduced pressure and the target compound isolated as defined below.

(E)-5'-Hydroxy-4'-methoxy-2'-phenylacetophenone O-4-Nitrobenzyl Oxime (CP30329)

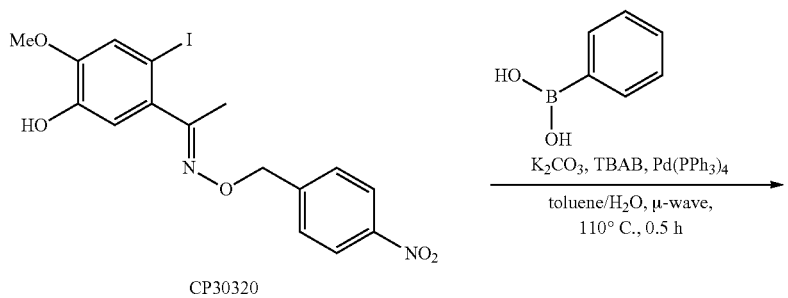

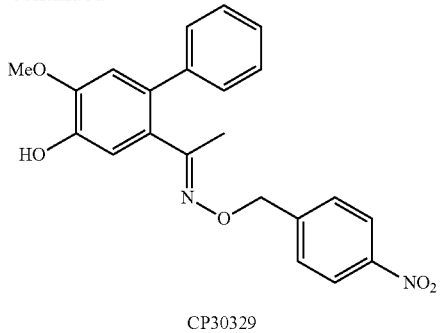

CP30329

Iodide CP30220 (100 mg, 0.226 mmol) was coupled with phenylboronic acid (44 mg, 0.361 mmol) according to the general procedure IV defined above. The residue thus obtained was subjected to flash chromatography (1:9 v/v ethyl acetate/hexane elution) to afford a ca. 2:1 mixture of the target compound CP30329 and the dehalogenated starting material CP30218 as a pale-yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30329 (25 mg, 28%) as a pale yellow oil, $R_t$ 18.9 min.

$^1$H NMR (300 MHz) δ 8.20 (d, J 8.9 Hz, 2H), 7.45 (d, J 8.8 Hz, 2H), 7.35-7.26 (complex m, 5H), 6.93 (s, 1H), 6.83 (s, 1H), 5.25 (s, 2H), 3.91 (s, 3H), 1.74 (s, 3H), signal due to Ar—OH not observed.

$^{13}$C NMR (75 MHz) δ 159.3 (C), 147.2 (C), 146.9 (C), 146.4 (C), 144.7 (C), 141.0 (C), 133.0 (C), 129.4 (C), 128.9 (2×CH), 128.3 (2×CH), 127.9 (2×CH), 127.1 (CH), 123.5 (2×CH), 115.3 (CH), 112.7 (CH), 74.2 (CH$_2$), 56.0 (CH$_3$), 17.1 (CH$_3$).

IR $v_{max}$/cm$^{-1}$ 3514, 3078, 2931, 2848, 1605, 1519, 1490, 1345, 1304, 1201, 1036, 859.

Mass Spectrum (EI) m/z 392 (M$^+$., 32), 240 (100).

HRMS Found: M$^+$., 392.1372. C$_{22}$H$_{20}$N$_2$O$_5$ requires M$^+$., 392.1372.

Concentration of fraction B gave the dehalogenated compound CP30218, $R_t$ 12.8 min, as a white solid that was identical, as judged by $^1$H NMR spectroscopic analysis, with authentic material.

(E)-5'-Hydroxy-4'-methoxy-2'-(3,4-dimethoxyphenyl)acetophenone O-4-Nitrobenzyl Oxime (CP30331)

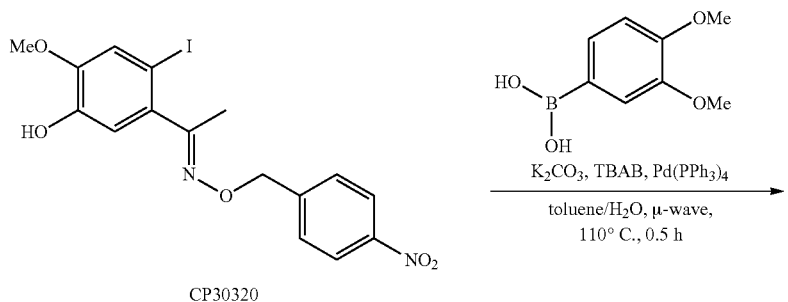

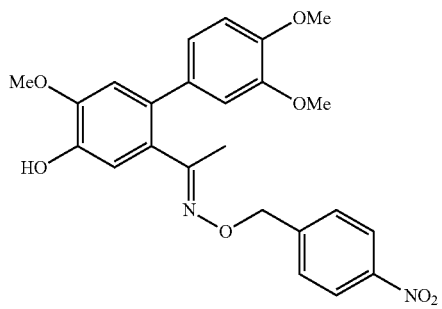

CP30331

Iodide CP30220 (80 mg, 0.181 mmol) was coupled with 3,4-dimethoxyphenylboronic acid (66 mg, 0.363 mmol) according to the general procedure IV defined above. The residue thus obtained was subjected to flash chromatography (1:9→2:8 v/v ethyl acetate/hexane gradient elution) to afford the target compound CP30331 (47 mg, 57%) as a pale-orange oil, $R_f$ 0.4 in 1:1 ethyl acetate/hexane.

$^1$H NMR (300 MHz) δ 8.19 (d, J 8.8 Hz, 2H), 7.46 (d, J 8.8 Hz, 2H), 6.90 (s, 1H), 6.83-6.82 (complex m, 4H), 5.66 (broad s, 1H), 5.25 (s, 2H), 3.91 (s, 3H), 3.90 (s, 3H), 3.81 (s, 3H), 1.75 (s, 3H).

$^{13}$C NMR (75 MHz) δ 159.8 (C), 148.8 (C), 148.5 (C), 147.5 (C), 147.1 (C), 146.4 (C), 144.8 (C), 133.9 (C), 133.0 (C), 129.6 (C), 128.2 (2×CH), 123.8 (2×CH), 121.5 (CH), 115.6 (CH), 112.7 (CH), 112.6 (6) (CH), 111.2 (CH), 74.5 (CH$_2$), 56.3 (CH$_3$), 56.1 (2×CH$_3$) 17.3 (CH$_3$).

IR $v_{max}$/cm$^{-1}$ 3436, 2930, 2852, 1605, 1520, 1504, 1345, 1254, 1027, 857, 735.

Mass Spectrum (EI) m/z 452 (M$^+$., 10), 300 (100).

HRMS Found: M$^+$., 452.1587. C$_{24}$H$_{24}$N$_2$O$_7$ requires M$^+$., 452.1584.

(E)-5'-Hydroxy-4'-methoxy-2'-(4-methoxyphenyl) acetophenone O-4-Nitrobenzyl Oxime (CP30338)

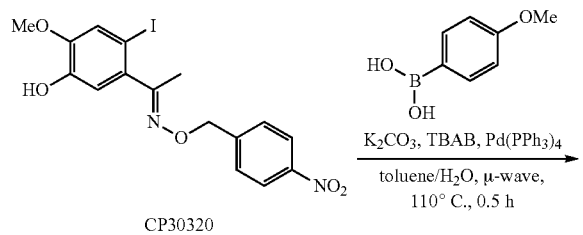

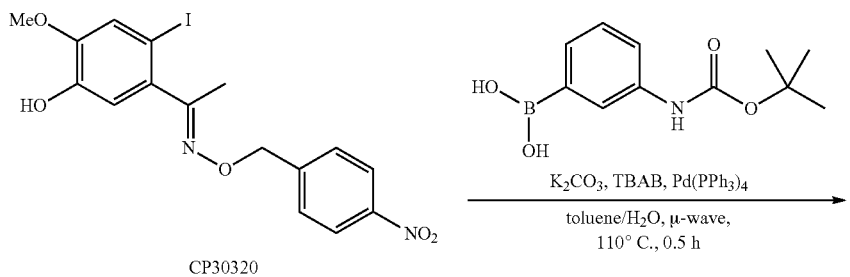

Iodide CP30220 (80 mg, 0.181 mmol) was coupled with 4-methoxyphenylboronic acid (55 mg, 0.362 mmol) according to the general procedure IV defined above. The residue thus obtained was subjected to flash chromatography (1:9→15:85 v/v ethyl acetate/hexane gradient elution) to afford the target compound CP30338 (50 mg, 66%) as a yellow oil, $R_f$ 0.4 in 1:1 ethyl acetate/hexane.

$^1$H NMR (300 MHz) δ 8.21 (d, J 8.9 Hz, 2H), 7.45 (d, J 8.9 Hz, 2H), 7.19 (d, J 8.8 Hz, 2H), 6.91 (s, 1H), 6.87 (d, J 8.8 Hz, 2H), 6.79 (s, 1H), 5.26 (s, 2H), 3.90 (s, 3H), 3.84 (s, 3H), 1.76 (s, 3H), signal due to Ar—OH not observed.

$^{13}$C NMR (75 MHz) δ 159.5 (C), 158.8 (C), 147.2 (C), 146.8 (C), 146.4 (C), 144.4 (C), 133.3 (C), 132.6 (C), 130.0 (2×CH), 129.3 (C), 127.9 (2×CH), 123.5 (2×CH), 115.3 (CH), 113.7 (2×CH), 112.6 (CH), 74.2 (CH$_2$), 56.0 (CH$_3$), 55.3 (CH$_3$), 17.1 (CH$_3$).

IR $v_{max}$/cm$^{-1}$ 3441, 2927, 1608, 1520, 1501, 1345, 1246, 1036, 859, 736.

Mass Spectrum (EI) m/z 422 (M$^+$., 82), 270 (100).

HRMS Found: M$^+$., 422.1476. C$_{23}$H$_{22}$N$_2$O$_6$ requires M$^+$., 422.1478.

(E)-2'-(3-tert-Butoxycarbonylaminophenyl)-5'-hydroxy-4'-methoxyacetophenone O-4-Nitrobenzyl Oxime (CP30339)

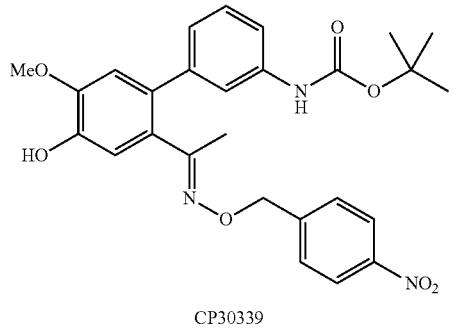

Iodide CP30220 (80 mg, 0.181 mmol) was coupled with 3-(tert-butoxycarbonylamino)phenylboronic acid (51 mg, 0.215 mmol) according to the general procedure IV defined above. The residue thus obtained was subjected to flash chromatography (1:9 v/v ethyl acetate/hexane gradient elution) to afford the target compound CP30339 (27 mg, 29%) as an orange waxy-oil, $R_f$ 0.4 in 1:1 ethyl acetate/hexane.

$^1$H NMR (300 MHz) δ 8.20 (d, J 8.8 Hz, 2H), 7.45 (d, J 8.8 Hz, 2H), 7.35-7.30 (complex m, 2H), 7.22 (m, 1H), 6.92 (m, 1H), 6.91 (s, 1H), 6.81 (s, 1H), 6.49 (broad s, 1H), 5.24 (s, 2H), 3.90 (s, 3H), 1.78 (s, 3H), 1.53 (s, 9H), signal due to Ar—OH not observed.

$^{13}$C NMR (75 MHz) δ 159.1 (C), 152.6 (C), 147.2 (C), 146.8 (C), 146.4 (C), 144.7 (C), 141.9 (C), 138.4 (C), 132.7 (C), 129.4 (C), 128.8 (CH), 127.9 (2×CH), 123.9 (CH), 123.5 (2×CH), 118.9 (CH), 117.0 (CH), 115.3 (CH), 112.6 (CH), 80.7 (C), 74.2 (CH$_2$), 56.1 (CH$_3$), 28.3 (3×CH$_3$), 17.1 (CH$_3$).

IR $v_{max}$/cm$^{-1}$ 3382, 2927, 1724, 1606, 1521, 1366, 1345, 1159, 1055, 853, 735.

Mass Spectrum (EI) m/z 507 (M$^+$., 2), 43 (100).

HRMS (ESI+) Found: (M+H)$^+$, 508.2068. C$_{27}$H$_{30}$N$_3$O$_7$ requires (M+H)$^+$, 508.2084.

(E)-2'-(4-Chlorophenyl)-5'-hydroxy-4'-methoxyacetophenone O-4-Nitrobenzyl Oxime (CP30340)

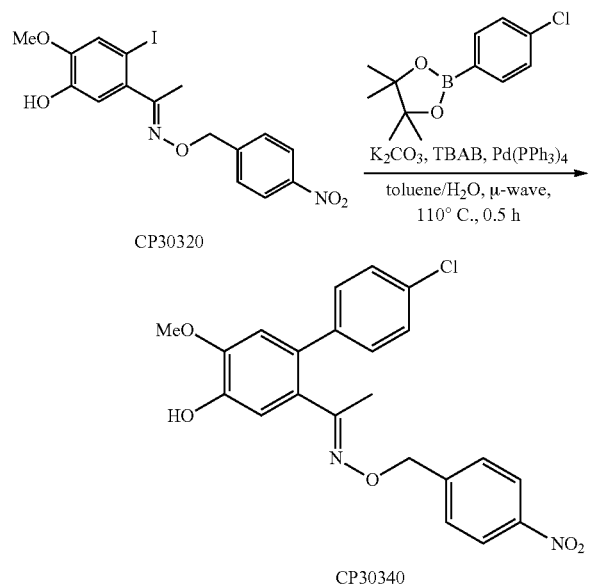

Iodide CP30220 (80 mg, 0.181 mmol) was coupled with 2-(4-chlorophenyl)-4,4,5,5-tetramethyl-1,3,2-dioxaborolane (86 mg, 0.361 mmol) according to the general procedure IV defined above. The residue thus obtained was subjected to flash chromatography (1:9 v/v ethyl acetate/hexane elution) to afford a ca. 2:3 mixture of the target compound CP30340 and the dehalogenated starting material CP30218 as a yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30340 (20 mg, 26%) as a yellow oil, $R_t$ 25.1 min.

$^1$H NMR (300 MHz) δ 8.22 (d, J 8.9 Hz, 2H), 7.44 (d, J 8.9 Hz, 2H), 7.30 (d, J 8.8 Hz, 2H), 7.20 (d, J 8.8 Hz, 2H), 6.92 (s, 1H), 6.77 (s, 1H), 5.23 (s, 2H), 3.91 (s, 3H), 1.79 (s, 3H), signal due to Ar—OH not observed.

$^{13}$C NMR (75 MHz) δ 158.7 (C), 147.3 (C), 146.9 (C), 146.1 (C), 144.9 (C), 139.5 (C), 133.1 (C), 131.6 (C), 130.2 (2×CH), 129.4 (C), 128.5 (2×CH), 127.9 (2×CH), 123.6 (2×CH), 115.4 (CH), 112.4 (CH), 74.3 (CH$_2$), 56.1 (CH$_3$), 17.2 (CH$_3$).

IR $v_{max}$/cm$^{-1}$ 3437, 2918, 1606, 1519, 1489, 1344, 1307, 1201, 1014, 804, 734.

Mass Spectrum (EI) m/z 426 (M$^+$., 85), 274 (100).

HRMS Found: M$^+$., 428.0975. C$_{22}$H$_{19}$N$_2$O$_5$$^{37}$Cl requires M$^+$., 428.0953. Found: M$^+$., 426.0982. C$_{22}$H$_{19}$N$_2$O$_5$$^{35}$Cl requires M$^+$., 426.0982.

Concentration of fraction B gave the dehalogenated compound CP30218, $R_t$ 13.1 min, as a white solid that was identical, as judged by $^1$H NMR spectroscopic analysis, with authentic material.

(E)-2'-(4-tert-Butoxycarbonylaminophenyl)-5'-hydroxy-4'-methoxyacetophenone O-4-Nitrobenzyl Oxime (CP30342)

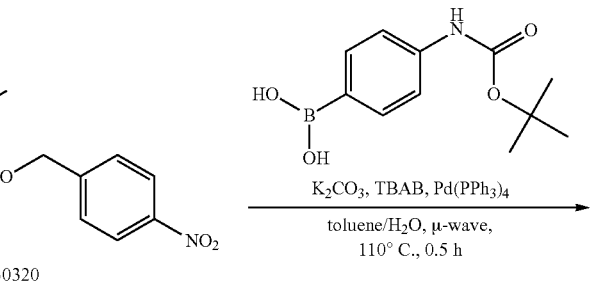

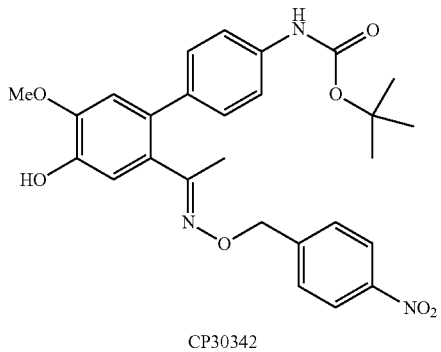

CP30342

Iodide CP30220 (80 mg, 0.181 mmol) was coupled with 4-(tert-butoxycarbonylamino)phenylboronic acid (86 mg, 0.363 mmol) according to the general procedure IV defined above. The residue thus obtained was subjected to flash chromatography (1:9→15:85 v/v ethyl acetate/hexane elution) to afford the target compound CP30342 (52 mg, 57%) as a pale-yellow solid, m.p. 91.0-96.8° C., $R_f$ 0.4 in 1:1 ethyl acetate/hexane.

$^1$H NMR (300 MHz) δ 8.21 (d, J 8.6 Hz, 2H), 7.46 (d, J 8.4 Hz, 2H), 7.35 (d, J 8.3 Hz, 2H), 7.20 (d, J 8.4 Hz, 2H), 6.90 (s, 1H), 6.79 (s, 1H), 6.57 (broad s, 1H), 5.62 (broad s, 1H), 5.25 (s, 2H), 3.90 (s, 3H), 1.75 (s, 3H), 1.55 (s, 9H).

$^{13}$C NMR (75 MHz) δ 159.3 (C), 152.7 (C), 147.3 (C), 146.9 (C), 146.3 (C), 144.6 (C), 137.5 (C), 135.6 (C), 132.5 (C), 129.5 (2×CH), 129.4 (C), 127.9 (2×CH), 123.5 (2×CH), 118.2 (2×CH), 115.3 (CH), 112.6 (CH), 80.8 (C), 74.2 (CH$_2$), 56.1 (CH$_3$), 28.3 (3×CH$_3$), 17.2 (CH$_3$).

IR $v_{max}$/cm$^{-1}$ 3371, 2926, 1715, 1607, 1520, 1344, 1158, 1054, 859, 735.

Mass Spectrum (EI) m/z 507 (M$^+$., 12), 57 (100).

HRMS Found: M$^+$., 507.2006. C$_{27}$H$_{29}$N$_3$O$_7$ requires M$^+$., 507.2006.

Elemental Analysis Found: C, 63.80; H, 5.98; N, 7.92. C$_{27}$H$_{29}$N$_3$O$_7$ requires C, 63.90; H, 5.76; N, 8.28%.

(E)-2'-(4-Trifluoromethoxyphenyl)-5'-hydroxy-4'-methoxyacetophenone O-4-Nitrobenzyl Oxime (CP30343)

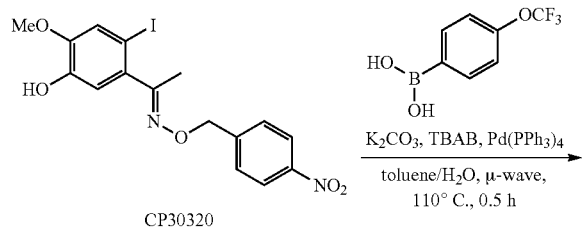

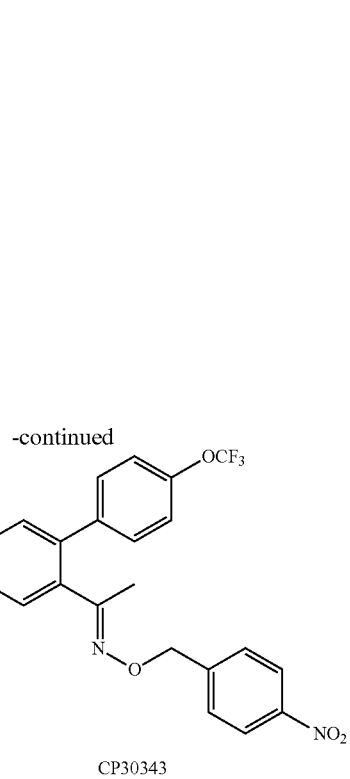

CP30343

Iodide CP30220 (80 mg, 0.181 mmol) was coupled with 4-trifluoromethoxyphenylboronic acid (75 mg, 0.364 mmol) according to the general procedure IV defined above. The residue thus obtained was subjected to flash chromatography (1:9 v/v ethyl acetate/hexane elution) to afford a ca. 1:4 mixture of the target compound CP30343 and the dehalogenated starting material CP30218 as a yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30343 (10 mg, 12%) as a colourless oil, $R_t$ 28.8 min.

$^1$H NMR (300 MHz) δ 8.22 (d, J 8.7 Hz, 2H), 7.46 (d, J 8.7 Hz, 2H), 7.30 (d, J 8.7 Hz, 2H), 7.19 (d, J 8.0 Hz, 2H), 6.93 (s, 1H), 6.79 (s, 1H), 5.22 (s, 2H), 3.92 (s, 3H), 1.77 (s, 3H), signal due to Ar—OH not observed.

$^{13}$C NMR (75 MHz) δ 158.7 (C), 148.3 (C), 147.3 (C), 146.9 (C), 146.0 (C), 145.0 (C), 139.7 (C), 131.5 (C), 130.3 (2×CH), 129.4 (C), 128.0 (2×CH), 123.6 (2×CH), 120.7 (2×CH), 120.4 (d, J$_{C,F}$ 256 Hz, C) 115.4 (CH), 112.5 (CH), 74.3 (CH$_2$), 56.1 (CH$_3$), 17.1 (CH$_3$).

IR $v_{max}$/cm$^{-1}$ 3435, 2928, 1521, 1500, 1345, 1259, 1203, 1166, 1053, 859, 736.

Mass Spectrum (EI) m/z 476 (M$^+$., 60), 324 (100).

HRMS Found: M$^+$., 476.1202. C$_{23}$H$_{19}$N$_2$O$_6$F$_3$ requires M$^+$., 476.1195.

Concentration of fraction B gave the dehalogenated compound CP30218, $R_t$ 13.0 min, as a white solid that was identical, as judged by $^1$H NMR spectroscopic analysis, with authentic material.

(E)-2'-(4-Fluorophenyl)-5'-hydroxy-4'-methoxyacetophenone O-4-Nitrobenzyl Oxime (CP30344)

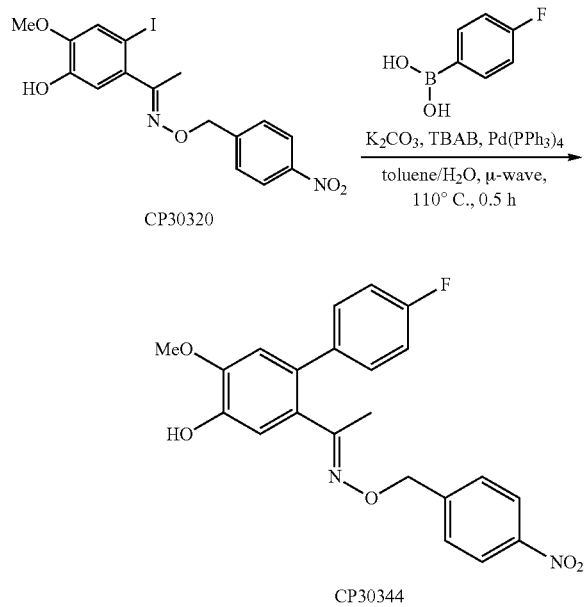 [SMILES: COc1cc(I)c(/C(C)=N/OCc2ccc([N+](=O)[O-])cc2)cc1O ; OB(O)c1ccc(F)cc1 ; COc1cc(-c2ccc(F)cc2)c(/C(C)=N/OCc2ccc([N+](=O)[O-])cc2)cc1O]

Iodide CP30220 (80 mg, 0.181 mmol) was coupled with 4-fluorophenylboronic acid (51 mg, 0.364 mmol) according to the general procedure IV defined above. The residue thus obtained was subjected to flash chromatography (1:9 v/v ethyl acetate/hexane elution) to afford a ca. 1:2 mixture of the target compound CP30344 and the dehalogenated starting material CP30218 as a yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30344 (18 mg, 24%) as a pale yellow oil, $R_t$ 22.1 min.

$^1$H NMR (300 MHz) δ 8.22 (d, J 8.8 Hz, 2H), 7.46 (d, J 8.9 Hz, 2H), 7.23 (m, 2H), 7.03 (m, 2H), 6.92 (s, 1H), 6.78 (s, 1H), 5.62 (broad s, 1H), 5.22 (s, 2H), 3.91 (s, 3H), 1.75 (s, 3H).

$^{13}$C NMR (75 MHz) δ 162.0 (d, $J_{C,F}$ 245 Hz, C), 158.9 (C), 147.3 (C), 146.9 (C), 146.2 (C), 144.7 (C), 137.0 (C), 131.8 (C), 130.5 (d, $J_{C,F}$ 8 Hz, 2×CH), 129.4 (C), 127.9 (2×CH), 123.5 (2×CH), 115.3 (CH), 115.2 (d, $J_{C,F}$ 21 Hz, 2×CH), 112.5 (CH), 74.2 (CH$_2$), 56.1 (CH$_3$), 17.1 (CH$_3$).

IR $v_{max}$/cm$^{-1}$ 3436, 2917, 1603, 1520, 1500, 1344, 1308, 1225, 1201, 1054, 839, 736.

Mass Spectrum (EI) m/z 410 (M$^+$., 100).

HRMS Found: M$^+$., 410.1280. C$_{22}$H$_{19}$N$_2$O$_5$F requires M$^+$., 410.1278.

Concentration of fraction B gave the dehalogenated compound CP30218, $R_t$ 14.9 min, as a white solid that was identical, as judged by $^1$H NMR spectroscopic analysis, with authentic material.

(E)-5'-Hydroxy-4'-methoxy-2'-(4-methylphenyl)acetophenone O-4-Nitrobenzyl Oxime (CP30345)

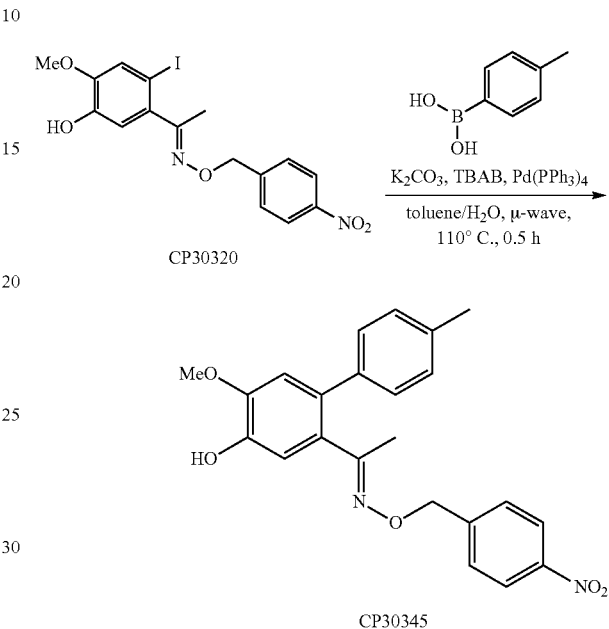

Iodide CP30220 (80 mg, 0.181 mmol) was coupled with 4-methylphenylboronic acid (51 mg, 0.364 mmol) according to the general procedure IV defined above. The residue thus obtained was subjected to flash chromatography (1:19→1:9 v/v ethyl acetate/hexane gradient elution) to afford a ca. 3:2 mixture of the target compound CP30345 and the dehalogenated starting material CP30218 as a yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30345 (31 mg, 42%) as a pale yellow solid, m.p. 105.9-108.7° C., $R_t$ 24.9 min.

$^1$H NMR (300 MHz) δ 8.21 (d, J 8.8 Hz, 2H), 7.46 (d, J 8.8 Hz, 2H), 7.17 (m, 4H), 6.91 (s, 1H), 6.81 (s, 1H), 5.57 (broad s, 1H), 5.27 (s, 2H), 3.90 (s, 3H), 2.40 (s, 3H), 1.74 (s, 3H).

$^{13}$C NMR (75 MHz) δ 159.7 (C), 147.2 (C), 146.9 (C), 146.3 (C), 144.4 (C), 138.0 (C), 136.9 (C), 133.0 (C), 129.2 (C), 129.0 (2×CH), 128.8 (2×CH), 127.8 (2×CH), 123.5 (2×CH), 115.3 (CH), 112.6 (CH), 74.1 (CH$_2$), 56.0 (CH$_3$), 21.1 (CH$_3$), 17.2 (CH$_3$).

IR $v_{max}$/cm$^{-1}$ 3503, 2922, 1606, 1521, 1502, 1345, 1304, 1201, 1054, 859, 735.

Mass Spectrum (EI) m/z 406 (M$^+$., 55), 254 (100).

HRMS Found: M$^+$., 406.1543. C$_{23}$H$_{22}$N$_2$O$_5$ requires M$^+$., 406.1529.

Elemental Analysis Found: C, 67.59; H, 5.50; N, 6.76. C$_{23}$H$_{22}$N$_2$O$_5$ requires C, 67.97; H, 5.46; N, 6.89%.

Concentration of fraction B gave the dehalogenated compound CP30218, $R_t$ 12.8 min, as a white solid that was identical, as judged by $^1$H NMR spectroscopic analysis, with authentic material.

(E)-2'-(4-Trifluoromethylphenyl)-5'-hydroxy-4'-methoxyacetophenone O-4-Nitrobenzyl Oxime (CP30346)

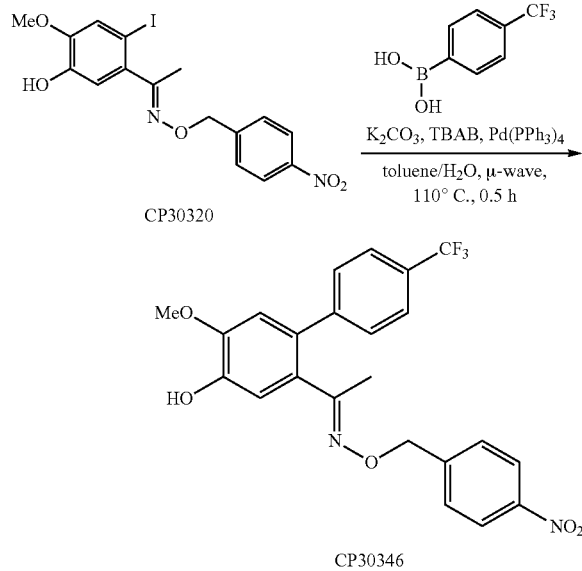

Iodide CP30220 (80 mg, 0.181 mmol) was coupled with 4-trifluoromethylphenylboronic acid (69 mg, 0.363 mmol) according to the general procedure IV defined above. The residue thus obtained was subjected to flash chromatography (1:9 v/v ethyl acetate/hexane elution) to afford a ca. 2:5 mixture of the target compound CP30346 and the dehalogenated starting material CP30218 as a yellow oil, $R_f$ 0.5 in 1:1 ethyl acetate/hexane. This mixture was subjected to semi-preparative HPLC (22×250 mm Alltima C18 column, 7:3 v/v acetonitrile/water containing 0.1% TFA) and two fractions, A and B, were thereby obtained.

Concentration of fraction A gave the target compound CP30346 (8 mg, 10%) as a white solid, m.p. 111.5–114.1° C., $R_t$ 25.6 min.

$^1$H NMR (300 MHz) δ 8.21 (d, J 8.8 Hz, 2H), 7.60 (d, J 8.0 Hz, 2H), 7.45 (d, J 8.8 Hz, 2H), 7.41 (d, J 8.1 Hz, 2H), 6.94 (s, 1H), 6.80 (s, 1H), 5.67 (broad s, 1H), 5.21 (s, 2H), 3.92 (s, 3H), 1.77 (s, 3H).

$^{13}$C NMR (75 MHz) δ 158.4 (C), 147.3 (C), 147.0 (C), 146.0 (C), 145.3 (C), 144.8 (C), 131.4 (C), 129.6 (C), 129.3 (2×CH), 128.9 (C), 127.9 (2×CH), 125.2 (d, $J_{C,F}$ 4 Hz, 2×CH), 124.1 (d, $J_{C,F}$ 270 Hz, C), 123.6 (2×CH), 115.5 (CH), 112.5 (CH), 74.3 (CH$_2$), 56.1 (CH$_3$), 17.2 (CH$_3$).

IR $v_{max}$/cm$^{-1}$ 3436, 2918, 1523, 1505, 1345, 1324, 1165, 1123, 1109, 1066, 844, 736.

Mass Spectrum (EI) m/z 460 (M$^+$., 45), 308 (100).

HRMS Found: M$^+$., 460.1247. C$_{23}$H$_{19}$N$_2$O$_5$F$_3$ requires M$^+$., 460.1246.

Concentration of fraction B gave the dehalogenated compound CP30218, $R_t$ 12.9 min, as a white solid that was identical, as judged by $^1$H NMR spectroscopic analysis, with authentic material.

(E)-2'-(4-Aminophenyl)-5'-hydroxy-4'-methoxyacetophenone O-4-Nitrobenzyl Oxime (CP30381)

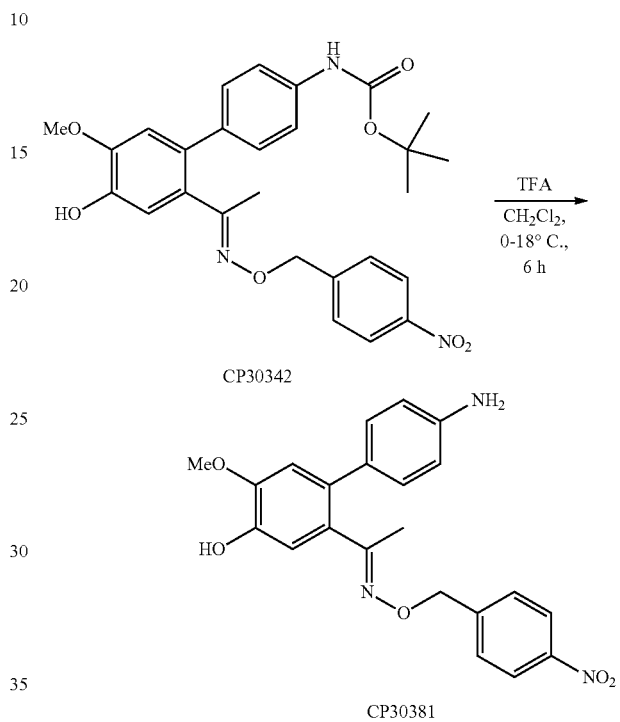

A magnetically stirred solution of carbamate CP30342 (20 mg, 0.039 mmol) in CH$_2$Cl$_2$ (0.5 mL) maintained at 0° C., was treated, dropwise, with trifluoroacetic acid (0.061 mL, 0.792 mmol) and the resulting mixture allowed to warm to 18° C., where it was stirred for 6 h. After this time, CH$_2$Cl$_2$ (10 mL) then NaOH (ca. 2 mL of a 0.1 M w/v aqueous solution) and H$_2$O (3 mL) were added to the reaction mixture, and the separated aqueous phase extracted with CH$_2$Cl$_2$ (1×5 mL). The combined organic fractions were then dried (MgSO$_4$), filtered and concentrated under reduced pressure and the ensuing residue subjected to flash chromatography (1:99 v/v methanol/dichloromethane elution) to afford the title compound CP30381 (12 mg, 75%) as a yellow oil, $R_f$ 0.5 in 1:19 v/v MeOH/CH$_2$Cl$_2$.

$^1$H NMR (300 MHz) δ 8.22 (d, J 8.4 Hz, 2H), 7.46 (d, J 8.7 Hz, 2H), 7.06 (d, J 7.9 Hz, 2H), 6.89 (s, 1H), 6.78 (s, 1H), 6.66 (d, J 8.1 Hz, 2H), 5.56 (broad s, 1H), 5.27 (s, 2H), 3.89 (s, 3H), 3.75 (broad s, 2H), 1.77 (s, 3H).

$^{13}$C NMR (75 MHz) δ 159.8 (C), 147.2 (C), 146.8 (C), 146.5 (C), 145.5 (C), 144.1 (C), 133.1 (C), 131.1 (C), 129.8 (2×CH), 129.1 (C), 127.9 (2×CH), 123.5 (2×CH), 115.2 (CH), 114.9 (2×CH), 112.5 (CH), 74.1 (CH$_2$), 56.0 (CH$_3$), 17.1 (CH$_3$).

IR $v_{max}$/cm$^{-1}$ 3370, 2929, 1608, 1518, 1502, 1344, 1201, 1054, 860, 735.

Mass Spectrum (EI) m/z 407 (M$^+$., 70), 255 (100).

HRMS (EI) Found: M$^+$., 407.1475. C$_{22}$H$_{21}$N$_3$O$_5$ requires M$^+$., 407.1481.

V) Synthesis of CP30347-8

4,4-Ethylenedioxycyclohexan-1-ol (41)

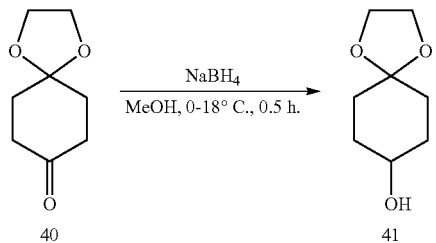 [SMILES: O=C1CCC2(CC1)OCCO2 ; "NaBH4" ; OC1CCC2(CC1)OCCO2]

Following protocols reported by Kitano et al.,[8] a magnetically stirred solution of 1,4-cyclohexanedione monoethylene acetal 40 (5.00 g, 32.0 mmol) in MeOH (30 mL), maintained at 0° C., was treated with sodium borohydride (1.57 g, 41.5 mmol). After 0.5 h, the reaction mixture was warmed to 18° C. and stirred at this temperature for an additional 0.5 h. The solvent was then removed under reduced pressure and the ensuing residue partitioned between $H_2O$ (30 mL) and $CH_2Cl_2$ (30 mL). The separated aqueous phase was extracted with $CH_2Cl_2$ (1×20 mL) and the combined organic fractions were then dried ($MgSO_4$), filtered and concentrated under reduced pressure to afford the title compound 41[8] (5.06 g, quant.) as a colourless oil.

$^1$H NMR (300 MHz) δ 3.96-3.88 (complex m, 4H), 3.77 (m, 1H), 1.90-1.75 (complex m, 5H), 1.68-1.50 (complex m, 4H).

4,4-Ethylenedioxy-1-bromocyclohexane (42)

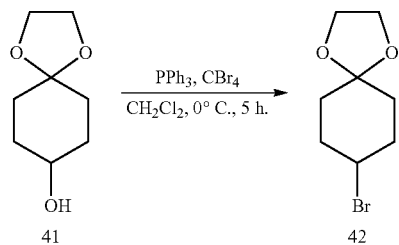

Following protocols reported by Kabalka et al.,[9] a magnetically stirred solution of alcohol 41 (3.00 g, 19.0 mmol) in dry $CH_2Cl_2$ (20 mL) was treated with carbon tetrabromide (7.55 g, 22.8 mmol) and the resulting mixture cooled to 0° C. Triphenylphosphine (5.97 g, 22.8 mmol) was then added and the stirring continued at 0° C. under a nitrogen atmosphere for 5 h. After this time $H_2O$ (50 mL) then $CH_2Cl_2$ (80 mL) were added to the reaction mixture, the organic phase separated and the aqueous phase extracted with $CH_2Cl_2$ (1×80 mL). The combined organic fractions were then dried ($MgSO_4$), filtered and concentrated under reduced pressure and the ensuing residue subjected to flash chromatography (hexane→1:19 v/v ethyl acetate/hexane gradient elution) to afford the title compound 42[9] (2.77 g, 66%) as a colourless oil, $R_f$ 0.6 in 1:1 v/v ethyl acetate/hexane.

$^1$H NMR (300 MHz) δ 4.32 (m, 1H), 3.99-3.89 (complex m, 4H), 2.20-2.01 (complex m, 4H), 1.95-1.87 (complex m, 2H), 1.65-1.56 (complex m, 2H).

4,4-(Ethylenedioxy)cyclohexyl(3-isopropoxy-4-methoxyphenyl)methanol (43)

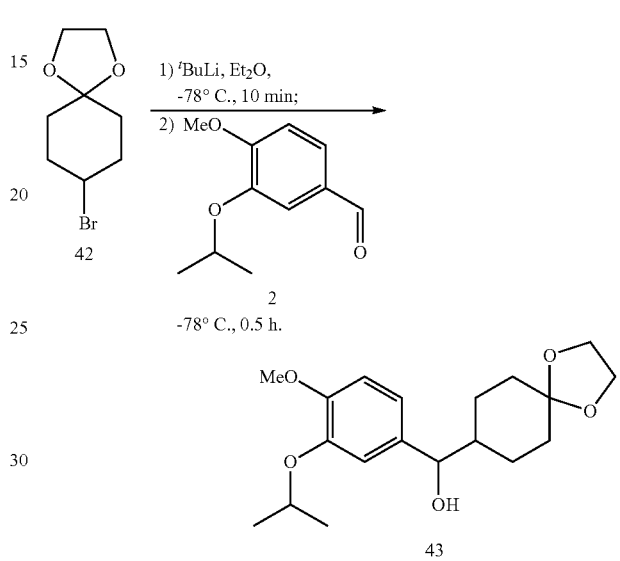

A magnetically stirred solution of bromide 42 (200 mg, 0.905 mmol) and N,N,N',N'-tetramethylethylenediamine (0.5 mL) in dry $Et_2O$ (4.5 mL) was cooled to −78° C. and treated, dropwise, with tert-butyllithium (1.7 M in pentane, 0.85 mL, 1.45 mmol). After 10 minutes, the mixture was treated, dropwise, with a solution of aldehyde 2 (263 mg, 1.36 mmol) in dry $Et_2O$ (5.0 mL). After 0.5 h at −78° C., the reaction mixture was treated with $NH_4Cl$ (6.0 mL of a 20% w/v aqueous solution), allowed to warm to 18° C., then extracted with $Et_2O$ (2×15 mL) and $CH_2Cl_2$ (1×10 mL). The combined organic fractions were dried ($MgSO_4$), filtered and concentrated under reduced pressure and the ensuing residue subjected to flash chromatography (15:85→3:7 v/v ethyl acetate/hexane gradient elution) to afford the title compound 43 (103 mg, 34%) as a colourless oil, $R_f$ 0.3 in 1:1 v/v ethyl acetate/hexane.

$^1$H NMR (300 MHz) δ 6.85-6.81 (complex m, 3H), 4.52 (septet, J 6.0 Hz, 1H), 4.26 (d, J 7.8 Hz, 1H), 3.90 (s, 4H), 3.82 (s, 3H), 2.08-1.12 (complex m, 10H), 1.34 (d, J 6.0 Hz, 3H), 1.33 (d, J 6.0 Hz, 3H).

$^{13}$C NMR (75 MHz) δ 149.7 (C), 147.0 (C), 136.1 (C), 119.1 (CH), 114.0 (CH), 111.5 (CH), 108.8 (C), 78.4 (CH), 71.2 (CH), 64.1 (2×$CH_2$), 55.9 ($CH_3$), 43.6 (CH), 34.2 ($CH_2$), 34.1 ($CH_2$), 26.5 ($CH_2$), 26.4 (5) ($CH_2$), 22.0 (2×$CH_3$).

IR $v_{max}$/cm$^{-1}$ 3436, 2932, 1507, 1443, 1372, 1259, 1106, 1033, 924.

Mass Spectrum (EI) m/z 336 (M$^+$., 32), 99 (100).

HRMS found: M$^+$., 336.1938. $C_{19}H_{28}O_5$ requires M$^+$., 336.1937.

4-[Hydroxyl(3-isopropoxy-4-methoxyphenyl)methyl]cyclohexenone (44)

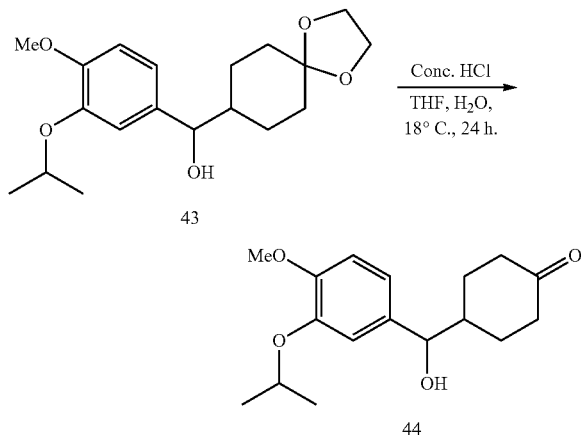

A solution of alcohol 43 (320 mg, 0.951 mmol) in THF (12 mL) and H$_2$O (4.0 mL) was treated with HCl (25 drops of conc. aqueous solution) and the resulting mixture stirred magnetically at 18° C. for 24 h. After this time H$_2$O (10 mL) then Et$_2$O (50 mL) were added to the reaction mixture, the organic phase separated and the aqueous phase extracted with Et$_2$O (1×50 mL) and CH$_2$Cl$_2$ (1×15 mL). The combined organic fractions were then dried (MgSO$_4$), filtered and concentrated under reduced pressure and the ensuing residue subjected to flash chromatography (3:7 v/v ethyl acetate/hexane elution) to afford the title compound 44 (260 mg, 94%) as a colourless oil, R$_f$ 0.2 in 1:1 v/v ethyl acetate/hexane.

$^1$H NMR (300 MHz) δ 6.88-6.82 (complex m, 3H), 4.52 (septet, J 6.0 Hz, 1H), 4.36 (d, J 7.5 Hz, 1H), 3.82 (s, 3H), 2.42-1.12 (complex m, 10H), 1.35 (d, J 6.0 Hz, 3H), 1.34 (d, J 6.0 Hz, 3H).

$^{13}$C NMR (75 MHz) δ 212.2 (C), 149.9 (C), 147.1 (C), 135.5 (C), 119.1 (CH), 113.8 (CH), 111.4 (CH), 77.6 (CH), 71.3 (CH), 55.9 (CH$_3$), 43.1 (CH), 40.4 (CH$_2$), 40.3 (6) (CH$_2$), 28.9 (CH$_2$), 28.7 (CH$_2$), 22.0 (2×CH$_3$).

IR v$_{max}$/cm$^{-1}$ 3433, 2926, 2855, 1712, 1509, 1425, 1261, 1231, 1135, 1109, 1029.

Mass Spectrum (EI) m/z 292 (M$^+$., 62), 195 (100).

HRMS found: M$^+$., 192.1673. C$_{17}$H$_{24}$O$_4$ requires M$^+$., 292.1675.

Ethyl 2-{4-[hydroxyl(3-isopropoxy-4-methoxyphenyl)methyl]cyclohexylidene} Acetate (45)

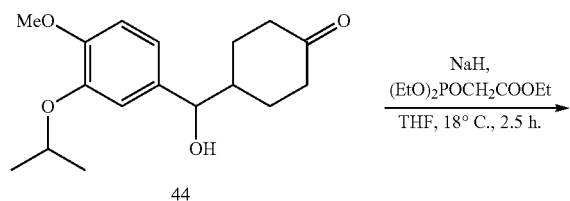

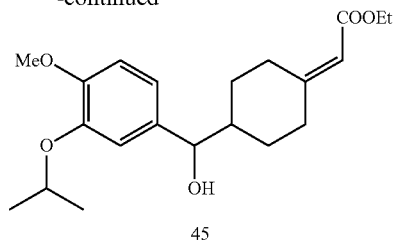

A mixture of sodium hydride (60% dispersion in mineral oil, 117 mg, 2.93 mmol) in dry THF (6.0 mL) was treated, dropwise, with triethyl phosphonoacetate (0.51 mL, 2.57 mmol) and the resulting mixture stirred magnetically at 18° C. until H$_2$ evolution ceased (ca. 5 minutes). A solution of ketone 44 (708 mg, 2.42 mmol) in dry THF (8.0 mL) was then added slowly to the reaction mixture, which was stirred for a further 2.5 h, then treated with H$_2$O (20 mL) and extracted with Et$_2$O (2×50 mL) and CH$_2$Cl$_2$ (1×20 mL). The combined organic fractions were then dried (MgSO$_4$), filtered and concentrated under reduced pressure and the ensuing residue subjected to flash chromatography (15:85 v/v ethyl acetate/hexane elution) to afford a ca. 1:1 mixture of diastereomers of the title compound 45 (795 mg, 91%) as a pale-yellow oil, R$_f$ 0.5 in 1:1 v/v ethyl acetate/hexane.

$^1$H NMR (300 MHz) δ 6.87-6.82 (complex m, 2×3H), 5.61 and 5.58 (2×s, 2×1H), 4.54 (septet, J 6.0 Hz, 2×1H), 4.30 and 4.29 (2×d, J 7.6 and 7.6 Hz, 2×1H), 4.13 and 4.11 (2×q, J 7.1 and 7.1 Hz, 2×2H), 3.84 (s, 2×3H), 2.36-0.83 (complex m, 2×10H), 1.37 (d, J 6.0 Hz, 2×3H), 1.36 (d, J 6.0 Hz, 2×3H), 1.26 and 1.25 (2×t, J 7.1 and 7.1 Hz, 2×3H).

$^{13}$C NMR (75 MHz) δ 166.7 (2×C), 162.6 and 162.5 (2×C), 149.8 (2×C), 147.0 (2×C), 135.8 and 135.7(5) (2×C), 119.2 and 119.1 (2×CH), 114.0 (2×CH), 113.3 and 113.2 (2×CH), 111.4 (2×CH), 78.3 (2×CH), 71.3 (2×CH), 59.5 (2×CH$_2$), 55.9 (2×CH$_3$), 44.4 (2×CH), 36.8 (2×CH$_2$), 30.5 and 30.4 (2×CH$_2$), 29.8 (2×CH$_2$), 28.5 (2×CH$_2$), 22.0 (4×CH$_3$), 14.2 (2×CH$_3$).

IR v$_{max}$/cm$^{-1}$ 3504, 2976, 2933, 1711, 1647, 1508, 1381, 1262, 1231, 1175, 1143, 1034.

Mass Spectrum (EI) m/z 362 (M$^+$., 44), 195 (100).

HRMS found: M$^+$., 362.2093. C$_{21}$H$_{30}$O$_5$ requires M$^+$., 362.2093.

A minor impurity is present in the sample post-chromatography (as indicated by a signal at δ 3.80 in the $^1$H NMR spectrum). Nevertheless, this material was used as obtained in the next step of the reaction sequence.

Ethyl 2-{4-[methoxymethoxy(3-isopropoxy-4-methoxyphenyl)methyl]-cyclohexylidene} Acetate (46)

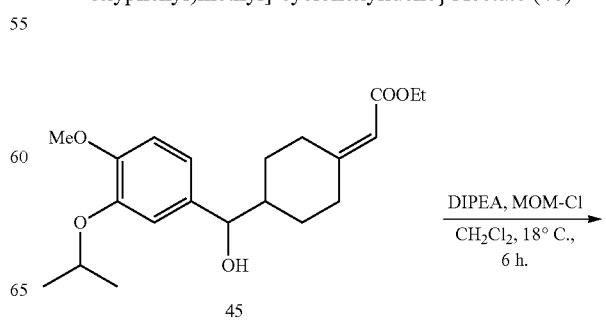

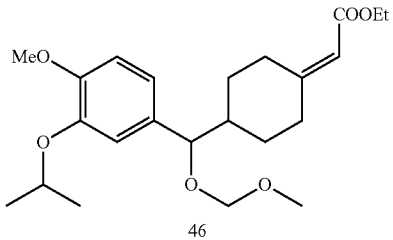

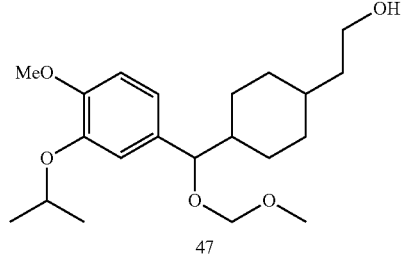

A solution of alcohol 45 (468 mg, 1.29 mmol) in dry CH$_2$Cl$_2$ (5.5 mL) was treated with N,N-diisopropylethylamine (1.0 mL, 5.75 mmol) and chloromethyl methyl ether (0.34 mL, 4.48 mmol) and the resulting mixture stirred magnetically at 18° C. under a nitrogen atmosphere for 5 h. Additional N,N-diisopropylethylamine (0.33 mL, 1.90 mmol) and chloromethyl methyl ether (0.10 mL, 1.32 mmol) were then added to the reaction mixture, which was stirred for a further 1 h at 18° C. The reaction mixture was then treated with H$_2$O (20 mL) and extracted with CH$_2$Cl$_2$ (2×40 mL) The combined organic fractions were dried (MgSO$_4$), filtered and concentrated, under reduced pressure, onto TLC-grade silica (ca. 600 mg) and the resulting free-flowing solid subjected to flash chromatography (1:19 v/v ethyl acetate/hexane elution) to afford a ca. 1:1 mixture of diastereomers of the title compound 46 (509 mg, 97%) as a colourless oil, $R_f$ 0.7 in 1:1 v/v ethyl acetate/hexane.

$^1$H NMR (300 MHz) δ 6.82-6.76 (complex m, 2×3H), 5.61 and 5.58 (2×s, 2×1H), 4.57-4.43 (complex m, 2×3H), 4.21-4.08 (complex m, 2×3H), 3.84 (s, 2×3H), 3.35 (s, 2×3H), 2.36-0.82 (complex m, 2×9H), 1.36 (d, J 6.0 Hz, 2×3H), 1.34 (d, J 6.0 Hz, 2×3H), 1.26 and 1.25 (2×t, J 7.1 and 7.1 Hz, 2×3H).

$^{13}$C NMR (75 MHz) δ 166.7 (2×C), 162.6 (2×C), 149.8 (2×C), 147.0 (2×C), 132.6 (2×C), 120.6 and 120.5 (2×CH), 114.6 (2×CH), 113.2 (2×CH), 111.3 and 111.2 (2×CH), 93.7 and 93.6 (2×CH$_2$), 81.2 (2×CH), 71.1 (2×CH), 59.5 (2×CH$_2$), 55.8 (2×CH$_3$), 55.6 (2×CH$_3$), 43.6 and 43.5(5) (2×CH), 36.8 (2×CH$_2$), 31.0, 30.7, 30.4 and 30.1 (4×CH$_2$), 28.5 and 28.4(6) (2×CH$_2$), 22.0 (2×CH$_3$), 21.9 (2×CH$_3$), 14.2 (2×CH$_3$).

IR $v_{max}$/cm$^{-1}$ 2976, 2933, 1713, 1650, 1508, 1443, 1381, 1261, 1238, 1179, 1144, 1033.

Mass Spectrum (EI) m/z 406 (M$^+$., 22), 45 (100).

HRMS found: M$^+$., 406.2365. C$_{23}$H$_{34}$O$_6$ requires M$^+$., 406.2355.

2-{4-[(3-Isopropoxy-4-methoxymethoxyphenyl)(methoxymethoxy)methyl]-cyclohexyl}ethanol (47)

A magnetically stirred solution of ester 46 (509 mg, 1.25 mmol) in dry Et$_2$O (18 mL) maintained at 0° C., was treated, dropwise, with lithium aluminium hydride (1.0 M in Et$_2$O, 5.6 mL, 5.60 mmol) and the resulting mixture allowed to warm to 18° C., where it was stirred under a nitrogen atmosphere for 3.5 h. The reaction mixture was then poured over ice, extracted with Et$_2$O (3×100 mL) and the combined organic fractions dried (MgSO$_4$), filtered and concentrated, under reduced pressure. A solution of the resulting residue in EtOAc (30 mL) maintained at 0° C., was then treated with rhodium (5% on Al$_2$O$_3$, 250 mg), and the resulting mixture stirred magnetically under a hydrogen atmosphere for 3 h. The reaction mixture was then filtered through a pad of Celite™ that was washed with EtOAc (2×30 mL) and the combined filtrates concentrated under reduced pressure. The ensuing residue was subjected to flash chromatography (3:7 v/v ethyl acetate/hexane elution) to afford a ca. 1:1 mixture of diastereomers of the title compound 47 (367 mg, 80%) as a colourless oil, $R_f$ 0.3 in 1:1 v/v ethyl acetate/hexane.

$^1$H NMR (300 MHz) δ 6.84-6.76 (complex m, 2×3H), 4.58-4.41 (complex m, 2×3H), 4.36 and 4.13 (2×d, J 8.7 and 8.1 Hz, 2×1H), 3.82 (s, 2×3H), 3.65 and 3.64 (2×t, J 6.7 and 6.7 Hz, 2×2H), 3.35 and 3.34 (2×s, 2×3H), 2.17-0.80 (complex m, 2×13H), 1.34 (d, J 6.0 Hz, 2×3H), 1.33 (d, J 6.0 Hz, 2×3H).

$^{13}$C NMR (75 MHz) δ 149.7 and 149.6 (2×C), 146.9 and 146.8 (2×C), 133.0 and 132.9(5) (2×C), 120.7 and 120.6 (2×CH), 114.6 and 114.5 (2×CH), 111.1 (2×CH), 93.7 (2×CH$_2$), 82.3 and 79.6 (2×CH), 71.0 (2×CH), 61.1 and 60.7 (2×CH$_2$), 55.8 (2×CH$_3$), 55.6 and 55.5 (2×CH$_3$), 44.1 and 42.0 (2×CH), 40.1 and 36.7 (2×CH$_2$), 34.1 and 31.3 (2×CH), 32.7 and 32.6 (6) (2×CH$_2$), 29.6, 29.1, 29.0 and 28.7 (4×CH$_2$), 25.2 (2×CH$_2$), 22.0 (2×CH$_3$), 21.9 (2×CH$_3$).

IR $v_{max}$/cm$^{-1}$ 3433, 2924, 1509, 1443, 1426, 1381, 1259, 1135, 1106, 1033.

Mass Spectrum (EI) m/z 366 (M$^+$., 8), 45 (100).

HRMS found: M$^+$., 366.2412. C$_{21}$H$_{34}$O$_5$ requires M$^+$., 366.2406.

2-{4-[(3-Isopropoxy-4-methoxyphenyl)(methoxymethoxy)methyl]cyclohexyl}ethoxy-tert-butyldiphenylsilane (48)

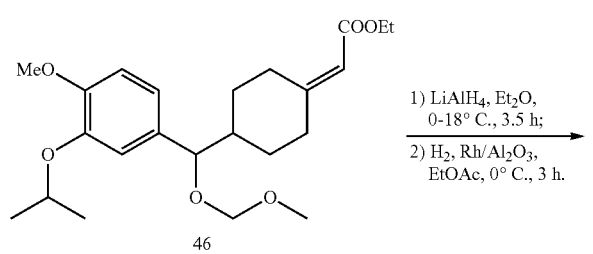

1) LiAlH$_4$, Et$_2$O, 0-18° C., 3.5 h;
2) H$_2$, Rh/Al$_2$O$_3$, EtOAc, 0° C., 3 h.

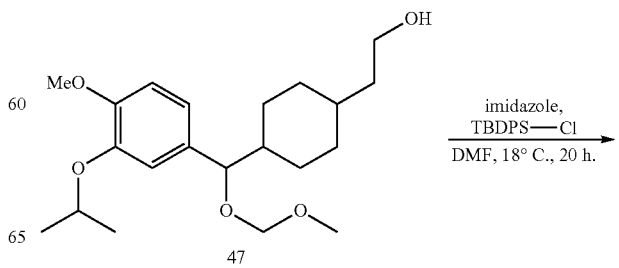

imidazole, TBDPS—Cl
DMF, 18° C., 20 h.

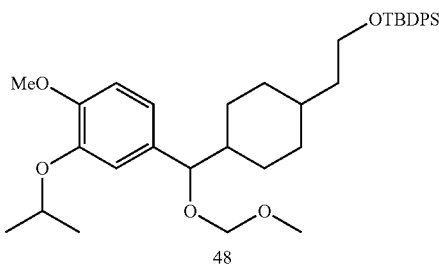

48

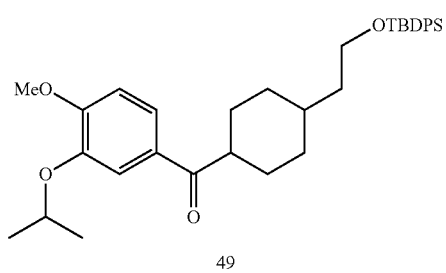

49

A solution of alcohol 47 (330 mg, 0.900 mmol) in DMF (17 mL) was treated with imidazole (153 mg, 2.25 mmol) and tert-butylchlorodiphenylsilane (0.46 mL, 1.80 mmol) and the resulting mixture stirred magnetically at 18° C. under a nitrogen atmosphere for 20 h. The reaction mixture was then treated with $Et_2O$ (100 mL), washed with HCl (1×40 mL of a 20% v/v aqueous solution) and brine (1×40 mL), then dried ($MgSO_4$), filtered and concentrated under reduced pressure. The ensuing residue was subjected to flash chromatography (1:99→1:19 v/v ethyl acetate/hexane gradient elution) to afford a ca. 1:1 mixture of diastereomers of the title compound 48 (452 mg, 83%) as a colourless oil, $R_f$ 0.5 in 15:85 v/v ethyl acetate/hexane.

$^1$H NMR (300 MHz) δ 7.69-7.64 (complex m, 2×4H), 7.42-7.36 (complex m, 2×6H), 6.83-6.78 (complex m, 2×3H), 4.57-4.42 (complex m, 2×3H), 4.34 and 4.13 (2×d, J 8.9 and 8.1 Hz, 2×1H), 3.84 (s, 2×3l4), 3.67 and 3.66 (2×t, J 6.5 and 6.5 Hz, 2×2H), 3.37 and 3.36 (2×s, 2×3H), 2.18-0.75 (complex m, 2×18H), 1.04 and 1.03 (2×s, 2×9H).

$^{13}$C NMR (75 MHz) δ 149.7 (2×C), 147.0 and 146.9 (2×C), 135.5 (8×CH), 134.0 (4×C), 133.2 and 133.1 (2×C), 129.5 (4×CH), 127.5 (8×CH), 120.7 and 120.6 (2×CH), 114.7 and 114.6 (2×CH), 111.1 (2×CH), 93.7 (2×$CH_2$), 82.4 and 79.8 (2×CH), 71.0 (2×CH), 62.4 and 61.9 (2×$CH_2$), 55.8 (2×$CH_3$), 55.6 and 55.5 (2×$CH_3$), 44.1 and 42.2 (2×CH), 39.9 and 36.5 (2×$CH_2$), 34.2 and 31.3 (2×CH), 32.8 and 32.7 (2×$CH_2$), 29.7, 29.3, 29.1 and 28.8 (4×$CH_2$), 26.8 (6×$CH_3$), 25.3 (2×$CH_2$), 22.0 (2×$CH_3$), 21.9 (2×$CH_3$), 19.1 (2×C).

IR $v_{max}$/cm$^{-1}$ 2929, 2856, 1507, 1427, 1383, 1259, 1110, 1034.

Mass Spectrum (EI) m/z 604 (M$^+$., 18), 239 (100).

HRMS found: M$^+$., 604.3582. $C_{37}H_{52}O_5Si$ requires M$^+$., 604.3584.

2-{4-[Oxy(3-isopropoxy-4-methoxyphenyl)methyl] cyclohexyl}ethoxy-tert-butyl diphenylsilane (49)

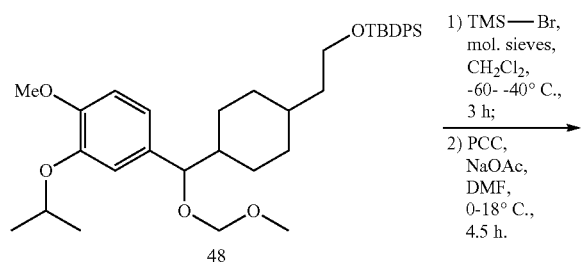

48

1) TMS—Br, mol. sieves, $CH_2Cl_2$, −60- −40° C., 3 h;
2) PCC, NaOAc, DMF, 0-18° C., 4.5 h.

A magnetically stirred solution of ether 48 (150 mg, 0.248 mmol) in dry $CH_2Cl_2$ (3.0 mL) containing molecular sieves (4 Å, ca. 20) was cooled to −60° C. then treated with bromotrimethylsilane (0.049 mL, 0.371 mmol) and the resulting mixture stirred between −40 and −60° C. under a nitrogen atmosphere for 3 h. The reaction mixture was then treated with $NaHCO_3$ (5.0 mL of saturated aqueous solution), allowed to warm to 0° C., and extracted with $CH_2Cl_2$ (3×10 mL). The combined organic fractions were then dried ($MgSO_4$) and filtered. The filtrate containing the terminal alcohol ($R_f$ 0.2 in 3:17 v/v ethyl acetate/hexane) was cooled to 0° C., then treated with pyridinium chlorochromate (69 mg, 0.320 mmol) and sodium acetate (6 mg, 0.073 mmol) and the resulting mixture stirred magnetically for 1 h. The reaction mixture was then warmed to 18° C. and stirred at this temperature for an additional 3.5 h, then filtered through a pad of Celite™ that was washed with $CH_2Cl_2$ (2×50 mL). The combined filtrates were then concentrated under reduced pressure and the ensuing residue subjected to flash chromatography (1:49→1:19 v/v ethyl acetate/hexane gradient elution) to afford a ca. 1:1 mixture of cis- and trans-isomeric fauns of the title compound 49 (100 mg, 72%) as a colourless oil, $R_f$ 0.4 in 15:85 v/v ethyl acetate/hexane.

$^1$H NMR (300 MHz) δ 7.70-7.68 (complex m, 2×4H), 7.59-7.54 (complex m, 2×2H), 7.42-7.37 (complex m, 2×6H), 6.89 (m, 2×1H), 4.64 (septet, J 6.0 Hz, 2×1l1), 3.92 (s, 2×3l1), 3.75-3.69 (complex m, 2×2H), 3.33 and 3.18 (2×m, 2×1H), 1.91-1.01 (complex m, 2×11H), 1.40 (d, J 6.0 Hz, 2×6H), 1.07 and 1.06 (2×s, 2×9H).

$^{13}$C NMR (75 MHz) δ 202.6 and 202.5 (2×C), 154.2 and 154.0 (2×C), 147.1 and 147.0(9) (2×C), 135.5 (8×CH), 133.9 (4) and 133.9(1) (4×C), 129.5 and 129.4 (4×CH), 129.2 (2×C), 127.5 (8×CH), 122.6 and 122.5 (2×CH), 114.3 (2×CH), 110.4 (2×CH), 71.2 (2×CH), 62.2 and 61.6 (2×$CH_2$), 55.9 (2×$CH_3$), 45.2 and 43.1 (2×CH), 39.8 and 36.1 (2×$CH_2$), 33.6 and 30.8 (2×CH), 32.5 and 29.5 (4×$CH_2$), 29.2 and 25.7 (4×$CH_2$), 26.8 (6×$CH_3$), 21.9 (4×$CH_3$), 19.1 (2×C).

IR $v_{max}$/cm$^{-1}$ 2929, 2856, 1671, 1592, 1511, 1426, 1262, 1111, 1024, 702.

Mass Spectrum (EI) m/z 558 (M$^+$., 1), 501 (100).

HRMS found: M$^+$., 501.2459. $C_{31}H_{37}O_4Si$ requires M$^+$., 501.2461.

4-(2-Hydroxyethyl)cyclohexyl(3-isopropoxy-4-methoxy)phenylmethanone (50)

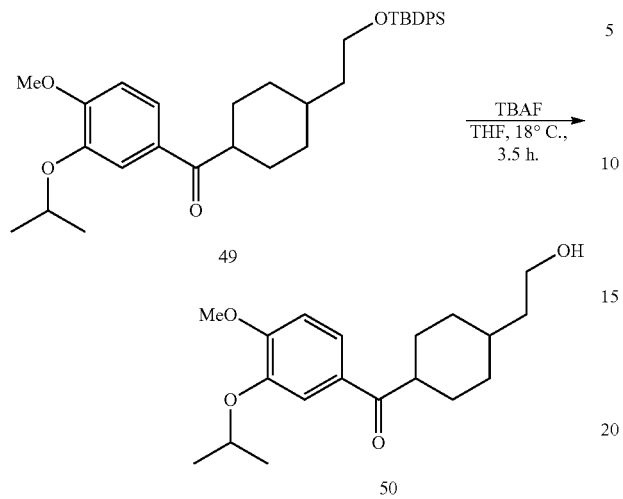

A solution of ketone 49 (95 mg, 0.170 mmol) in dry THF (4.0 mL) was treated with tetra-n-butylammonium fluoride (1.0 M in THF, 0.31 mL, 0.31 mmol) and the resulting mixture stirred magnetically at 18° C. under a nitrogen atmosphere for 3.5 h. After this time $Et_2O$ (15 mL) was added and the mixture washed with HCl (1×5.0 mL of 1.0 M aqueous solution) and brine (1×5.0 mL), then dried ($MgSO_4$), filtered and concentrated under reduced pressure. The ensuing residue was subjected to flash chromatography (3:7 v/v ethyl acetate/hexane elution) to afford a ca. 1:1 mixture of the cis- and trans-isomeric forms of the title compound 50 (50 mg, 93%) as a colourless oil, $R_f$ 0.2 in 1:1 v/v ethyl acetate/hexane.

$^1$H NMR (300 MHz) δ 7.58-7.51 (complex m, 2×2H), 6.88 (m, 2×1H), 4.63 (septet, J 6.1 Hz, 2×1H), 3.92 (s, 2×3H), 3.72 and 3.69 (2×t, J 6.7 and 6.7 Hz, 2×2H), 3.36 and 3.18 (m, 2×1H), 1.92-1.05 (complex m, 2×12H), 1.39 (d, J 6.1 Hz, 2×6H).

$^{13}$C NMR (75 MHz) δ 202.6 and 202.4 (2×C), 154.2 and 154.0 (2×C), 147.1 and 147.0(7) (2×C), 129.2 and 129.1 (2×C), 122.6 and 122.5(6) (2×CH), 114.4 (2×CH), 110.4 (2×CH), 71.2 (2×CH), 60.9 and 60.5 (2×$CH_2$), 55.9 (2×$CH_3$), 45.1 and 42.8 (2×CH), 40.0 and 36.5 (2×$CH_2$), 33.6 and 30.8 (2×CH), 32.5 and 29.4 (4×$CH_2$), 29.2 and 25.7 (4×$CH_2$), 21.9 (4×$CH_3$).

IR $v_{max}$/cm$^{-1}$ 3436, 2927, 1668, 1592, 1510, 1424, 1263, 1148, 1021.

Mass Spectrum (EI) m/z 320 (M$^+$., 12), 69 (100).

HRMS found: M$^+$., 320.1986. $C_{19}H_{28}O_4$ requires M$^+$., 320.1988.

(3-Hydroxy-4-methoxyphenyl)-4-(2-hydroxyethyl)cyclohexylmethanone (51)

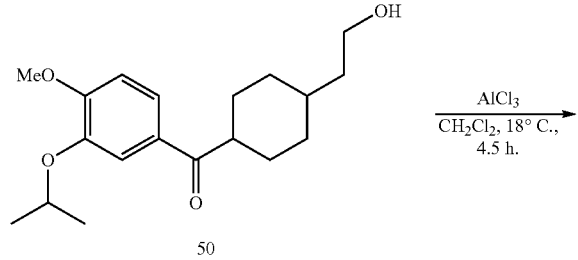

A solution of ketone 50 (250 mg, 0.780 mmol) in dry $CH_2Cl_2$ (4.0 mL) was treated with $AlCl_3$ (312 mg, 2.34 mmol) and the resulting mixture stirred magnetically at 18° C. under a nitrogen atmosphere for 4.5 h then partitioned between $H_2O$ (15 mL) and $CH_2Cl_2$ (15 mL). The separated aqueous phase was extracted with $CH_2Cl_2$ (1×10 mL) and the combined organic fractions dried ($MgSO_4$), filtered and concentrated, under reduced pressure, onto TLC-grade silica (ca. 250 mg). The resulting free-flowing solid was subjected to flash chromatography (1:1 v/v ethyl acetate/hexane elution) to afford a ca. 1:1 mixture of the cis- and trans-isomeric fauns of compound 51 (195 mg, 90%) as a white solid, $R_f$ 0.4 in ethyl acetate.

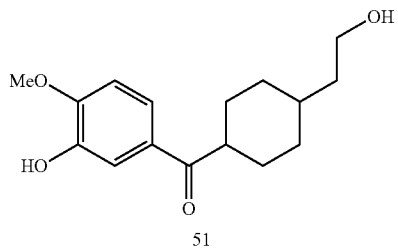

This mixture was subjected to semi-preparative HPLC (22×250 mm Alltima C18 column, 56:44 v/v 25 mM $KH_2PO_4$ buffer/MeOH) and two fractions, A and B, were thereby obtained.

Concentration of fraction A gave the cis-isomer of the title compound as a white solid, m.p. 107.1-108.7° C., $R_t$ 74.4 min.

$^1$H NMR (300 MHz) δ 7.53-7.50 (complex m, 2H), 6.89 (d, J 8.1 Hz, 1H), 5.67 (broad s, 1H), 3.96 (s, 3H), 3.68 (t, J 6.5 Hz, 2H), 3.32 (m, 1H), 1.91-1.48 (complex m, 12H).

$^{13}$C NMR (75 MHz) δ 202.6 (C), 150.2 (C), 145.3 (C), 130.1 (C), 121.6 (CH), 114.4 (CH), 109.9 (CH), 61.1 ($CH_2$), 56.0 ($CH_3$), 43.1 (CH), 36.5 ($CH_2$), 30.8 (CH), 29.2 (2×$CH_2$), 25.7 (2×$CH_2$).

IR $v_{max}$/cm$^{-1}$ 3401, 2930, 2855, 1661, 1607, 1583, 1512, 1439, 1275, 1119, 1023.

Mass Spectrum (EI) m/z 278 (M$^+$., 12), 151 (100).

HRMS found: M$^+$., 278.1521. $C_{16}H_{22}O_4$ requires M$^+$., 278.1518.

Elemental Analysis found: C, 68.87; H, 7.78%. $C_{16}H_{22}O_4$ requires C, 69.04; H, 7.97%.

Recrystallisation (MeOH) of the solid derived from concentration of fraction B gave the trans-isomer of the title compound as a white solid, m.p. 152.0-154.7° C., $R_t$ 79.7 min.

$^1$H NMR (300 MHz) δ 7.56-7.52 (complex m, 2H), 6.89 (d, J 8.4 Hz, 1H), 5.65 (broad s, 1H), 3.96 (s, 3H), 3.72 (t, J 6.6 Hz, 2H) 3.15 (m, 1H), 1.91-1.04 (complex m, 12H).

$^{13}$C NMR (75 MHz) δ 202.4 (C), 150.3 (C), 145.3 (C), 130.0 (C), 121.6 (CH), 114.4 (CH), 109.9 (CH), 60.8 ($CH_2$), 56.0 ($CH_3$), 45.3 (CH), 40.1 ($CH_2$), 33.7 (CH), 32.6 (2×$CH_2$), 29.3 (2×$CH_2$).

IR $v_{max}$/cm$^{-1}$ 3401, 2918, 2850, 1655, 1607, 1515, 1439, 1276, 1127, 1022.

Mass Spectrum (EI) m/z 278 (M$^+$., 12), 151 (100).

HRMS found: M$^+$., 278.1518. $C_{16}H_{22}O_4$ requires M$^+$., 278.1518.

Elemental Analysis found: C, 68.95; H, 7.84%. $C_{16}H_{22}O_4$ requires C, 69.04; H, 7.97%.

trans-(3-Hydroxy-4-methoxyphenyl)-4-(2-hydroxyethyl)cyclohexylmethanone O-4-Nitrobenzyl Oxime (CP30347)

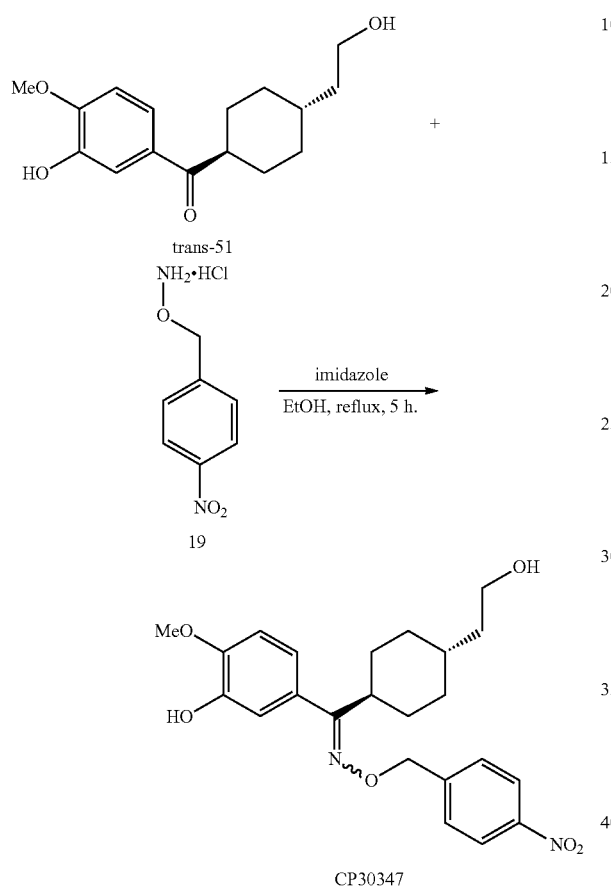

A magnetically stirred solution of the trans-isomer of ketone 51 (35 mg, 0.126 mmol) in EtOH (2.5 mL) was treated with compound 19 (51 mg, 0.249 mmol) and imidazole (11 mg, 0.162 mmol). The resulting mixture was heated at reflux for 5 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (1×10 mL). The combined organic fractions were then dried ($MgSO_4$), filtered and concentrated under reduced pressure. The resulting mixture was subjected to flash chromatography (1:9→1:1 v/v ethyl acetate/hexane gradient elution) to afford a ca. 6:5 mixture of the E- and Z-isomeric forms of the title compound CP30347 (50 mg, 93%) as a pale-yellow oil, $R_f$ 0.5 in ethyl acetate.

$^1$H NMR (300 MHz) δ 8.22 and 8.18 (2×d, J 8.7 and 8.8 Hz, 2×2H), 7.52 and 7.41 (2×d, J 8.8 and 8.8 Hz, 2×2H), 6.93-6.73 (complex m, 2×3H), 5.65 and 5.61 (2×broad s, 2×1H), 5.25 and 5.13 (2×s, 2×2H), 3.91 and 3.88 (2×s, 2×3H), 3.66 (complex m, 2×2H), 3.17 and 2.37 (2×m, 2×1H), 1.79-0.85 (complex m, 2×12H).

$^{13}$C NMR (75 MHz) δ 164.4 and 162.8 (2×C), 147.2, 147.1, 147.0, 146.5, 146.4 and 146.1 (6×C), 145.1 (2×C), 128.9 and 127.0 (2×C), 128.0 and 127.9 (4×CH), 123.5 and 123.4 (4×CH), 119.9 and 119.3 (2×CH), 114.2 and 113.9 (2×CH), 110.1 and 110.0 (2×CH), 74.3 and 74.0 (2×$CH_2$), 60.6 and 60.5 (2×$CH_2$), 55.9 and 55.8 (2×$CH_3$), 44.2 and 39.1 (2×CH), 40.0 and 39.9 (2×$CH_2$), 33.6 (2×CH), 32.8 and 32.7 (4×$CH_2$), 30.3 and 28.9 (4×$CH_2$).

IR $v_{max}$/cm$^{-1}$ 3369, 2926, 2854, 1606, 1519, 1449, 1345, 1283, 1260, 1014, 736.

Mass Spectrum (EI) m/z 428 (M$^+$., 32), 276 (100).

HRMS found: M$^+$., 428.1944. $C_{23}H_{28}N_2O_6$ requires M$^+$., 428.1947.

cis-(3-Hydroxy-4-methoxyphenyl)-4-(2-hydroxyethyl)cyclohexylmethanone O-4-Nitrobenzyl Oxime (CP30348)

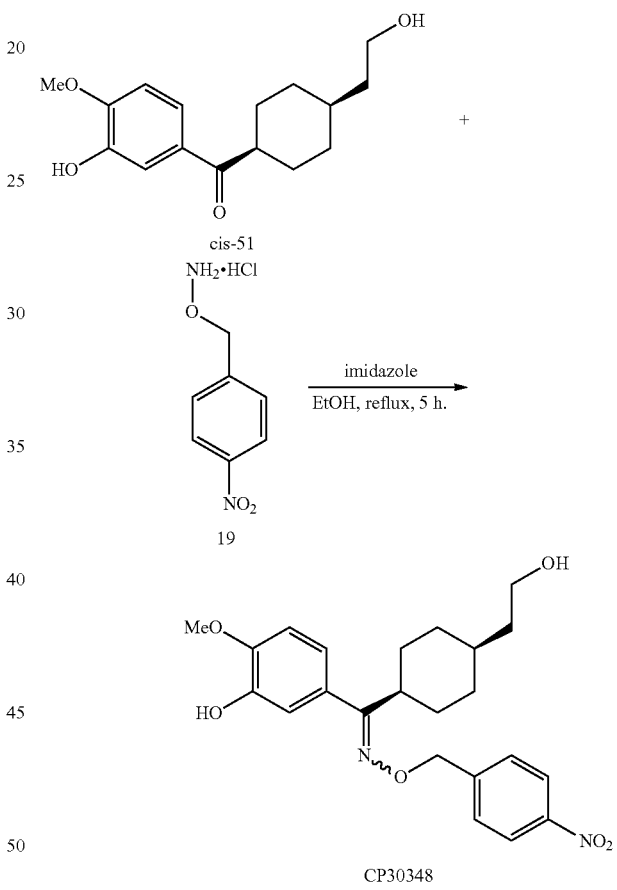

A magnetically stirred solution of the cis-isomer of ketone 51 (35 mg, 0.126 mmol) in EtOH (2.5 mL) was treated with compound 19 (51 mg, 0.249 mmol) and imidazole (11 mg, 0.162 mmol). The resulting mixture was heated at reflux for 5 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (1×10 mL). The combined organic fractions were then dried ($MgSO_4$), filtered and concentrated under reduced pressure. The resulting mixture of the E- and Z-isomeric forms of the title compound CP30348 was subjected to flash chromatography (1:9→1:1 v/v ethyl acetate/hexane gradient elution) and two fractions, A and B, were thereby obtained.

Recrystallisation of the solid derived from concentration of fraction A gave the Z-isomer of the title compound, CP30348-1 (18 mg, 33%) as a white solid, m.p. 131.8-135.8° C., $R_f$ 0.5 in ethyl acetate.

$^1$H NMR (300 MHz) δ 8.18 (d, J 8.8 Hz, 2H), 7.44 (d, J 8.7 Hz, 2H), 6.87 (d, J 8.2 Hz, 1H), 6.84 (d, J 1.9 Hz, 1H), 6.74 (dd, J 8.2 and 1.9 Hz, 1H), 5.69 (broad s, 1H), 5.13 (s, 2H), 3.91 (s, 3H), 3.61 (t, J 6.7 Hz, 2H), 2.61 (m, 1H), 1.63-1.25 (complex m, 12H).

$^{13}$C NMR (75 MHz) δ 161.6 (C), 147.2 (C), 146.7 (C), 146.5 (C), 145.2 (C), 128.1 (2×CH), 127.1 (C), 123.4 (2×CH), 119.2 (CH), 113.8 (CH), 110.1 (CH), 74.2 (CH$_2$), 61.0 (CH$_2$), 55.8 (CH$_3$), 41.7 (CH), 37.0 (CH$_2$), 31.2 (CH), 29.0 (2×CH$_2$), 26.2 (2×CH$_2$).

IR $v_{max}$/cm$^{-1}$ 3400, 2926, 2854, 1606, 1519, 1441, 1345, 1280, 1012, 736.

Mass Spectrum (EI) m/z 428 (M$^+$., 28), 276 (100).

HRMS found: M$^+$., 428.1947. C$_{23}$H$_{28}$N$_2$O$_6$ requires M$^+$., 428.1947.

Elemental Analysis found: C, 64.39; H, 6.74; N, 6.18%. C$_{23}$H$_{28}$N$_2$O$_6$ requires C, 64.47; H, 6.59; N, 6.54%.

Concentration of fraction B gave a ca. 22:1 mixture of the E- and Z-isomers of the title compound, CP30348-2 (20 mg, 37%) as a pale-yellow oil, $R_f$ 0.5 in ethyl acetate.

$^1$H NMR (300 MHz) δ (major isomer) 8.22 (d, J 8.8 Hz, 2H), 7.44 (d, J 8.8 Hz, 2H), 6.93 (d, J 1.8 Hz, 1H), 6.84-6.81 (complex m, 2H), 5.65 (broad s, 1H), 5.25 (s, 2H), 3.89 (s, 3H), 3.64 (t, J 6.9 Hz, 2H), 3.18 (m, 1H), 1.89-0.85 (complex m, 12H).

$^{13}$C NMR (75 MHz) δ 164.3 (C), 147.3 (C), 147.0 (C), 146.0 (C), 145.2 (C), 129.1 (C), 128.0 (2×CH), 123.6 (2×CH), 119.8 (CH), 114.1 (CH), 110.2 (CH), 74.4 (CH$_2$), 61.6 (CH$_2$), 55.9 (CH$_3$), 39.5 (CH), 34.0 (CH$_2$), 29.7 (2×CH$_2$), 28.5 (CH), 23.5 (2×CH$_2$).

IR $v_{max}$/cm$^{-1}$ 3369, 2926, 1606, 1518, 1453, 1344, 1260, 1213, 1059, 736.

Mass Spectrum (EI) m/z 428 (M$^+$., 5), 57 (100).

HRMS found: M$^+$., 428.1953. C$_{23}$H$_{28}$N$_2$O$_6$ requires M$^+$., 428.1947.

VI) Synthesis of CP30424

2'-Cyclohexyl-5'-isopropoxy-4'-methoxyacetophenone (52)

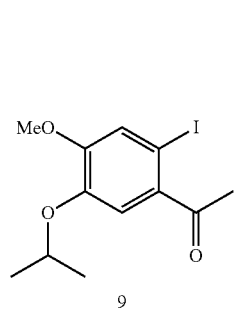
9

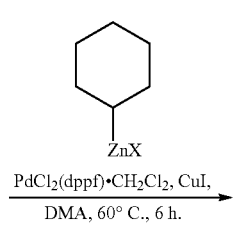

PdCl$_2$(dppf)·CH$_2$Cl$_2$, CuI,
DMA, 60° C., 6 h.

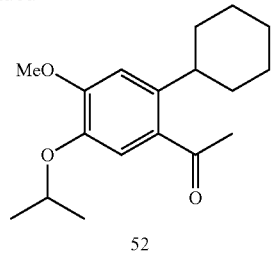
52

A magnetically stirred solution of bromocyclohexane (0.18 mL, 1.46 mmol) in dry Et$_2$O (3.0 mL), under a nitrogen atmosphere, was cooled to −78° C. and treated, dropwise, with tert-butyllithium (1.7 M in pentane, 1.9 mL, 3.23 mmol). After 10 minutes, the mixture was treated, dropwise, with a solution of anhydrous zinc iodide (495 mg, 1.55 mmol) in dry THF (1.7 mL). After 10 minutes at −78° C., the reaction mixture was allowed to warm to 18° C. and then slowly transferred to a mixture of iodide 9 (370 mg, 1.11 mmol), [1,1'-bis(diphenylphosphino)ferrocene]dichloropalladium (II).CH$_2$Cl$_2$ (18 mg, 0.022 mmol) and copper(I) iodode (8 mg, 0,042 mmol) in N,N-dimethylacetamide (1.0 mL). The resulting mixture was then stirred at 60° C., under a nitrogen atmosphere, for 6 h. The cooled mixture was filtered through a pad of Celite™ and the solids thus retained washed with EtOAC (1×50 mL). The filtrate was then washed with HCl (1×10 mL of a 1.0 M aqueous solution) and brine (1×10 mL), then dried (MgSO$_4$), filtered and concentrated under reduced pressure and the ensuing residue subjected to flash chromatography (1:19→1:9 v/v ethyl acetate/hexane gradient elution) to afford the title compound 52 (65 mg, 20%) as a yellow oil, $R_f$ 0.7 in 1:1 v/v ethyl acetate/hexane.

$^1$H NMR (300 MHz) δ 7.13 (s, 1H), 6.86 (s, 1H), 4.49 (septet, J 6.0 Hz, 1H), 3.89 (s, 3H), 3.23 (m, 1H), 2.53 (s, 3H), 1.85-1.21 (complex m, 10H), 1.36 (d, J 6.0 Hz, 3H).

$^{13}$C NMR (75 MHz) δ 201.4 (C), 153.0 (C), 144.0 (C), 142.7 (C), 130.3 (C), 117.4 (CH), 110.2 (CH), 72.1 (CH), 55.8 (CH$_3$), 39.5 (CH), 34.7 (2×CH$_2$), 30.3 (CH$_3$), 26.9 (2×CH$_2$), 26.3 (CH$_2$), 22.1 (2×CH$_3$).

IR $v_{max}$/cm$^{-1}$ 2926, 2850, 1677, 1512, 1302, 1267, 1150, 1110, 1060.

Mass Spectrum (EI) m/z 290 (M$^+$., 62), 233 (100).

HRMS found: M$^+$., 290.1880. C$_{18}$H$_{26}$O$_3$ requires M$^+$., 290.1882.

2'-Cyclohexyl-5'-hydroxy-4'-methoxyacetophenone (53)

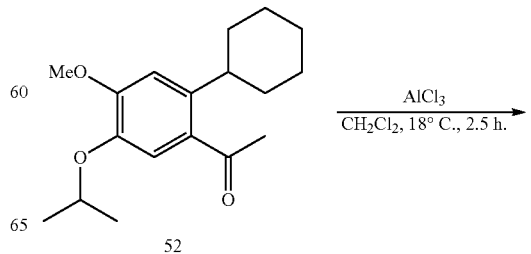
52

AlCl$_3$
CH$_2$Cl$_2$, 18° C., 2.5 h.

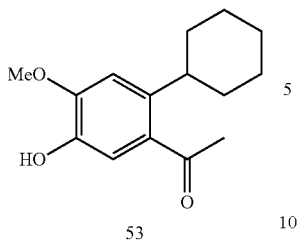

53

A solution of ketone 52 (50 mg, 0.172 mmol) in dry CH$_2$Cl$_2$ (1.5 mL) was treated with AlCl$_3$ (0.069 mg, 0.517 mmol) and the resulting mixture stirred magnetically at 18° C. under a nitrogen atmosphere for 2.5 h then partitioned between H$_2$O (10 mL) and CH$_2$Cl$_2$ (10 mL). The separated aqueous phase was extracted with CH$_2$Cl$_2$ (1×10 mL) and the combined organic fractions dried (MgSO$_4$), filtered and concentrated, under reduced pressure, onto TLC-grade silica (ca. 80 mg). The resulting free-flowing solid was subjected to flash chromatography (1:19→15:85 v/v ethyl acetate/hexane gradient elution) to afford the title compound 53 (31 mg, 72%) as a colourless oil, R$_f$ 0.6 in 1:1 v/v ethyl acetate/hexane.

$^1$H NMR (300 MHz) δ 7.18 (s, 1H), 6.84 (s, 1H), 5.59 (broad s, 1H), 3.93 (s, 3H), 3.24 (m, 1H), 2.52 (s, 3H), 1.88-1.13 (complex m, 10H).

$^{13}$C NMR (75 MHz) δ 201.5 (C), 148.8 (C), 142.4 (C), 141.5 (C), 130.6 (C), 115.2 (CH), 109.0 (CH), 55.8 (CH$_3$), 39.3 (CH), 34.8 (2×CH$_2$), 30.2 (CH$_3$), 26.9 (2×CH$_2$), 26.2 (CH$_2$).

IR ν$_{max}$/cm$^{-1}$ 3401, 2925, 2850, 1674, 1574, 1512, 1359, 1277, 1194, 1149, 1060, 869.

Mass Spectrum (EI) m/z 248 (M$^+$., 2), 233 (100).

HRMS found: M$^+$., 248.1412. C$_{15}$H$_{20}$O$_3$ requires M$^+$., 248.1412.

2'-Cyclohexyl-5'-hydroxy-4'-methoxyacetophenone O-4-Nitrobenzyl Oxime (CP30424)

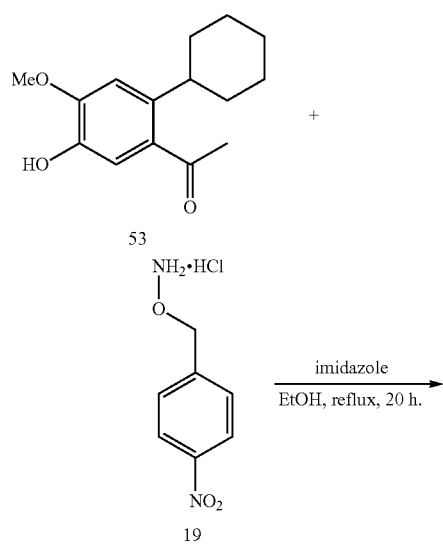

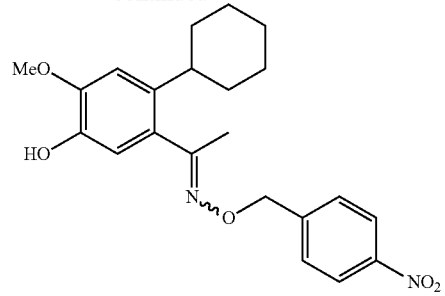

CP30424

A magnetically stirred solution of ketone 53 (28 mg, 0.113 mmol) in EtOH (1.0 mL) was treated with compound 19 (46 mg, 0.225 mmol) and imidazole (12 mg, 0.176 mmol). The resulting mixture was heated at reflux for 20 h then cooled and the solvent removed under reduced pressure. The ensuing residue was partitioned between CH$_2$Cl$_2$ (10 mL) and H$_2$O (10 mL) and the separated aqueous fraction extracted with CH$_2$Cl$_2$ (1×15 mL). The combined organic fractions were then dried (MgSO$_4$), filtered and concentrated under reduced pressure. The resulting mixture was subjected to flash chromatography (1:19→1:9 v/v ethyl acetate/hexane gradient elution) to afford a ca. 4:1 mixture of the E- and Z-isomeric fowls of the title compound CP30424 (26 mg, 58%) as a colourless oil, R$_f$ 0.6 in 1:1 v/v ethyl acetate/hexane.

$^1$H NMR (300 MHz) δ (major isomer) 8.22 (d, J 8.8 Hz, 2H), 7.54 (d, J 8.8 Hz, 2H), 6.73 (s, 1H), 6.70 (s, 1H), 5.47 (s, 1H), 5.27 (s, 2H), 3.88 (s, 3H), 2.54 (m, 1H), 2.22 (s, 3H), 1.76-1.12 (complex m, 10H); δ (minor isomer) 8.17 (d, J 8.8 Hz, 2H), 7.42 (d, J 8.8 Hz, 2H), 6.76 (s, 1H), 6.58 (s, 1H), 5.53 (s, 1H), 5.10 (s, 2H), 3.90 (s, 3H), 2.26 (m, 1H), 2.08 (s, 3H), 1.76-1.12 (complex m, 10H).

$^{13}$C NMR (75 MHz) δ (major isomer) 158.2 (C), 147.3 (C), 146.8 (C), 146.4 (C), 143.2 (C), 137.9 (C), 129.0 (C), 128.0 (2×CH), 123.6 (2×CH), 114.1 (CH), 108.7 (CH), 74.2 (CH$_2$), 55.9 (CH$_3$), 40.4 (CH), 34.7 (2×CH$_2$), 26.8 (2×CH$_2$), 26.0 (CH$_2$), 17.6 (CH$_3$); δ (minor isomer) 157.2 (C), 146.6 (C), 146.2 (C), 143.6 (C), 136.0 (C), 128.1 (2×CH), 127.5 (C), 123.5 (2×CH), 111.7 (CH), 108.3 (CH), 74.0 (CH$_2$), 55.7 (CH$_3$), 41.3 (CH), 23.1 (CH$_3$), signals due to 1×C and 5×CH$_2$ obscured or overlapping.

IR ν$_{max}$/cm$^{-1}$ 3503, 2926, 2850, 1520, 1345, 1198, 1049, 856.

Mass Spectrum (EI) m/z 398 (M$^+$., 5), 246 (100).

HRMS found: M$^+$., 398.1837. C$_{22}$H$_{26}$N$_2$O$_5$ requires M$^+$., 398.1842.

VII) Synthesis of CP30450-3

Ethyl 4-[(tert-butyldimethylsilyl)oxy]cyclohexanecarboxylate (55)

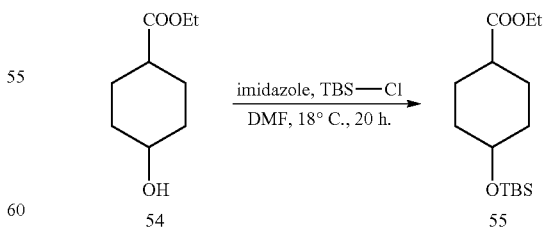

Following protocols reported by Wild,[10] a solution of Ethyl 4-hydroxycylohexanecarboxylate (54) (1.0 mL, 6.20 mmol) in DMF (3.0 mL) was treated with imidazole (929 mg, 13.6 mmol) and tert-butyldimethylsilyl chloride (1.22 g, 8.09 mmol) and the resulting mixture stirred magnetically at 18°

C. under a nitrogen atmosphere for 20 h. The reaction mixture was then treated with Et$_2$O (50 mL), washed with HCl (1×5 mL of a 1 M aqueous solution), then dried (MgSO$_4$), filtered and concentrated under reduced pressure. The ensuing residue was subjected to flash chromatography (hexane→1:49 v/v ethyl acetate/hexane gradient elution) to afford a ca. 1:1 mixture of the cis- and trans-isomeric forms of the title compound 55 (1.78 g, quant.) as a colourless oil, R$_f$ 0.7 in 3:7 v/v ethyl acetate/hexane.

$^1$H NMR (300 MHz) δ 4.12 and 4.11 (2×q, J 7.1 and 7.1 Hz, 2×2H), 3.89 and 3.56 (2×m, 2×1H), 2.33-2.16 (complex m, 2×1H), 1.98-1.87 (complex m, 2×2H), 1.68-1.22 (complex m, 2×6H), 1.25 and 1.24 (2×t, J 7.1 and 7.1 Hz, 2×3H), 0.88 and 0.87(8) (2×s, 2×9H), 0.05 and 0.03 (2×s, 2×6H).

$^{13}$C NMR (75 MHz) δ 175.8 and 175.7 (2×C), 70.5 and 66.6 (2×CH), 60.1 and 60.0 (2×CH$_2$), 42.2 and 42.0 (2×CH), 34.8 and 32.8 (4×CH$_2$), 27.2 and 23.4 (4×CH$_2$), 25.8 and 25.7(7) (6×CH$_3$), 18.2 and 18.1 (2×C), 14.2 (2×CH$_3$), −4.7 and −4.9 (4×CH$_3$).

IR ν$_{max}$/cm$^{-1}$ 2934, 2858, 1734, 1463, 1252, 1096, 1049, 835, 774.

Mass Spectrum (EI) m/z 229 [(M-C$_4$H$_9$)$^+$., 92], 57 (100).

HRMS found: (M-C$_4$H$_9$)$^+$., 229.1256. C$_{15}$H$_{30}$O$_3$Si requires (M-C$_4$H$_9$)$^+$., 229.1260.

Ethyl 4-[(tert-butyldimethylsilyl)oxy]-1-methylcyclohexanecarboxylate (56)

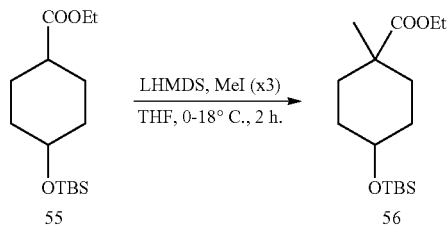 [SMILES: CCOC(=O)C1CCC(O[Si](C)(C)C(C)(C)C)CC1 ; CCOC(=O)C1(C)CCC(O[Si](C)(C)C(C)(C)C)CC1]

A magnetically stirred solution of ester 55 (7.00 g, 24.4 mmol) in dry THF (60 mL) maintained at 0° C. was treated with lithium bis(trimethylsilyl)amide (1.0 M in THF, 37 mL, 37.0 mmol). The mixture was then warmed to 18° C., where it was stirred under a nitrogen atmosphere for 0.5 h, then treated with iodomethane (15 mL, 241 mmol) and stirred for an additional 1.5 h. The reaction mixture was then treated with H$_2$O (40 mL), extracted with Et$_2$O (2×150 mL) and the combined organic fractions dried (MgSO$_4$), filtered and concentrated under reduced pressure [Note: any salts may be removed via filtration with Et$_2$O]. The above procedure was then performed an additional two times. Following the three reaction cycles the ensuing residue was subjected to flash chromatography (hexane→3:97 v/v Et$_2$O/hexane gradient elution) to afford a ca. 3:1 mixture of the cis- and trans-isomeric forms of the title compound 56 (4.64 g, 63%) as a pale-yellow oil, R$_f$ 0.7 in 1:9 v/v ethyl acetate/hexane.

$^1$H NMR (300 MHz) δ (major isomer) 4.13 (q, J 7.1 Hz, 2H), 3.56 (m, 1H), 2.21-1.08 (complex m, 8H), 1.25 (t, J 7.1 Hz, 3H), 1.13 (s, 3H), 0.87 (s, 9H), 0.04 (s, 6H); δ (minor isomer) 4.12 (q, J 7.1 Hz, 2H), 3.77 (m, 1H), 2.21-1.08 (complex m, 8H), 1.24 (t, J 7.1 Hz, 3H), 1.17 (s, 3H), 0.88 (s, 9H), 0.03 (s, 6H).

$^{13}$C NMR (75 MHz) δ (major isomer) 177.0 (C), 70.6 (CH), 60.3 (CH$_2$), 42.5 (C), 32.9 (2×CH$_2$), 31.1 (2×CH$_2$), 26.8 (CH$_3$), 25.9 (3×CH$_3$), 18.2 (C), 14.2 (CH$_3$), −4.7 (2×CH$_3$); δ (minor isomer) 178.0 (C), 67.8 (CH), 60.1 (CH$_2$), 42.3 (C), 33.5 (2×CH$_2$), 30.7 (2×CH$_2$), 25.8 (3×CH$_3$), 22.7 (CH$_3$), 18.1 (C), −4.8 (2×CH$_3$), signals due to 1×CH$_3$ obscured or overlapping.

IR ν$_{max}$/cm$^{-1}$ 2932, 2857, 1729, 1462, 1252, 1201, 1109, 1090, 1049, 835, 773.

Mass Spectrum (EI) m/z 243 [(M-C$_4$H$_9$)$^+$., 100].

HRMS found: (M-C$_4$H$_9$)$^+$., 243.1416. C$_{16}$H$_{32}$O$_3$Si requires (M-C$_4$H$_9$)$^+$., 243.1416.

[(4-Hydroxy-1-methylcyclohexyl)methoxy]-tert-butyldiphenylsilane (57)

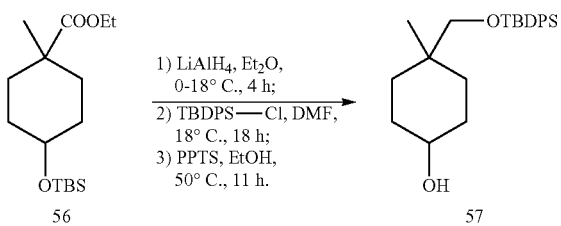

A magnetically stirred solution of ester 56 (1.46 g, 4.86 mmol) in dry Et$_2$O (60 mL) maintained at 0° C., was treated, dropwise, with lithium aluminium hydride (1.0 M in Et$_2$O, 20 mL, 20.0 mmol) and the resulting mixture allowed to warm to 18° C., where it was stirred under a nitrogen atmosphere for 4 h. The reaction mixture was then diluted with Et$_2$O (30 mL), cooled to 0° C. and treated, dropwise, sequentially with H$_2$O (0.8 mL), NaOH (0.8 mL of a 3.0 M aqueous solution) and H$_2$O (2.4 mL) then dried (MgSO$_4$), filtered and concentrated, under reduced pressure. A solution of the resulting residue (R$_f$ 0.2 in 1:9 v/v ethyl acetate/hexane) in DMF (70 mL) was then treated with imidazole (850 mg, 12.5 mmol) and tert-butylchlorodiphenylsilane (2.6 mL, 10.2 mmol) and the resulting mixture stirred magnetically under a nitrogen atmosphere for 18 h. The reaction mixture was then treated with Et$_2$O (150 mL), washed with HCl (1×30 ml of a 1 M aqueous solution) and brine (1×30 mL) then dried (MgSO$_4$), filtered and concentrated under reduced pressure. The ensuing residue was subjected to flash chromatography (hexane→1:19 v/v ethyl acetate/hexane gradient elution) and the concentrated relevant fractions used as obtained, in the next step of the reaction sequence.

A solution of the resulting residue (R$_f$ 0.3 in hexane) in EtOH (20 mL) was treated with pyridinium p-toluenesulfonate (376 mg, 1.50 mmol) and the resulting mixture stirred magnetically at 50° C. for 11 h. The solvent was then removed under reduced pressure and the resulting residue taken up into ethyl acetate (80 mL), washed with brine (1×20 mL), then dried (MgSO$_4$), filtered and concentrated under reduced pressure. The ensuing residue was subjected to flash chromatography (hexane→15:85 v/v ethyl acetate/hexane gradient elution) to afford a ca. 3:1 mixture of the cis- and trans-isomeric forms of the title compound 57 (1.77 g, 95%) as a colourless oil, R$_f$ 0.1 in 1:79 v/v ethyl acetate/hexane.

$^1$H NMR (300 MHz) δ (major isomer) 7.71-7.68 (complex m, 4H), 7.45-7.38 (complex m, 6H), 3.71 (m, 1H), 3.46 (s, 2H), 1.77-0.88 (complex m, 9H), 1.09 (s, 9H), 1.00 (s, 3H); δ (minor isomer) 7.71-7.68 (complex m, 4H), 7.47-7.38 (complex m, 6H), 3.57 (m, 1H), 3.33 (s, 2H), 1.77-0.88 (complex m, 9H), 1.08 (7) (s, 9H), 0.99 (s, 3H).

$^{13}$C NMR (75 MHz) δ (major isomer) 135.6 (4×CH), 133.8 (2×C), 129.5 (2×CH), 127.6 (4×CH), 69.8 (CH$_2$), 69.4 (CH), 34.8 (C), 30.9 (2×CH$_2$), 30.3 (2×CH$_2$), 26.9 (3×CH$_3$), 24.5

(CH$_3$), 19.4 (C); δ (minor isomer) 73.6 (CH$_2$), 71.0 (CH), 35.1 (C), 31.9 (2×CH$_2$), 30.8 (2×CH$_2$), 20.4 (CH$_3$), signals due to 3×C, 10×CH and 3×CH$_3$ obscured or overlapping.

IR $v_{max}$/cm$^{-1}$ 3341, 2931, 2857, 1471, 1427, 1111, 701.

Mass Spectrum (EI) m/z 325 [(M-C$_4$H$_9$)$^+$., 5], 109 (100).

HRMS found: (M-C$_4$H$_9$)$^+$., 325.1629. C$_{24}$H$_{34}$O$_2$Si requires (M-C$_4$H$_9$)$^+$., 325.1624.

[(4-Bromo-1-methylcyclohexyl)methoxy]-tert-butyl-diphenylsilane (58)

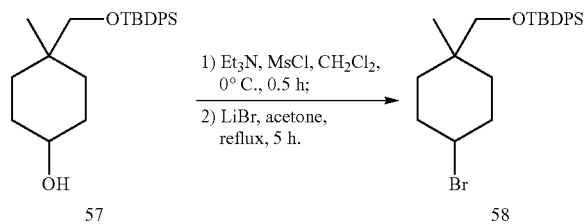

A magnetically stirred solution of alcohol 57 (1.27 g, 3.32 mmol) in dry CH$_2$Cl$_2$ (20 mL), maintained at 0° C., was treated with triethylamine (0.69 mL, 4.98 mmol) and methanesulfonylchloride (0.28 mL, 3.60 mmol) and the resulting mixture stirred at 0° C. under a nitrogen atmosphere for 0.5 h. The solvent was removed under reduced pressure and the residue taken up into dry acetone (10 mL) then filtered (using additional 10 mL dry acetone). Lithium bromide (1.90 g, 21.9 mmol) was added to the filtrate and the resulting mixture stirred at reflux under a nitrogen atmosphere for 5 h. After this time H$_2$O (25 mL) then CH$_2$Cl$_2$ (50 mL) were added to the reaction mixture, the organic phase separated and the aqueous phase extracted with CH$_2$Cl$_2$ (2×40 mL). The combined organic fractions were then dried (MgSO$_4$), filtered and concentrated under reduced pressure and the ensuing residue subjected to flash chromatography (hexane→1:99 v/v Et$_2$O/hexane gradient elution) to afford a ca. 3:1 mixture of the cis- and trans-isomeric forms of the title compound 58 (631 mg, 43%) as a pale-yellow oil, R$_f$ 0.4 in hexane.

$^1$H NMR (300 MHz) δ (major isomer) 7.70-7.63 (complex m, 4H), 7.47-7.35 (complex m, 6H), 4.05 (m, 1H), 3.29 (s, 2H), 2.12-0.84 (complex m, 8H), 1.06 (s, 9H), 1.00 (s, 3H); δ (minor isomer) 7.70-7.63 (complex m, 4H), 7.47-7.35 (complex m, 6H), 4.37 (m, 1H), 3.42 (s, 2H), 2.12-0.84 (complex m, 8H), 1.08 (s, 9H), 0.94 (s, 3H)

$^{13}$C NMR (75 MHz) δ (major isomer) 135.6 (4×CH), 133.6 (2×C), 129.6 (2×CH), 127.6 (4×CH), 73.0 (CH$_2$), 53.1 (CH), 34.8 (C), 33.9 (2×CH$_2$), 33.1 (2×CH$_2$), 26.9 (3×CH$_3$), 20.9 (CH$_3$), 19.4 (C); δ (minor isomer) 135.7 (4×CH), 133.7 (2×C), 71.1 (CH$_2$), 54.0 (CH), 34.9 (C), 31.9 (2×CH$_2$), 31.4 (2×CH$_2$), 23.4 (CH$_3$); signals due to 1×C, 6×CH and 4×CH$_3$ obscured or overlapping.

IR $v_{max}$/cm$^{-1}$ 3071, 2931, 2856, 1471, 1427, 1112, 825, 701.

Mass Spectrum (EI) m/z 389 and 387 [(M-C$_4$H$_9$)$^+$., 45 and 43], 199 (100).

HRMS Found: (M-C$_4$H$_9$)$^+$., 389.0766. C$_{24}$H$_{33}$$^{81}$BrOSi requires (M-C$_4$H$_9$)$^+$% 389.0759. Found: (M-C$_4$H$_9$)$^+$., 387.0784. C$_{24}$H$_{33}$$^{79}$BrOSi requires (M-C$_4$H$_9$)$^+$., 387.0780.

2'-(4-hydroxymethyl-4-methyl)cyclohexyl-5'-isopropoxy-4'-methoxyacetophenone (59)

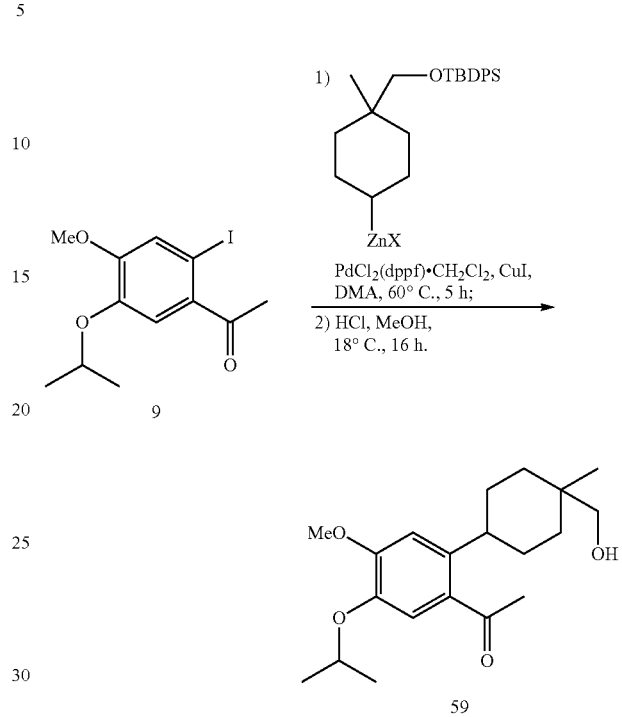

A magnetically stirred solution of bromocyclohexane 58 (188 mg, 0.422 mmol) and N,N,N',N'-tetramethylenediamine (0.1 mL) in dry Et$_2$O (0.9 mL), under a nitrogen atmosphere, was cooled to −78° C. and treated, dropwise, with tert-butyllithium (1.7 M in pentane, 0.55 mL, 0.935 mmol). After 20 minutes, the mixture was treated, dropwise, with a solution of anhydrous zinc chloride (ca. 1 M in THF, 0.5 mL, 0.500 mmol). After 10 minutes at −78° C., the reaction mixture was allowed to warm to 18° C. and then slowly transferred to a mixture of iodide 9 (108 mg, 0.323 mmol), copper(I) iodode (11 mg, 0.058 mmol) and [1,1'-bis(diphenylphosphino)ferrocene]dichloropalladium(II).CH$_2$Cl$_2$ (26 mg, 0.032 mmol) in N,N-dimethylacetamide (0.5 mL). The resulting mixture was then stirred at 60° C., under a nitrogen atmosphere, for 5 h. The cooled mixture was filtered through a pad of Celite™ and the solids thus retained washed with ethyl acetate (1×40 mL). The filtrate was then washed with HCl (1×10 mL of a 1.0 M aqueous solution) and brine (1×10 mL), then dried (MgSO$_4$), filtered and concentrated under reduced pressure. The ensuing residue was subjected to flash chromatography (1:49→1:19 v/v ethyl acetate/hexane gradient elution) and the concentrated relevant fractions used as obtained, in the next step of the reaction sequence.

A solution of the resulting residue (R$_f$ 0.5 in 15:85 v/v ethyl acetate/hexane) in MeOH (3.5 mL) was treated with HCl (ca. 1.5 mL of conc. aqueous solution) and the resulting mixture stirred magnetically at 18° C. for 16 h. The mixture was then treated with H$_2$O (8 mL), extracted with CH$_2$Cl$_2$ (3×15 mL), and the combined organic fractions dried (MgSO$_4$), filtered and concentrated under reduced pressure. The ensuing residue was subjected to flash chromatography (1:9→3:7 v/v ethyl acetate/hexane gradient elution) to afford a ca. 2:1 mixture the cis- and trans-isomeric forms of the title compound 59 (23 mg, 21%) as a colourless oil, $R_f$ 0.4 in 1:1 v/v ethyl acetate/hexane.

$^1$H NMR (300 MHz) δ (major isomer) 7.15 (s, 1H), 6.89 (s, 1H), 4.49 (septet, J 6.1 Hz, 1H), 3.91 (s, 3H), 3.33 (s, 2H), 3.17 (m, 1H), 2.53 (s, 3H), 1.74-0.84 (complex m, 9H), 1.36 (d, J 6.1 Hz, 6H), 1.03 (s, 3H); δ (minor isomer) 7.15 (s, 1H), 6.84 (s, 1H), 4.48 (5) (septet, J 6.1 Hz, 1H), 3.88 (s, 3H), 3.63 (s, 2H), 3.21 (m, 1H), 2.53 (s, 3H), 1.74-0.84 (complex m, 9H), 1.35 (d, J 6.1 Hz, 6H), 0.95 (s, 3H).

$^{13}$C NMR (75 MHz) δ (major isomer) 201.3 (C), 153.0 (9) (C), 144.1 (C), 142.3 (C), 130.3 (C), 117.8 (CH), 110.2 (CH), 74.7 (CH$_2$), 72.2 (CH), 55.9 (CH$_3$), 39.8 (CH), 34.8 (C), 34.1 (2×CH$_2$), 30.2 (CH$_3$), 29.4 (2×CH$_2$), 22.1 (2×CH$_3$), 19.6 (CH$_3$); δ (minor isomer) 201.2 (C), 153.1 (C), 130.2 (C), 117.9 (CH), 110.1 (CH), 67.0 (CH$_2$), 39.4 (CH), 36.6 (C), 34.7 (2×CH$_2$), 29.8 (2×CH$_2$), 27.4 (CH$_3$), signals due to 2×C, 1×CH and 4×CH$_3$ obscured or overlapping.

IR $v_{max}$/cm$^{-1}$ 3436, 2929, 2854, 1675, 1512, 1357, 1264, 1147, 1110, 1058, 940.

Mass Spectrum (EI) m/z 334 (M$^+$., 80), 43 (100).

HRMS found: M$^+$., 334.2142. C$_{20}$H$_{30}$O$_4$ requires M$^+$., 334.2144.

2'-(4-hydroxymethyl-4-methyl)cyclohexyl-5'-hydroxy-4'-methoxyacetophenone (60)

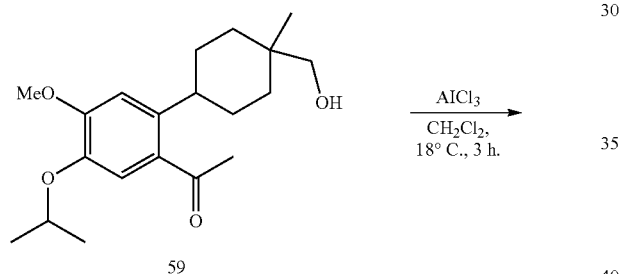

A solution of ketone 59 (64 mg, 0.191 mmol) in dry CH$_2$Cl$_2$ (1.0 mL) was treated with AlCl$_3$ (77 mg, 0.577 mmol) and the resulting mixture stirred magnetically at 18° C. under a nitrogen atmosphere for 3 h. The mixture was then treated with H$_2$O (5 mL), extracted with CH$_2$Cl$_2$ (3×10 mL), and the combined organic fractions dried (MgSO$_4$), filtered and concentrated under reduced pressure. The ensuing residue was subjected to flash chromatography (3:7→1:1 v/v ethyl acetate/hexane gradient elution) to afford a ca. 2:1 mixture the cis- and trans-isomeric forms of the title compound 60 (44 mg, 79%) as a pale yellow oil, $R_f$ 0.2 in 1:1 v/v ethyl acetate/hexane.

This mixture was subjected to semi-preparative HPLC (22×250 mm Alltima C18 column, 60:40 v/v 25 mM KH$_2$PO$_4$ buffer/CH$_3$CN) and two fractions, A and B, were thereby obtained.

Concentration of fraction A gave the trans-isomer of the title compound as a white solid, m.p. 139.7-144.3° C., $R_t$ 14.7 min.

$^1$H NMR (300 MHz) δ 7.21 (s, 1H), 6.87 (s, 1H), 5.56 (broad s, 1H), 3.96 (s, 3H), 3.34 (s, 2H), 3.19 (m, 1H), 2.52 (s, 3H), 1.75-1.25 (complex m, 9H), 1.03 (s, 3H).

$^{13}$C NMR (75 MHz) δ 201.2 (C), 148.8 (C), 142.6 (C), 141.0 (C), 130.7 (C), 115.5 (CH), 108.8 (CH), 74.8 (CH$_2$), 55.9 (CH$_3$), 39.7 (CH), 34.8 (C), 34.1 (2×CH$_2$), 30.2 (CH$_3$), 29.5 (2×CH$_2$), 19.6 (CH$_3$).

IR $v_{max}$/cm$^{-1}$ 3369, 2928, 1670, 1571, 1513, 1359, 1279, 1197, 1145, 1042, 871.

Mass Spectrum (EI) m/z 292 (M$^+$., 85), 202 (100).

HRMS found: M$^+$., 292.1674. C$_{17}$H$_{24}$O$_4$ requires M$^+$., 292.1675.

Concentration of fraction B gave the cis-isomer of the title compound as a white solid, m.p. 113.6-116.7° C., $R_t$ 17.3 min.

$^1$H NMR (300 MHz) δ 7.21 (s, 1H), 6.83 (s, 1H), 5.52 (broad s, 1H), 3.93 (s, 3H), 3.64 (s, 2H), 3.24 (m, 1H), 2.52 (s, 3H), 1.74-1.25 (complex m, 9H), 0.96 (s, 3H).

$^{13}$C NMR (75 MHz) δ 201.2 (C), 148.8 (C), 142.6 (C), 140.9 (C), 130.7 (C), 115.5 (CH), 108.8 (CH), 67.1 (CH$_2$), 55.9 (CH$_3$), 39.2 (CH), 34.7 (2×CH$_2$), 34.2 (C), 30.2 (CH$_3$), 30.0 (2×CH$_2$), 27.4 (CH$_3$).

IR $v_{max}$/cm$^{-1}$ 3369, 2929, 1670, 1572, 1513, 1360, 1281, 1196, 1159, 1041, 871.

Mass Spectrum (EI) m/z 292 (M$^+$., 82), 202 (100).

HRMS found: M$^+$., 292.1679. C$_{17}$H$_{24}$O$_4$ requires M$^+$., 292.1675.

2'-(4-hydroxymethyl-4-methyl)cyclohexyl-5'-hydroxy-4'-methoxyacetophenone O-4-Nitrobenzyl Oxime (CP30450)

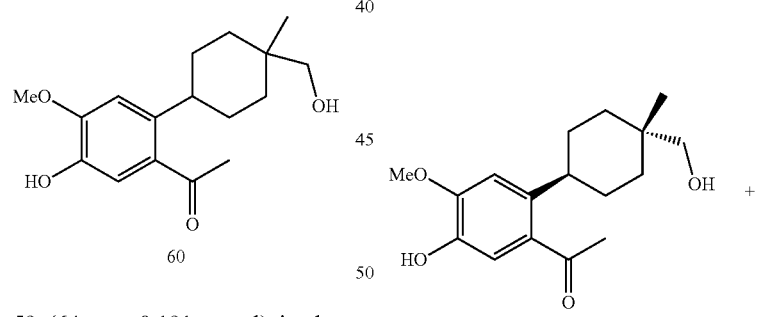

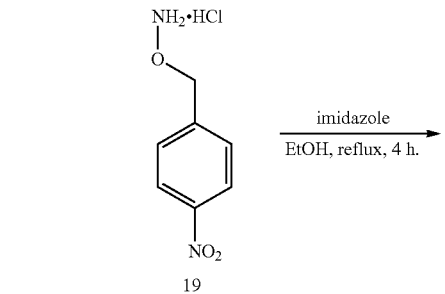

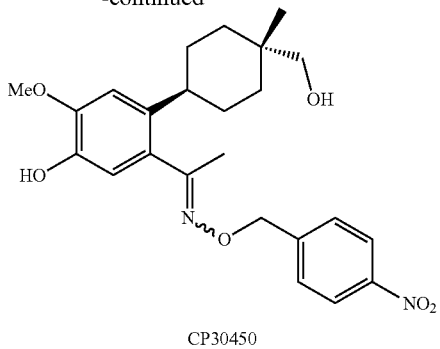

CP30450

A magnetically stirred solution of the trans-isomer of ketone 60 (30 mg, 0.103 mmol) in EtOH (1.5 mL) was treated with compound 19 (42 mg, 0.205 mmol) and imidazole (10 mg, 0.162 mmol). The resulting mixture was heated at reflux for 4 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (2×10 mL). The combined organic fractions were then dried ($MgSO_4$), filtered and concentrated under reduced pressure. The resulting mixture of the E- and Z-isomeric forms of the title compound CP30450 was subjected to flash chromatography (1:9→6:7 v/v ethyl acetate/hexane gradient elution) and two fractions, A and B, were thereby obtained.

Concentration of fraction A gave the major-isomer of the title compound, CP30450-A (19 mg, 42%) as a pale-yellow oil-foam, $R_f$ 0.4 in 1:1 v/v ethyl acetate/hexane.

$^1$H NMR (300 MHz) δ 8.22 (d, J 8.8 Hz, 2H), 7.54 (d, J 8.8 Hz, 2H), 6.75 (s, 1H), 6.70 (s, 1H), 5.54 (broad s, 1H), 5.26 (s, 2H), 3.90 (s, 3H), 3.27 (s, 2H), 2.43 (m, 1H), 2.22 (s, 3H), 1.60-1.02 (complex m, 9H), 0.98 (s, 3H).

$^{13}$C NMR (75 MHz) δ 158.1 (C), 147.3 (C), 146.8 (C), 146.4 (C), 143.4 (C), 137.2 (C), 129.2 (C), 128.0 (2×CH), 123.6 (2×CH), 114.1 (CH), 108.6 (CH), 74.4 ($CH_2$), 74.2 ($CH_2$), 55.9 ($CH_3$), 40.6 (CH), 34.6 (C), 33.8 (2×$CH_2$), 29.6 (2×$CH_2$), 19.5 ($CH_3$), 17.6 ($CH_3$).

IR $\nu_{max}$/cm$^{-1}$ 3401, 2929, 2855, 1520, 1345, 1201, 1046, 856.

Mass Spectrum (EI) m/z 442 (M$^+$., 5), 290 (100).

HRMS found: M$^+$., 442.2101. $C_{24}H_{30}N_2O_6$ requires M$^+$., 442.2104.

Concentration of fraction B gave a ca. 2:1 mixture of the major- and minor-isomers of the title compound, CP30450-B (13 mg, 29%) as a pale-yellow oil-foam, $R_f$ 0.4 in 1:1 v/v ethyl acetate/hexane.

$^1$H NMR (300 MHz) δ (minor isomer) 8.17 (d, J 8.8 Hz, 2H), 7.42 (d, J 8.8 Hz, 2H), 6.77 (s, 1H), 6.58 (s, 1H), 5.57 (broad s, 1H), 5.09 (s, 2H), 3.92 (s, 3H), 3.31 (s, 2H), 2.43 (m, 1H), 2.07 (s, 3H), 1.60-1.02 (complex m, 9H), 1.02 (s, 3H).

$^{13}$C NMR (75 MHz) δ (minor isomer) 157.0 (C), 146.6 (C), 146.1 (C), 143.7 (C), 135.4 (C), 128.2 (2×CH), 127.5 (C), 123.5 (2×CH), 111.8 (CH), 108.2 (CH), 74.0 ($CH_2$), 55.8 ($CH_3$), 41.4 (CH), 34.7 (C), 23.1 ($CH_3$), 19.5 ($CH_3$), signals due to 1×C and 5×$CH_2$ obscured or overlapping.

IR $\nu_{max}$/cm$^{-1}$ 3401, 2928, 2855, 1520, 1345, 1201, 1045, 856.

Mass Spectrum (EI) m/z 442 (M$^+$., 5), 290 (100).

HRMS found: M$^+$., 442.2101. $C_{24}H_{30}N_2O_6$ requires M$^+$., 442.2104.

2'-(4-hydroxymethyl-4-methyl)cyclohexyl-5'-hydroxy-4'-methoxyacetophenone O-4-Nitrobenzyl Oxime (CP30451)

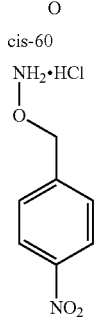

cis-60

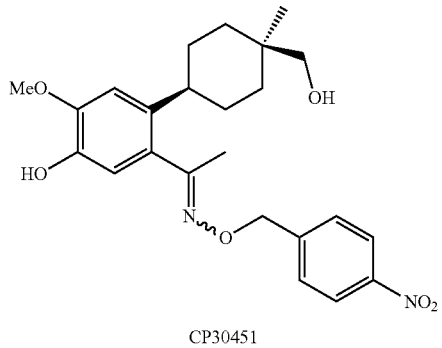

CP30451

A magnetically stirred solution of the cis-isomer of ketone 60 (15 mg, 0.051 mmol) in EtOH (1.0 mL) was treated with compound 19 (21 mg, 0.103 mmol) and imidazole (5 mg, 0.073 mmol). The resulting mixture was heated at reflux for 16 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (2×10 mL). The combined organic fractions were then dried ($MgSO_4$), filtered and concentrated under reduced pressure. The resulting mixture was subjected to flash chromatography (1:9→3:7 v/v ethyl acetate/hexane gradient elution) to afford a ca. 5:1 mixture of the E- and Z-isomeric forms of the title compound CP30451 (12 mg, 52%) as a pale-yellow oil-foam, $R_f$ 0.2 in 1:1 v/v ethyl acetate/hexane.

$^1$H NMR (300 MHz) δ (major isomer) 8.23 (d, J 8.7 Hz, 2H), 7.54 (d, J 8.7 Hz, 2H), 6.71 (s, 1H), 6.70 (s, 1H), 5.50 (broad s, 1H), 5.27 (s, 2H), 3.87 (s, 3H), 3.60 (s, 2H), 2.50 (m, 1H), 2.23 (s, 3H), 1.65-0.87 (complex m, 9H), 0.88 (s, 3H); δ (minor isomer) 8.18 (d, J 8.7 Hz, 2H), 7.43 (d, J 8.7 Hz, 2H), 6.72 (s, 1H), 6.58 (s, 1H), 5.55 (broad s, 1H), 5.09 (s, 2H), 3.89 (s, 3H), 3.64 (s, 2H), 2.50 (m, 1H), 2.08 (s, 3H), 1.65-0.87 (complex m, 9H), 0.93 (s, 3H).

$^{13}$C NMR (75 MHz) δ (major isomer) 158.0 (C), 147.3 (C), 146.8 (C), 146.5 (C), 143.4 (C), 137.1 (C), 129.1 (C), 128.0 (2×CH), 123.6 (2×CH), 114.1 (CH), 108.5 (CH), 74.2 (CH$_2$), 66.8 (CH$_2$), 55.9 (CH$_3$), 40.1 (CH), 34.6 (2×CH$_2$), 33.9 (C), 29.9 (2×CH$_2$), 27.3 (CH$_3$), 17.5 (CH$_3$); δ (minor isomer) 157.0 (C), 146.6 (C), 146.1 (C), 143.7 (C), 135.3 (C), 128.2 (2×CH), 127.5 (C), 123.5 (2×CH), 111.8 (CH), 108.1 (CH), 74.0 (CH$_2$), 55.8 (CH$_3$), 41.1 (CH), 34.0 (C), 27.4 (CH$_3$), 23.1 (CH$_3$), signals due to 1×C and 5×CH$_2$ obscured or overlapping.

IR $v_{max}$/cm$^{-1}$ 3404, 2927, 1519, 1344, 1200, 1044, 854.

Mass Spectrum (EI) m/z 442 (M$^+$., 5), 290 (100).

HRMS found: M$^+$., 442.2105. C$_{24}$H$_{30}$N$_2$O$_6$ requires M$^+$., 442.2104.

2'-(4-Hydroxymethyl-4-methyl)cyclohexyl-5'-hydroxy-4'-methoxyacetophenone O-(benzofurazan-5-yl)methyl Oxime (CP30452)

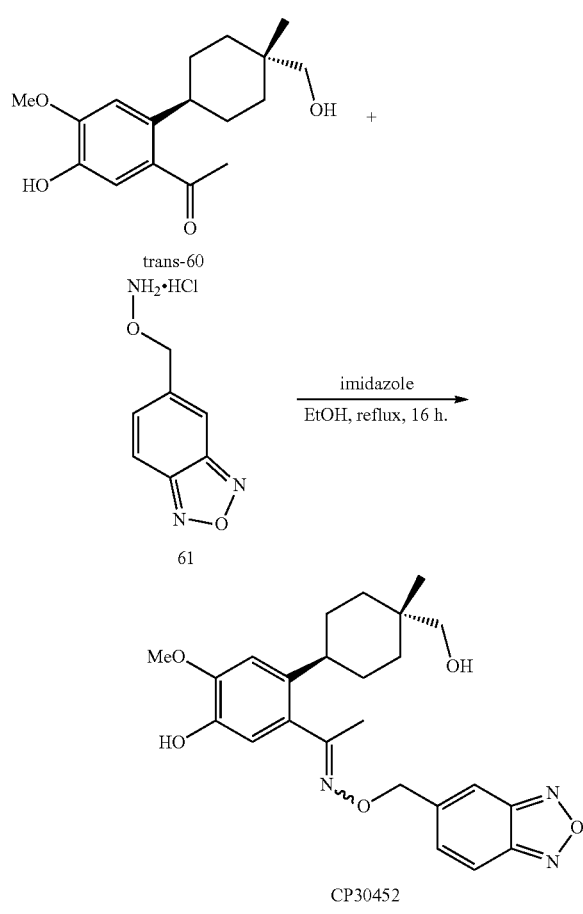

A magnetically stirred solution of the trans-isomer of ketone 60 (16 mg, 0.055 mmol) in EtOH (1.0 mL) was treated with O-(benofurazan-5-yl)methylhydroxylamine hydrochloride 61 (22 mg, 0.109 mmol) and imidazole (6 mg, 0.088 mmol). The resulting mixture was heated at reflux for 16 h then cooled and the solvent removed under reduced pressure. The ensuing residue was partitioned between CH$_2$Cl$_2$ (10 mL) and H$_2$O (10 mL) and the separated aqueous fraction extracted with CH$_2$Cl$_2$ (2×10 mL). The combined organic fractions were then dried (MgSO$_4$), filtered and concentrated under reduced pressure. The resulting mixture was subjected to flash chromatography (1:9→3:7 v/v ethyl acetate/hexane gradient elution) to afford a ca. 7:1 mixture of the E- and Z-isomeric forms of the title compound CP30452 (12 mg, 50%) as a pale-yellow oil-foam, R$_f$ 0.3 in 1:1 v/v ethyl acetate/hexane.

$^1$H NMR (300 MHz) δ (major isomer) 7.83 (dd, J 9.3 and 0.8 Hz, 1H), 7.77 (dd, J 1.2 and 1.2 Hz, 1H), 7.41 (dd, J 9.3 and 1.2 Hz, 1H), 6.75 (s, 1H), 6.72 (s, 1H), 5.54 (broad s, 1H), 5.24 (s, 2H), 3.89 (s, 3H), 3.21 (s, 2H), 2.46 (m, 1H), 2.25 (s, 3H), 1.60-0.88 (complex m, 9H), 0.96 (s, 3H); δ (minor isomer) 7.66 (dd, J 1.2 and 1.2 Hz, 1H), 7.31 (dd, J 9.2 and 1.2 Hz, 1H), 6.78 (s, 1H), 6.60 (s, 1H), 5.61 (broad s, 1H), 5.07 (s, 2H), 3.92 (s, 3H), 3.31 (s, 2H), 2.46 (m, 1H), 2.09 (s, 3H), 1.60-0.88 (complex m, 9H), 1.01 (s, 3H), signal due to 1×Ar—H obscured or overlapping.

$^{13}$C NMR (75 MHz) δ (major isomer) 158.4 (C), 149.2 (C), 148.9 (C), 146.9 (C), 143.4 (C), 143.2 (C), 137.2 (C), 131.7 (CH), 129.1 (C), 116.4 (CH), 114.0 (CH), 113.0 (CH), 108.6 (CH), 74.4 (CH$_2$), 74.2 (CH$_2$), 55.9 (CH$_3$), 40.7 (CH), 34.6 (C), 33.8 (2×CH$_2$), 29.6 (2×CH$_2$), 19.5 (CH$_3$), 17.6 (CH$_3$); δ (minor isomer) 157.3 (C), 146.7 (C), 143.8 (C), 142.8 (C), 135.4 (C), 131.8 (CH), 127.4 (C), 116.3 (CH), 113.3 (CH), 111.8 (CH), 108.2 (CH), 55.8 (CH$_3$), 41.5 (CH), 34.7 (C), 23.1 (CH$_3$), 19.6 (CH$_3$), signals due to 2×C and 6×CH$_2$ obscured or overlapping.

IR $v_{max}$/cm$^{-1}$ 3414, 2928, 1511, 1258, 1201, 1047, 1008.

Mass Spectrum (EI) m/z 439 (M$^+$., 5), 290 (100).

HRMS found: M$^+$., 439.2115. C$_{24}$H$_{29}$N$_3$O$_5$ requires M$^+$., 439.2107.

2'-(4-Hydroxymethyl-4-methyl)cyclohexyl-5'-hydroxy-4'-methoxyacetophenone O-(benzofurazan-5-yl)methyl Oxime (CP30453)

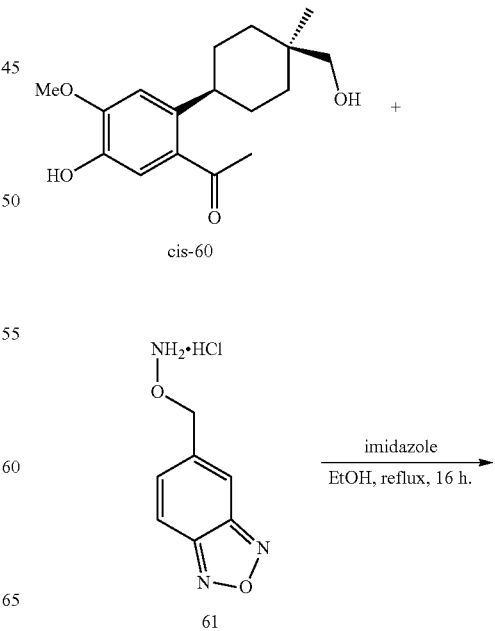

-continued

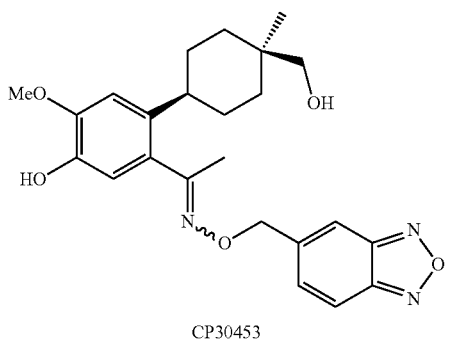

CP30453

A magnetically stirred solution of the cis-isomer of ketone 60 (20 mg, 0.068 mmol) in EtOH (1.0 mL) was treated with O-(benofurazan-5-yl)methylhydroxylamine hydrochloride 61 (28 mg, 0.139 mmol) and imidazole (7 mg, 0.103 mmol). The resulting mixture was heated at reflux for 16 h then cooled and the solvent removed under reduced pressure. The ensuing residue was partitioned between $CH_2Cl_2$ (10 mL) and $H_2O$ (10 mL) and the separated aqueous fraction extracted with $CH_2Cl_2$ (2×10 mL). The combined organic fractions were then dried ($MgSO_4$), filtered and concentrated under reduced pressure. The resulting mixture was subjected to flash chromatography (1:9→3:7 v/v ethyl acetate/hexane gradient elution) to afford a ca. 5:1 mixture of the E- and Z-isomeric forms of the title compound CP30453 (8 mg, 27%) as a pale-yellow oil-foam, $R_f$ 0.3 in 1:1 v/v ethyl acetate/hexane.

$^1$H NMR (300 MHz) δ (major isomer) 7.83 (dd, J 9.2 and 1.0 Hz, 1H), 7.78 (dd, J 1.2 and 1.2 Hz, 1H), 7.43 (dd, J 9.2 and 1.2 Hz, 1H), 6.72 (s, 1H), 6.70 (s, 1H), 5.50 (broad s, 1H), 5.25 (s, 2H), 3.87 (s, 3H), 3.57 (s, 2H), 2.51 (m, 1H), 2.26 (s, 3H), 1.59-0.85 (complex m, 9H), 0.79 (s, 3H); δ (minor isomer) 7.78 (dd, J 9.2 and 1.0 Hz, 1H), 7.66 (dd, J 1.2 and 1.2 Hz, 1H), 7.33 (dd, J 9.2 and 1.2 Hz, 1H), 6.73 (s, 1H), 6.59 (s, 1H), 5.57 (broad s, 1H), 5.07 (s, 2H), 3.90 (s, 3H), 3.63 (s, 2H), 2.51 (m, 1H), 2.09 (s, 3H), 1.59-0.85 (complex m, 9H), 0.92 (s, 3H).

$^{13}$C NMR (75 MHz) δ (major isomer) 158.2 (C), 149.2 (C), 148.9 (C), 146.9 (C), 143.4 (C), 143.0 (C), 137.1 (C), 131.7 (CH), 129.0 (C), 116.4 (CH), 114.1 (CH), 113.2 (CH), 108.5 (CH), 74.4 ($CH_2$), 66.8 ($CH_2$), 55.9 ($CH_3$), 40.2 (CH), 34.5 (2×$CH_2$), 33.9 (C), 29.9 (2×$CH_2$), 27.1 ($CH_3$), 17.6 ($CH_3$); δ (minor isomer) 157.3 (C), 146.6 (C), 143.7 (C), 142.6 (C), 135.3 (C), 131.9 (CH), 127.3 (C), 116.3 (CH), 113.6 (CH), 111.7 (CH), 108.1 (CH), 74.3 ($CH_2$), 55.8 ($CH_3$), 41.1 (CH), 34.6 (2×$CH_2$), 34.0 (C), 27.3 ($CH_3$), 23.1 ($CH_3$), signals due to 2×C and 3×$CH_2$ obscured or overlapping.

IR $v_{max}$/cm$^{-1}$ 3400, 2927, 1512, 1258, 1200, 1045, 1013.

Mass Spectrum (EI) m/z 439 (M$^+$., 12), 290 (100).

HRMS found: M$^+$., 439.2107. $C_{24}H_{29}N_3O_5$ requires M$^+$., 439.2107.

VIII) Synthesis of Further Compounds (E)-6,7-Dimethoxy-3,4-dihydronaphthalen-1(2H)-one O-4-Nitrobenzyl Oxime (1-TB-39)

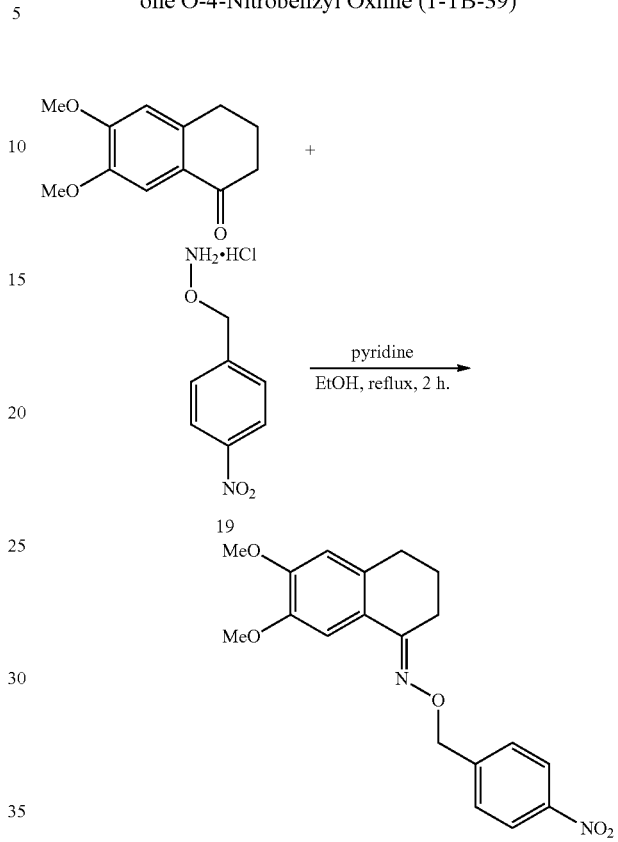

(4-Nitrobenzyl)hydroxylamine hydrochloride (119 mg, 0.58 mmol) and pyridine (0.5 mL, 6.45 mmol) were added to a magnetically stirred solution of 6,7-dimethoxy-1-tetralone (100 mg, 0.48 mmol) in ethanol (2 mL) and the ensuing mixture heated at reflux for 2 h. The cooled reaction mixture was concentrated under reduced pressure and the residue thus obtained partitioned between $CH_2Cl_2$ (5 mL) and water (5 mL). The separated aqueous layer was washed with $CH_2Cl_2$ (1×5 mL) and the combined organic extracts were then dried ($MgSO_4$), filtered and concentrated under reduced pressure. The ensuing residue was subjected to flash chromatography (3:7 v/v ethyl acetate/hexane elution) and concentration of the appropriate fractions gave the title compound (148 mg, 86%) as yellow crystals, m.p. 124-127° C., $R_f$ 0.3.

$^1$H NMR (300 MHz, CDCl$_3$) δ 8.22 (d, J 8.8 Hz, 2H), 7.56 (d, J 8.8 Hz, 2H), 7.45 (s, 1H), 6.60 (s, 1H), 5.34 (s, 2H), 3.87 (s, 6H), 2.78 (t, J 6.5 Hz, 2H), 2.70 (t, J 6.5 Hz, 2H), 1.86 (p, J 6.4 Hz, 2H).

$^{13}$C NMR (75 MHz, CDCl$_3$) δ 155.6, 150.7, 147.9, 147.6, 146.3, 133.7, 128.4, 123.8, 122.4, 111.0, 106.6, 74.8, 56.2, 56.1, 29.5, 24.5, 21.9.

IR $v_{max}$/cm$^{-1}$ 2935, 2835, 1601, 1510, 1464, 1344, 1286, 1255, 1220, 1153, 1068, 1035, 871, 791, 736.

EI MS m/z (70 eV) 356 (M$^+$., 100), 220 (48), 192 (42), 160 (22), 106 (33).

HRMS Found: M+., 356.1382. $C_{19}H_{20}N_2O_5$ requires M+., 356.1372.

(E)-5,6-Dimethoxy-2,3-dihydroinden-1-one O-4-Nitrobenzyl Oxime (1-TB-54)

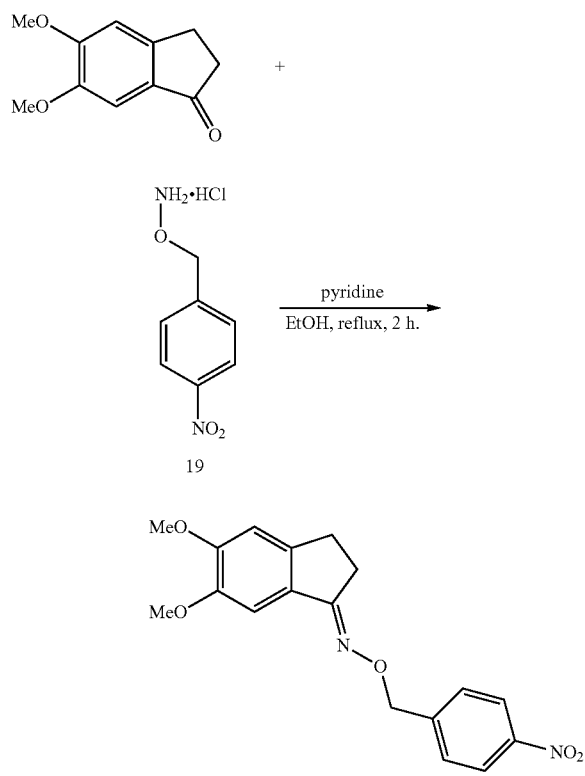

5,6-Dimethoxy-1-indanone (104 mg, 0.54 mmol) was subjected to reaction with (4-nitrobenzyl)hydroxylamine hydrochloride (125 mg, 0.61 mmol) in ethanol (5 mL) and pyridine (0.7 mL, 9.03 mmol) under the same conditions as described for (E)-6,7-dimethoxy-3,4-dihydronaphthalen-1(2H)-one O-4-nitrobenzyl oxime. Subjection of the material obtained on work up to flash chromatography (3:7 v/v ethyl acetate/hexane elution) afforded a ca. 3:1 mixture of the E- and Z-isomeric forms of the title compound (98 mg, 53%) as a pale-yellow crystalline solid, m.p. 139-144° C., $R_f$ 0.3.

$^1$H NMR (300 MHz, CDCl$_3$) δ 8.23 (d, J 8.2 Hz, 2H), 7.59 (d, J 8.2 Hz, 2H), 7.23 (s, 1H), 6.80 (s, 1H), 5.38 (s, 2H), 3.90 (s, 3H), 3.89 (s, 3H), 3.00 (m, 4H)

$^{13}$C NMR (75 MHz, CDCl$_3$) δ (major isomer) 164.9, 152.4, 149.2, 147.6, 146.4, 142.5, 128.3, 127.6, 123.9, 107.5, 103.5, 74.7, 56.3, 56.2, 28.7, 27.7.

IR $v_{max}$/cm$^{-1}$ 2929, 1696, 1603, 1518, 1466, 1344, 1262, 1215, 1135, 1044, 859, 735.

EI MS m/z (70 eV) 342 (M+., 100), 206 (96), 190 (24), 176 (93), 161 (23), 106 (23).

HRMS Found: M+., 342.1211. $C_{18}H_{18}N_2O_5$ requires M+., 342.1216

(E)-7-Hydroxy-6-methoxy-3,4-dihydronaphthalen-1 (2H)-one O-4-Nitrobenzyl Oxime (1-TB-76)

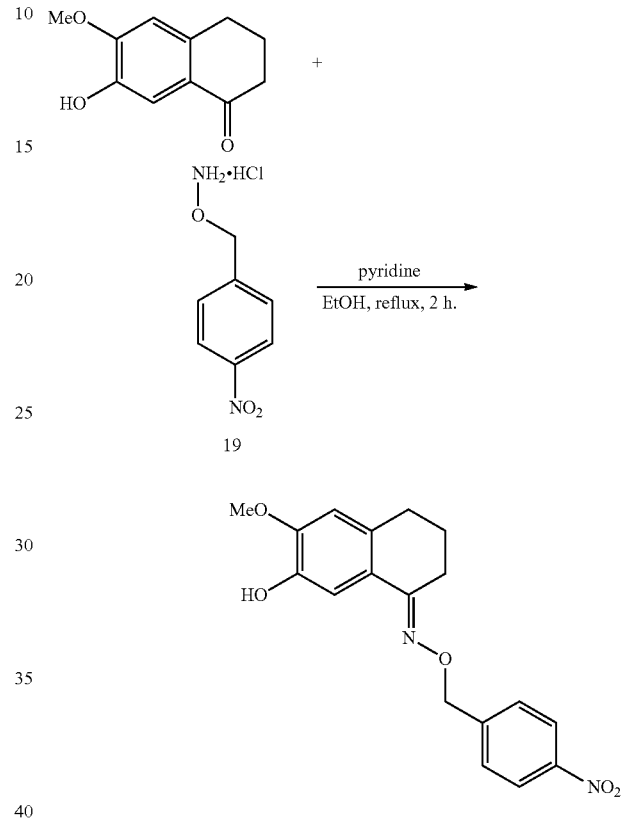

7-Hydroxy-6-methoxy-1-tetralone (105 mg, 0.55 mmol) was subjected to reaction with (4-nitrobenzyl)hydroxylamine hydrochloride (122 mg, 0.60 mmol) in ethanol (5 mL) and pyridine (0.5 mL, 6.45 mmol) under the same conditions as described for (E)-6,7-dimethoxy-3,4-dihydronaphthalen-1 (2R)-one O-4-nitrobenzyl oxime. The solid obtained on work up was recrystallised (isopropanol) to yield the title compound (103 mg, 55%) as off-white crystals, m.p. 125-127° C.

$^1$H NMR (300 MHz, CDCl$_3$) δ 8.21 (d, J 8.8 Hz, 2H), 7.54 (d, J 8.8 Hz, 2H), 7.46 (s, 1H), 6.57 (s, 1H), 5.28 (s, 2H), 3.88 (s, 3H), 2.75 (t, J 6.6 Hz, 2H), 2.67 (t, J 6.6 Hz, 2H), 1.84 (p, J 6.6 Hz, 2H), signal due to OH not observed.

$^{13}$C NMR (75 MHz, CDCl$_3$) δ 155.1, 148.1, 147.5, 146.5, 144.3, 132.8, 128.5, 123.8, 123.4, 110.4, 109.9, 74.8, 56.1, 29.6, 24.4, 21.9.

IR $v_{max}$/cm$^{-1}$ 2937, 1603, 1519, 1506, 1450, 1344, 1307, 1261, 1213, 1149, 1066, 1034, 860, 800, 736.

EI MS m/z (70 eV) 342 (M+., 75), 206 (23), 191 (81), 174 (18), 161 (22), 106 (23), 81 (53), 69 (100), 57 (38), 55 (40), 43 (45), 41 (55).

HRMS Found: M+., 342.1216. $C_{18}H_{18}N_2O_5$ requires M+., 342.1216

(E)-6-Hydroxy-5-methoxy-2,3-dihydroinden-1-one O-4-Nitrobenzyl Oxime (1-TB-81)

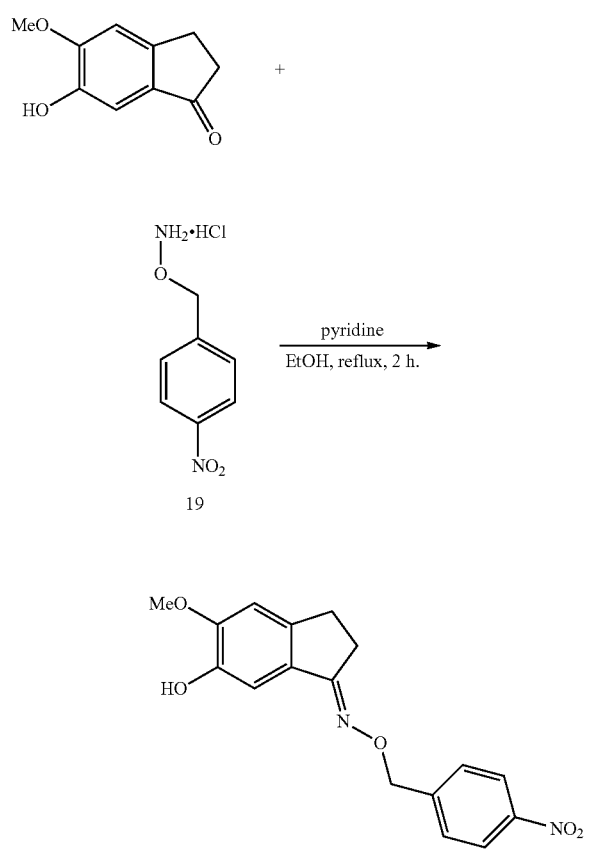

6-Hydroxy-5-methoxy-1-indanone (114 mg, 0.64 mmol) was subjected to reaction with (4-nitrobenzyl)hydroxylamine hydrochloride (149 mg, 0.73 mmol) in ethanol (5 mL) and pyridine (0.6 mL, 7.74 mmol) under the same conditions as described for (E)-6,7-dimethoxy-3,4-dihydronaphthalen-1(2H)-one O-4-nitrobenzyl oxime. The solid obtained on work up was recrystallized (isopropanol) to yield the title compound (101 mg, 48%) as off-white crystals, m.p. 146-149° C.

$^1$H NMR (300 MHz, CDCl$_3$) δ 8.21 (d, J 8.8 Hz, 2H), 7.56 (d, J 8.8 Hz, 2H), 7.19 (s, 1H), 6.77 (s, 1H), 5.28 (s, 2H), 3.91 (s, 3H), 2.95 (m, 4H), signal due to OH not observed.

$^{13}$C NMR (75 MHz, CDCl$_3$) δ 164.2, 149.7, 146.5, 145.6, 141.3, 128.6, 128.4, 123.8, 107.0, 106.8, 74.7, 56.2, 28.7, 27.4.

IR $v_{max}$/cm$^{-1}$ 2924, 2850, 1605, 1519, 1494, 1453, 1343, 1285, 1262, 1205, 1130, 1040, 915, 861, 832, 736.

EI MS m/z (70 eV) 328 (M+., 92), 192 (100), 162 (87), 147 (30), 106 (21), 69 (25).

HRMS Found: M+., 328.1060. $C_{17}H_{16}N_2O_5$ requires M+., 328.1059

7,8-Dimethoxy-2-(4-nitrophenyl)-4,5-dihydro-2H-benzo[g]indazole (2-TB-39)

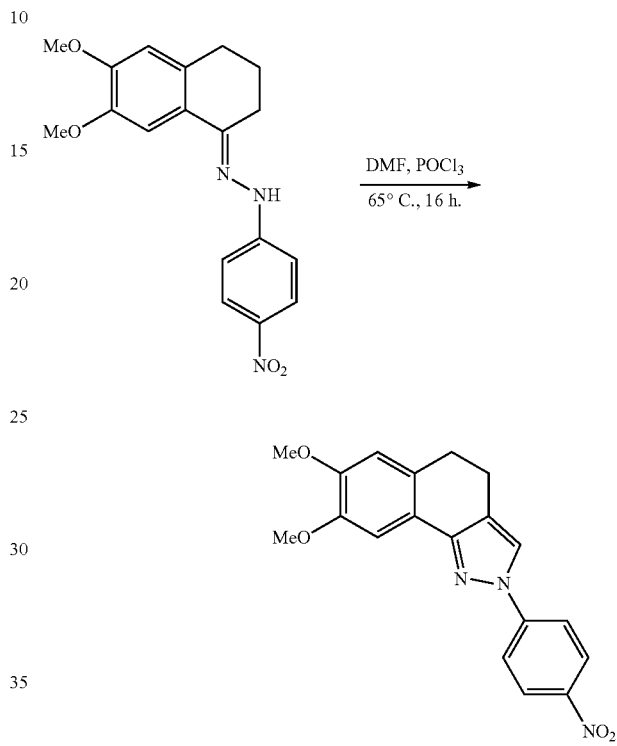

Phosphorous oxytrichloride (0.2 mL) was added, over a period of 0.5 h, to a magnetically solution of (E)-1-[6,7-dimethoxy-3,4-dihydronaphthalen-1(2H)-ylidene]-2-(4-nitro-phenyl)hydrazine (56 mg, 0.16 mmol) in DMF (5 mL) maintained at 0° C. under a nitrogen atmosphere. The ensuing mixture was allowed to warm to 18° C. and left stirring at this temperature for 1 h then heated to 65° C. and stirred at this temperature for a further 16 h. The hot reaction mixture was poured onto crushed ice and the crystals so-formed were collected by filtration. Recrystallisation (ethyl acetate/hexane) of this material then afforded the title compound (31 mg, 54%) as orange crystals, m.p. 150° C. (with decomposition).

$^1$H NMR (300 MHz, CDCl$_3$) δ 8.33 (d, J 9.2 Hz, 2H), 7.83 (d, J 9.2 Hz, 2H), 7.79 (s, 1H), 7.51 (s, 1H), 6.78 (s, 1H), 3.99 (s, 3H), 3.92 (s, 3H), 2.91 (complex m, 4H).

$^{13}$C NMR (75 MHz, CDCl$_3$) δ 150.7, 148.4, 147.1, 143.6, 143.5, 129.3, 124.4, 122.5, 119.9, 119.2, 116.6, 110.5, 104.8, 55.1, 54.9, 27.8, 18.4.

IR $v_{max}$/cm$^{-1}$ 2936, 1593, 1505, 1490, 1364, 1330, 1276, 1239, 1180, 1110, 1047, 943, 852, 793, 749.

EI MS m/z (70 eV) 351 (M+., 100), 336 (9), 321 (15), 262 (15).

HRMS Found: M+., 351.1223. $C_{19}H_{17}N_3O_4$ requires M+., 351.1219.

(E)-6,7-Dimethoxy-3,4-dihydronaphthalen-1(2H)-one O-Benzo[c][1,2,5]oxadiazol-5-ylmethyl oxime (2-TB-141)

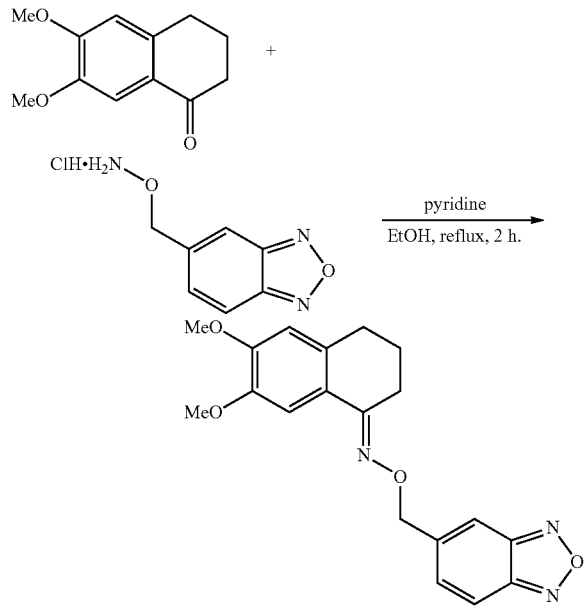

6,7-Dimethoxy-1-tetralone (40 mg, 0.19 mmol) was subjected to reaction with 0-(benzo[c][1,2,5]oxadiazol-5-ylmethyl)hydroxylamine hydrochloride (41 mg, 0.20 mmol) in ethanol (2 mL) and pyridine (0.2 mL, 2.58 mmol) under the same conditions as described for (E)-6,7-dimethoxy-3,4-dihydronaphthalen-1(2H)-one O-4-nitrobenzyl oxime. Subjection of the material obtained on work up to flash chromatography (3:7 v/v ethyl acetate/hexane elution) afforded the title compound as white crystals (60 mg, 88%), m.p. 139-140° C., $R_f$ 0.4.

$^1$H NMR (300 MHz, CDCl$_3$) δ 7.81 (d, J 9 Hz, 1H), 7.78 (s, 1H), 7.42 (d, J 9 Hz, 1H), 7.40 (s, 1H), 6.59 (s, 1H), 5.28 (s, 2H), 3.87 (s, 3H), 3.86 (s, 3H), 2.80 (t, J 6 Hz, 2H), 2.69 (t, J 6 Hz, 2H), 1.86 (p, J 6 Hz, 2H).

$^{13}$C NMR (75 MHz, CDCl$_3$) δ 155.6, 150.6, 149.5, 149.1, 147.8, 143.1, 133.6, 132.1, 122.5, 116.6, 113.5, 111.0, 106.5, 75.0, 56.2, 29.5, 24.5, 21.9.

IR $v_{max}$/cm$^{-1}$ 2937, 1592, 1364, 1255, 1220, 1036.

EI MS m/z (70 eV) 353 (M+., 100) 220 (59), 41 (89).

HRMS Found: M+., 353.1377. $C_{19}H_{19}N_3O_4$ requires M+. 353.1376.

(E)-5,6-Dimethoxy-2,3-dihydro-1H-inden-1-one O-Benzo[c][1,2,5]oxadiazol-5-ylmethyl oxime (2-TB-142)

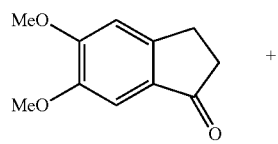

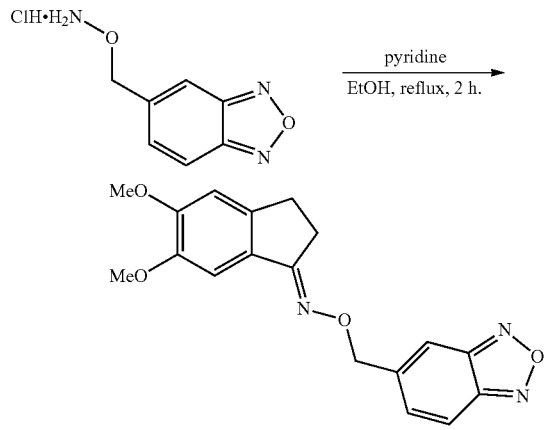

5,6-Dimethoxy-1-indanone (38 mg, 0.19 mmol) was subjected to reaction with O-(benzo[c][1,2,5]oxadiazol-5-ylmethyl)hydroxylamine hydrochloride (39 mg, 0.19 mmol) in ethanol (2 mL) and pyridine (0.2 mL, 2.58 mmol) under the same conditions as described for (E)-6,7-dimethoxy-3,4-dihydronaphthalen-1(2H)-one O-4-nitrobenzyl oxime. Subjection of the material obtained on work up to flash chromatography (3:7 v/v ethyl acetate/hexane elution) afforded the title compound as off-white crystals (55 mg, 82%), m.p. 163-166° C., $R_f$ 0.4.

$^1$H NMR (300 MHz, CDCl$_3$) δ 7.80 (d, J 9 Hz, 1H), 7.78 (s, 1H), 7.43 (d, J 9 Hz, 1H), 7.07 (s, 1H), 6.78 (s, 1H), 5.25 (s, 2H), 3.89 (s, 3H), 3.87 (s, 3H), 2.98 (complex m, 4H).

$^{13}$C NMR (75 MHz, CDCl$_3$) δ 164.8, 152.3, 149.5, 149.2, 143.2, 142.3, 132.0, 127.8, 116.6, 113.5, 107.5, 103.3, 74.9, 56.3, 28.7, 27.6.

IR $v_{max}$/cm$^{-1}$ 2924, 1608, 1507, 1332, 1214, 1047.

EI MS m/z (70 eV) 339 (M+., 69) 206 (100), 176 (80).

HRMS Found: M+. 339.1220. $C_{18}H_{17}N_3O_4$ requires M+. 339.1219.

(E)-7-Hydroxy-6-methoxy-3,4-dihydronaphthalen-1(2H)-one O-benzo[c][1,2,5]oxadiazol-5-ylmethyl oxime (2-TB-146)

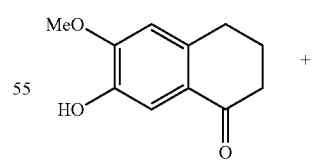

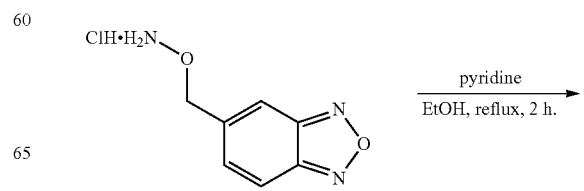

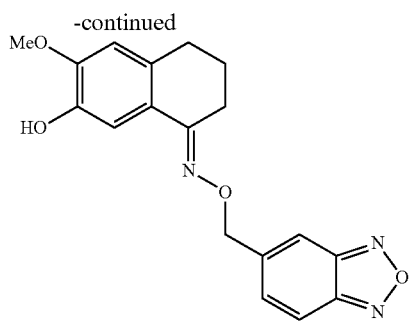

7-Hydroxy-6-methoxy-1-tetralone (83 mg, 0.43 mmol) was subjected to reaction with O-(benzo[c][1,2,5]oxadiazol-5-ylmethyl)hydroxylamine hydrochloride (96 mg, 0.48 mmol) in ethanol (2 mL) and pyridine (0.2 mL, 2.58 mmol) under the same conditions as described for (E)-6,7-dimethoxy-3,4-dihydronaphthalen-1(2H)-one O-4-nitrobenzyl oxime. Subjection of the material obtained on work up to flash chromatography (3:7 v/v ethyl acetate/hexane elution) afforded the title compound as off-white crystals (13 mg, 9%), m.p. 138° C. (with decomposition), $R_f$ 0.4.

$^1$H NMR (300 MHz, CDCl$_3$) δ 7.81 (d, J 9 Hz, 1H), 7.79 (s, 1H), 7.47 (d, J 9 Hz, 1H), 7.45 (s, 1H), 6.58 (s, 1H), 5.44 (s, 1H), 5.28 (s, 2H), 3.89 (s, 3H), 2.78 (t, J 6 Hz, 2H), 2.68 (t, J 6 Hz, 2H), 1.86 (p, J 6 Hz, 2H).

$^{13}$C NMR (75 MHz, CDCl$_3$) δ 155.3, 149.5, 149.1, 148.2, 144.3, 143.1, 132.8, 132.2, 123.4, 116.5, 113.7, 110.3, 109.9, 75.0, 56.1, 29.6, 24.5, 21.9.

IR $v_{max}$/cm$^{-1}$ 3427, 2930, 1627, 1509, 1442, 1292, 1035.

ESI MS m/z 362 ([M+Na]$^+$, 24), 340 ([M+H]$^+$, 40), 207 (50), 55 (100).

HRMS Found: [M+H]$^+$ 340.129916. C$_{18}$H$_{17}$N$_3$O$_4$ requires [M+H]$^+$ 340.129196.

(E)-6-Hydroxy-5-methoxy-2,3-dihydro-1H-inden-1-one O-benzo[c][1,2,5]oxadiazol-5-ylmethyl oxime (2-TB-147)

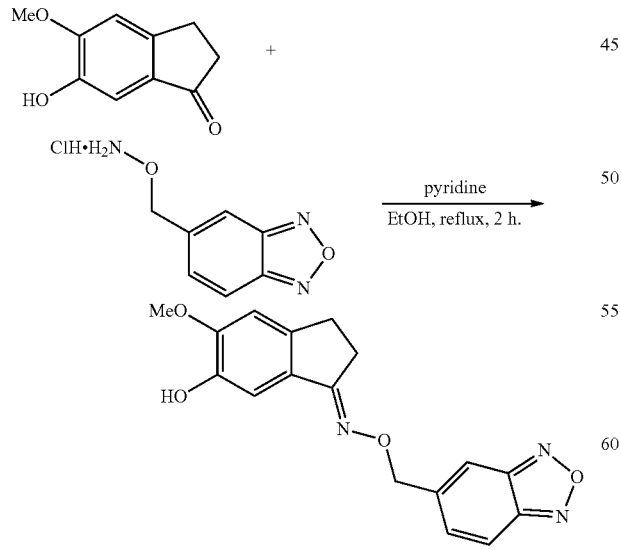

6-Hydroxy-5-methoxy-1-indanone (76 mg, 0.43 mmol) was subjected to reaction with O-(benzo[c][1,2,5]oxadiazol-5-ylmethyl)hydroxylamine hydrochloride (97 mg, 0.48 mmol) in ethanol (2 mL) and pyridine (0.2 mL, 2.58 mmol) under the same conditions as described for (E)-6,7-dimethoxy-3,4-dihydronaphthalen-1(2H)-one O-4-nitrobenzyl oxime. Subjection of the material obtained on work up to flash chromatography (3:7 v/v ethyl acetate/hexane elution) afforded the title compound as off-white crystals (13 mg, 9%), m.p. 145° C. (with decomposition), $R_f$ 0.3.

$^1$H NMR (300 MHz, CDCl$_3$) δ 7.81 (d, J 9 Hz, 1H), 7.79 (s, 1H), 7.45 (d, J 9 Hz, 1H), 7.17 (s, 1H), 6.78 (s, 1H), 5.59 (s, 1H), 5.25 (s, 2H), 3.92 (s, 3H), 2.98 (complex m, 4H).

$^{13}$C NMR (75 MHz, DMSO-d$_6$) δ 164.4, 151.7, 149.6, 149.3, 146.9, 144.9, 141.1, 133.6, 127.8, 116.8, 113.1, 108.9, 107.1, 74.5, 56.3, 28.6, 27.7.

IR $v_{max}$/cm$^{-1}$ 3256, 3018, 2937, 1660, 1623, 1519, 1464, 1342, 1217, 1110.

EI MS m/z (70 eV) 325 (M$^+$., 57) 192 (100), 162 (77).

HRMS Found: M$^+$. 325.1063. C$_{17}$H$_{15}$N$_3$O$_4$ requires M$^+$. 325.1063.

Preparation of 6-(Benzo[c][1,2,5]oxadiazol-5-yl)methoxyamine hydrochloride

This compound is used a starting material in preparing certain compounds according to the present invention.

(Benzo[c][1,2,5]oxadiazol-5-yl)methoxyphthalimide

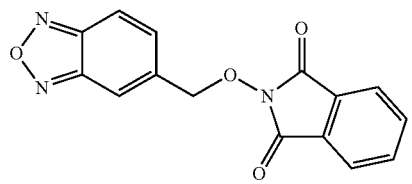 [SMILES: O=C1c2ccccc2C(=O)N1OCc1ccc2nonc2c1]

5-(Bromomethyl)benzo[c][1,2,5]oxadiazole (0.441 g, 2.07 mmol) was added to a solution of N-hydroxyphthalimide (0.336 g, 2.06 mmol) in dry tetrahydrofuran (15 ml). N,N-Diisopropylethylamine (0.519 g, 4.02 mmol) was added and the solution was stirred at reflux under nitrogen for 23 h and cooled to room temperature. The suspension was concentrated in vacuo to a pale beige solid. This was diluted with water and filtered. The residue was washed with plenty of water and dried under vacuum to give (benzo[c][1,2,5]oxadiazol-5-yl)methoxyphthalimide (0.571 g, 94%).

Rf~0.50 (100% dichloromethane)

$^1$H nmr (CDCl$_3$): δ 5.30 (s, 2H); 7.75-7.78 (m, 3H); 7.83-7.85 (m, 2H); 7.91 (d, J 1.46 Hz, 1H); 7.92 (d, J 9.8 Hz, 1H).

(Benzo[c][1,2,5]oxadiazol-5-yl)methoxyamine hydrochloride

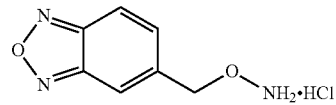

Concentrated hydrochloric acid (2 ml) was added to a suspension of (benzo[c][1,2,5]oxadiazol-5-yl)methoxyphthalimide (0.571 g, 1.94 mmol) in ethanol (15 ml). The suspension was stirred at reflux for 18 h and allowed to cool down slightly before water was added. The aqueous phase was washed with chloroform (×3), then concentrated to give (benzo[c][1,2,5]oxadiazol-5-yl)methoxyamine hydrochloride as an off-white solid (0.390 g, 99%).

¹H nmr (d6-DMSO): δ 5.15 (s, 2H); 7.61 (dd, J 9.3, 1.4 Hz, 1H); 8.09 (t, J 1.0 Hz, 1H); 8.11 (d, J 9.3, 1.0 Hz, 1H).

MS ESI +ve: M⁺+H, 166.1.

1-(3-hydroxy-4-methoxyphenyl)ethanone-O-[(benzo [c][1,2,5]oxadiazol-5-yl)methyl]oxime (CP 9-33)

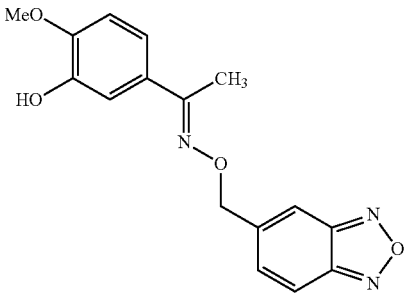 [SMILES: COc1ccc(/C(C)=N/OCc2ccc3nonc3c2)cc1O]

A solution of 3-hydroxy-4-methoxyacetophenone (0.070 g, 0.421 mmol), (benzo[c][1,2,5]oxadiazol-5-yl)methoxyamine hydrochloride (0.126 g, 0.625 mmol) and pyridine (0.16 ml, 1.98 mmol) in ethanol (6 ml) was stirred at reflux under nitrogen for 4 h and cooled to room temperature. The solution was concentrated to a yellow oil which was diluted with water. The resultant suspension was extracted with dichloromethane (×3). The combined organic phases were washed with water, dried over magnesium sulphate, filtered and concentrated to a yellow oil. The crude product was purified by column chromatography (SiO₂), eluting with 8:2 petrol/ethyl acetate, to give a slightly sticky solid which was further triturated with petroleum spirit (40-60°), to give 1-(3-hydroxy-4-methoxyphenyl)ethanone-O -[(benzo[c][1,2,5] oxadiazol-5-yl)methyl]oxime (CP9-33) as a light yellow solid (0.119 g, 90%).

Rf~0.38 (7:3 petroleum spirit (40-60°)/ethyl acetate).

¹H nmr (CDCl₃): δ2.29 (s, 3H); 3.91 (s, 3H); 5.28 (s, 2H); 5.60 (s, 1H); 6.82 (d, J 8.6 Hz, 1H); 7.13 (dd, J 8.4, 2.1 Hz, 1H); 7.25 (d, J 2.1 Hz, 1H); 7.44 (dd, J 9.4, 1.1 Hz, 1H); 7.79 (d, J 1.1 Hz, 1H); 7.81 (d, J 9.7 Hz, 1H).

MS ESI +ve: M⁺+H, 314.3.

MS ESI –ve: M⁺–H, 312.3 m.p. 77-78° C.

3-O-(Ethoxycarbonylmethyl)-2-methoxy-6-[(4-nitrobenzyloxy)imino]estradiol (CP8-133)

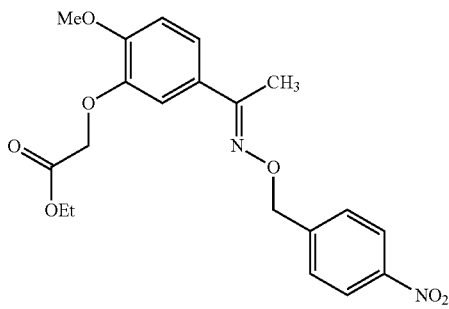 [SMILES: CCOC(=O)COc1cc(/C(C)=N/OCc2ccc([N+](=O)[O-])cc2)ccc1OC]

Anhydrous potassium carbonate (0.486 g, 3.52 mmol) was added to a solution of CP30218 (0.151 g, 0.477 mmol) in acetonitrile (20 ml). Ethyl bromoacetate (0.0525 ml, 0.474 mmol) was added. The suspension was stirred at reflux under nitrogen for 4 h and cooled to room temperature. Water (~20 ml) was added and the mixture was extracted with ethyl acetate (×3). The combined organic extracts were washed with water (×1) and brine (×1), dried over magnesium sulphate, filtered and concentrated to an orange oil. This was purified by column chromatography (silica), eluting with 8:2 petroleum spirit (40-60°)/ethyl acetate to give a yellow oil which, after further drying under high vacuum, gave CP8-133 as a yellow solid (0.116 g, 60%).

Rf~0.16 (8:2 petrol/ethyl acetate).

¹H nmr (CDCl₃): δ 1.26 (t, J 7.0 Hz, 3H); 2.26 (s, 3H); 3.90 (s, 3H); 4.24 (q, J 7.0 Hz, 2H); 4.69 (s, 2H); 5.30 (s, 2H); 6.87 (d, J 9.1 Hz, 1H); 7.19-7.22 (m, 2H); 7.54 (d, J 8.4 Hz, 2H); 8.22 (d, J 8.7 Hz, 1H).

MS ESI +ve: M⁺+H, 403.3 m.p. 62-63° C.

3'-Fluoro-4'-methoxyacetophenone-O-3,4-difluorobenzyloxime (CP9-126)

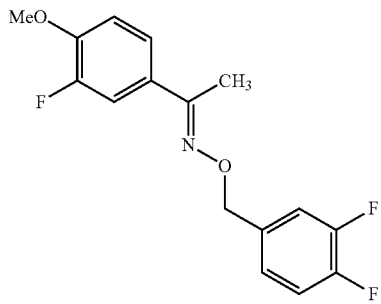 [SMILES: COc1ccc(/C(C)=N/OCc2ccc(F)c(F)c2)cc1F]

A solution of 3-fluoro-4-methoxyacetophenone (0.054 g, 0.319 mmol), O-(3,4-difluorobenzyl)hydroxylamine hydrochloride (0.089 g, 0.452 mmol) and pyridine (0.12 ml, 1.48 mmol) in ethanol (5 ml) was stirred at reflux under nitrogen for 4 h and cooled to room temperature. The solution was concentrated to a pale yellow oil which was diluted with water. The suspension was extracted with dichloromethane (×3). The combined organic phases were washed with water and brine, dried over magnesium sulphate, filtered and concentrated to a white solid. The crude product was purified by column chromatography (SiO₂), eluting with 9:1 petrol/ethyl acetate, to give 3'-fluoro-4'-methoxyacetophenone-O-3,4-difluorobenzyloxime (CP9-126) as a white solid (0.090 g, 91%), m.p. 62-63°.

Rf~0.82 (7:3 petrol/ethyl acetate).

¹H nmr (CDCl₃): δ2.22 (s, 3H); 3.90 (s, 3H); 5.14 (s, 2H); 6.93 (apparent t, J 8.6 Hz, 1H); 7.10-7.17 (m, 2H); 7.22 (ddd, J 10.7, 7.7, 1.9 Hz, 1H); 7.33 (apparent dt, J 8.6, 1.3 Hz, 1H); 7.43 (dd, J 12.7, 1.2 Hz, 1H).

MS ESI +ve: M⁺+H, 310.2.

3'-Fluoro-4'-methoxyacetophenone-O—[(benzo[c][1,2,5]oxadiazol-5-yl)methyl]oxime (CP9-121)

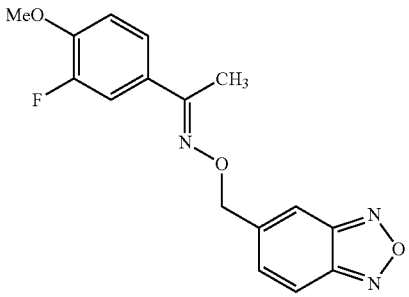 [SMILES: COc1ccc(/C(C)=N/OCc2ccc3nonc3c2)cc1F]

A solution of 3-fluoro-4-methoxyacetophenone (0.062 g, 0.369 mmol), (benzo[c][1,2,5]oxadiazol-5-yl)methoxyamine hydrochloride (0.114 g, 0.563 mmol) and pyridine (0.14 ml, 1.73 mmol) in ethanol (5 ml) was stirred at reflux under nitrogen for 4 h and cooled to room temperature. The solution was concentrated to a white solid which was diluted with water. The resultant suspension was extracted with dichloromethane (×3). The combined organic phases were washed with water, dried over magnesium sulphate, filtered and concentrated to a white solid. The crude product was purified by column chromatography (SiO$_2$), eluting with 9:1 petrol/ethyl acetate, to give 3'-fluoro-4'-methoxyacetophenone-β-[(benzo[c][1,2,5]oxadiazol-5-yl)methyl]oxime (CP9-121) as a white solid (0.099 g, 85%), m.p. 111-112°.

Rf~0.60 (7:3 petrol/ethyl acetate).

$^1$H nmr (CDCl$_3$): δ2.28 (s, 3H); 3.90 (s, 3H); 5.28 (d, J 0.8 Hz, 2H); 6.93 (apparent t, J 8.6 Hz, 1H); 7.33 (apparent dt, J 8.6, 1.6 Hz, 1H); 7.40-7.45 (m, 2H); 7.78 (brs, 1H); 7.82 (d, J 9.4 Hz, 1H).

MS ESI +ve: M$^+$+H, 316.2.

3'-Fluoro-4'-methoxyacetophenone-O-4-nitrobenzyloxime (CP9-123)

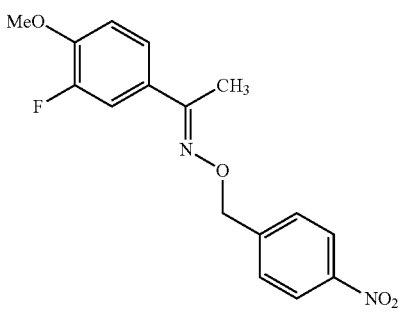 [SMILES: COc1ccc(/C(C)=N/OCc2ccc([N+](=O)[O-])cc2)cc1F]

A solution of 3-fluoro-4-methoxyacetophenone (0.064 g, 0.380 mmol), O-(4-nitrobenzyl)hydroxylamine hydrochloride (0.111 g, 0.552 mmol) and pyridine (0.14 ml, 1.73 mmol) in ethanol (7 ml) was stirred at reflux under nitrogen for 4 h and cooled to room temperature. The solution was concentrated to a yellow oil which was diluted with water/dichloromethane. The suspension was extracted with dichloromethane (×3). The combined organic phases were washed with water and brine, dried over magnesium sulphate, filtered and concentrated to a yellow oil. The crude product was purified by column chromatography (SiO$_2$), eluting with 9:1 petrol/ethyl acetate, to give a yellow oil which was triturated with petrol, and the resultant off white solid was further washed with petrol to give 3'-fluoro-4'-methoxyacetophenone-O-4-nitrobenzyloxime (CP9-123) as a white solid (0.079 g, 65%), m.p. 67-68°.

Rf~0.64 (7:3 petrol/ethyl acetate).

$^1$H nmr (CDCl$_3$): δ2.26 (s, 3H); 3.90 (s, 3H); 5.30 (s, 2H); 6.92 (apparent t, J 8.6 Hz, 1H); 7.32 (apparent dt, J 8.6, 1.6 Hz, 1H); 7.42 (dd, J 12.6, 2.1 Hz, 1H); 7.54 (d, J 8.6 Hz, 2H); 8.22 (d, J 8.6 Hz, 1H).

MS ESI +ve: M$^+$+H, 319.2.

3'-Fluoro-4'-methoxyacetophenone-O-3-fluorobenzyloxime (CP9-125)

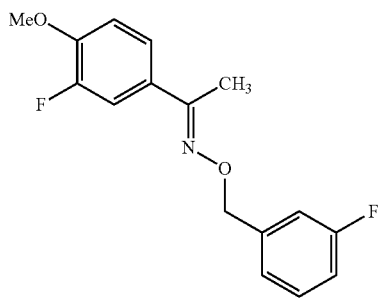 [SMILES: COc1ccc(/C(C)=N/OCc2cccc(F)c2)cc1F]

A solution of 3-fluoro-4-methoxyacetophenone (0.063 g, 0.377 mmol), O-(3-fluorobenzyl)hydroxylamine hydrochloride (0.100 g, 0.569 mmol) and pyridine (0.14 ml, 1.73 mmol) in ethanol (5 ml) was stirred at reflux under nitrogen for 4 h and cooled to room temperature. The solution was concentrated to a pale yellow oil which was diluted with water. The suspension was extracted with dichloromethane (×3). The combined organic phases were washed with water and brine, dried over magnesium sulphate, filtered and concentrated to a white solid. The crude product was purified by column chromatography (SiO$_2$), eluting with 95:5 petrol/ethyl acetate, to give 3'-fluoro-4'-methoxyacetophenone-O-3-fluorobenzyloxime (CP9-126) as a white solid (0.099 g, 90%), m.p. 67°.

Rf~0.82 (7:3 petrol/ethyl acetate).

$^1$H nmr (CDCl$_3$): δ2.23 (s, 3H); 3.90 (s, 3H); 5.20 (s, 2H); 6.92 (apparent t, J 8.6 Hz, 1H); 6.99 (apparent td, J 10.2, 2.5 Hz, 2H); 7.11 (brd, J 9.7 Hz, 1H); 7.16 (brd, J 7.6 Hz, 1H); 7.29-7.35 (m, 2H); 7.44 (d, J 12.9, 1.1 Hz, 1H).

MS ESI +ve: M$^+$+H, 292.2.

4'-Fluoro-3'-hydroxyacetophenone-O—[(benzo[c][1,2,5]oxadiazol-5-yl)methyl]oxime (CP9-135)

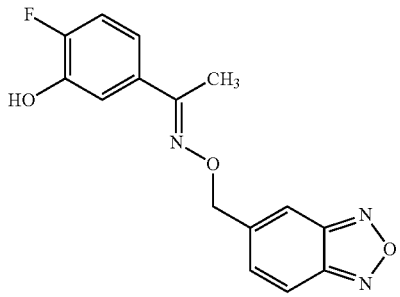 [SMILES: C/C(=N\OCc1ccc2nonc2c1)c1ccc(F)c(O)c1]

A solution of 4-fluoro-3-hydroxyacetophenone (0.041 g, 0.263 mmol), (benzo[c][1,2,5]oxadiazol-5-yl)methoxyamine hydrochloride (0.047 g, 0.232 mmol) and pyridine (0.09 ml, 1.11 mmol) in ethanol (5 ml) was stirred at reflux under nitrogen for 4 h and cooled to room temperature. The solution was concentrated to a yellow oil which was diluted with water/dichloromethane. The resultant mixture was extracted with dichloromethane (×3). The combined organic phases were washed with water and brine, dried over magnesium sulphate, filtered and concentrated to a pale yellow solid. The crude product was purified by column chromatography (SiO$_2$), eluting with 8:2 petrol/ethyl acetate, to give 3'-fluoro-4'-hydroxyacetophenone-O-[(benzo[c][1,2,5]oxadiazol-5-yl)methyl]oxime (CP9-135) as a light orange solid (0.050 g, 72%), m.p. 125-126°.

Rf~0.61 (7:3 petrol/ethyl acetate).

$^1$H nmr (CDCl$_3$): δ2.29 (s, 3H); 5.19 (d, J 4.0 Hz, 1H); 5.29 (d, J 1.0 Hz, 1H); 7.05 (dd, J 10.5, 9.4 Hz, 1H); 7.13 (ddd, J 9.4, 7.0, 2.1 Hz, 1H); 7.31 (dd, J 8.5, 2.1 Hz, 1H); 7.43 (dd, J 9.4, 1.1 Hz, 1H); 7.78 (apparent pentet, J 1.2 Hz, 1H); 7.82 (dd, J 9.5, 1.0 Hz, 1H).

MS ESI +ve: M$^+$+H, 302.2.

MS ESI −ve: M$^+$−H, 300.1.

4-Fluoro-3-hydroxyacetophenone

A suspension of 4-fluoro-3-methoxyacetophenone (0.316 g, 1.88 mmol) in 48% hydrobromic acid (10 ml) was stirred at reflux under nitrogen for 16 h. After cooling to room temperature, the suspension was poured over crushed ice and extracted with dichloromethane (×3). The combined organic extracts were washed with water (×2), dried over magnesium sulphate, filtered and concentrated to an orange oil. The crude product was purified by column chromatography (SiO$_2$), eluting with 9:1 petrol/ethyl acetate to give a 4-fluoro-3-hydroxyacetophenone as an orange solid (0.041 g, 14.0%).

Rf~0.33 (7:3 petrol/ethyl acetate).

$^1$H nmr (CDCl$_3$): δ2.57 (s, 3H); 5.35 (d, J 4.0 Hz, 1H); 7.15 (dd, J 10.0, 8.3 Hz, 1H); 7.30 (ddd, J 8.4, 4.7, 2.1 Hz, 1H); 7.63 (dd, J 8.5, 2.1 Hz, 1H).

MS ESI +ve: M$^+$+H, 155.0.

MS ESI −ve: M$^+$−H, 152.9.

3'-Fluoro-4'-hydroxyacetophenone-O-[(benzo[c][1,2,5]oxadiazol-5-yl)methyl]oxime (CP9-128)

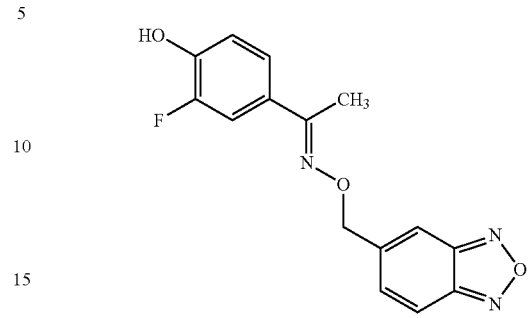

A solution of 3-fluoro-4-hydroxyacetophenone (0.061 g, 0.398 mmol), (benzo[c][1,2,5]oxadiazol-5-yl)methoxyamine hydrochloride (0.095 g, 0.470 mmol) and pyridine (0.13 ml, 1.61 mmol) in ethanol (5 ml) was stirred at reflux under nitrogen for 4 h and cooled to room temperature. The solution was concentrated to a pale yellow oil which was diluted with water. The resultant suspension was extracted with dichloromethane (×3). The combined organic phases were washed with water and brine, dried over magnesium sulphate, filtered and concentrated to an off-white solid. The crude product was purified by column chromatography (SiO$_2$), eluting with 9:1 petrol/ethyl acetate, to give a pale beige solid which was further washed with petrol/dichloromethane to give 3'-fluoro-4'-hydroxyacetophenone-O-[(benzo[c][1,2,5]oxadiazol-5-yl)methyl]oxime (CP9-128) as a pale beige solid (0.098 g, 82%), m.p. 139-140°.

Rf~0.57 (7:3 petrol/ethyl acetate).

$^1$H nmr (CDCl$_3$): δ2.28 (s, 3H); 5.28 (d, J 1.0 Hz, 2H); 5.30 (d, J 4.0 Hz, 1H); 6.97 (apparent t, J 8.7 Hz, 1H); 7.30 (ddd, J 8.1, 1.6, 1.0 Hz, 1H); 7.42 (dd, J 11.8, 1.7 Hz, 1H); 7.42 (dd, J 9.3, 1.2 Hz, 1H); 7.78 (apparent pentet, J 1.0 Hz 1H); 7.82 (dd, J 9.2, 1.0 Hz, 1H).

MS ESI +ve: M$^+$+H, 302.1.

MS ESI −ve: M$^+$−H, 300.1.

4'-Fluoro-3'-methoxyacetophenone-O-[(benzo[c][1,2,5]oxadiazol-5-yl)methyl]oxime (CP9-129)

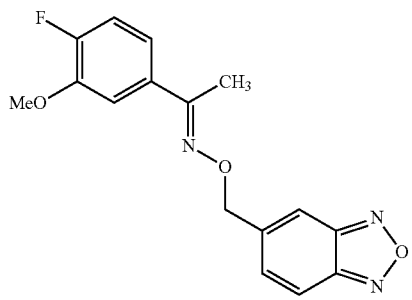 [SMILES: COc1cc(/C(C)=N/OCc2ccc3nonc3c2)ccc1F]

A solution of 4-fluoro-3-methoxyacetophenone (0.056 g, 0.332 mmol), (benzo[c][1,2,5]oxadiazol-5-yl)methoxyamine hydrochloride (0.072 g, 0.359 mmol) and pyridine (0.10 ml, 1.24 mmol) in ethanol (5 ml) was stirred at reflux under nitrogen for 4 h and cooled to room temperature. The solution was concentrated to a pale yellow oil which was diluted with dichloromethane/water. The resultant mixture was extracted with dichloromethane (×3). The combined organic phases were washed with water and brine, dried over magnesium sulphate, filtered and concentrated to a white solid. The crude product was purified by column chromatography (SiO$_2$), eluting with 9:1 petrol/ethyl acetate, to give a 4'-fluoro-3'-methoxyacetophenone-O-[(benzo[c][1,2,5]oxadiazol-5-yl)methyl]oxime (CP9-129) as a white solid (0.078 g, 74%), m.p. 65°.

Rf~0.61 (7:3 petrol/ethyl acetate).

$^1$H nmr (CDCl$_3$): δ2.31 (s, 3H); 3.90 (s, 3H); 5.31 (d, J 1.5 Hz, 2H); 7.06 (dd, J 10.8, 8.5 Hz, 1H); 7.13 (ddd, J 8.5, 4.0, 2.0 Hz, 1H); 7.29 (dd, J 8.2, 2.1 Hz, 1H); 7.43 (dd, J 9.3, 1.4 Hz, 1H); 7.80 (m, 1H); 7.83 (dd, J 9.3, 1.2 Hz, 1H).

MS ESI +ve: M$^+$+H, 316.2.

3',4'-Difluoroacetophenone-O—[(benzo[c][1,2,5]oxadiazol-5-yl)methyl]oxime (CP9-131)

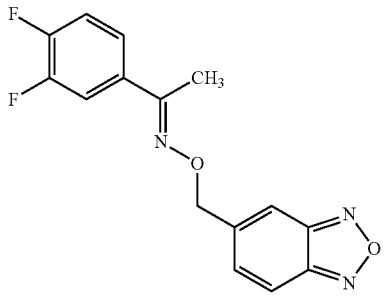 [SMILES: C/C(=N\OCc1ccc2nonc2c1)c1ccc(F)c(F)c1]

A solution of 3,4-difluoroacetophenone (0.073 g, 0.468 mmol), (benzo[c][1,2,5]oxadiazol-5-yl)methoxyamine hydrochloride (0.118 g, 0.586 mmol) and pyridine (0.15 ml, 1.85 mmol) in ethanol (5 ml) was stirred at reflux under nitrogen for 4 h and cooled to room temperature. The solution was concentrated to a pale yellow oil which was diluted with dichloromethane/water. The resultant mixture was extracted with dichloromethane (×3). The combined organic phases were washed with water and brine, dried over magnesium sulphate, filtered and concentrated to a white solid. The crude product was purified by column chromatography (SiO$_2$), eluting with 9:1 petrol/ethyl acetate, to give a 3',4'-difluoroacetophenone-β-[(benzo[c][1,2,5]oxadiazol-5-yl)methyl]oxime (CP9-131) as a white solid (0.124 g, 88%), m.p. 67-68°.

Rf~0.69 (7:3 petrol/ethyl acetate).

$^1$H nmr (CDCl$_3$): δ2.30 (s, 3H); 5.30 (d, J 1.2 Hz, 1H); 7.15 (m, 1H); 7.35 (m, 1H); 7.42 (dd, J 9.4, 1.1 Hz, 1H); 7.49 (ddd, J 12.0, 7.6, 2.1 Hz, 1H); 7.79 (brs, 1H); 7.83 (d, J 9.3 Hz, 1H).

3'-Fluoro-4'-hydroxyacetophenone-O-4-nitrobenzyloxime (CP9-132)

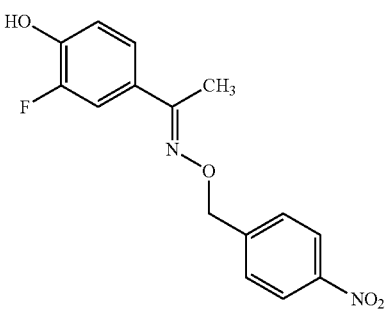 [SMILES: C/C(=N\OCc1ccc([N+](=O)[O-])cc1)c1ccc(O)c(F)c1]

A solution of 3'-fluoro-4'-hydroxyacetophenone (0.063 g, 0.411 mmol), O-(4-nitrobenzyl)hydroxylamine hydrochloride (0.100 g, 0.491 mmol) and pyridine (0.13 ml, 1.61 mmol) in ethanol (5 ml) was stirred at reflux under nitrogen for 5h and cooled to room temperature. The solution was concentrated to a pale yellow oil which was diluted with dichloromethane/water. The resultant mixture was extracted with dichloromethane (×3). The combined organic phases were washed with water and brine, dried over magnesium sulphate, filtered and concentrated to an off-white solid. The crude product was purified by column chromatography (SiO$_2$), eluting with 8:2 petrol/ethyl acetate, to give a 3'-fluoro-4'-hydroxyacetophenone-O-4-nitrobenzyloxime (CP9-132) as light yellow solid (0.081 g, 65%), m.p. 93-94°.

Rf~0.53 (7:3 petrol/ethyl acetate).

$^1$H nmr (CDCl$_3$): δ2.25 (s, 3H); 5.27 (d, J 4.0 Hz, 1H); 5.30 (s, 1H); 6.98 (apparent t, J 8.7 Hz, 1H); 7.30 (ddd, J 8.5, 2.2, 1.2 Hz, 1H); 7.41 (d, J 12.0, 2.0 Hz, 1H); 7.54 (d, J 9.0, 2H); 8.22 (d, J 8.7 Hz, 2H).

MS ESI +ve: M$^+$+H, 305.2.

MS ESI −ve: M$^+$−H, 303.1.

Compounds AA-1-53, AA-1-54, AA-1-55, AA1-56, AA-1-58, 10-OK-07a, AA-1-66-, AA-1-68, AA-1-69, AA-1-73, AA-1-39-2, AA-1-78, AA-1-79, AA-1-80, AA-1-81

The following compounds provide further examples of preferred compounds in accordance with the first aspect of the present invention. They made be synthesised in accordance with the general synthetic methods previously described.

(AA-1-53)

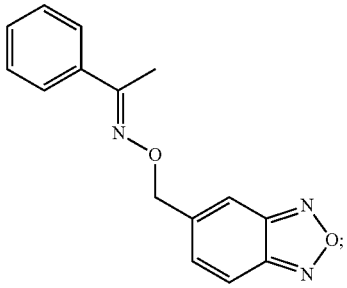

(AA-1-54)

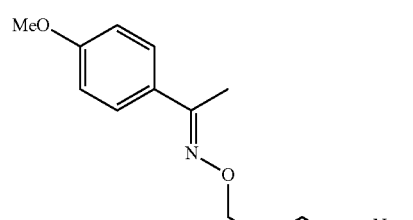

(AA-1-55)

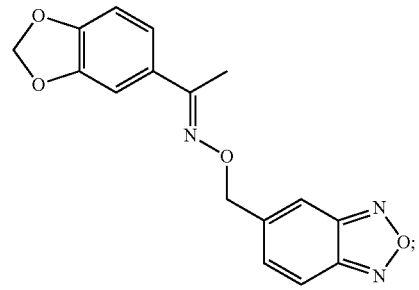

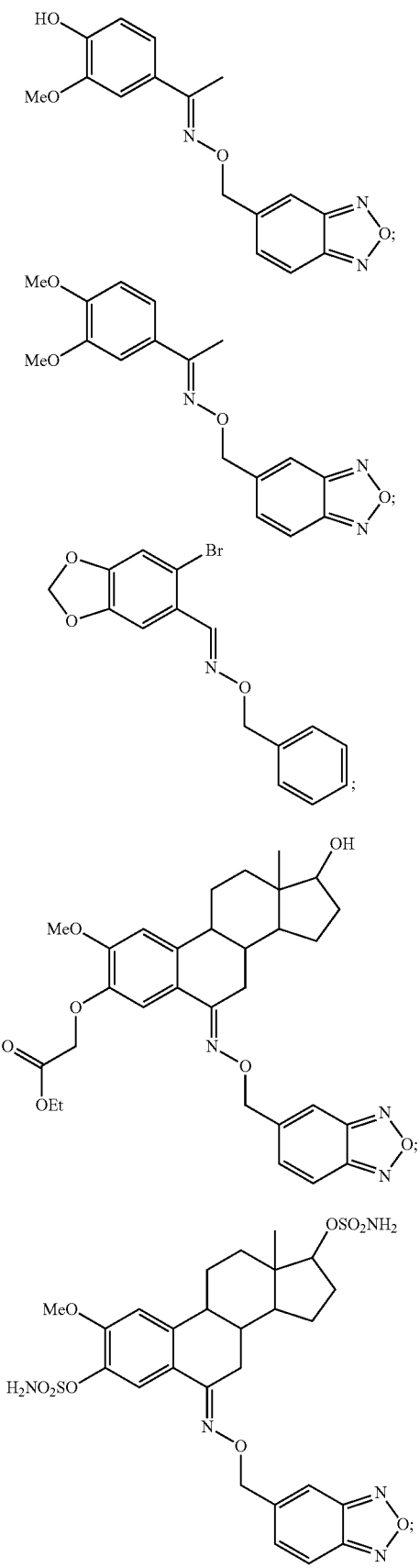
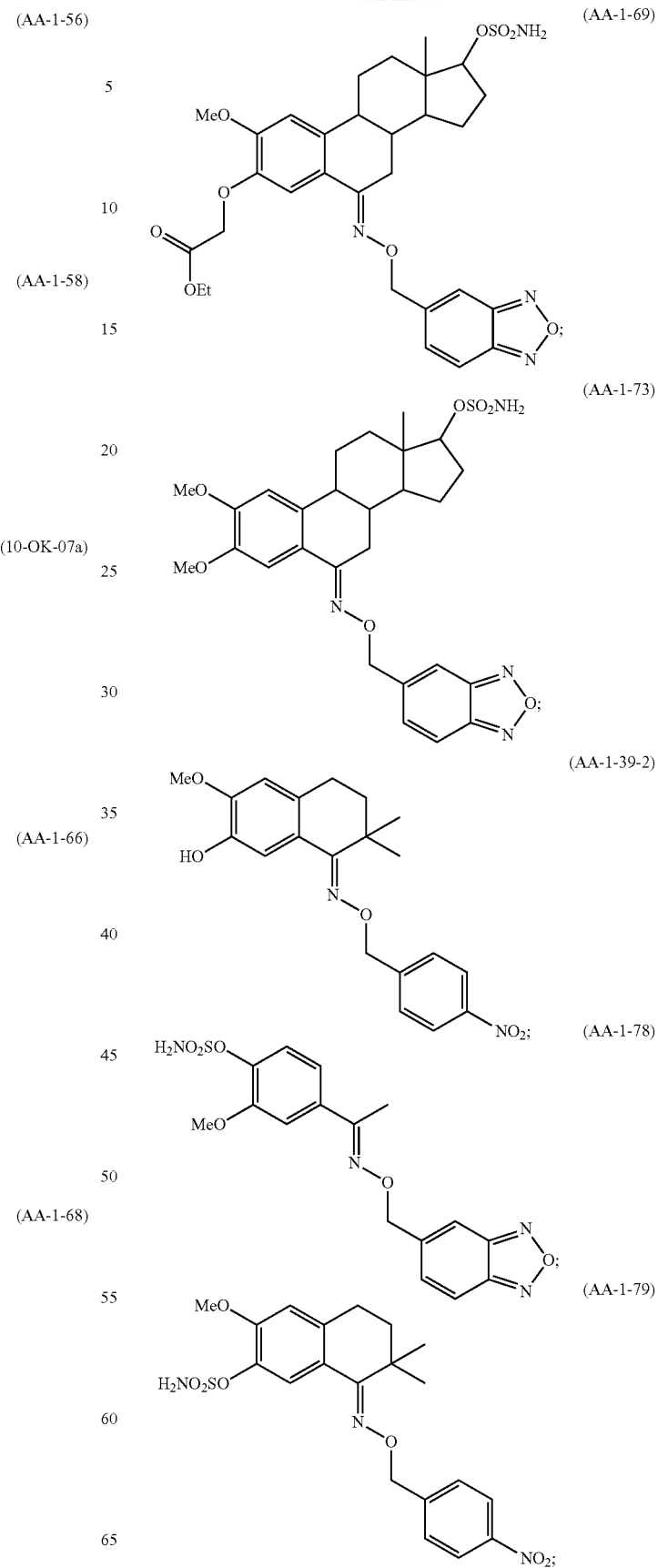

-continued

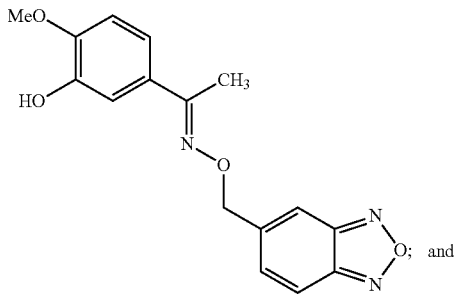
(AA-1-80)

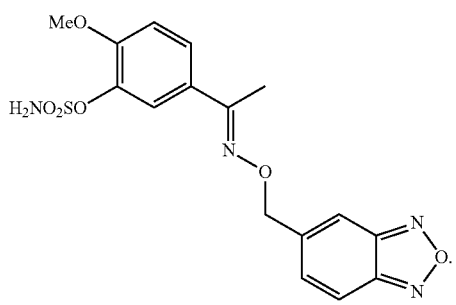
(AA-1-81)

Biological Activity
1. LPS Mouse Model of Acute Lung Injury

The compounds of the present invention may be tested for anti-inflammatory activity using the LPS Mouse model of acute lung injury.

The model used is very similar to the one described by Bozinovski, S., Jones, J. E., Vlahos, R., Hamilton, J. A. & Anderson, G. P. (2002). Granulocyte/macrophage-colony-stimulating factor (GM-CSF) regulates lung innate immunity to lipopolysaccharide through Akt/Erk activation of NFkappa B and AP-1 in vivo. *J Biol Chem*, 277, 42808-14.

Intratracheal administration of Lipopolysachamide (LPS) to mice results in injury to the lung and a resulting increase in total recoverable bronchoalveolar lavage (BAL) total cells mainly due to the infiltration of neutrophils to the site of injury. The LPS injury also results in increased expression of genes involved in the inflammatory response including ICAM, GM-CSF and COX-2. The effect of the compounds of the present invention on BAL cell number, total BAL protein and inflammatory gene expression may be analysed. As an example, female Balb/c mice (17-21 g) may be given a single intraperitoneal (i.p.) injection of vehicle or CP92 (150, 50, 15 and 5 mg/kg in peanut oil DMSO). Two hours after the mice would be anaesthetised with methoxyflurane and a droplet of LPS (1 μg in saline) or sterile saline would be applied to the nose. As the animals breathe through their nose, the LPS or saline would be inhaled and gain access to the lung tissue. Twenty four hours post-LPS administration, mice would be euthanized with a mixture of 200 μl ketamine and 10 μl xylazine i.p., tracheotomised and bronchoalveolar lavage (BAL) performed for the assessment of cell number, cell type and protein content. The lungs would be removed and weighed as an indicator of any adverse effects of the drug treatment. Total RNA would be isolated from the lung tissues for analysis of gene expression (mRNA) using RT-PCR.

2. Zymosan Challenge as a Model of Peritonitis

The peritonitis model is conducted in C57BL/6 mice. Compounds of the present invention would be administered subcutaneously in a vehicle of 10% DMSO 90% peanut oil in a volume of 100 μL 2 hours before administration of 1 mg zymosan (50 mg/kg, ip) into the peritoneal cavity in a volume of 100 pt. After a period of 4 hours, the mice would be killed by inhalational anaesthetic, methoxyfluorane and the peritoneal cavity lavaged using 1 ml of phosphate buffered saline. The number of viable cells and the protein content of the recovered lavage fluid would be measured by haemocytometer counting of propidium iodide excluding cells and Bradford protein assay, respectively.

The model would be conducted according to the methods described by Robert Hannon, Jamie D. Croxtall, Stephen J. Getting, Fiorentina Roviezzo, Ü Simon Yona, Mark J. Paul-Clark, Felicity N. E. Gavins, Mauro Perretti, John F. Morris, Julia C. Buckingham, and Roderick J. Flower. Aberrant inflammation and resistance to glucocorticoids in Annexin 1−/− Mouse. The FASEB Journal, FASEB J 2003 February 17(2):253-5.

3. Effects of Compounds on the Proliferation of Cells in Response to the Proliferative Stimulus of Either Thrombin (Human Airway Smooth Muscle) or Basic Fibroblast Growth Factor (bFGF)(Human Lung Parenchymal Fibroblasts, pFb)

The effects of compounds of the present invention on the proliferation of cells in response to the proliferative stimulus of either thrombin (human airway smooth muscle) or basic fibroblast growth factor (bFGF)(human lung parenchymal fibroblasts, pFb) were investigated. Cells were seeded onto 6-well plates at a density of $1.5 \times 10^4$ cells $cm^2$, made quiescent by removal of serum-containing media for 24 hours and then stimulated for 48 h with either thrombin (0.3 U/ml) or bFGF (300 pM). The test compounds were pre-incubated with HASM or pFb cells for 30 minutes before the addition of thrombin. At the end of the 48 hour incubation period, cells were detached from the culture plate by trypsin (0.5% w/v in PBS containing 1 mM EDTA), incubated for 5 minutes at ambient temperature in PBS containing 0.5% (w/v) trypan blue, washed twice (2% FCS in PBS), isolated by centrifugation (12,000×g, 5 min) and resuspended in 200 μl 2% FCS in PBS for counting in a haemocytometer chamber.

Methods

Human airway smooth muscle (HASM) cells were cultured from macroscopically normal bronchi (0.5-2 cm diameter) obtained from lung resection or heart-lung transplant specimens provided by the Alfred Hospital (Melbourne) according to methods published in detail previously (Fernandes et al., 1999).

Approximately 0.1 g of smooth muscle was stripped from the wall of the bronchus for each cell culture. Dissected tissue was immersed in Dulbecco's modified Eagle's medium (DMEM) (Flow Laboratories, Scotland), supplemented with 100 U/mL penicillin G (CSL, Australia) and 100 μg/mL streptomycin (CSL, Australia). The tissue was rinsed in phosphate buffered saline (PBS; Oxoid, England) and the airway smooth muscle was chopped into 2 $mm^3$ pieces and digested for 2 hours in DMEM containing elastase (0.5 mg/mL: Worthington Biochemical, USA) followed by a 12 hour incubation in DMEM containing collagenase (1 mg/mL) (Worthington Biochemical, USA), at 37° C. with agitation.

The resulting cell suspension was centrifuged and washed three times in phosphate buffered saline (PBS). Following the last centrifugation step, the cells were resuspended in 25 mL of DMEM supplemented with L-glutamine (2 mM: Sigma, USA), penicillin G (100 U/mL), streptomycin (100 μg/mL), amphotericin B (2 μg/mL: Wellcome, UK) and heat-inactivated FCS (10% v/v: CSL, Australia) and seeded into 25 $cm^2$ culture flasks. The primary isolates were incubated for 7 to 14 days to reach confluence.

Cells were harvested weekly by 10 min exposure to trypsin (0.5%: CSL, Australia) and EDTA (1 mM in PBS: BDH, Australia) and passaged at a 1:3 ratio into 75 cm² flasks.

Human Lung Parenchymal Fibroblast Cell Culture

Human lung parenchymal fibroblast cell culture (pFb) were cultured from macroscopically normal parenchymal tissue of patients without fibrotic disease obtained from lung resection or heart-lung transplant specimens provided by the Alfred Hospital (Melbourne). Subpleural biopsy tissue measuring 5×5×5 mm was extensively rinsed in sterile PBS, chopped into 1 fragments and adhered to the bottom of 1 well of a 6 well plastic culture dish in a minimum volume of medium (~200 ml), after approximately 4-6 h to allow tissue adherence the wells were flooded with 2 ml DMEM. Cultures were grown in DMEM (containing 10% v v$^{-1}$ FCS, 100 U ml$^{-1}$ Penicillin-G, 100 μg ml$^{-1}$, 2 μg ml$^{-1}$ amphotericin B, 1% v v$^{-1}$ non-essential amino acids, and 1% v v$^{-1}$ Sodium Pyruvate) until monolayer confluence was reached.

In Vitro Fibroblast Proliferation Assay

Human pFb were grown to confluence and serum-deprived for 24 h to synchronise cells in $G_0/G_1$-phase of the cell-cycle prior to stimulation with FCS (10% v v$^{-1}$, or bFGF, 300 pM). A growth supplement containing factors essential for cell mitogenesis including insulin, transferrin, and selenium (1% v v$^{-1}$ Monomed A, JRH Biosciences, USA) was added (in experiments using bFGF as the mitogen) and after 48 h cells were detached from the culture plate by the addition of trypsin, washed twice (2% FCS in PBS), isolated by centrifugation (12,000×g, 5 min) and resuspended in 300 μl (2% FCS in PBS, containing 0.5% w v$^{-1}$ trypan blue) before counting in a haemocytometer.

It will be understood that such assays could be readily utilized to determine the ability of disclosed compounds to inhibit Thrombin or bFGF-induced proliferation of human airway smooth muscle cells. These assays may also be used to test the ability of such compounds to inhibit the Thrombin or bFGF-induced proliferation of smooth muscle cells from other regions.

The results of these assays using compounds of the present invention are presented in Table 2 below.

TABLE 2

| Compound | Log IC$_{50}$ HASM | Log IC$_{50}$ pFb |
|---|---|---|
| CP30218 | −5.23 | −8.18 |
| CP30220-minor (Z-) | −7.41 | — |
| CP30222 | −8.08 | — |
| CP30221 | −5.54 | — |

Macrophage Cell Lines and Prostaglandin $E_2$ Production
U937 Monocytic Cell

The U937 monocytic cell line (available from the ATCC, USA) is commonly used to evaluate anti-inflammatory agents. In the present experiment, U937 cells maintained in culture in a medium comprising RPMI containing (5% FCS v/v; supplemented with 100 U/ml penicillin, and 100 mg/ml streptomycin) were treated with phorbol myristate acetate (10 nM) then immediately dispersed into a 24 well cell culture plate at a concentration of 2×10⁵ cells per ml in a volume of 1 ml per well. After 24 hours by which time the cells had adhered to the plastic substrate, they were treated with one of several analogues or with the vehicle of 0.1% DMSO. After a further 24 hour incubation period the supernatant was harvested and the content of prostaglandin $E_2$ was measured by a radioimmunoassay, as described by Vlahos, R., & Stewart, A. G. (1999). ("Interleukin-1α and Tumour necrosis factor-α inhibit airway smooth muscle DNA synthesis by a glucocorticoid-sensitive induction of cyclo-oxygenase-2. *British Journal of Pharmacology*, 126, 1315-1324). Most of the analogues were found to decrease the concentration of Prostaglandin $E_2$ in the supernatant, consistent with these compounds having an anti-inflammatory effect, although certain compounds had a stimulatory action. The data in the table are presented as percentage of the control level of Prostaglandin $E_2$.

J774 Cell Line

The J774A.1 murine macrophage cell line (from American Type Culture Collection) was cultured in phenol red-free Dulbecco's modified Eagle's medium (DMEM) (Gibco) supplemented with 5% (v/v) heat-inactivated foetal calf serum (FCS) (JRH Biosciences), 15 mM HEPES, 2 mM L-glutamine (SAFC Biosciences), 0.2% sodium bicarbonate, 50 iu/ml penicillin and 50 μg/ml streptomycin, maintained at 37° C. in a humidified atmosphere containing 5% $CO_2$. All cell culture reagents were certified endotoxin-free. Cells were passaged by scraping, and washed twice in 2% FCS in PBS (once before scraping, once after) prior to plating in order to remove debris that may have accumulated in the medium. Cells were seeded on 24-well culture plates at a density of 1.5×10⁵ cells/ml/well (7.5×10⁴ cells/cm²). Before stimulation with LPS (1 mg/ml) and IFNγ (0.1 iu/ml), cells were pre-treated with CP analogue for 30 min and after a further 24 hour incubation period, the supernatant was harvested and the content of prostaglandin $E_2$ was measured by a radioimmunoassay.

Competitive Binding Assays

Compounds of the present invention were assessed in a competitive binding assay using the radioligand [4-³H] 2-methoxy-6-(4-nitrobenzyloxyimino)estradiol ([³H]-CP2117) bound to proteins in rat lung membranes.

The compound CP-2117 has been shown in vitro to have anti-inflammatory activity. See, for example, WO 2004/101595.

Preparation of [4-³H] 2-methoxy-6-(4-nitrobenzyloxyimino)estradiol ([³H]-CP2117)

[4-³H] 2-methoxy-6-(4-nitrobenzyloxyimino)estradiol was prepared in accordance with the reaction scheme below.

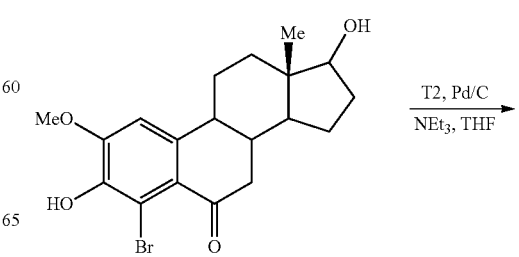

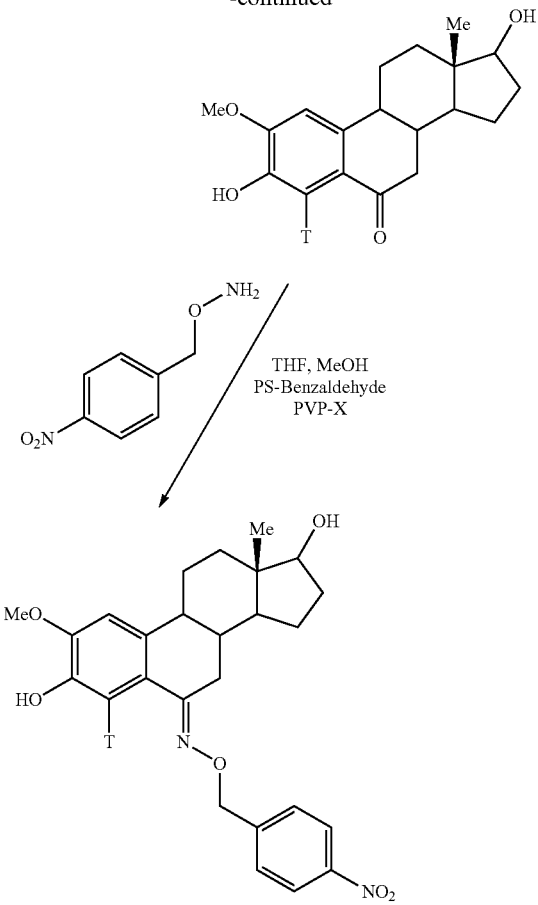

Synthesis of ³H—CP2117

³H-CP2117 was custom-tritiated on the 4 position using a 4-bromo-2-methoxy-2-oxo-3,17-bisacetyl-estratriene by Eagle Picher Pharmaceutical Services, LLC of Lenexa, Kans., USA. The final product isolated by preparatory HPLC. The batch of radiochemical supplied by Eagle Picher was 95% pure by HPLC with a specific activity of 6 Ci/mmol at a concentration of 0.4 mCi/ml in 9:1 toluene:ethanol. The compound presented as a clear colourless liquid and was stored under inert atmosphere at −20° C. and protected from light. The material was stored at −20° C. and aliquots were taken as required, evaporated to dryness under a stream of $N_2$ and resuspended in TEG buffer at the required concentration ³H-CP2117 of 10 nM.

Receptor Preparation

Male and female Sprague Dawley rats 200-400 g are killed by anaesthetic overdose and exsanguinated. Lungs are removed, snap frozen in liquid N2 and pulverized using a mortar and pestle. Pulverised tissue is added to extraction buffer (Tris 50 mM buffer pH 7.00 containing EDTA 1 mM, glycerol 10% v/v, (TEG) PMSF 1 mM, $CaCl_2$ 2 mM) in a volume of 10 ml/g wet tissue weight. Tissue is homogenised by three 15 s burst on medium speed in an Ultra Turrax homogeniser with 45 s on ice between bursts to avoid heating extraction solution. The tissue is strained through gauze, subjected to centrifugation at 100 g for 15 min at 4° C. The pellet is discarded and dithiothreitol 1 mM/25 mM sodium molybdate is added to the supernatant prior to isolation of the particulate fraction by centrifugation at 30,000 g for 60 min. The supernatant (cytosolic fraction is stored) and the pellet (particulate fraction) is resuspended in 5 ml of TEG/PMSF buffer. A further centrifugation at 30,000 g for 60 min at 4° C. is carried out, and the pellet is resuspended in 10 ml TEG/PMSF buffer and used for radioligand binding studies as described below.

Binding Studies

Affinities of the compounds of the present invention were determined using rat lung membranes as a source of binding proteins. The membranes were diluted to contain approximately 0.1 mg/mL protein as determined using the Bradford method (Biorad). Binding assays were carried out by overnight incubation at 4° C. in 300 mL of the above described buffer, comprising 200 mL of RLM, 50 µL of displacer (compounds over a suitable range of concentrations to yield a displacement curve up to a maximum of 10 mM) and 504 of 10 nM [³H]-CP2117 (prepared as described above). Separation of bound from free radioligand was achieved by the addition of 500 µL of dextran-coated charcoal (400 mg dextran clinical grade C and 2 g of charcoal, Norit A in 100 mL of Tris buffer) and centrifugation at 4° C. in a Sorval RT7 at 2000×g for 10 min. Saturation analysis over the range 1-100 nM [³H]-CP2117 indicated that the concentration of 10 nM in the final incubation described above was sub-saturating and therefore was a suitable concentration for displacement studies. Analyses of CP analogues were carried out over the range 30 nM-3 µM in 0.5 to 1.0 log increments. The data were fitted by non-linear regression (GraphPad Ver 4.0) and the data are presented as $pIC_{50}$ (negative logarithm of the concentration producing 50% of the maximum displacement of radiolabel).

The activity of CP933 was investigated in a model of pulmonary inflammation induced by intra-nasal delivery of LPS. The agent CP933 was administered by intraperitoneal injection in a dose of 150 mg/kg (vehicle comprising 10% DMSO in peanut oil at a volume of 10 ml/kg), ip to mice 2 hours after intranasal dosing with 1 mg LPS in a volume of 35 µL The effects of dexamethasone at 1 mg/kg, ip were established in the same study. As shown in FIGS. 1A and 1B, CP933 reduced accumulation of protein in the boncho-alveolar lavage (BAL) fluid and attenuated the airspace neutrophilia (more than 90% of the cells attracted into the airspaces by the LPS challenges have the morphological characteristics of neutrophils. Dexemathasone, also administered 2 hours after the LPS, had no significant effect on the neutrophilia, but produced a similar reduction in the BAL protein levels to that of CP933.

Several analogues were evaluated for their actions on the release of $PGE_2$ from the human U937macrophage cell line. Cells were stimulated by exposure to PMA 1 nM and after a period allowed for adherence of cells to the plastic culture dish, the cell were treated with one of several CP analogues. FIG. 2 shows the action of compounds CP1-56 and CP1-58 on the release of $PGE_2$ from the U937macrophage cell line. The chemical structures of CP1-56 and CP1-58 are as follows:

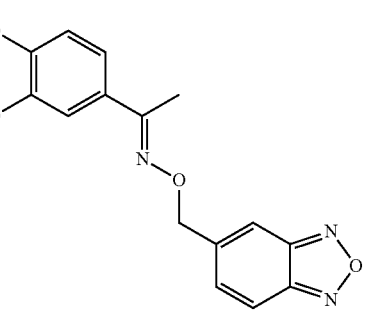

CP1-56

-continued

CPI-58

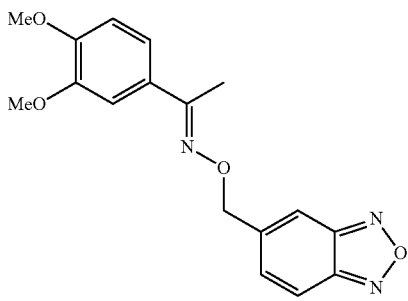

Figure 3:
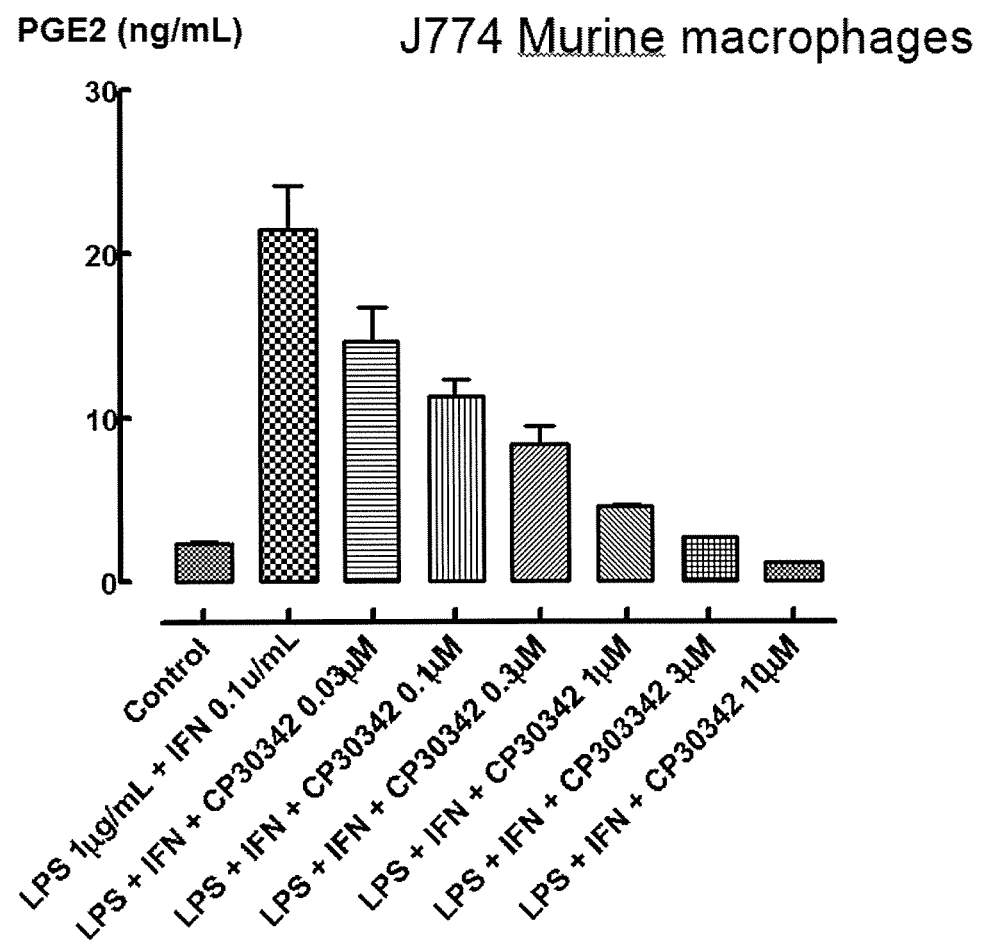
FIG. 3: Shows the evaluation of CP30342, a preferred compounds of the first aspect of the present invention, for its action on the release of $PGE_2$ from the murine J 774 macrophage cell line.

Several analogues were also evaluated for their actions on the release of $PGE_2$ from the murine J774 macrophage cell line. Cells were stimulated by exposure to LPS (1 µg/ml) and IFNγ 0.1 iu/ml) after 30 min of pretreatment with CP analogue. An example using CP30342 as the analogue is shown in FIG. 3.

Biological results for other compounds tested are set out in Table 3.

TABLE 3

| Analogue | Log IC50 RLM binding | Effects on PGE2 release in U937 cells at 1 µM as a % of PMA control | | Effects on PGE2 release in J774 macrophages at 1 µM as a % of LPS/IFNγ control | | Effects on PGE2 release in J774 macrophages at 10 µM as a % of LPS/IFNγ control | |
|---|---|---|---|---|---|---|---|
| | | mean | sem | mean | sem | mean | sem |
| CP30218 | −6.44 | | | 218 | 36 | 188 | 57 |
| CP30280 | −6.5 | | | | | | |
| CP30220 | NA | | | | | | |
| CP30221 | NA | | | | | | |
| CP30222 | NA | | | | | | |
| CP933 | −6.185 | | | 109 | 17 | 87 | 21 |
| CP30255 | ND | | | | | | |
| CP30257 | ND | | | | | | |
| CP30252 | ND | | | | | | |
| CP30262 | −6.88 | | | | | | |
| CP30253 | ND | | | 47 | 9 | 4 | |
| CP30254 | ND | | | | | | |
| CP30260 | ND | | | | | | |
| CP30263 | −6.46 | | | | | | |
| CP30264 | −6.96 | | | 77 | 3 | 74 | 5 |
| CP30281 | −6.16 | | | | | | |
| CP30282 | −6.41 | | | | | | |
| CP30283 | −6.05 | | | | | | |
| CP30274 | −6.86 | | | | | | |
| CP30275 | NA | | | | | | |
| CP30266 | −6.9 | | | | | | |
| CP30329 | −6.2 | | | | | 55 | 12.4 |
| CP30331 | −6.14 | | | | | 28 | 5.3 |
| CP30338 | −6.88 | | | 110 | 11.4 | | |
| CP30339 | −6.64 | | | | | 36 | 4.3 |
| CP30340 | −6.26 | | | | | 51 | 4.4 |
| CP30342 | −6.79 | | | 19 | 1 | 0 | 0 |
| CP30343 | −6.23 | | | 65 | 3 | 51 | 4 |
| CP30344 | −5.43 | | | 111 | 12.7 | 94 | 8 |
| CP30345 | −6.33 | | | 76 | 7.3 | 1 | 3 |
| CP30346 | −5.99 | | | 78 | 11.2 | 34 | 10 |
| CP30347 | −5.75 | | | 102 | 10.6 | 68 | 10 |
| CP30348-1 | −6.02 | | | 124 | 16.8 | 91 | 19 |
| CP30348-2 | −5.6 | | | 85 | 8.5 | 111 | 18 |
| CP30381 | −5.83 | | | 62 | 5.1 | | |
| CP8133 | NA | | | | | | |
| CP9121 | ND | | | | | | |
| CP9123 | ND | | | | | | |
| CP9125 | −5.5 | | | | | | |
| CP9126 | nd | | | | | | |
| CP9128 | −5.9 | | | 62 | 3 | 65 | 9 |
| CP9129 | nd | | | | | | |
| CP9131 | NA | | | | | | |
| CP9132 | NA | | | | | | |
| CP9135 | −5.28 | | | 66 | 9 | 90 | 5 |
| TB39 | NA | | | | | | |
| TB76 | −6.48 | | | | | | |
| TB81 | −6.16 | | | | | | |
| TB54 | ND | | | 95 | 4.1 | 78 | 9 |
| CP30261 | −6.65 | | | | | | |
| 2-TB39 | ND | | | | | | |
| 2-TB-141 | nd | | | | | | |
| 2-TB-142 | nd | | | | | | |

TABLE 3-continued

| Analogue | Log IC50 RLM binding | Effects on PGE2 release in U937 cells at 1 μM as a % of PMA control | | Effects on PGE2 release in J774 macrophages at 1 μM as a % of LPS/IFNγ control | | Effects on PGE2 release in J774 macrophages at 10 μM as a % of LPS/IFNγ control | |
|---|---|---|---|---|---|---|---|
| | | mean | sem | mean | sem | mean | sem |
| 2-TB-146 | −6.91 | | | 138 | 34 | 214 | 48 |
| 2-TB-147 | −6.43 | | | | | | |
| CP30424 | −6.18 | | | 83 | 3.48 | | |
| AA36 | −6.59 | | | 70 | 2.51 | | |
| AA-1-39-2 | −6.19 | 100 | 2.9 | | | | |
| AA-1-53 | ND | 91 | 1.7 | | | | |
| AA-1-54 | ND | 76 | 2 | | | | |
| AA-1-55 | ND | 90 | 2.1 | | | | |
| AA-1-56 | −6.21 | 16 | 0.6 | | | | |
| AA-1-58 | −4.74 | 111 | 5 | | | | |
| AA-1-78 | −4.87 | 19 | 1.4 | | | | |
| AA-1-79 | −4.58 | 113 | 1.3 | | | | |
| AA-1-80 | −6.33 | 38 | 2.7 | | | | |
| AA-1-81 | −5.25 | 43 | 2.8 | | | | |
| 10-OK-07a | −4.76 | 114 | 4.4 | | | | |
| CP30381 | −5.137 | | | | | | |
| CP30450A | −5.81 | 80 | 3.9 | | | | |
| CP30450B | −5.85 | 77 | 3.2 | | | | |
| CP30451 | −5.73 | 67 | 1.5 | | | | |
| CP30452 | −5.54 | 89 | 1.2 | | | | |
| CP30453 | −5.81 | | | | | | |
| 2-TB-264 | −5.63 | | | | | | |
| 2-TB-288 | −5.61 | | | | | | |

ND- not detected
NA- not available

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Ishii, H., Chen, I.-S., Ishikawa, T. *J. Chem. Soc. Perkin Trans.* 1 1987, 671-676.
2. Banwell, M. G., Flynn, B. L., Willis, A. C., Hamel, E. *Aust. J. Chem.* 1999, 52, 767-774.
3. McCoubrey, A., Iyengar, N. K., *J. Chem. Soc.* 1951, 3430-3433.
4. Brossi, A., Gurien, H., Rachlin, A. I., Teitel, S. *J. Org. Chem.* 1967, 32, 1269-1270.
5. Hamor, G. H., Breslow, D. M., Fisch, G. W. *J. Pharm. Sci.* 1970, 59, 1752-1756.
6. Brady, O. L., Klein, L. *J. Chem. Soc.* 1927, 874-894.
7. Flynn, B. L., Hessian, K. O. *Org. Lett.* 2003, 5, 4377-4380.
8. Kitano, Y., Ito, T., Suzuki, T., Nogata, Y., Shinshima, K., Yoshimura, E., Chiba, K., Tada, M., Sakaguchi, I., *J. Chem. Soc., Perkin Trans.* 1 2002, 2251-2255.
9. Kabalka, G. W., Wu, Z. Z., Yao, M., -L., Natarajan, N., *Appl. Radiat. Isotopes* 2004, 61-1111-1115.
10. Wild, H., *J. Org. Chem.* 1994, 59, 2748-2761.
11. Vlahos, R., & Stewart, A. G. "Interleukin-1α and Tumour necrosis factor-α inhibit airway smooth muscle DNA synthesis by a glucocorticoid-sensitive induction of cyclooxygenase-2. *British Journal of Pharmacology*, 1999, 126, 1315-1324.
12. Mark J. Paul-Clark, Felicity N. E. Gavins, Mauro Perretti, John F. Morris, Julia C.

Buckingham, and Roderick J. Flower. Aberrant inflammation and resistance to glucocorticoids in Annexin 1−/− Mouse. The FASEB Journal, FASEB J 2003 February 17(2): 253-5.
13. Bozinovski, S., Jones, J. E., Vlahos, R., Hamilton, J. A. & Anderson, G. P. (2002). Granulocyte/macrophage-colony-stimulating factor (GM-CSF) regulates lung innate immunity to lipopolysaccharide through Akt/Erk activation of NFkappa B and AP-1 in vivo. *J Biol Chem*, 277, 42808-14.
14. Fernandes, D. J., Guida, E., Kalafatis, V., Harris, T., Wilson, J., and Stewart, A. G., *American Journal of Respiratory Cell Molecular Biology* 1999 21:77-88.

The invention claimed is:
1. A compound, selected from the group consisting of:
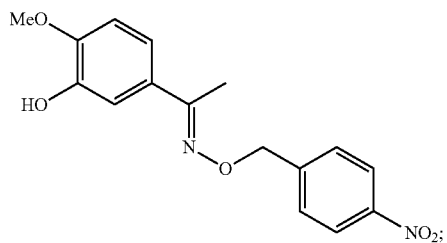
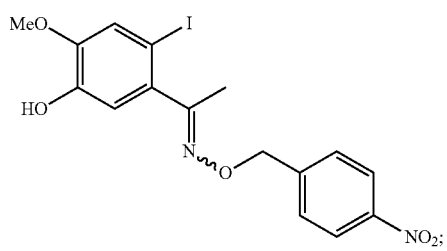
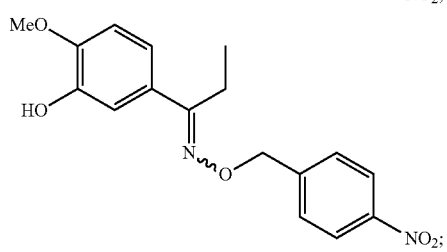
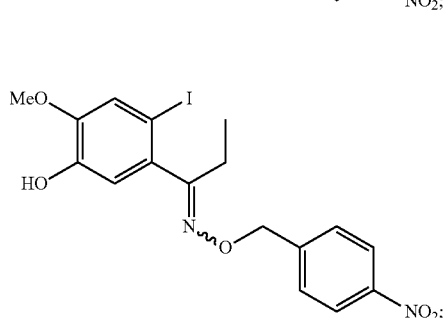
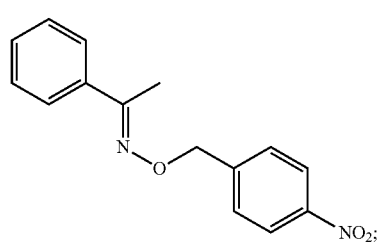
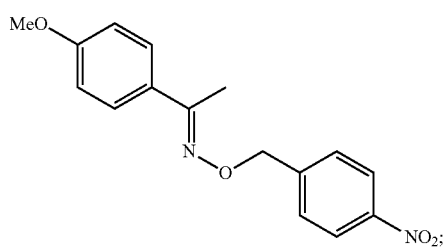
-continued
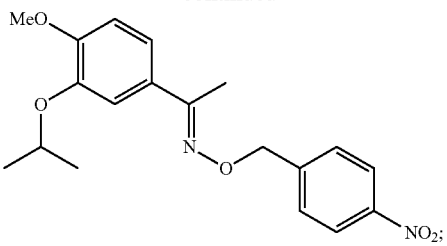
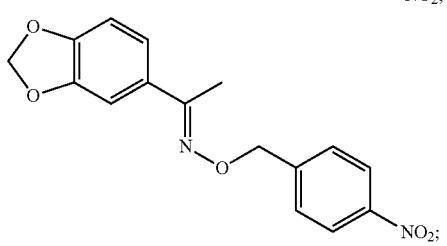
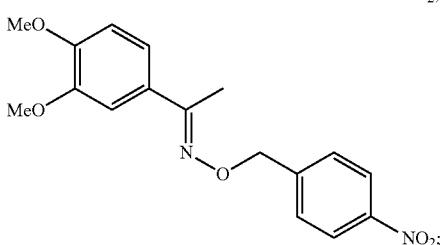
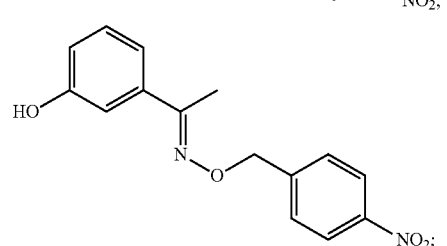
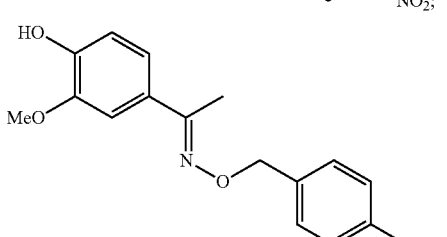
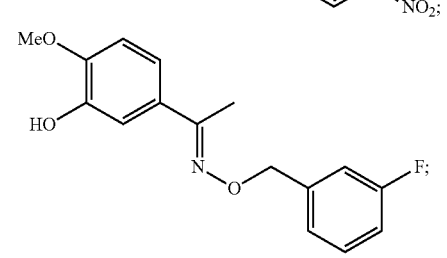
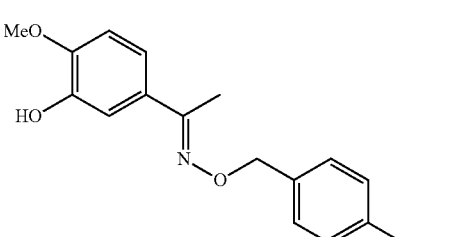

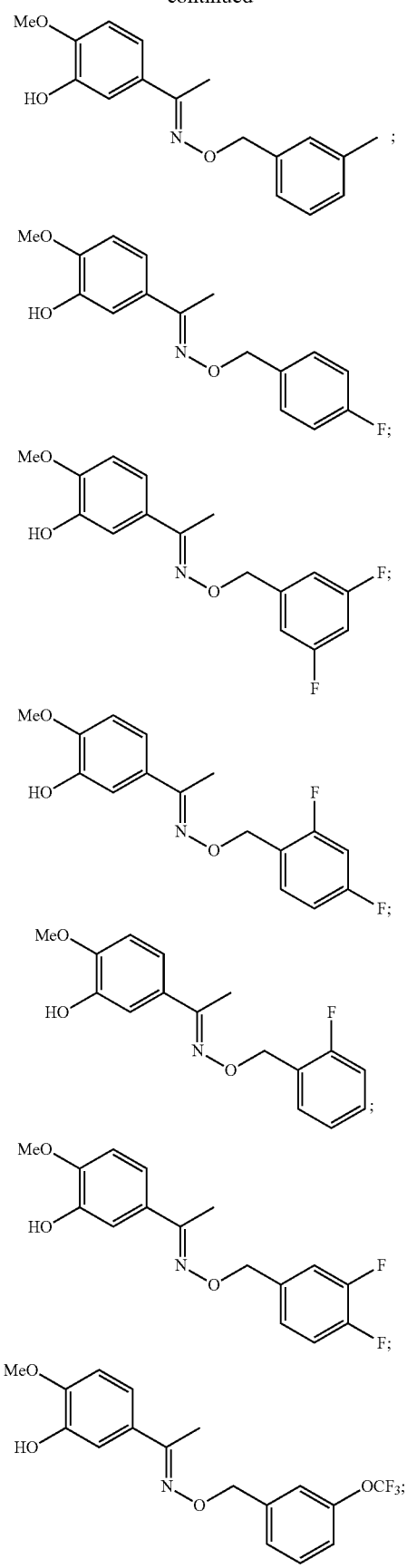
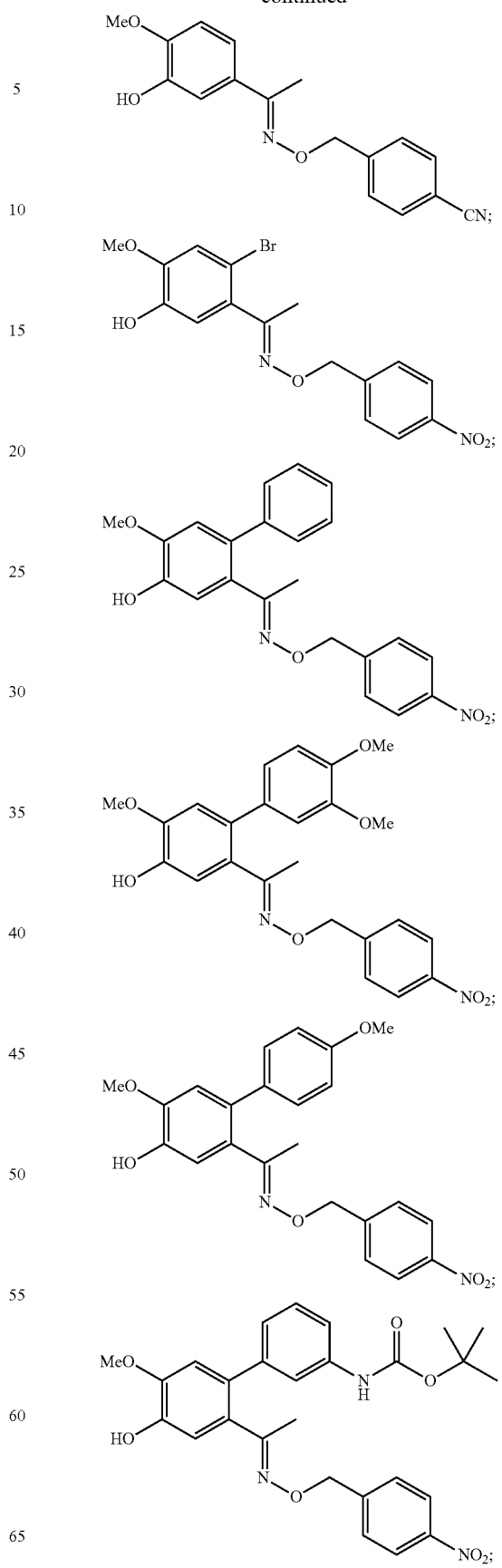

137 -continued
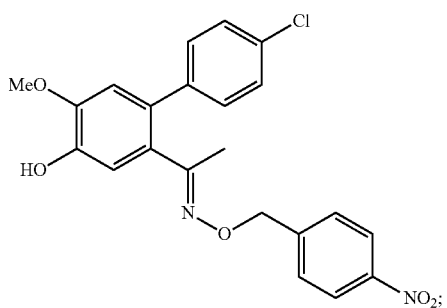
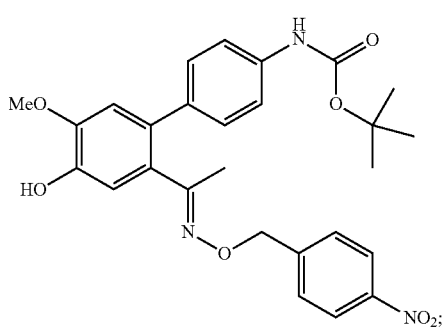
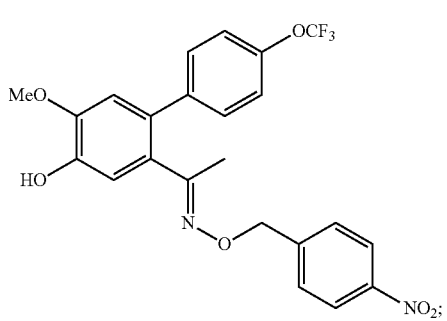
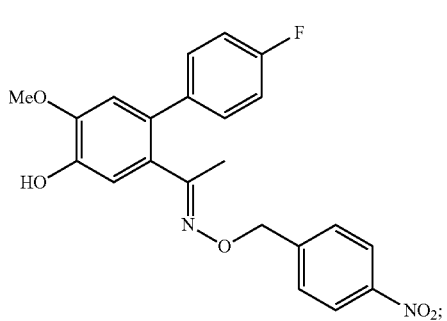
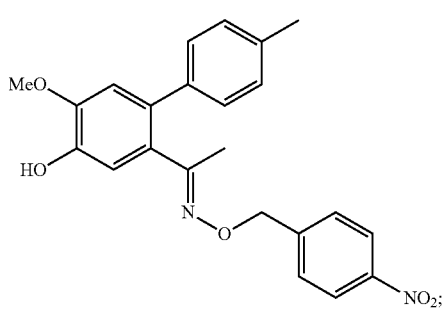
138 -continued
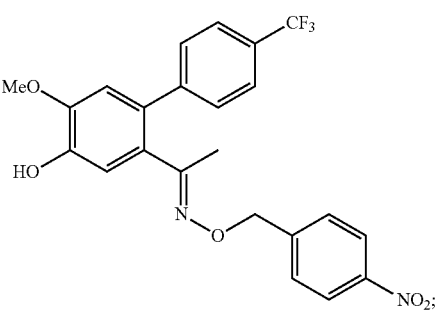
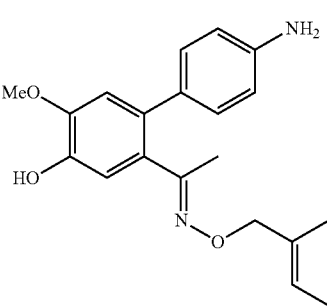
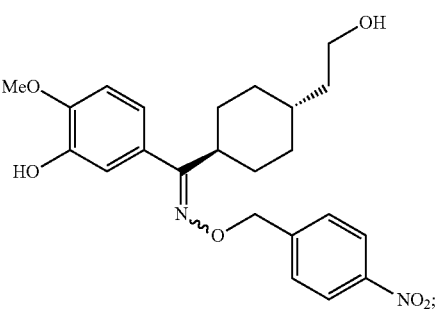
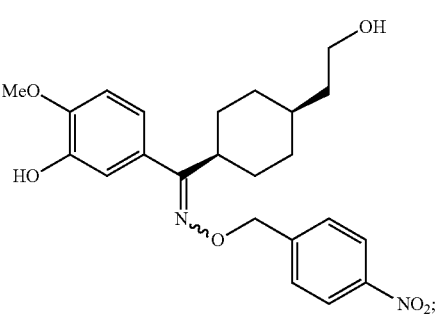
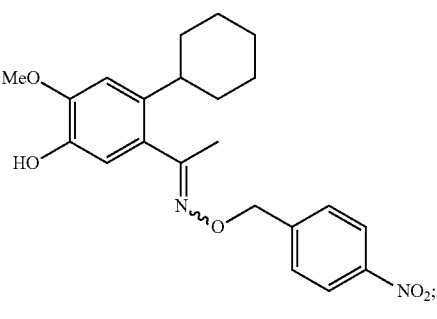

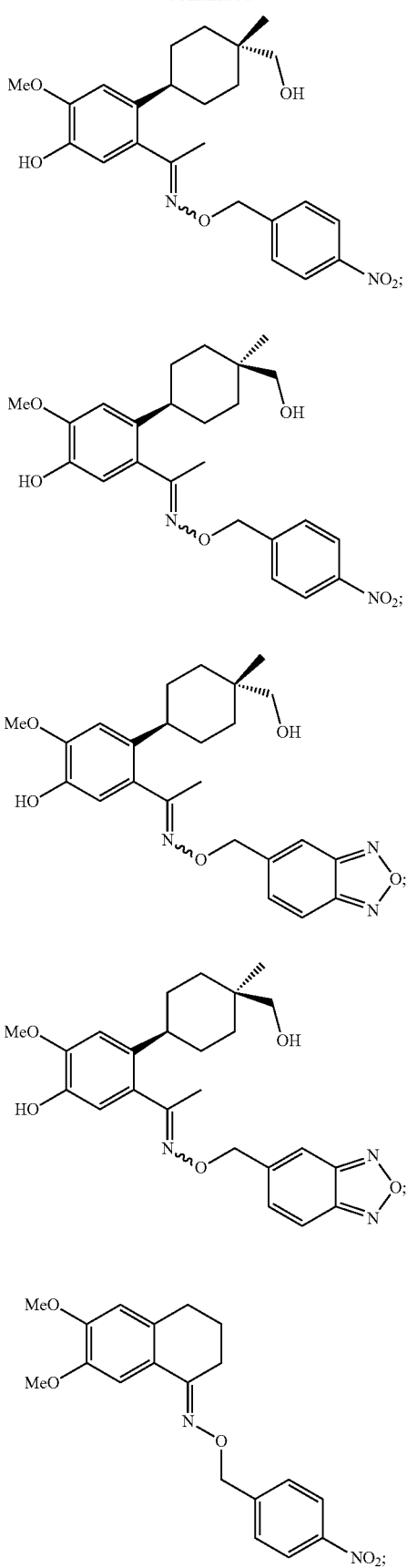

141
-continued
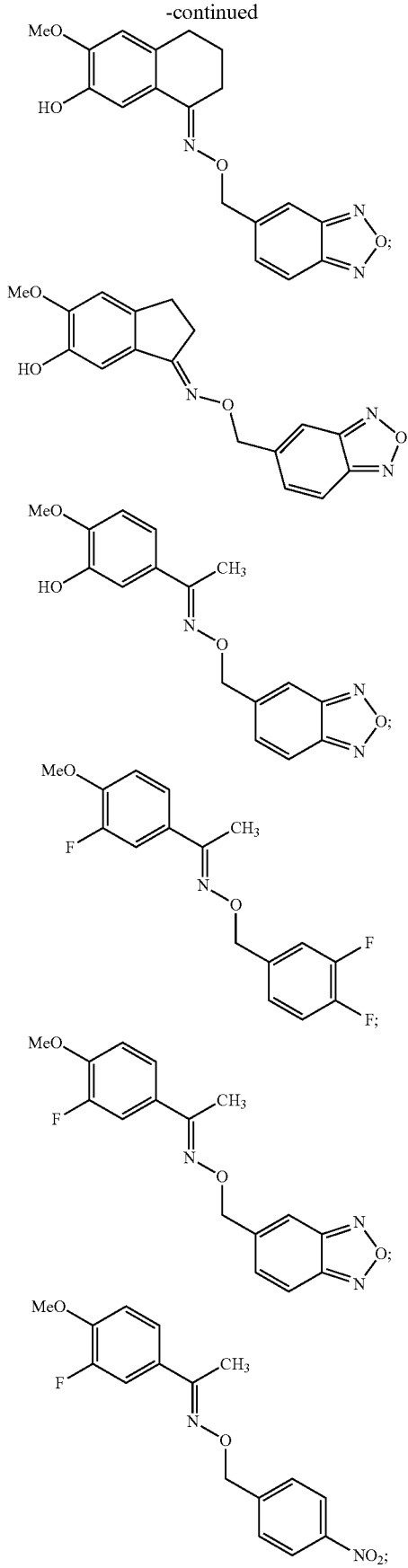
142
-continued
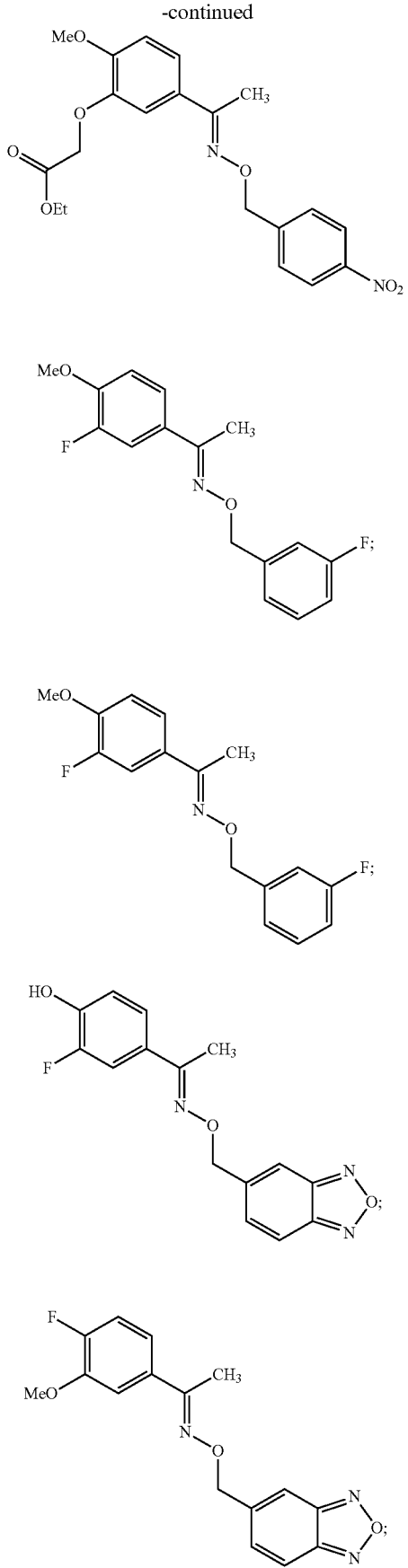

143
-continued
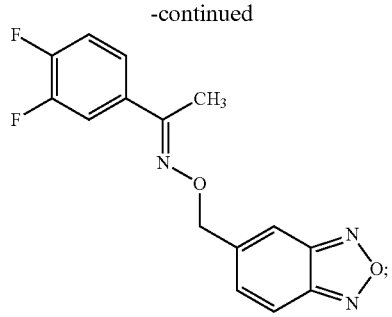
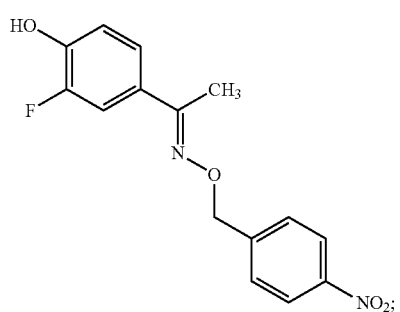
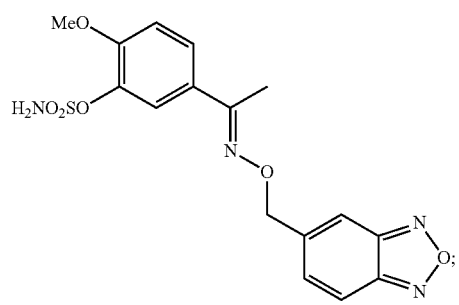
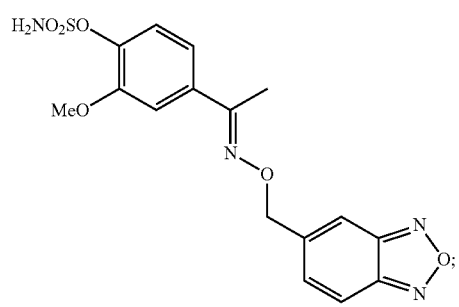
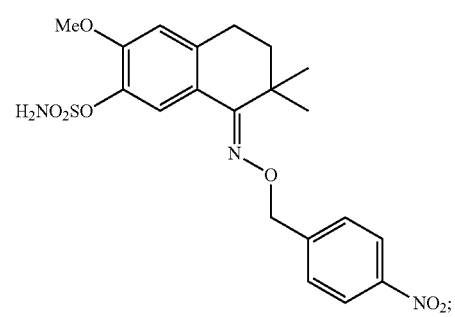
144
-continued
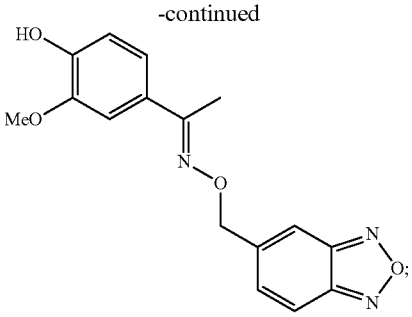
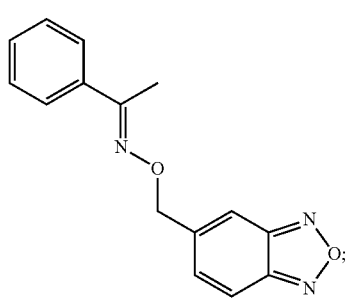
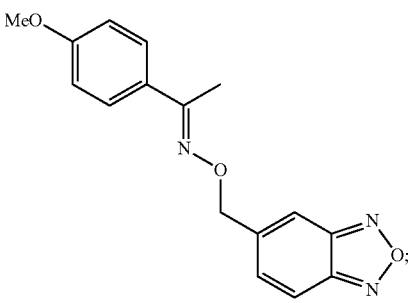
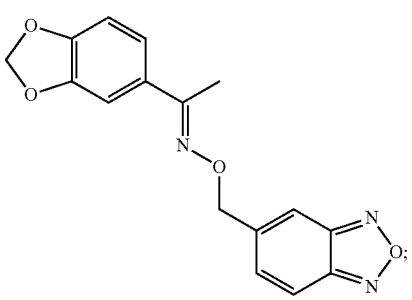
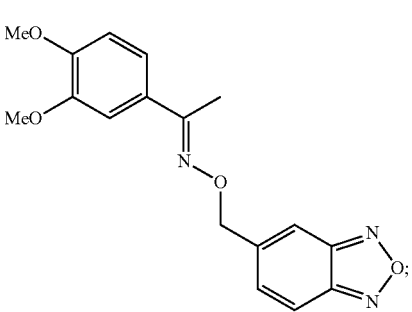

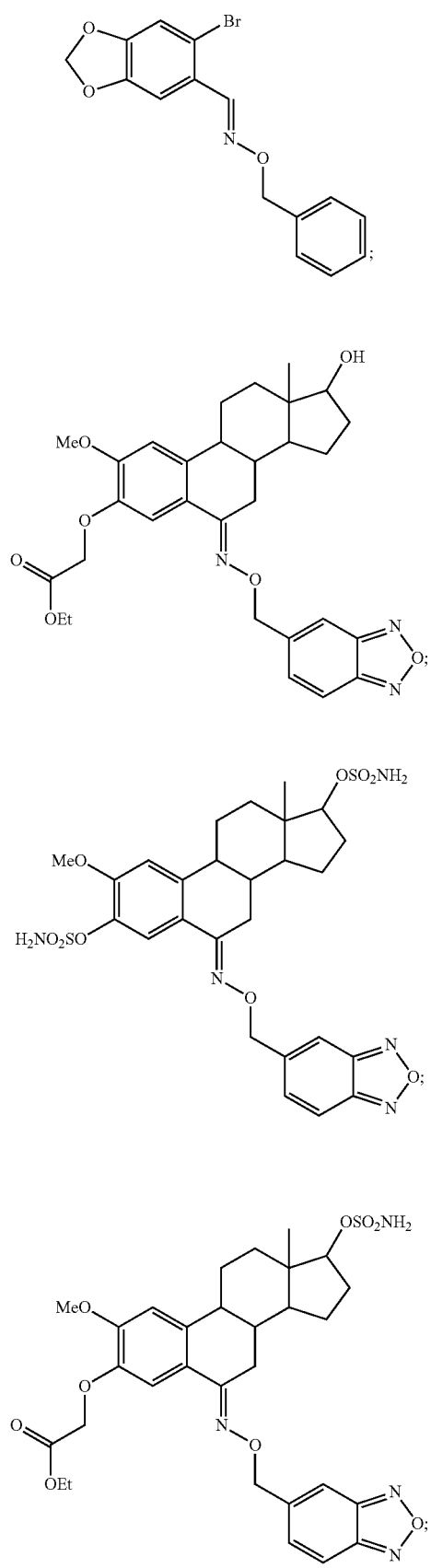

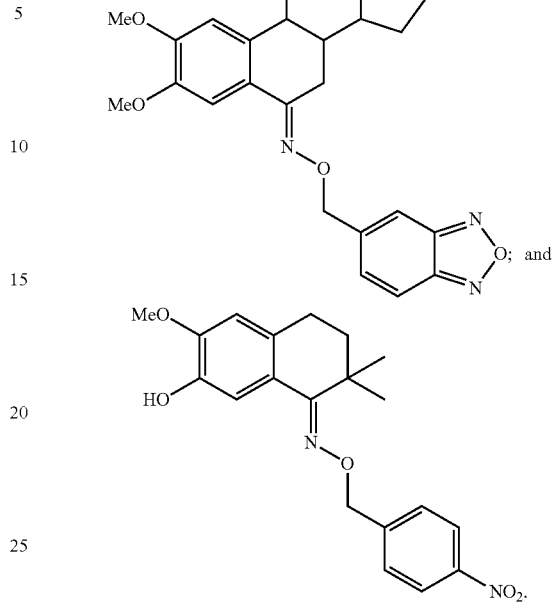

or a pharmaceutically acceptable salt, derivative, or prodrug thereof.

2. The compound according to claim 1, wherein the conformation around the C=N double bond is the "E" conformation.

3. The compound according to claim 1, wherein the compound is in substantially pure isomeric form at one or more asymmetric centres.

4. A pharmaceutical composition comprising a compound as claimed in claim 1 and a pharmaceutically acceptable carrier, diluent and/or excipient.

5. A pharmaceutical composition according to claim 4 further comprising a glucocorticoid.

6. A pharmaceutical composition according to claim 4 further comprising a β2-adrenoceptor agonist.

7. A method of treating a condition or disease associated with an allergic disease, comprising: administering an effective amount of a pharmaceutical composition as claimed in claim 4 to a subject in need thereof, wherein the allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

8. A method of treating a condition or disease associated with an allergic disease, comprising: administering an effective amount of a compound as claimed in claim 1 to a subject in need thereof,
wherein the allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

9. The method according to claim 8 wherein the compound is administered to the subject by parental administration, oral administration or by inhalation.

10. The method according to claim 8, wherein the allergic disease is a respiratory allergic disease.

11. The method according to claim 10 wherein the respiratory allergic disease is selected from the group consisting of asthma, allergic rhinitis, and hypersensitivity lung disease.

12. The method according to claim 8, wherein the disease or condition is asthma.

13. The method according to claim 8, wherein the subject to be treated is a human.

* * * * *